US010259880B2

(12) United States Patent
Campbell et al.

(10) Patent No.: US 10,259,880 B2
(45) Date of Patent: Apr. 16, 2019

(54) ANTI-LIGHT ANTIBODIES

(71) Applicant: KYMAB LIMITED, Cambridge (GB)

(72) Inventors: Jamie Iain Campbell, Cambridge (GB); Bettina Franz, Cambridge (GB); Steve Holmes, Cambridge (GB); Ian Kirby, Cambridge (GB); Anais Legent, Cambridge (GB)

(73) Assignee: KYMAB LIMITED, Cambridge (GB)

( * ) Notice: Subject to any disclaimer, the term of this patent is extended or adjusted under 35 U.S.C. 154(b) by 0 days.

(21) Appl. No.: 15/110,487

(22) PCT Filed: Jan. 13, 2015

(86) PCT No.: PCT/GB2015/050054
§ 371 (c)(1),
(2) Date: Jul. 8, 2016

(87) PCT Pub. No.: WO2015/107331
PCT Pub. Date: Jul. 23, 2015

(65) Prior Publication Data
US 2017/0291951 A1 Oct. 12, 2017

(30) Foreign Application Priority Data
Jan. 14, 2014 (GB) .................................. 1400597.9
Aug. 6, 2014 (GB) .................................. 1413950.5

(51) Int. Cl.
*C07K 16/28* (2006.01)
*A61K 39/00* (2006.01)
*C12N 15/63* (2006.01)

(52) U.S. Cl.
CPC .......... *C07K 16/2875* (2013.01); *A61K 39/00* (2013.01); *C12N 15/635* (2013.01); *C07K 2317/32* (2013.01); *C07K 2317/33* (2013.01); *C07K 2317/56* (2013.01); *C07K 2317/73* (2013.01); *C07K 2317/76* (2013.01); *C07K 2317/92* (2013.01)

(58) Field of Classification Search
CPC ........................... C07K 16/2875; A61K 39/00
See application file for complete search history.

(56) References Cited

FOREIGN PATENT DOCUMENTS

| WO | 2008/027338 | 3/2008 |
| WO | 2010/111180 | 9/2010 |
| WO | 2013/148350 | 10/2013 |

OTHER PUBLICATIONS

Rudikoff et al (Proc Natl Acad Sci USA 1982 vol. 79 p. 1979).*
Brummell et al. (Biochemistry 32:1180-1187 (1993)).*
Ward (Nature 341:544-546 (1989)).*
Casset et al. ((2003) BBRC 307, 198-205).*
De Pascalis et al. The Journal of Immunology (2002) 169, 3076-3084.*
Padlan et al. (PNAS 1989, 86:5938-5942).*
Lamminmaki et al. (JBC 2001,276:36687-36694).*
Lloyd et al. Protein Engineering, Design & Selection 2009, 22:159-168 (Year: 2009).*
Edwards et al., J Mol Biol. Nov. 14, 2013;334(1):103-118 (Year: 2003).*
D'Angelo et al., Front Immunol. 2018; 9: 395 (Year: 2018).*
Cheung et al., "Polymorphic variants of LIGHT (TNF superfamily-14) alter receptor avidity and bioavailability." The Journal of Immunology 185(3):1949-1958 (2010).
Bujotzek et al., "VH-VL orientation prediction for antibody humanization candidate selection: A case study." MABS 8 (2):288-305 (2016).
Xu et al., "Diversity in the CDR3 region of VH is sufficient for most antibody specificities." Immunity 13(1):37-45 (2000).

* cited by examiner

*Primary Examiner* — Daniel C Gamett
(74) *Attorney, Agent, or Firm* — Nixon Peabody LLP; David S. Resnick; Nicole D. Kling

(57) ABSTRACT

The present invention relates to anti-human LIGHT antibodies, new medical uses and methods.

30 Claims, 20 Drawing Sheets
Specification includes a Sequence Listing.

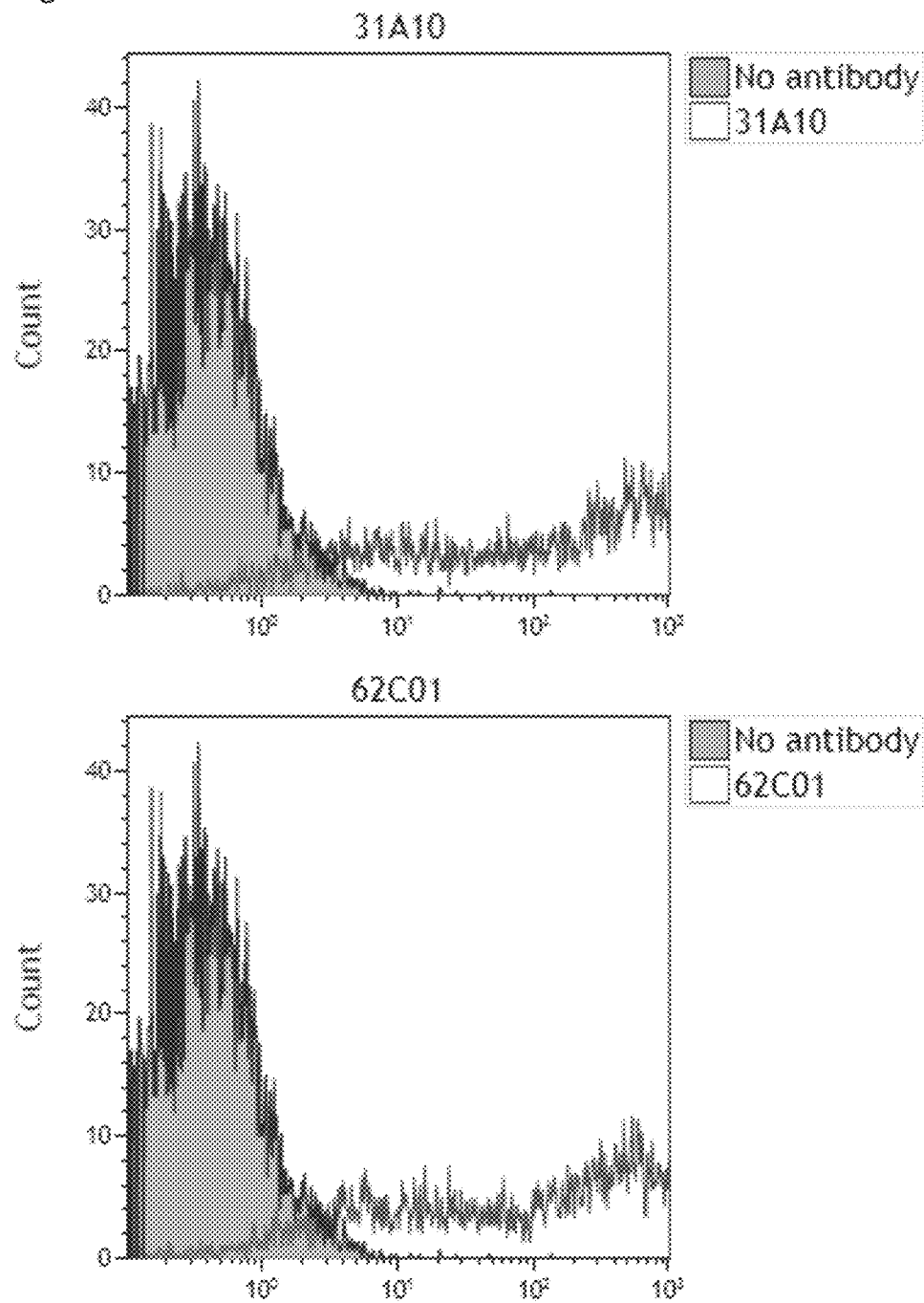

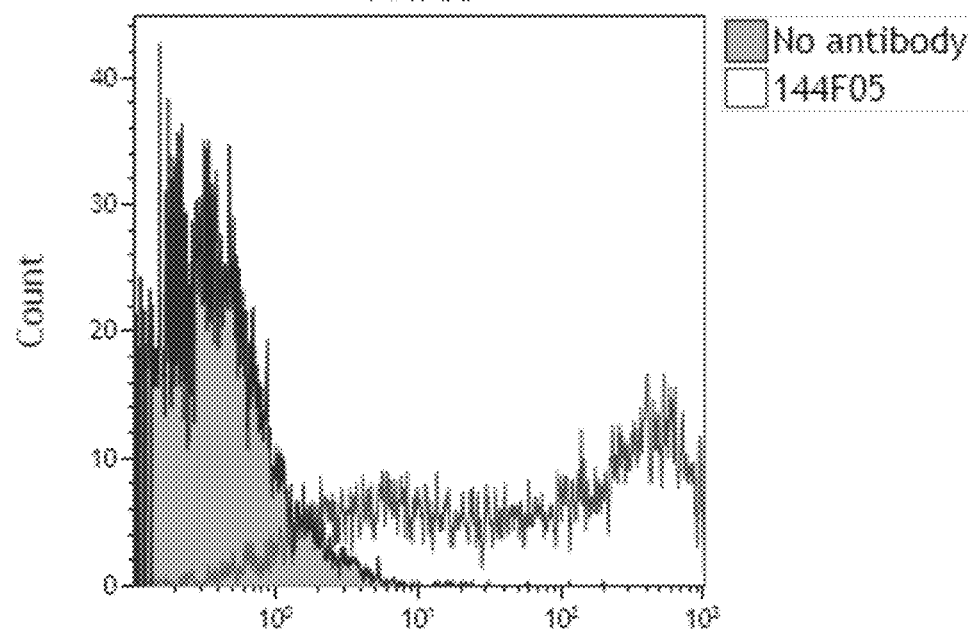
Fig. 2 (continued)
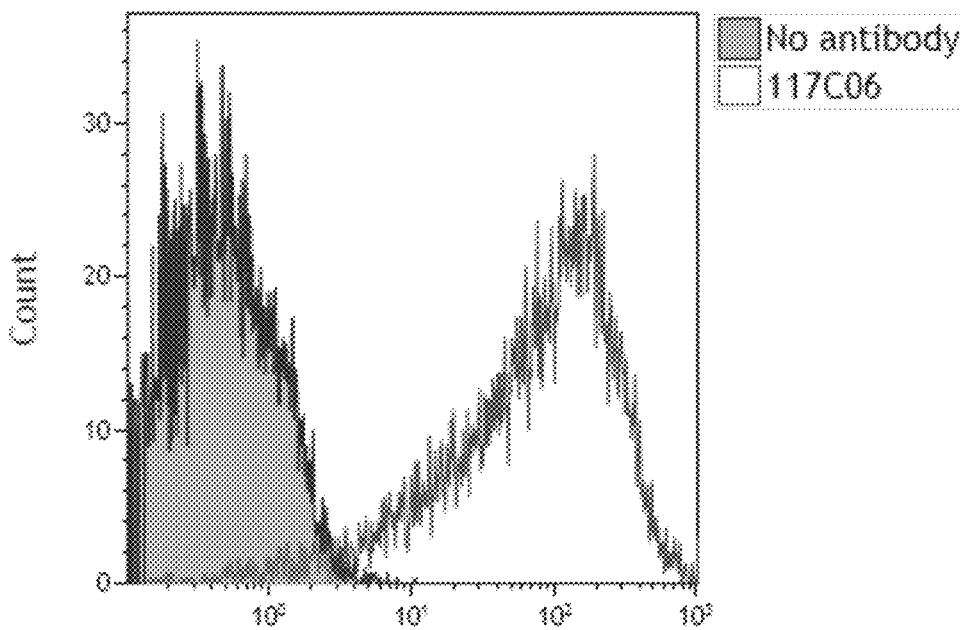

SEQUENCE LISTING

<160> NUMBER OF SEQ ID NOS: 427

<210> SEQ ID NO 1
<211> LENGTH: 363
<212> TYPE: DNA
<213> ORGANISM: Homo sapiens

<400> SEQUENCE: 1
caggtgcagc tgcaggagtc gggcccagga ctggtgaagc cttcgggac cctgtccctc      60 acctgcgctg tctctggtgg ctccatcagc agtattaatt ggtggaattg ggtccgccag    120
cccccaggga aggggctgga gtggattggg gaagtctctc atagtgggat caccaactat    180

```
aacccgtcccc tcaagagtcg agtcaccatg tcagtagaca aggccaagaa tcagttctcc    240
ctgaagctga actctgtgac cgccgcggac acggccgtgt attattgtgc gagagaaagg    300
gcagtggctg actaccacgg tatggacgtc tggggccaag gaccacggt caccgtctcc    360 tca                                                                   363
```

```
<210> SEQ ID NO 2
<211> LENGTH: 121
<212> TYPE: PRT
<213> ORGANISM: Homo sapiens

<400> SEQUENCE: 2
```

Gln Val Gln Leu Gln Glu Ser Gly Pro Gly Leu Val Lys Pro Ser Gly
1               5                   10                  15

Thr Leu Ser Leu Thr Cys Ala Val Ser Gly Ser Ile Ser Ser Ile
            20                  25                  30

Asn Trp Trp Asn Trp Val Arg Gln Pro Pro Gly Lys Gly Leu Glu Trp
        35                  40                  45

Ile Gly Glu Val Ser His Ser Gly Ile Thr Asn Tyr Asn Pro Ser Leu
    50                  55                  60

Lys Ser Arg Val Thr Met Ser Val Asp Lys Ala Lys Asn Gln Phe Ser
65                  70                  75                  80

Leu Lys Leu Asn Ser Val Thr Ala Ala Asp Thr Ala Val Tyr Tyr Cys
                85                  90                  95

Ala Arg Glu Arg Ala Val Ala Asp Tyr His Gly Met Asp Val Trp Gly
            100                 105                 110

Gln Gly Thr Thr Val Thr Val Ser Ser
        115                 120

```
<210> SEQ ID NO 3
<211> LENGTH: 27
<212> TYPE: DNA
<213> ORGANISM: Homo sapiens

<400> SEQUENCE: 3
ggtggctcca tcagcagtat taattgg                                          27

<210> SEQ ID NO 4
<211> LENGTH: 9
<212> TYPE: PRT
<213> ORGANISM: Homo sapiens

<400> SEQUENCE: 4
```

Gly Gly Ser Ile Ser Ser Ile Asn Trp
1               5

```
<210> SEQ ID NO 5
<211> LENGTH: 21
<212> TYPE: DNA
<213> ORGANISM: Homo sapiens

<400> SEQUENCE: 5
gtctctcata gtgggatcac c                                                21

<210> SEQ ID NO 6
<211> LENGTH: 7
<212> TYPE: PRT
<213> ORGANISM: Homo sapiens

<400> SEQUENCE: 6
```

```
Val Ser His Ser Gly Ile Thr
1               5

<210> SEQ ID NO 7
<211> LENGTH: 42
<212> TYPE: DNA
<213> ORGANISM: Homo sapiens

<400> SEQUENCE: 7
gcgagagaaa gggcagtggc tgactaccac ggtatggacg tc                          42

<210> SEQ ID NO 8
<211> LENGTH: 14
<212> TYPE: PRT
<213> ORGANISM: Homo sapiens

<400> SEQUENCE: 8

Ala Arg Glu Arg Ala Val Ala Asp Tyr His Gly Met Asp Val
1               5                   10

<210> SEQ ID NO 9
<211> LENGTH: 18
<212> TYPE: DNA
<213> ORGANISM: Homo sapiens

<400> SEQUENCE: 9
agtattaatt ggtggaat                                                     18

<210> SEQ ID NO 10
<211> LENGTH: 6
<212> TYPE: PRT
<213> ORGANISM: Homo sapiens

<400> SEQUENCE: 10

Ser Ile Asn Trp Trp Asn
1               5

<210> SEQ ID NO 11
<211> LENGTH: 48
<212> TYPE: DNA
<213> ORGANISM: Homo sapiens

<400> SEQUENCE: 11
gaagtctctc atagtgggat caccaactat aacccgtccc tcaagagt                    48

<210> SEQ ID NO 12
<211> LENGTH: 16
<212> TYPE: PRT
<213> ORGANISM: Homo sapiens

<400> SEQUENCE: 12

Glu Val Ser His Ser Gly Ile Thr Asn Tyr Asn Pro Ser Leu Lys Ser
1               5                   10                  15

<210> SEQ ID NO 13
<211> LENGTH: 35
<212> TYPE: DNA
<213> ORGANISM: Homo sapiens

<400> SEQUENCE: 13
aaagggcagt ggctgactac cacggtatgg acgtc                                  35

<210> SEQ ID NO 14
```

```
<211> LENGTH: 12
<212> TYPE: PRT
<213> ORGANISM: Homo sapiens

<400> SEQUENCE: 14

Glu Arg Ala Val Ala Asp Tyr His Gly Met Asp Val
1               5                   10

<210> SEQ ID NO 15
<211> LENGTH: 321
<212> TYPE: DNA
<213> ORGANISM: Homo sapiens

<400> SEQUENCE: 15
gccatccagt tgacccagtc tccatcctcc ctgtctgcat ctgtgggaga tagagtcacc      60
atcacttgcc gggcaagtca gggcattagc agtgctttag cctggtttca gcagaaacca    120 gggaaaccte ctaagctcct gatctttgat gcctccgatt tggaaagtgg ggtctcatca    180
aggttcagcg gcagtggatc tgggacagat ttcactctca ccatcagcag cctgcagcct    240
ggagattttg caacttatta ctgtcaacag tttaatagtt acccgatcac cttcggccaa    300
gggacacgac tggagatcaa a                                              321

<210> SEQ ID NO 16
<211> LENGTH: 107
<212> TYPE: PRT
<213> ORGANISM: Homo sapiens

<400> SEQUENCE: 16

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Phe Gln Gln Lys Pro Gly Lys Pro Pro Lys Leu Leu Ile
        35                  40                  45

Phe Asp Ala Ser Asp Leu Glu Ser Gly Val Ser Ser Arg Phe Ser Gly
    50                  55                  60

Ser Gly Ser Gly Thr Asp Phe Thr Leu Thr Ile Ser Ser Leu Gln Pro
65                  70                  75                  80

Gly Asp Phe Ala Thr Tyr Tyr Cys Gln Gln Phe Asn Ser Tyr Pro Ile
                85                  90                  95

Thr Phe Gly Gln Gly Thr Arg Leu Glu Ile Lys
            100                 105

<210> SEQ ID NO 17
<211> LENGTH: 18
<212> TYPE: DNA
<213> ORGANISM: Homo sapiens

<400> SEQUENCE: 17
cagggcatta gcagtgct                                                   18

<210> SEQ ID NO 18
<211> LENGTH: 6
<212> TYPE: PRT
<213> ORGANISM: Homo sapiens

<400> SEQUENCE: 18

Gln Gly Ile Ser Ser Ala
1               5
```

<210> SEQ ID NO 19

<400> SEQUENCE: 19

000

<210> SEQ ID NO 20

<400> SEQUENCE: 20

000

<210> SEQ ID NO 21
<211> LENGTH: 60
<212> TYPE: DNA
<213> ORGANISM: Homo sapiens

<400> SEQUENCE: 21
ctgcagcctg gagattttgc aacttattac tgtcaacagt ttaatagtta cccgatcacc    60

<210> SEQ ID NO 22
<211> LENGTH: 9
<212> TYPE: PRT
<213> ORGANISM: Homo sapiens

<400> SEQUENCE: 22

Gln Gln Phe Asn Ser Tyr Pro Ile Thr
1               5

<210> SEQ ID NO 23
<211> LENGTH: 33
<212> TYPE: DNA
<213> ORGANISM: Homo sapiens

<400> SEQUENCE: 23
cgggcaagtc agggcattag cagtgcttta gcc                                 33

<210> SEQ ID NO 24
<211> LENGTH: 11
<212> TYPE: PRT
<213> ORGANISM: Homo sapiens

<400> SEQUENCE: 24

Arg Ala Ser Gln Gly Ile Ser Ser Ala Leu Ala
1               5                   10

<210> SEQ ID NO 25
<211> LENGTH: 21
<212> TYPE: DNA
<213> ORGANISM: Homo sapiens

<400> SEQUENCE: 25
gatgcctccg atttggaaag t                                              21

<210> SEQ ID NO 26
<211> LENGTH: 7
<212> TYPE: PRT
<213> ORGANISM: Homo sapiens

<400> SEQUENCE: 26

Asp Ala Ser Asp Leu Glu Ser
1               5

<210> SEQ ID NO 27

```
<211> LENGTH: 60
<212> TYPE: DNA
<213> ORGANISM: Homo sapiens

<400> SEQUENCE: 27
ctgcagcctg agatttttgc aacttattac tgtcaacagt ttaatagtta cccgatcacc      60

<210> SEQ ID NO 28
<211> LENGTH: 9
<212> TYPE: PRT
<213> ORGANISM: Homo sapiens

<400> SEQUENCE: 28

Gln Gln Phe Asn Ser Tyr Pro Ile Thr
1               5

<210> SEQ ID NO 29
<211> LENGTH: 348
<212> TYPE: DNA
<213> ORGANISM: Homo sapiens

<400> SEQUENCE: 29
caggtgcagt tggtggagtc tgggggaggc ttggtcaagc ctggagggtc cctgagactc      60
tcctgtgcag cctctggatt caccttcagt gactactaca tgagctggat ccgccaggct     120
ccagggaagg gactggagtg gtttcatac attagtagaa gtagtttcat atactactca     180
gagtctgtga agggccgatt caccatctcc agggacaacg ccaagaactc actgtatctg     240
caaatgaaca gcctgagagc cgaggacacg gccgtgtatt actgtgcgcg atgggagcta     300
tccccttttg actactgggg ccagggaacc ctggtcaccg tctcctca                  348

<210> SEQ ID NO 30
<211> LENGTH: 116
<212> TYPE: PRT
<213> ORGANISM: Homo sapiens

<400> SEQUENCE: 30

Gln Val Gln Leu Val Glu Ser Gly Gly Gly Leu Val Lys Pro Gly Gly
1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Ser Ser Phe Ile Tyr Tyr Ser Glu Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Trp Glu Leu Ser Pro Phe Asp Tyr Trp Gly Gln Gly Thr Leu Val
            100                 105                 110

Thr Val Ser Ser
        115

<210> SEQ ID NO 31
<211> LENGTH: 24
<212> TYPE: DNA
<213> ORGANISM: Homo sapiens

<400> SEQUENCE: 31
```

```
ggattcacct tcagtgacta ctac                                    24
```

<210> SEQ ID NO 32
<211> LENGTH: 8
<212> TYPE: PRT
<213> ORGANISM: Homo sapiens

<400> SEQUENCE: 32

```
Gly Phe Thr Phe Ser Asp Tyr Tyr
1               5
```

<210> SEQ ID NO 33
<211> LENGTH: 21
<212> TYPE: DNA
<213> ORGANISM: Homo sapiens

<400> SEQUENCE: 33

```
attagtagaa gtagtttcat a                                       21
```

<210> SEQ ID NO 34
<211> LENGTH: 7
<212> TYPE: PRT
<213> ORGANISM: Homo sapiens

<400> SEQUENCE: 34

```
Ile Ser Arg Ser Ser Phe Ile
1               5
```

<210> SEQ ID NO 35
<211> LENGTH: 30
<212> TYPE: DNA
<213> ORGANISM: Homo sapiens

<400> SEQUENCE: 35

```
gcgcgatggg agctatcccc ttttgactac                              30
```

<210> SEQ ID NO 36
<211> LENGTH: 10
<212> TYPE: PRT
<213> ORGANISM: Homo sapiens

<400> SEQUENCE: 36

```
Ala Arg Trp Glu Leu Ser Pro Phe Asp Tyr
1               5                   10
```

<210> SEQ ID NO 37
<211> LENGTH: 15
<212> TYPE: DNA
<213> ORGANISM: Homo sapiens

<400> SEQUENCE: 37

```
gactactaca tgagc                                              15
```

<210> SEQ ID NO 38
<211> LENGTH: 5
<212> TYPE: PRT
<213> ORGANISM: Homo sapiens

<400> SEQUENCE: 38

```
Asp Tyr Tyr Met Ser
1               5
```

<210> SEQ ID NO 39
<211> LENGTH: 48

<212> TYPE: DNA
<213> ORGANISM: Homo sapiens

<400> SEQUENCE: 39
tacattagta gaagtagttt catatactac tcagagtctg tgaagggc            48

<210> SEQ ID NO 40
<211> LENGTH: 16
<212> TYPE: PRT
<213> ORGANISM: Homo sapiens

<400> SEQUENCE: 40

Tyr Ile Ser Arg Ser Ser Phe Ile Tyr Tyr Ser Glu Ser Val Lys Gly
1               5                   10                  15

<210> SEQ ID NO 41
<211> LENGTH: 24
<212> TYPE: DNA
<213> ORGANISM: Homo sapiens

<400> SEQUENCE: 41
tgggagctat cccctttga ctac            24

<210> SEQ ID NO 42
<211> LENGTH: 8
<212> TYPE: PRT
<213> ORGANISM: Homo sapiens

<400> SEQUENCE: 42

Trp Glu Leu Ser Pro Phe Asp Tyr
1               5

<210> SEQ ID NO 43
<211> LENGTH: 321
<212> TYPE: DNA
<213> ORGANISM: Homo sapiens

<400> SEQUENCE: 43
gacatccaga tgacccagtc tccatcctca ctgtctgcat ctgtaggaga cagagtcacc     60
atcacttgtc gggcgagtca gggcattagc aattatttag cctggtttca gcagaaacca    120
gggaaagccc ctaagtccct gatctatgct gcatccagtt tgcaaagtgg ggtcccatca    180
aagttcagcg gcagtggatc tgggacagat ttcactctca ccatcagcag cctgcagcct    240
gaagattttg caacttattt ctgccaacag tataatactt acccattcac tttcggccct    300
gggaccaaag tggatatcaa a                                              321

<210> SEQ ID NO 44
<211> LENGTH: 107
<212> TYPE: PRT
<213> ORGANISM: Homo sapiens

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Phe Cys Gln Gln Tyr Asn Thr Tyr Pro Phe
                 85                  90                  95

Thr Phe Gly Pro Gly Thr Lys Val Asp Ile Lys
            100                 105
```

<210> SEQ ID NO 45
<211> LENGTH: 18
<212> TYPE: DNA
<213> ORGANISM: Homo sapiens

<400> SEQUENCE: 45
cagggcatta gcaattat                                                 18

<210> SEQ ID NO 46
<211> LENGTH: 6
<212> TYPE: PRT
<213> ORGANISM: Homo sapiens

<400> SEQUENCE: 46

```
Gln Gly Ile Ser Asn Tyr
 1               5
```

<210> SEQ ID NO 47

<400> SEQUENCE: 47

000

<210> SEQ ID NO 48

<400> SEQUENCE: 48

000

<210> SEQ ID NO 49
<211> LENGTH: 27
<212> TYPE: DNA
<213> ORGANISM: Homo sapiens

<400> SEQUENCE: 49
caacagtata atacttaccc attcact                                       27

<210> SEQ ID NO 50
<211> LENGTH: 9
<212> TYPE: PRT
<213> ORGANISM: Homo sapiens

<400> SEQUENCE: 50

```
Gln Gln Tyr Asn Thr Tyr Pro Phe Thr
 1               5
```

<210> SEQ ID NO 51
<211> LENGTH: 33
<212> TYPE: DNA
<213> ORGANISM: Homo sapiens

<400> SEQUENCE: 51
cgggcgagtc agggcattag caattattta gcc                                33

<210> SEQ ID NO 52
<211> LENGTH: 11
<212> TYPE: PRT

```
<213> ORGANISM: Homo sapiens

<400> SEQUENCE: 52

Arg Ala Ser Gln Gly Ile Ser Asn Tyr Leu Ala
1               5                   10

<210> SEQ ID NO 53
<211> LENGTH: 21
<212> TYPE: DNA
<213> ORGANISM: Homo sapiens

<400> SEQUENCE: 53
gctgcatcca gtttgcaaag t                                              21

<210> SEQ ID NO 54
<211> LENGTH: 7
<212> TYPE: PRT
<213> ORGANISM: Homo sapiens

<400> SEQUENCE: 54

Ala Ala Ser Ser Leu Gln Ser
1               5

<210> SEQ ID NO 55
<211> LENGTH: 27
<212> TYPE: DNA
<213> ORGANISM: Homo sapiens

<400> SEQUENCE: 55
caacagtata atacttaccc attcact                                        27

<210> SEQ ID NO 56
<211> LENGTH: 9
<212> TYPE: PRT
<213> ORGANISM: Homo sapiens

<400> SEQUENCE: 56

Gln Gln Tyr Asn Thr Tyr Pro Phe Thr
1               5

<210> SEQ ID NO 57
<211> LENGTH: 360
<212> TYPE: DNA
<213> ORGANISM: Homo sapiens

<400> SEQUENCE: 57
gaggtgcagc tggtggagtc tgggggaggc ttggtacagc ctggggggtc cctgagactc    60
tcctgtgcag cctctggatt cacctttagc agctatgtca tgagctgggt ccgccaggct   120
ccagggaagg ggctggagtg ggtctcagtt attagttcta gtggtgttac cacgtactac   180
gcagactccg tgaagggccg attcaccatc tccagagaca attccaagaa cacgctgtat   240
ctgcaaatga acagcctgag agccgaggag acggccgtat attactgtgc gaaaggggaac   300 tatgggtcgg ggagtttttg tgactactgg ggccagggaa ccccggtcac cgtctcctca   360

<210> SEQ ID NO 58
<211> LENGTH: 120
<212> TYPE: PRT
<213> ORGANISM: Homo sapiens

<400> SEQUENCE: 58

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Phe Thr Phe Ser Ser Tyr
            20                  25                  30

Val Met Ser Trp Val Arg Gln Ala Pro Gly Lys Gly Leu Glu Trp Val
        35                  40                  45

Ser Val Ile Ser Ser Gly Val Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Glu Thr Ala Val Tyr Tyr Cys
                85                  90                  95

Ala Lys Gly Asn Tyr Gly Ser Gly Ser Phe Cys Asp Tyr Trp Gly Gln
            100                 105                 110

Gly Thr Pro Val Thr Val Ser Ser
        115                 120

<210> SEQ ID NO 59
<211> LENGTH: 24
<212> TYPE: DNA
<213> ORGANISM: Homo sapiens

<400> SEQUENCE: 59
ggattcacct ttagcagcta tgtc                                      24

<210> SEQ ID NO 60
<211> LENGTH: 8
<212> TYPE: PRT
<213> ORGANISM: Homo sapiens

<400> SEQUENCE: 60

Gly Phe Thr Phe Ser Ser Tyr Val
1               5

<210> SEQ ID NO 61
<211> LENGTH: 24
<212> TYPE: DNA
<213> ORGANISM: Homo sapiens

<400> SEQUENCE: 61
attagttcta gtggtgttac cacg                                      24

<210> SEQ ID NO 62
<211> LENGTH: 8
<212> TYPE: PRT
<213> ORGANISM: Homo sapiens

<400> SEQUENCE: 62

Ile Ser Ser Ser Gly Val Thr Thr
1               5

<210> SEQ ID NO 63
<211> LENGTH: 39
<212> TYPE: DNA
<213> ORGANISM: Homo sapiens

<400> SEQUENCE: 63
gcgaaaggga actatgggtc ggggagtttt tgtgactac                      39

<210> SEQ ID NO 64
<211> LENGTH: 13
<212> TYPE: PRT
<213> ORGANISM: Homo sapiens -continued

<400> SEQUENCE: 64

Ala Lys Gly Asn Tyr Gly Ser Gly Ser Phe Cys Asp Tyr
1               5                   10

<210> SEQ ID NO 65
<211> LENGTH: 15
<212> TYPE: DNA
<213> ORGANISM: Homo sapiens

<400> SEQUENCE: 65
agctatgtca tgagc                                             15

<210> SEQ ID NO 66
<211> LENGTH: 5
<212> TYPE: PRT
<213> ORGANISM: Homo sapiens

<400> SEQUENCE: 66

Ser Tyr Val Met Ser
1               5

<210> SEQ ID NO 67
<211> LENGTH: 51
<212> TYPE: DNA
<213> ORGANISM: Homo sapiens

<400> SEQUENCE: 67
gttattagtt ctagtggtgt taccacgtac tacgcagact ccgtgaaggg c       51

<210> SEQ ID NO 68
<211> LENGTH: 17
<212> TYPE: PRT
<213> ORGANISM: Homo sapiens

<400> SEQUENCE: 68

Val Ile Ser Ser Ser Gly Val Thr Thr Tyr Tyr Ala Asp Ser Val Lys
1               5                   10                  15

Gly

<210> SEQ ID NO 69
<211> LENGTH: 33
<212> TYPE: DNA
<213> ORGANISM: Homo sapiens

<400> SEQUENCE: 69
gggaactatg ggtcggggag tttttgtgac tac                          33

<210> SEQ ID NO 70
<211> LENGTH: 11
<212> TYPE: PRT
<213> ORGANISM: Homo sapiens

<400> SEQUENCE: 70

Gly Asn Tyr Gly Ser Gly Ser Phe Cys Asp Tyr
1               5                   10

<210> SEQ ID NO 71
<211> LENGTH: 324
<212> TYPE: DNA
<213> ORGANISM: Homo sapiens

<400> SEQUENCE: 71

```
tcctatgtgc tgactcagcc accctcagtg tcagtggccc caggaaagac ggccaggatt    60
acctgtgggg gaaacaacat tggaagtaaa agtgtgcact ggtaccagca gaggccaggc   120
caggccccta tactggtcat ctattatgat agcgaccggc cctcagggat ccctgagcga   180
ttctctggct ccaactctgg gaactcggcc accctgacca tcagcagggt cgaagccggg   240
gatgaggccg actatcactg tcaggtgtgg gaaagtagta gtgatcatcc ggtgttcggc   300
ggagggacca agctgaccgt ccta                                          324
```

```
<210> SEQ ID NO 72
<211> LENGTH: 108
<212> TYPE: PRT
<213> ORGANISM: Homo sapiens

<400> SEQUENCE: 72

Ser Tyr Val Leu Thr Gln Pro Pro Ser Val Ser Val Ala Pro Gly Lys
1               5                   10                  15

Thr Ala Arg Ile Thr Cys Gly Gly Asn Asn Ile Gly Ser Lys Ser Val
            20                  25                  30

His Trp Tyr Gln Gln Arg Pro Gly Gln Ala Pro Ile Leu Val Ile Tyr
        35                  40                  45

Tyr Asp Ser Asp Arg Pro Ser Gly Ile Pro Glu Arg Phe Ser Gly Ser
    50                  55                  60

Asn Ser Gly Asn Ser Ala Thr Leu Thr Ile Ser Arg Val Glu Ala Gly
65                  70                  75                  80

Asp Glu Ala Asp Tyr His Cys Gln Val Trp Glu Ser Ser Ser Asp His
                85                  90                  95

Pro Val Phe Gly Gly Gly Thr Lys Leu Thr Val Leu
            100                 105

<210> SEQ ID NO 73
<211> LENGTH: 18
<212> TYPE: DNA
<213> ORGANISM: Homo sapiens

<400> SEQUENCE: 73
aacattggaa gtaaaagt                                                  18

<210> SEQ ID NO 74
<211> LENGTH: 6
<212> TYPE: PRT
<213> ORGANISM: Homo sapiens

<400> SEQUENCE: 74

Asn Ile Gly Ser Lys Ser
1               5

<210> SEQ ID NO 75

<400> SEQUENCE: 75

000

<210> SEQ ID NO 76

<400> SEQUENCE: 76

000

<210> SEQ ID NO 77
<211> LENGTH: 33
```

```
<212> TYPE: DNA
<213> ORGANISM: Homo sapiens

<400> SEQUENCE: 77
caggtgtggg aaagtagtag tgatcatccg gtg                          33

<210> SEQ ID NO 78
<211> LENGTH: 11
<212> TYPE: PRT
<213> ORGANISM: Homo sapiens

<400> SEQUENCE: 78

Gln Val Trp Glu Ser Ser Ser Asp His Pro Val
1               5                   10

<210> SEQ ID NO 79
<211> LENGTH: 33
<212> TYPE: DNA
<213> ORGANISM: Homo sapiens

<400> SEQUENCE: 79 ggggaaaca acattggaag taaaagtgtg cac                           33

<210> SEQ ID NO 80
<211> LENGTH: 11
<212> TYPE: PRT
<213> ORGANISM: Homo sapiens

<400> SEQUENCE: 80

Gly Gly Asn Asn Ile Gly Ser Lys Ser Val His
1               5                   10

<210> SEQ ID NO 81
<211> LENGTH: 21
<212> TYPE: DNA
<213> ORGANISM: Homo sapiens

<400> SEQUENCE: 81
tatgatagcg accggccctc a                                       21

<210> SEQ ID NO 82
<211> LENGTH: 7
<212> TYPE: PRT
<213> ORGANISM: Homo sapiens

<400> SEQUENCE: 82

Tyr Asp Ser Asp Arg Pro Ser
1               5

<210> SEQ ID NO 83
<211> LENGTH: 33
<212> TYPE: DNA
<213> ORGANISM: Homo sapiens

<400> SEQUENCE: 83
caggtgtggg aaagtagtag tgatcatccg gtg                          33

<210> SEQ ID NO 84
<211> LENGTH: 11
<212> TYPE: PRT
<213> ORGANISM: Homo sapiens

<400> SEQUENCE: 84

Gln Val Trp Glu Ser Ser Ser Asp His Pro Val
```

<210> SEQ ID NO 85
<211> LENGTH: 348
<212> TYPE: DNA
<213> ORGANISM: Homo sapiens

<400> SEQUENCE: 85
caggagcagc tggtgcagtc tggggctgag gtgaagaagc ctggggcctc agtgaaggtc    60
tcctgcaagg cttctggata cactttcacc agttatgata tcaactgggt gcgacaggcc   120
actggacaag gcttgagtg gatgggatgg atgaaccta acagtggtta cacaggctat    180
gcacagaagt tccagggcag agtcaccatg accaggaaca cctccataag aacagtctac   240
atggagctga gcagcctgag atctgaggac acggccgtgt attactgtgc gagaggaggg   300
gagacttttg atatctgggg ccaagggaca atggtcaccg tctcttca               348

<210> SEQ ID NO 86
<211> LENGTH: 116
<212> TYPE: PRT
<213> ORGANISM: Homo sapiens

<400> SEQUENCE: 86

Gln Glu Gln Leu Val Gln Ser Gly Ala Glu Val Lys Lys Pro Gly Ala
1               5                  10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Met Asn Pro Asn Ser Gly Tyr Thr Gly Tyr Ala Gln Lys Phe
        50                  55                  60

Gln Gly Arg Val Thr Met Thr Arg Asn Thr Ser Ile Arg Thr Val Tyr
65                  70                  75                  80

Met Glu Leu Ser Ser Leu Arg Ser Glu Asp Thr Ala Val Tyr Tyr Cys
                85                  90                  95

Ala Arg Gly Gly Glu Thr Phe Asp Ile Trp Gly Gln Gly Thr Met Val
                100                 105                 110

Thr Val Ser Ser
        115

<210> SEQ ID NO 87
<211> LENGTH: 24
<212> TYPE: DNA
<213> ORGANISM: Homo sapiens

<400> SEQUENCE: 87
ggatacactt tcaccagtta tgat                                            24

<210> SEQ ID NO 88
<211> LENGTH: 8
<212> TYPE: PRT
<213> ORGANISM: Homo sapiens

<400> SEQUENCE: 88

Gly Tyr Thr Phe Thr Ser Tyr Asp
1               5

<210> SEQ ID NO 89
<211> LENGTH: 24
<212> TYPE: DNA

<210> SEQ ID NO 89
<211> LENGTH: 24
<212> TYPE: DNA
<213> ORGANISM: Homo sapiens

<400> SEQUENCE: 89
atgaacccta acagtggtta caca         24

<210> SEQ ID NO 90
<211> LENGTH: 8
<212> TYPE: PRT
<213> ORGANISM: Homo sapiens

<400> SEQUENCE: 90

Met Asn Pro Asn Ser Gly Tyr Thr
1               5

<210> SEQ ID NO 91
<211> LENGTH: 27
<212> TYPE: DNA
<213> ORGANISM: Homo sapiens

<400> SEQUENCE: 91
gcgagaggag gggagacttt tgatatc         27

<210> SEQ ID NO 92
<211> LENGTH: 9
<212> TYPE: PRT
<213> ORGANISM: Homo sapiens

<400> SEQUENCE: 92

Ala Arg Gly Gly Glu Thr Phe Asp Ile
1               5

<210> SEQ ID NO 93
<211> LENGTH: 15
<212> TYPE: DNA
<213> ORGANISM: Homo sapiens

<400> SEQUENCE: 93
agttatgata tcaac         15

<210> SEQ ID NO 94
<211> LENGTH: 5
<212> TYPE: PRT
<213> ORGANISM: Homo sapiens

<400> SEQUENCE: 94

Ser Tyr Asp Ile Asn
1               5

<210> SEQ ID NO 95
<211> LENGTH: 51
<212> TYPE: DNA
<213> ORGANISM: Homo sapiens

<400> SEQUENCE: 95
tggatgaacc ctaacagtgg ttacacaggc tatgcacaga gttccaggg c         51

<210> SEQ ID NO 96
<211> LENGTH: 17
<212> TYPE: PRT
<213> ORGANISM: Homo sapiens

<400> SEQUENCE: 96

Trp Met Asn Pro Asn Ser Gly Tyr Thr Gly Tyr Ala Gln Lys Phe Gln
1               5                   10                  15

Gly

<210> SEQ ID NO 97
<211> LENGTH: 21
<212> TYPE: DNA
<213> ORGANISM: Homo sapiens

<400> SEQUENCE: 97 ggagggggaga cttttgatat c                                      21

<210> SEQ ID NO 98
<211> LENGTH: 7
<212> TYPE: PRT
<213> ORGANISM: Homo sapiens

<400> SEQUENCE: 98

Gly Gly Glu Thr Phe Asp Ile
1               5

<210> SEQ ID NO 99
<211> LENGTH: 324
<212> TYPE: DNA
<213> ORGANISM: Homo sapiens

<400> SEQUENCE: 99
tcctatgagc tgacacagcc accctcggtg tcagtgtccc caggacaaac ggccaggatc    60
acctgctctg gagatgcatt gccaaaaaaa tatgcttatt ggtaccagca gaagtcaggc   120
caggcccctg tgctggtcat ctatgaggac agcaaacgac cctccgggat ccctgagaga   180
ttctctggct ccagctcagg gacaatggcc accttgacta tcagtggggc ccaggtggag   240
gatgaagctg actactactg ttactcaaca gacagcagtg ataatcatag tgtcttcgga   300
actgggacca aggtcaccgt ccta                                          324

<210> SEQ ID NO 100
<211> LENGTH: 108
<212> TYPE: PRT
<213> ORGANISM: Homo sapiens

<400> SEQUENCE: 100

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
                20                  25                  30

Tyr Trp Tyr Gln Gln Lys Ser Gly Gln Ala Pro Val Leu Val Ile Tyr
            35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Asp Asn His
                85                  90                  95

Ser Val Phe Gly Thr Gly Thr Lys Val Thr Val Leu
            100                 105

<210> SEQ ID NO 101
<211> LENGTH: 18
<212> TYPE: DNA
<213> ORGANISM: Homo sapiens

<210> SEQ ID NO 101

<400> SEQUENCE: 101
gcattgccaa aaaaatat                                                  18

<210> SEQ ID NO 102
<211> LENGTH: 6
<212> TYPE: PRT
<213> ORGANISM: Homo sapiens

<400> SEQUENCE: 102

Ala Leu Pro Lys Lys Tyr
1               5

<210> SEQ ID NO 103

<400> SEQUENCE: 103

000

<210> SEQ ID NO 104

<400> SEQUENCE: 104

000

<210> SEQ ID NO 105
<211> LENGTH: 33
<212> TYPE: DNA
<213> ORGANISM: Homo sapiens

<400> SEQUENCE: 105
tactcaacag acagcagtga taatcatagt gtc                                 33

<210> SEQ ID NO 106
<211> LENGTH: 11
<212> TYPE: PRT
<213> ORGANISM: Homo sapiens

<400> SEQUENCE: 106

Tyr Ser Thr Asp Ser Ser Asp Asn His Ser Val
1               5                   10

<210> SEQ ID NO 107
<211> LENGTH: 33
<212> TYPE: DNA
<213> ORGANISM: Homo sapiens

<400> SEQUENCE: 107
tctggagatg cattgccaaa aaaatatgct tat                                 33

<210> SEQ ID NO 108
<211> LENGTH: 11
<212> TYPE: PRT
<213> ORGANISM: Homo sapiens

<400> SEQUENCE: 108

Ser Gly Asp Ala Leu Pro Lys Lys Tyr Ala Tyr
1               5                   10

<210> SEQ ID NO 109
<211> LENGTH: 21
<212> TYPE: DNA
<213> ORGANISM: Homo sapiens

<400> SEQUENCE: 109
gaggacagca aacgaccctc c                                                                21

<210> SEQ ID NO 110
<211> LENGTH: 7
<212> TYPE: PRT
<213> ORGANISM: Homo sapiens

<400> SEQUENCE: 110

Glu Asp Ser Lys Arg Pro Ser
1               5

<210> SEQ ID NO 111
<211> LENGTH: 33
<212> TYPE: DNA
<213> ORGANISM: Homo sapiens

<400> SEQUENCE: 111
tactcaacag acagcagtga taatcatagt gtc                                                   33

<210> SEQ ID NO 112
<211> LENGTH: 11
<212> TYPE: PRT
<213> ORGANISM: Homo sapiens

<400> SEQUENCE: 112

Tyr Ser Thr Asp Ser Ser Asp Asn His Ser Val
1               5                   10

<210> SEQ ID NO 113
<211> LENGTH: 351
<212> TYPE: DNA
<213> ORGANISM: Homo sapiens

<400> SEQUENCE: 113
caggtccagc ttgtgcagtc tggggctgag gtgaagaagc ctggggcctc agtgaaggtt        60
tcctgcaggg cttctggata caccttcact agctatctta tgcattgggt gcgccaggcc      120
cccggacaaa ggcttgagtg gatgggatgg atcaacgttg gcaatggtaa cacaaaatat      180
tcacagaagt tccagggcag agtcaccatt accaggaca catccgcgag cacagcctac      240
atggagctga gcggcctgag atctgaagac acggctgtgt attactgtgc ccggaactac      300
tacaactggt tcgaccctg gggccaggga accctggtca ccgtctcctc a                351

<210> SEQ ID NO 114
<211> LENGTH: 117
<212> TYPE: PRT
<213> ORGANISM: Homo sapiens

<400> SEQUENCE: 114

Gln Val Gln Leu Val Gln Ser Gly Ala Glu Val Lys Lys Pro Gly Ala
1               5                   10                  15

Ser Val Lys Val Ser Cys Arg Ala Ser Gly Tyr Thr Phe Thr Ser Tyr
                20                  25                  30

Leu Met His Trp Val Arg Gln Ala Pro Gly Gln Arg Leu Glu Trp Met
            35                  40                  45

Gly Trp Ile Asn Val Gly Asn Gly Asn Thr Lys Tyr Ser Gln Lys Phe
        50                  55                  60

Gln Gly Arg Val Thr Ile Thr Arg Asp Thr Ser Ala Ser Thr Ala Tyr
65                  70                  75                  80

Met Glu Leu Ser Gly Leu Arg Ser Glu Asp Thr Ala Val Tyr Tyr Cys
                85                  90                  95

Ala Arg Asn Tyr Tyr Asn Trp Phe Asp Pro Trp Gly Gln Gly Thr Leu
            100                 105                 110
Val Thr Val Ser Ser
        115

<210> SEQ ID NO 115
<211> LENGTH: 24
<212> TYPE: DNA
<213> ORGANISM: Homo sapiens

<400> SEQUENCE: 115
ggatacacct tcactagcta tctt                                           24

<210> SEQ ID NO 116
<211> LENGTH: 8
<212> TYPE: PRT
<213> ORGANISM: Homo sapiens

<400> SEQUENCE: 116

Gly Tyr Thr Phe Thr Ser Tyr Leu
1               5

<210> SEQ ID NO 117
<211> LENGTH: 24
<212> TYPE: DNA
<213> ORGANISM: Homo sapiens

<400> SEQUENCE: 117
atcaacgttg gcaatggtaa caca                                           24

<210> SEQ ID NO 118
<211> LENGTH: 8
<212> TYPE: PRT
<213> ORGANISM: Homo sapiens

<400> SEQUENCE: 118

Ile Asn Val Gly Asn Gly Asn Thr
1               5

<210> SEQ ID NO 119
<211> LENGTH: 30
<212> TYPE: DNA
<213> ORGANISM: Homo sapiens

<400> SEQUENCE: 119
gcccggaact actacaactg gttcgacccc                                     30

<210> SEQ ID NO 120
<211> LENGTH: 10
<212> TYPE: PRT
<213> ORGANISM: Homo sapiens

<400> SEQUENCE: 120

Ala Arg Asn Tyr Tyr Asn Trp Phe Asp Pro
1               5                   10

<210> SEQ ID NO 121
<211> LENGTH: 15
<212> TYPE: DNA
<213> ORGANISM: Homo sapiens

<400> SEQUENCE: 121
agctatctta tgcat                                                     15

<210> SEQ ID NO 122
<211> LENGTH: 5
<212> TYPE: PRT
<213> ORGANISM: Homo sapiens

<400> SEQUENCE: 122

Ser Tyr Leu Met His
1               5

<210> SEQ ID NO 123
<211> LENGTH: 51
<212> TYPE: DNA
<213> ORGANISM: Homo sapiens

<400> SEQUENCE: 123
tggatcaacg ttggcaatgg taacacaaaa tattcacaga agttccaggg c         51

<210> SEQ ID NO 124
<211> LENGTH: 17
<212> TYPE: PRT
<213> ORGANISM: Homo sapiens

<400> SEQUENCE: 124

Trp Ile Asn Val Gly Asn Gly Asn Thr Lys Tyr Ser Gln Lys Phe Gln
1               5                   10                  15
Gly

<210> SEQ ID NO 125
<211> LENGTH: 24
<212> TYPE: DNA
<213> ORGANISM: Homo sapiens

<400> SEQUENCE: 125
aactactaca actggttcga cccc                                        24

<210> SEQ ID NO 126
<211> LENGTH: 8
<212> TYPE: PRT
<213> ORGANISM: Homo sapiens

<400> SEQUENCE: 126

Asn Tyr Tyr Asn Trp Phe Asp Pro
1               5

<210> SEQ ID NO 127
<211> LENGTH: 330
<212> TYPE: DNA
<213> ORGANISM: Homo sapiens

<400> SEQUENCE: 127
cagtctgccc tgactcagcc tgcctccgtg tctgggtctc ctggacagtc gatcaccatc    60
tcctgcactg gaaccagcag tgatgttggt ggttataact atgtctcctg gtaccaacag   120
cacccaggca agcccccaa actcatgatt tatgatgtca gtaagcggcc ctcaggggtt    180
tctaatcgct tctctggctc caagtctggc aacacggcct ccctgacaat ctctgggctc   240
caggctgagg acgaggctga ttattactgc ttctcatatg caggtagtag cactgtggta   300
ttcggcggag ggaccaagct gaccgtccta                                   330

<210> SEQ ID NO 128
<211> LENGTH: 110

<210> SEQ ID NO 128
<211> LENGTH: (not shown)
<212> TYPE: PRT
<213> ORGANISM: Homo sapiens

<400> SEQUENCE: 128

```
Gln Ser Ala Leu Thr Gln Pro Ala Ser Val Ser Gly Ser Pro Gly Gln
1               5                   10                  15
Ser Ile Thr Ile Ser Cys Thr Gly Thr Ser Ser Asp Val Gly Gly Tyr
            20                  25                  30
Asn Tyr Val Ser Trp Tyr Gln Gln His Pro Gly Lys Ala Pro Lys Leu
        35                  40                  45
Met Ile Tyr Asp Val Ser Lys Arg Pro Ser Gly Val Ser Asn Arg Phe
    50                  55                  60
Ser Gly Ser Lys Ser Gly Asn Thr Ala Ser Leu Thr Ile Ser Gly Leu
65                  70                  75                  80
Gln Ala Glu Asp Glu Ala Asp Tyr Tyr Cys Phe Ser Tyr Ala Gly Ser
                85                  90                  95
Ser Thr Val Val Phe Gly Gly Gly Thr Lys Leu Thr Val Leu
            100                 105                 110
```

<210> SEQ ID NO 129
<211> LENGTH: 27
<212> TYPE: DNA
<213> ORGANISM: Homo sapiens

<400> SEQUENCE: 129
agcagtgatg ttggtggtta taactat                                       27

<210> SEQ ID NO 130
<211> LENGTH: 9
<212> TYPE: PRT
<213> ORGANISM: Homo sapiens

<400> SEQUENCE: 130

```
Ser Ser Asp Val Gly Gly Tyr Asn Tyr
1               5
```

<210> SEQ ID NO 131

<400> SEQUENCE: 131

000

<210> SEQ ID NO 132

<400> SEQUENCE: 132

000

<210> SEQ ID NO 133
<211> LENGTH: 30
<212> TYPE: DNA
<213> ORGANISM: Homo sapiens

<400> SEQUENCE: 133
ttctcatatg caggtagtag cactgtggta                                    30

<210> SEQ ID NO 134
<211> LENGTH: 10
<212> TYPE: PRT
<213> ORGANISM: Homo sapiens

<400> SEQUENCE: 134

Phe Ser Tyr Ala Gly Ser Ser Thr Val Val
1               5                   10

<210> SEQ ID NO 135
<211> LENGTH: 42
<212> TYPE: DNA
<213> ORGANISM: Homo sapiens

<400> SEQUENCE: 135
actggaacca gcagtgatgt tggtggttat aactatgtct cc          42

<210> SEQ ID NO 136
<211> LENGTH: 14
<212> TYPE: PRT
<213> ORGANISM: Homo sapiens

<400> SEQUENCE: 136

Thr Gly Thr Ser Ser Asp Val Gly Gly Tyr Asn Tyr Val Ser
1               5                   10

<210> SEQ ID NO 137
<211> LENGTH: 21
<212> TYPE: DNA
<213> ORGANISM: Homo sapiens

<400> SEQUENCE: 137
gatgtcagta agcggccctc a                                 21

<210> SEQ ID NO 138
<211> LENGTH: 7
<212> TYPE: PRT
<213> ORGANISM: Homo sapiens

<400> SEQUENCE: 138

Asp Val Ser Lys Arg Pro Ser
1               5

<210> SEQ ID NO 139
<211> LENGTH: 30
<212> TYPE: DNA
<213> ORGANISM: Homo sapiens

<400> SEQUENCE: 139
ttctcatatg caggtagtag cactgtggta                        30

<210> SEQ ID NO 140
<211> LENGTH: 10
<212> TYPE: PRT
<213> ORGANISM: Homo sapiens

<400> SEQUENCE: 140

Phe Ser Tyr Ala Gly Ser Ser Thr Val Val
1               5                   10

<210> SEQ ID NO 141
<211> LENGTH: 351
<212> TYPE: DNA
<213> ORGANISM: Homo sapiens

<400> SEQUENCE: 141
caggttcagc tggtgcagtc tggagctgag gtgaagaagc ctggggcctc agtgaaggtc    60
tcctgcaagg cttctggtta tacctttacc agctatggta tcagctgggt gcgacaggcc   120
cctggacaag gcttgagtg gatgggatgg atcagcgctc acaatgctaa cacaaactat   180

```
gcacagaagc tccagggcag agtcaccatg accacagaca catccacgag cacagcctac    240
atggagctga ggagcctgag atctgacgac acggccatgt attactgtgc gagactgtac    300
cgcaactggt tcgacccctg gggccaggga accctggtca ccgtctcctc a             351
```

```
<210> SEQ ID NO 142
<211> LENGTH: 117
<212> TYPE: PRT
<213> ORGANISM: Homo sapiens

<400> SEQUENCE: 142
```

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala His Asn Ala Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Leu Tyr Arg Asn Trp Phe Asp Pro Trp Gly Gln Gly Thr Leu
            100                 105                 110

Val Thr Val Ser Ser
        115

```
<210> SEQ ID NO 143
<211> LENGTH: 24
<212> TYPE: DNA
<213> ORGANISM: Homo sapiens

<400> SEQUENCE: 143
ggttatacct ttaccagcta tggt                                            24

<210> SEQ ID NO 144
<211> LENGTH: 8
<212> TYPE: PRT
<213> ORGANISM: Homo sapiens

<400> SEQUENCE: 144
```

Gly Tyr Thr Phe Thr Ser Tyr Gly
1               5

```
<210> SEQ ID NO 145
<211> LENGTH: 24
<212> TYPE: DNA
<213> ORGANISM: Homo sapiens

<400> SEQUENCE: 145
atcagcgctc acaatgctaa caca                                            24

<210> SEQ ID NO 146
<211> LENGTH: 8
<212> TYPE: PRT
<213> ORGANISM: Homo sapiens

<400> SEQUENCE: 146
```

Ile Ser Ala His Asn Ala Asn Thr

<210> SEQ ID NO 147
<211> LENGTH: 30
<212> TYPE: DNA
<213> ORGANISM: Homo sapiens

<400> SEQUENCE: 147
gcgagactgt accgcaactg gttcgacccc                                30

<210> SEQ ID NO 148
<211> LENGTH: 10
<212> TYPE: PRT
<213> ORGANISM: Homo sapiens

<400> SEQUENCE: 148

Ala Arg Leu Tyr Arg Asn Trp Phe Asp Pro
1               5                   10

<210> SEQ ID NO 149
<211> LENGTH: 15
<212> TYPE: DNA
<213> ORGANISM: Homo sapiens

<400> SEQUENCE: 149
agctatggta tcagc                                                15

<210> SEQ ID NO 150
<211> LENGTH: 5
<212> TYPE: PRT
<213> ORGANISM: Homo sapiens

<400> SEQUENCE: 150

Ser Tyr Gly Ile Ser
1               5

<210> SEQ ID NO 151
<211> LENGTH: 51
<212> TYPE: DNA
<213> ORGANISM: Homo sapiens

<400> SEQUENCE: 151
tggatcagcg ctcacaatgc taacacaaac tatgcacaga agctccaggg c          51

<210> SEQ ID NO 152
<211> LENGTH: 17
<212> TYPE: PRT
<213> ORGANISM: Homo sapiens

<400> SEQUENCE: 152

Trp Ile Ser Ala His Asn Ala Asn Thr Asn Tyr Ala Gln Lys Leu Gln
1               5                   10                  15
Gly

<210> SEQ ID NO 153
<211> LENGTH: 24
<212> TYPE: DNA
<213> ORGANISM: Homo sapiens

<400> SEQUENCE: 153
ctgtaccgca actggttcga cccc                                      24

<210> SEQ ID NO 154

<211> LENGTH: 8
<212> TYPE: PRT
<213> ORGANISM: Homo sapiens

<400> SEQUENCE: 154

Leu Tyr Arg Asn Trp Phe Asp Pro
1               5

<210> SEQ ID NO 155
<211> LENGTH: 330
<212> TYPE: DNA
<213> ORGANISM: Homo sapiens

<400> SEQUENCE: 155
cagtctgccc tgactcagcc tgcctccgtg tctgggtctc ctggacagtc gatcaccatc     60
tcctgcactg gaaccagcag tgatgttggt ggttataact atgtctcctg gtaccaacag    120
cacccaggca aagcccccaa actcatgatt tatgatgtca gtaagcggcc ctcagggggtt   180 tctaatcgct tctctggctc caagtctggc aacacggcct ccctgacaat ctctgggctc    240
caggctgagg acgaggctga ttattactgc tgctcatatg caggtagtag cactttgctg    300
ttcggcggag ggaccaagct gaccgtccta                                     330

<210> SEQ ID NO 156
<211> LENGTH: 110
<212> TYPE: PRT
<213> ORGANISM: Homo sapiens

<400> SEQUENCE: 156

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Tyr Val Ser Trp Tyr Gln Gln His Pro Gly Lys Ala Pro Lys Leu
        35                  40                  45

Met Ile Tyr Asp Val Ser Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Cys Ser Tyr Ala Gly Ser
                85                  90                  95

Ser Thr Leu Leu Phe Gly Gly Gly Thr Lys Leu Thr Val Leu
            100                 105                 110

<210> SEQ ID NO 157
<211> LENGTH: 27
<212> TYPE: DNA
<213> ORGANISM: Homo sapiens

<400> SEQUENCE: 157
agcagtgatg ttggtggtta taactat                                        27

<210> SEQ ID NO 158
<211> LENGTH: 9
<212> TYPE: PRT
<213> ORGANISM: Homo sapiens

<400> SEQUENCE: 158

Ser Ser Asp Val Gly Gly Tyr Asn Tyr
1               5

<210> SEQ ID NO 159

<400> SEQUENCE: 159

000

<210> SEQ ID NO 160

<400> SEQUENCE: 160

000

<210> SEQ ID NO 161
<211> LENGTH: 30
<212> TYPE: DNA
<213> ORGANISM: Homo sapiens

<400> SEQUENCE: 161
tgctcatatg caggtagtag cactttgctg                          30

<210> SEQ ID NO 162
<211> LENGTH: 10
<212> TYPE: PRT
<213> ORGANISM: Homo sapiens

<400> SEQUENCE: 162

Cys Ser Tyr Ala Gly Ser Ser Thr Leu Leu
1               5                   10

<210> SEQ ID NO 163
<211> LENGTH: 42
<212> TYPE: DNA
<213> ORGANISM: Homo sapiens

<400> SEQUENCE: 163
actggaacca gcagtgatgt tggtggttat aactatgtct cc             42

<210> SEQ ID NO 164
<211> LENGTH: 14
<212> TYPE: PRT
<213> ORGANISM: Homo sapiens

<400> SEQUENCE: 164

Thr Gly Thr Ser Ser Asp Val Gly Gly Tyr Asn Tyr Val Ser
1               5                   10

<210> SEQ ID NO 165
<211> LENGTH: 21
<212> TYPE: DNA
<213> ORGANISM: Homo sapiens

<400> SEQUENCE: 165
gatgtcagta agcggccctc a                                   21

<210> SEQ ID NO 166
<211> LENGTH: 7
<212> TYPE: PRT
<213> ORGANISM: Homo sapiens

<400> SEQUENCE: 166

Asp Val Ser Lys Arg Pro Ser
1               5

<210> SEQ ID NO 167

-continued

<211> LENGTH: 30
<212> TYPE: DNA
<213> ORGANISM: Homo sapiens

<400> SEQUENCE: 167
tgctcatatg caggtagtag cactttgctg        30

<210> SEQ ID NO 168
<211> LENGTH: 10
<212> TYPE: PRT
<213> ORGANISM: Homo sapiens

<400> SEQUENCE: 168

Cys Ser Tyr Ala Gly Ser Ser Thr Leu Leu
1               5                   10

<210> SEQ ID NO 169
<211> LENGTH: 345
<212> TYPE: DNA
<213> ORGANISM: Homo sapiens

<400> SEQUENCE: 169
caggttcagt tggtgcagtc tggagctgag gtgaagaagc ctggggcctc agtgaaggtc        60
tcctgcaagg cttctggtta cacctttgtc aactttggta tcagctgggt gcgacaggcc       120
cctggacaag gcttgagtg gatgggatgg atcagtgttt acagtggtaa cacaaactat        180
gcacagaagc tccagggcag agtcaccttg accacagaca catccacgac cacagcctac       240
atggaactga ggagcctgag atctgacgac acggccgttt attactgtgc gagacacaac       300
tggaacgact actggggcca gggaaccctg gtcaccgtct cctca                       345

<210> SEQ ID NO 170
<211> LENGTH: 115
<212> TYPE: PRT
<213> ORGANISM: Homo sapiens

<400> SEQUENCE: 170

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Val Asn Phe
                20                  25                  30

Gly Ile Ser Trp Val Arg Gln Ala Pro Gly Gln Gly Leu Glu Trp Met
            35                  40                  45

Gly Trp Ile Ser Val Tyr Ser Gly Asn Thr Asn Tyr Ala Gln Lys Leu
        50                  55                  60

Gln Gly Arg Val Thr Leu Thr Thr Asp Thr Ser Thr Thr Thr Ala Tyr
65                  70                  75                  80

Met Glu Leu Arg Ser Leu Arg Ser Asp Asp Thr Ala Val Tyr Tyr Cys
                85                  90                  95

Ala Arg His Asn Trp Asn Asp Tyr Trp Gly Gln Gly Thr Leu Val Thr
                100                 105                 110

Val Ser Ser
        115

<210> SEQ ID NO 171
<211> LENGTH: 24
<212> TYPE: DNA
<213> ORGANISM: Homo sapiens

<400> SEQUENCE: 171

```
ggttacacct ttgtcaactt tggt                                              24
```

<210> SEQ ID NO 172
<211> LENGTH: 8
<212> TYPE: PRT
<213> ORGANISM: Homo sapiens

<400> SEQUENCE: 172

Gly Tyr Thr Phe Val Asn Phe Gly
1               5

<210> SEQ ID NO 173
<211> LENGTH: 24
<212> TYPE: DNA
<213> ORGANISM: Homo sapiens

<400> SEQUENCE: 173

```
atcagtgttt acagtggtaa caca                                              24
```

<210> SEQ ID NO 174
<211> LENGTH: 8
<212> TYPE: PRT
<213> ORGANISM: Homo sapiens

<400> SEQUENCE: 174

Ile Ser Val Tyr Ser Gly Asn Thr
1               5

<210> SEQ ID NO 175
<211> LENGTH: 24
<212> TYPE: DNA
<213> ORGANISM: Homo sapiens

<400> SEQUENCE: 175

```
gcgagacaca actggaacga ctac                                              24
```

<210> SEQ ID NO 176
<211> LENGTH: 8
<212> TYPE: PRT
<213> ORGANISM: Homo sapiens

<400> SEQUENCE: 176

Ala Arg His Asn Trp Asn Asp Tyr
1               5

<210> SEQ ID NO 177
<211> LENGTH: 15
<212> TYPE: DNA
<213> ORGANISM: Homo sapiens

<400> SEQUENCE: 177

```
aactttggta tcagc                                                        15
```

<210> SEQ ID NO 178
<211> LENGTH: 5
<212> TYPE: PRT
<213> ORGANISM: Homo sapiens

<400> SEQUENCE: 178

Asn Phe Gly Ile Ser
1               5

<210> SEQ ID NO 179
<211> LENGTH: 51

<212> TYPE: DNA
<213> ORGANISM: Homo sapiens

<400> SEQUENCE: 179
tggatcagtg tttacagtgg taacacaaac tatgcacaga agctccaggg c        51

<210> SEQ ID NO 180
<211> LENGTH: 17
<212> TYPE: PRT
<213> ORGANISM: Homo sapiens

<400> SEQUENCE: 180

Trp Ile Ser Val Tyr Ser Gly Asn Thr Asn Tyr Ala Gln Lys Leu Gln
1               5                   10                  15

Gly

<210> SEQ ID NO 181
<211> LENGTH: 18
<212> TYPE: DNA
<213> ORGANISM: Homo sapiens

<400> SEQUENCE: 181
cacaactgga acgactac                                              18

<210> SEQ ID NO 182
<211> LENGTH: 6
<212> TYPE: PRT
<213> ORGANISM: Homo sapiens

<400> SEQUENCE: 182

His Asn Trp Asn Asp Tyr
1               5

<210> SEQ ID NO 183
<211> LENGTH: 321
<212> TYPE: DNA
<213> ORGANISM: Homo sapiens

<400> SEQUENCE: 183
gaaattgtgt tgacgcagtc tccaggcacc ctgtctttgt ctccagggga aagagccacc    60
ctctcctgca gggccagtca gagtgttagc agcagctact taacctggta ccagcagaaa   120
cctggccagg ctcccaggct cctcatctat ggtgcatcca gcagggccac tggcatccca   180
gacaggttca gtggcagtgg gtctgggaca gacttcactc tcaccatcag cagactggag   240
cctgaagatt ttgcagtcta ttactgtcag cagtttggta gctcacctag ttttggccag   300
gggaccaagc tggagatcaa a                                            321

<210> SEQ ID NO 184
<211> LENGTH: 107
<212> TYPE: PRT
<213> ORGANISM: Homo sapiens

<400> SEQUENCE: 184

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
                20                  25                  30

Tyr Leu Thr Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser

```
            50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Phe Gly Ser Ser Pro
                 85                  90                  95

Ser Phe Gly Gln Gly Thr Lys Leu Glu Ile Lys
            100                 105
```

<210> SEQ ID NO 185
<211> LENGTH: 21
<212> TYPE: DNA
<213> ORGANISM: Homo sapiens

<400> SEQUENCE: 185
cagagtgtta gcagcagcta c                                       21

<210> SEQ ID NO 186
<211> LENGTH: 7
<212> TYPE: PRT
<213> ORGANISM: Homo sapiens

<400> SEQUENCE: 186

```
Gln Ser Val Ser Ser Ser Tyr
 1               5
```

<210> SEQ ID NO 187

<400> SEQUENCE: 187

000

<210> SEQ ID NO 188

<400> SEQUENCE: 188

000

<210> SEQ ID NO 189
<211> LENGTH: 24
<212> TYPE: DNA
<213> ORGANISM: Homo sapiens

<400> SEQUENCE: 189
cagcagtttg gtagctcacc tagt                                    24

<210> SEQ ID NO 190
<211> LENGTH: 8
<212> TYPE: PRT
<213> ORGANISM: Homo sapiens

<400> SEQUENCE: 190

```
Gln Gln Phe Gly Ser Ser Pro Ser
 1               5
```

<210> SEQ ID NO 191
<211> LENGTH: 36
<212> TYPE: DNA
<213> ORGANISM: Homo sapiens

<400> SEQUENCE: 191
agggccagtc agagtgttag cagcagctac ttaacc                       36

<210> SEQ ID NO 192

```
<211> LENGTH: 12
<212> TYPE: PRT
<213> ORGANISM: Homo sapiens

<400> SEQUENCE: 192

Arg Ala Ser Gln Ser Val Ser Ser Ser Tyr Leu Thr
1               5                   10

<210> SEQ ID NO 193
<211> LENGTH: 21
<212> TYPE: DNA
<213> ORGANISM: Homo sapiens

<400> SEQUENCE: 193
ggtgcatcca gcagggccac t                                       21

<210> SEQ ID NO 194
<211> LENGTH: 7
<212> TYPE: PRT
<213> ORGANISM: Homo sapiens

<400> SEQUENCE: 194

Gly Ala Ser Ser Arg Ala Thr
1               5

<210> SEQ ID NO 195
<211> LENGTH: 24
<212> TYPE: DNA
<213> ORGANISM: Homo sapiens

<400> SEQUENCE: 195
cagcagtttg gtagctcacc tagt                                    24

<210> SEQ ID NO 196
<211> LENGTH: 8
<212> TYPE: PRT
<213> ORGANISM: Homo sapiens

<400> SEQUENCE: 196

Gln Gln Phe Gly Ser Ser Pro Ser
1               5

<210> SEQ ID NO 197
<211> LENGTH: 366
<212> TYPE: DNA
<213> ORGANISM: Homo sapiens

<400> SEQUENCE: 197
caggtgcagc tgcaggagtc gggcccagga ctggtgaagc cttcggggac cctgtccctc    60
acctgcgctg tctctggtgg ctccatcagc agtactcact ggtggaattg ggtccgccag   120
cccccaggga aggggctgga gtggattgga gaaatctatc atagtgggag caccaactgc   180
aacccgtccc tcaagagtcg agtcaccata tcagtcgaca gtccaagaa ccagttctcc    240 ctgaagatga actctgtgac cgccgcggac acggccgtgt attactgtac aagggggtggg   300 gcagcagctg gtacgaacta cggttttgga gtctggggcc aagggaccac ggtcaccgtc   360
tcctca                                                              366

<210> SEQ ID NO 198
<211> LENGTH: 122
<212> TYPE: PRT
<213> ORGANISM: Homo sapiens
```

<400> SEQUENCE: 198

Gln Val Gln Leu Gln Glu Ser Gly Pro Gly Leu Val Lys Pro Ser Gly
1               5                   10                  15
Thr Leu Ser Leu Thr Cys Ala Val Ser Gly Gly Ser Ile Ser Ser Thr
            20                  25                  30
His Trp Trp Asn Trp Val Arg Gln Pro Pro Gly Lys Gly Leu Glu Trp
        35                  40                  45
Ile Gly Glu Ile Tyr His Ser Gly Ser Thr Asn Cys Asn Pro Ser Leu
    50                  55                  60
Lys Ser Arg Val Thr Ile Ser Val Asp Lys Ser Lys Asn Gln Phe Ser
65                  70                  75                  80
Leu Lys Met Asn Ser Val Thr Ala Ala Asp Thr Ala Val Tyr Tyr Cys
                85                  90                  95
Thr Arg Gly Gly Ala Ala Ala Gly Thr Asn Tyr Gly Leu Asp Val Trp
            100                 105                 110
Gly Gln Gly Thr Thr Val Thr Val Ser Ser
        115                 120

<210> SEQ ID NO 199
<211> LENGTH: 27
<212> TYPE: DNA
<213> ORGANISM: Homo sapiens

<400> SEQUENCE: 199
ggtggctcca tcagcagtac tcactgg                                           27

<210> SEQ ID NO 200
<211> LENGTH: 9
<212> TYPE: PRT
<213> ORGANISM: Homo sapiens

<400> SEQUENCE: 200

Gly Gly Ser Ile Ser Ser Thr His Trp
1               5

<210> SEQ ID NO 201
<211> LENGTH: 21
<212> TYPE: DNA
<213> ORGANISM: Homo sapiens

<400> SEQUENCE: 201
atctatcata gtgggagcac c                                                 21

<210> SEQ ID NO 202
<211> LENGTH: 7
<212> TYPE: PRT
<213> ORGANISM: Homo sapiens

<400> SEQUENCE: 202

Ile Tyr His Ser Gly Ser Thr
1               5

<210> SEQ ID NO 203
<211> LENGTH: 45
<212> TYPE: DNA
<213> ORGANISM: Homo sapiens

<400> SEQUENCE: 203 acaagggggtg gggcagcagc tggtacgaac tacggtttgg acgtc                      45

<210> SEQ ID NO 204
<211> LENGTH: 15
<212> TYPE: PRT
<213> ORGANISM: Homo sapiens

<400> SEQUENCE: 204

Thr Arg Gly Gly Ala Ala Ala Gly Thr Asn Tyr Gly Leu Asp Val
1               5                   10                  15

<210> SEQ ID NO 205
<211> LENGTH: 18
<212> TYPE: DNA
<213> ORGANISM: Homo sapiens

<400> SEQUENCE: 205
agtactcact ggtggaat                                                   18

<210> SEQ ID NO 206
<211> LENGTH: 6
<212> TYPE: PRT
<213> ORGANISM: Homo sapiens

<400> SEQUENCE: 206

Ser Thr His Trp Trp Asn
1               5

<210> SEQ ID NO 207
<211> LENGTH: 48
<212> TYPE: DNA
<213> ORGANISM: Homo sapiens

<400> SEQUENCE: 207
gaaatctatc atagtgggag caccaactgc aacccgtccc tcaagagt                  48

<210> SEQ ID NO 208
<211> LENGTH: 16
<212> TYPE: PRT
<213> ORGANISM: Homo sapiens

<400> SEQUENCE: 208

Glu Ile Tyr His Ser Gly Ser Thr Asn Cys Asn Pro Ser Leu Lys Ser
1               5                   10                  15

<210> SEQ ID NO 209
<211> LENGTH: 45
<212> TYPE: DNA
<213> ORGANISM: Homo sapiens

<400> SEQUENCE: 209
acaaggggtg gggcagcagc tggtacgaac tacggtttgg acgtc                     45

<210> SEQ ID NO 210
<211> LENGTH: 15
<212> TYPE: PRT
<213> ORGANISM: Homo sapiens

<400> SEQUENCE: 210

Thr Arg Gly Gly Ala Ala Ala Gly Thr Asn Tyr Gly Leu Asp Val
1               5                   10                  15

<210> SEQ ID NO 211
<211> LENGTH: 321
<212> TYPE: DNA
<213> ORGANISM: Homo sapiens

<400> SEQUENCE: 211

```
gacatccaga tgacccagtc tccatcctcc ctgtctgcat ctgtaggaga cagagtctcc    60
atcacttgcc aggcgagtca ggacattagc aactatttaa attggtatca gcagaaacca   120
gggaaagccc ctaagctcct gatctacgat gcatccaatt tggaaacagg ggtcccatca   180
aggttcagtg gaagtggatc tgggacagat tttactttca ccatcagcag cctgcagcct   240
gaagatattg caacatatta ctgtcaacag tatgataatc tcccactcac tttcggcgga   300
gggaccaagg tggagatcaa a                                             321
```

<210> SEQ ID NO 212
<211> LENGTH: 107
<212> TYPE: PRT
<213> ORGANISM: Homo sapiens

<400> SEQUENCE: 212

```
Asp Ile Gln Met Thr Gln Ser Pro Ser Ser Leu Ser Ala Ser Val Gly
1               5                   10                  15
Asp Arg Val Ser Ile Thr Cys Gln Ala Ser Gln Asp Ile Ser Asn Tyr
            20                  25                  30
Leu Asn Trp Tyr Gln Gln Lys Pro Gly Lys Ala Pro Lys Leu Leu Ile
        35                  40                  45
Tyr Asp Ala Ser Asn Leu Glu Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Ile Ala Thr Tyr Tyr Cys Gln Gln Tyr Asp Asn Leu Pro Leu
                85                  90                  95
Thr Phe Gly Gly Gly Thr Lys Val Glu Ile Lys
            100                 105
```

<210> SEQ ID NO 213
<211> LENGTH: 18
<212> TYPE: DNA
<213> ORGANISM: Homo sapiens

<400> SEQUENCE: 213

```
caggacatta gcaactat                                                  18
```

<210> SEQ ID NO 214
<211> LENGTH: 6
<212> TYPE: PRT
<213> ORGANISM: Homo sapiens

<400> SEQUENCE: 214

```
Gln Asp Ile Ser Asn Tyr
1               5
```

<210> SEQ ID NO 215

<400> SEQUENCE: 215

000

<210> SEQ ID NO 216

<400> SEQUENCE: 216

000

<210> SEQ ID NO 217
<211> LENGTH: 27
<212> TYPE: DNA
<213> ORGANISM: Homo sapiens

<400> SEQUENCE: 217
caacagtatg ataatctccc actcact                                          27

<210> SEQ ID NO 218
<211> LENGTH: 9
<212> TYPE: PRT
<213> ORGANISM: Homo sapiens

<400> SEQUENCE: 218

Gln Gln Tyr Asp Asn Leu Pro Leu Thr
1               5

<210> SEQ ID NO 219
<211> LENGTH: 27
<212> TYPE: DNA
<213> ORGANISM: Homo sapiens

<400> SEQUENCE: 219
caggcgagtc aggacattag caactat                                          27

<210> SEQ ID NO 220
<211> LENGTH: 11
<212> TYPE: PRT
<213> ORGANISM: Homo sapiens

<400> SEQUENCE: 220

Gln Ala Ser Gln Asp Ile Ser Asn Tyr Leu Asn
1               5                   10

<210> SEQ ID NO 221
<211> LENGTH: 21
<212> TYPE: DNA
<213> ORGANISM: Homo sapiens

<400> SEQUENCE: 221
gatgcatcca atttggaaac a                                                21

<210> SEQ ID NO 222
<211> LENGTH: 7
<212> TYPE: PRT
<213> ORGANISM: Homo sapiens

<400> SEQUENCE: 222

Asp Ala Ser Asn Leu Glu Thr
1               5

<210> SEQ ID NO 223
<211> LENGTH: 27
<212> TYPE: DNA
<213> ORGANISM: Homo sapiens

<400> SEQUENCE: 223
caacagtatg ataatctccc actcact                                          27

<210> SEQ ID NO 224
<211> LENGTH: 9
<212> TYPE: PRT
<213> ORGANISM: Homo sapiens

<400> SEQUENCE: 224

Gln Gln Tyr Asp Asn Leu Pro Leu Thr
1               5

<210> SEQ ID NO 225
<211> LENGTH: 354
<212> TYPE: DNA
<213> ORGANISM: Homo sapiens

<400> SEQUENCE: 225
gaggtgcagc tggtggagtc tgggggaggc ttggtacagc ctggggggtc cctgagactc      60
tcctgtgcag cctctggatt cacctttagc aactatgcca tgagctgggt ccgccaggct     120
ccagggaagg gctggagtg gtctcagct attagtggta gtggtggtag cacatattat       180
gcagattccg tgaagggccg cttcaccatc tccagagaca attccaagaa cacgctgtat     240
ctgcaaatga atagcctgag agccgaggac acggccgtat attactgtgc gaaagatatt     300
actatggttc ggggaatcaa ctggggccaa gggacaatgg tcatcgtctc ttca           354

<210> SEQ ID NO 226
<211> LENGTH: 118
<212> TYPE: PRT
<213> ORGANISM: Homo sapiens

<400> SEQUENCE: 226

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Thr Met Val Arg Gly Ile Asn Trp Gly Gln Gly Thr
            100                 105                 110

Met Val Ile Val Ser Ser
        115

<210> SEQ ID NO 227
<211> LENGTH: 24
<212> TYPE: DNA
<213> ORGANISM: Homo sapiens

<400> SEQUENCE: 227
ggattcacct ttagcaacta tgcc                                             24

<210> SEQ ID NO 228
<211> LENGTH: 8
<212> TYPE: PRT
<213> ORGANISM: Homo sapiens

<400> SEQUENCE: 228

Gly Phe Thr Phe Ser Asn Tyr Ala
1               5

<210> SEQ ID NO 229

```
<211> LENGTH: 24
<212> TYPE: DNA
<213> ORGANISM: Homo sapiens

<400> SEQUENCE: 229
attagtggta gtggtggtag caca                                          24

<210> SEQ ID NO 230
<211> LENGTH: 8
<212> TYPE: PRT
<213> ORGANISM: Homo sapiens

<400> SEQUENCE: 230

Ile Ser Gly Ser Gly Gly Ser Thr
1               5

<210> SEQ ID NO 231
<211> LENGTH: 33
<212> TYPE: DNA
<213> ORGANISM: Homo sapiens

<400> SEQUENCE: 231
gcgaaagata ttactatggt tcggggaatc aac                                33

<210> SEQ ID NO 232
<211> LENGTH: 11
<212> TYPE: PRT
<213> ORGANISM: Homo sapiens

<400> SEQUENCE: 232

Ala Lys Asp Ile Thr Met Val Arg Gly Ile Asn
1               5                   10

<210> SEQ ID NO 233
<211> LENGTH: 15
<212> TYPE: DNA
<213> ORGANISM: Homo sapiens

<400> SEQUENCE: 233
aactatgcca tgagc                                                    15

<210> SEQ ID NO 234
<211> LENGTH: 5
<212> TYPE: PRT
<213> ORGANISM: Homo sapiens

<400> SEQUENCE: 234

Asn Tyr Ala Met Ser
1               5

<210> SEQ ID NO 235
<211> LENGTH: 51
<212> TYPE: DNA
<213> ORGANISM: Homo sapiens

<400> SEQUENCE: 235
gctattagtg gtagtggtgg tagcacatat tatgcagatt ccgtgaaggg c             51

<210> SEQ ID NO 236
<211> LENGTH: 17
<212> TYPE: PRT
<213> ORGANISM: Homo sapiens

<400> SEQUENCE: 236
```

```
Ala Ile Ser Gly Ser Gly Gly Ser Thr Tyr Tyr Ala Asp Ser Val Lys
1               5                   10                  15

Gly

<210> SEQ ID NO 237
<211> LENGTH: 27
<212> TYPE: DNA
<213> ORGANISM: Homo sapiens

<400> SEQUENCE: 237
gatattacta tggttcgggg aatcaac                                           27

<210> SEQ ID NO 238
<211> LENGTH: 9
<212> TYPE: PRT
<213> ORGANISM: Homo sapiens

<400> SEQUENCE: 238

Asp Ile Thr Met Val Arg Gly Ile Asn
1               5

<210> SEQ ID NO 239
<211> LENGTH: 321
<212> TYPE: DNA
<213> ORGANISM: Homo sapiens

<400> SEQUENCE: 239
gacatccaga tgacccagtc tccatcttcc gtgtctgcat ctgtaggaga cagagtcacc        60
atcacttgtc gggcgagtca gggtattagc aactggttag cctggtatca gcagaaacca      120
gggaaagccc ctaaactcct gatctttgct gcatccagtt tgcaaagtgg ggtcccatca      180
aggttcagcg gcagtggctc tgggacagat ttcactctca ccatcagcag cctgcagcct      240
gaagattttg caacttacta ttgtcaacag tctaacagtt tccctctcac tttcggcgga      300
gggaccaagg tggagatcaa a                                                321

<210> SEQ ID NO 240
<211> LENGTH: 107
<212> TYPE: PRT
<213> ORGANISM: Homo sapiens

<400> SEQUENCE: 240

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Gly Lys Ala Pro Lys Leu Leu Ile
        35                  40                  45

Phe Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Asn Ser Phe Pro Leu
                85                  90                  95

Thr Phe Gly Gly Gly Thr Lys Val Glu Ile Lys
            100                 105

<210> SEQ ID NO 241
<211> LENGTH: 18
<212> TYPE: DNA
```

<213> ORGANISM: Homo sapiens

<400> SEQUENCE: 241
cagggtatta gcaactgg                                                18

<210> SEQ ID NO 242
<211> LENGTH: 6
<212> TYPE: PRT
<213> ORGANISM: Homo sapiens

<400> SEQUENCE: 242

Gln Gly Ile Ser Asn Trp
1               5

<210> SEQ ID NO 243

<400> SEQUENCE: 243

000

<210> SEQ ID NO 244

<400> SEQUENCE: 244

000

<210> SEQ ID NO 245
<211> LENGTH: 27
<212> TYPE: DNA
<213> ORGANISM: Homo sapiens

<400> SEQUENCE: 245
caacagtcta acagtttccc tctcact                                      27

<210> SEQ ID NO 246
<211> LENGTH: 9
<212> TYPE: PRT
<213> ORGANISM: Homo sapiens

<400> SEQUENCE: 246

Gln Gln Ser Asn Ser Phe Pro Leu Thr
1               5

<210> SEQ ID NO 247
<211> LENGTH: 33
<212> TYPE: DNA
<213> ORGANISM: Homo sapiens

<400> SEQUENCE: 247
cgggcgagtc agggtattag caactggtta gcc                               33

<210> SEQ ID NO 248
<211> LENGTH: 11
<212> TYPE: PRT
<213> ORGANISM: Homo sapiens

<400> SEQUENCE: 248

Arg Ala Ser Gln Gly Ile Ser Asn Trp Leu Ala
1               5                   10

<210> SEQ ID NO 249
<211> LENGTH: 21
<212> TYPE: DNA
<213> ORGANISM: Homo sapiens

```
<400> SEQUENCE: 249
gctgcatcca gtttgcaaag t                                              21

<210> SEQ ID NO 250
<211> LENGTH: 7
<212> TYPE: PRT
<213> ORGANISM: Homo sapiens

<400> SEQUENCE: 250

Ala Ala Ser Ser Leu Gln Ser
1               5

<210> SEQ ID NO 251
<211> LENGTH: 27
<212> TYPE: DNA
<213> ORGANISM: Homo sapiens

<400> SEQUENCE: 251
caacagtcta acagtttccc tctcact                                        27

<210> SEQ ID NO 252
<211> LENGTH: 9
<212> TYPE: PRT
<213> ORGANISM: Homo sapiens

<400> SEQUENCE: 252

Gln Gln Ser Asn Ser Phe Pro Leu Thr
1               5

<210> SEQ ID NO 253
<211> LENGTH: 981
<212> TYPE: DNA
<213> ORGANISM: Homo sapiens

<400> SEQUENCE: 253
gcttccacca agggcccatc cgtcttcccc ctggcgccct gctccaggag cacctccgag     60
agcacagccg ccctgggctg cctggtcaag gactacttcc ccgaaccggt gacggtgtcg    120
tggaactcag gcgccctgac cagcggcgtg cacaccttcc cggctgtcct acagtcctca    180
ggactctact ccctcagcag cgtggtgacc gtgccctcca gcagcttggg cacgaagacc    240
tacacctgca acgtagatca caagcccagc aacaccaagg tggacaagag agttgagtcc    300
aaatatggtc ccccatgccc atcatgccca gcacctgagt tcctgggggg accatcagtc    360
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcggagg agcagttcaa cagcacgtac    540
cgtgtggtca gcgtcctcac cgtcctgcac caggactggc tgaacggcaa ggagtacaag    600
tgcaaggtct ccaacaaagg cctcccgtcc tccatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggctcct tcttcctcta cagcaggcta accgtggaca agagcaggtg gcaggagggg    900
aatgtcttct catgctccgt gatgcatgag gctctgcaca accactacac acagaagagc    960
ctctccctgt ctctgggtaa a                                             981
```

<210> SEQ ID NO 254
<211> LENGTH: 327
<212> TYPE: PRT
<213> ORGANISM: Homo sapiens

<400> SEQUENCE: 254

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 255
<211> LENGTH: 981
<212> TYPE: DNA
<213> ORGANISM: Homo sapiens

<400> SEQUENCE: 255
gcttccacca agggcccatc cgtcttcccc ctggcgccct gctccaggag cacctccgag      60

-continued

```
agcacagccg ccctgggctg cctggtcaag gactacttcc ccgaaccggt gacggtgtcg      120
tggaactcag gcgccctgac cagcggcgtg cacaccttcc cggctgtcct acagtcctca      180
ggactctact ccctcagcag cgtggtgacc gtgccctcca gcagcttggg cacgaagacc      240
tacacctgca acgtagatca caagcccagc aacaccaagg tggacaagag agttgagtcc      300
aaatatggtc cccgtgccc  atcatgccca gcacctgagt tcctgggggg accatcagtc      360
ttcctgttcc ccccaaaacc caaggacact ctcatgatct cccggacccc tgaggtcacg      420
tgcgtggtgg tggacgtgag ccaggaagac cccgaggtcc agttcaactg gtacgtggat      480
ggcgtggagg tgcataatgc caagacaaag ccgcgggagg agcagttcaa cagcacgtac      540
cgtgtggtca gcgtcctcac cgtcgtgcac caggactggc tgaacggcaa ggagtacaag      600
tgcaaggtct ccaacaaagg cctcccgtcc tccatcgaga aaaccatctc caaagccaaa      660
gggcagcccc gagagccaca ggtgtacacc ctgcccccat cccaggagga gatgaccaag      720
aaccaggtca gcctgacctg cctggtcaaa ggcttctacc ccagcgacat cgccgtggag      780
tgggagagca atgggcagcc ggagaacaac tacaagacca cgcctcccgt gctggactcc      840
gacggctcct tcttcctcta cagcaggcta accgtggaca agagcaggtg gcaggagggg      900
aatgtcttct catgctccgt gatgcatgag gctctgcaca accactacac gcagaagagc      960
ctctccctgt ctctgggtaa a                                                981
```

<210> SEQ ID NO 256
<211> LENGTH: 327
<212> TYPE: PRT
<213> ORGANISM: Homo sapiens

<400> SEQUENCE: 256

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Val His Gln Asp
            180                 185                 190

Trp Leu Asn Gly Lys Glu Tyr Lys Cys Lys Val Ser Asn Lys Gly Leu
        195                 200                 205
```

Pro Ser Ser Ile Glu Lys Thr Ile Ser Lys Ala Lys Gly Gln Pro Arg
        210                 215                 220

Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Gln Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 257
<211> LENGTH: 981
<212> TYPE: DNA
<213> ORGANISM: Homo sapiens

<400> SEQUENCE: 257
gcttccacca agggcccatc cgtcttcccc ctggcgccct gctccaggag cacctccgag      60
agcacagccg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc cccatgccca tcatgccca gcacctgagt tcctgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtcc tccatcgaga aaaccatctc caaagccaaa     660
gggcagcccc gagagccaca ggtgtacacc ctgcccccat cccaggagga tgaccaag     720 aaccaggtca gcctgacctg cctggtcaaa ggcttctacc ccagcgacat cgccgtggag     780
tgggagagca atgggcagcc ggagaacaac tacaagacca cgcctcccgt gctggactcc     840
gacggctcct tcttcctcta cagcaagctc accgtggaca agagcaggtg gcaggagggg     900
aacgtcttct catgctccgt gatgcatgag gctctgcaca accactacac gcagaagagc     960
ctctccctgt ctctgggtaa a                                               981

<210> SEQ ID NO 258
<211> LENGTH: 327
<212> TYPE: PRT
<213> ORGANISM: Homo sapiens

<400> SEQUENCE: 258

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr 20                  25                  30
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Lys Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 259
<211> LENGTH: 981
<212> TYPE: DNA
<213> ORGANISM: Homo sapiens

<400> SEQUENCE: 259
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctgaat tgagggggg accatcagtc      360

```
ttcctgttcc ccccaaaacc caaggacact ctcatgatct cccggacccc tgaggtcacg    420
tgcgtggtgg tggacgtgag ccaggaagac cccgaggtcc agttcaactg gtacgtggat    480
ggcgtggagg tgcataatgc caagacaaag ccgcgggagg agcagttcaa cagcacgtac    540
cgtgtggtca gcgtcctcac cgtcctgcac caggactggc tgaacggcaa ggagtacaag    600
tgcaaggtct ccaacaaagg cctcccgtca tcgatcgaga aaaccatctc caaagccaaa    660
gggcagcccc gagagccaca ggtgtacacc ctgcccccat cccaggagga gatgaccaag    720
aaccaggtca gcctgacctg cctggtcaaa ggcttctacc ccagcgacat cgccgtggag    780
tgggagagca atgggcagcc ggagaacaac tacaagacca cgcctcccgt gctggactcc    840
gacggatcct tcttcctcta cagcaggcta accgtggaca agagcaggtg gcaggagggg    900
aatgtcttct catgctccgt gatgcatgag gctctgcaca accactacac acagaagagc    960 ctctcccctgt ctctgggtaa a                                             981
```

<210> SEQ ID NO 260
<211> LENGTH: 327
<212> TYPE: PRT
<213> ORGANISM: Homo sapiens

<400> SEQUENCE: 260

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
```

260                 265                 270
Thr Thr Pro Pro Val Leu Asp Ser Asp Gly Ser Phe Phe Leu Tyr Ser
                275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 261
<211> LENGTH: 981
<212> TYPE: DNA
<213> ORGANISM: Homo sapiens

<400> SEQUENCE: 261
gcctccacca agggacctag cgtgttccct ctcgccccct gttccaggtc cacaagcgag      60
tccaccgctg ccctcggctg tctggtgaaa gactactttc ccgagcccgt gaccgtctcc     120
tggaatagcg gagccctgac ctccggcgtg cacacatttc cgccgtgctg cagagcagc     180 ggactgtata gcctgagcag cgtggtgacc gtgcccagct ccagcctcgg caccaaaacc     240
tacacctgca acgtggacca caagccctcc aacaccaagg tggacaagcg ggtggagagc     300
aagtacggcc cccttgccc tccttgtcct gcccctgagt cgagggagg accctccgtg      360 ttcctgtttc cccccaaacc caaggacacc ctgatgatct cccggacacc cgaggtgacc     420
tgtgtggtcg tggacgtcag ccaggaggac cccgaggtgc agttcaactg gtatgtggac     480
ggcgtggagg tgcacaatgc caaaaccaag cccagggagg agcagttcaa ttccacctac     540
agggtggtga gcgtgctgac cgtcctgcat caggattggc tgaacggcaa ggagtacaag     600
tgcaaggtgt ccaacaaggg actgcccagc tccatcgaga agaccatcag caaggctaag     660
ggccagccga gggagcccca ggtgtatacc ctgcctccta gccaggaaga gatgaccaag     720
aaccaagtgt ccctgacctg cctggtgaag ggattctacc cctccgacat cgccgtggag     780
tgggagagca atggccagcc cgagaacaac tacaaaacaa cccctcccgt gctcgatagc     840
gacggcagct tctttctcta cagccggctg acagtggaca agagcaggtg gcaggagggc     900
aacgtgttct cctgttccgt gatgcacgag gccctgcaca tcactacac ccagaagagc     960 ctctccctgt ccctgggcaa g                                              981

<210> SEQ ID NO 262
<211> LENGTH: 981
<212> TYPE: DNA
<213> ORGANISM: Homo sapiens

<400> SEQUENCE: 262
gccagcacca agggcccttc cgtgttcccc ctggcccctt gcagcaggag cacctccgaa      60
tccacagctg ccctgggctg tctggtgaag gactactttc ccgagcccgt gaccgtgagc     120
tggaacagcg gcgctctgac atccggcgtc cacaccttc ctgccgtcct gcagtcctcc     180
ggcctctact ccctgtcctc cgtggtgacc gtgcctagct cctccctcgg caccaagacc     240
tacacctgta acgtggacca caaaccctcc aacaccaagg tggacaaacg ggtcgagagc     300
aagtacggcc ctccctgccc tccttgtcct gccccgagt cgaaggcgg acccagcgtg      360 ttcctgttcc ctcctaagcc caaggacacc ctcatgatca gcggacacc cgaggtgacc     420 tgcgtggtgg tggatgtgag ccaggaggac cctgaggtcc agttcaactg gtatgtggat     480

```
ggcgtggagg tgcacaacgc caagacaaag ccccgggaag agcagttcaa ctccacctac      540
agggtggtca gcgtgctgac cgtgctgcat caggactggc tgaacggcaa ggagtacaag      600
tgcaaggtca gcaataaggg actgcccagc agcatcgaga agaccatctc caaggctaaa      660
ggccagcccc gggaacctca ggtgtacacc ctgcctccca gccaggagga gatgaccaag      720
aaccaggtga gcctgacctg cctggtgaag ggattctacc cttccgacat cgccgtggag      780
tgggagtcca acggccagcc cgagaacaat tataagacca cccctcccgt cctcgacagc      840
gacggatcct tctttctgta ctccaggctg accgtggata agtccaggtg caggaaggc       900 aacgtgttca gctgctccgt gatgcacgag gccctgcaca atcactacac ccagaagtcc      960
ctgagcctgt ccctgggaaa g                                                981
```

<210> SEQ ID NO 263
<211> LENGTH: 981
<212> TYPE: DNA
<213> ORGANISM: Homo sapiens

<400> SEQUENCE: 263

```
gcctccacca agggcccatc cgtcttcccc ctggcgccct gctccaggag cacctccgag      60
agcacggccg ccctgggctg cctggtcaag gactacttcc ccgaaccagt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacgaagacc     240
tacacctgca acgtagatca caagcccagc aacaccaagg tggacaagag agttgagtcc     300
aaatatggtc ccccatgccc accatgccca gcgcctccag ttgcgggggg accatcagtc     360
ttcctgttcc ccccaaaacc caaggacact ctcatgatct cccggacccc tgaggtcacg     420
tgcgtggtgg tggacgtgag ccaggaagac cccgaggtcc agttcaactg gtacgtggat     480
ggcgtggagg tgcataatgc caagacaaag ccgcgggagg agcagttcaa cagcacgtac     540
cgtgtggtca gcgtcctcac cgtcctgcac caggactggc tgaacggcaa ggagtacaag     600
tgcaaggtct ccaacaaagg cctcccgtca tcgatcgaga aaaccatctc caaagccaaa     660
gggcagcccc gagagccaca ggtgtacacc ctgcccccat cccaggagga gatgaccaag     720
aaccaggtca gcctgacctg cctggtcaaa ggcttctacc cagcgacat cgccgtggag      780 tgggagagca atgggcagcc ggagaacaac tacaagacca cgcctcccgt gctggactcc     840
gacggatcct tcttcctcta cagcaggcta accgtggaca gagcaggtg gcaggagggg      900 aatgtcttct catgctccgt gatgcatgag gctctgcaca accactacac acagaagagc     960
ctctccctgt ctctgggtaa a                                                981
```

<210> SEQ ID NO 264
<211> LENGTH: 327
<212> TYPE: PRT
<213> ORGANISM: Homo sapiens

<400> SEQUENCE: 264

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
```

```
            50                  55                  60
Leu Ser Ser Val Val Thr Val Pro Ser Ser Leu Gly Thr Lys Thr
 65                  70                  75                  80

Tyr Thr Cys Asn Val Asp His Lys Pro Ser Asn Thr Lys Val Asp Lys
                 85                  90                  95

Arg Val Glu Ser Lys Tyr Gly Pro Pro Cys Pro Pro Cys Pro Ala Pro
            100                 105                 110

Pro Val Ala Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 265
<211> LENGTH: 990
<212> TYPE: DNA
<213> ORGANISM: Homo sapiens

<400> SEQUENCE: 265
gcctccacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagaa agtggagccc     300
aaatcttgtg acaaaactca cacatgccca ccgtgcccag cacctgaact cgcggggggca    360 ccgtcagtct tcctcttccc cccaaaaccc aaggacaccc tcatgatctc ccggacccct     420
gaggtcacat gcgtggtggt ggacgtgagc cacgaagacc ctgaggtcaa gttcaactgg     480
tacgtggacg gcgtggaggt gcataatgcc aagacaaagc cgcggagga gcagtacaac     540
```

```
agcacgtacc gtgtggtcag cgtcctcacc gtcctgcacc aggactggct gaatggcaag    600
gagtacaagt gcaaggtctc caacaaagcc ctcccagccc ccatcgagaa aaccatctcc    660
aaagccaaag ggcagccccg agaaccacag gtgtacaccc tgccccatc ccgggatgag     720 ctgaccaaga accaggtcag cctgacctgc ctggtcaaag gcttctatcc cagcgacatc    780
gccgtggagt gggagagcaa tgggcagccg gagaacaact acaagaccac gcctcccgtg    840
ctggactccg acggctcctt cttcctctac agcaagctca ccgtggacaa gagcaggtgg    900
cagcagggga acgtcttctc atgctccgtg atgcatgagg ctctgcacaa ccactacacg    960
cagaagagcc tctccctgtc tccgggtaaa                                     990
```

```
<210> SEQ ID NO 266
<211> LENGTH: 330
<212> TYPE: PRT
<213> ORGANISM: Homo sapiens

<400> SEQUENCE: 266

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Ala Gly Ala Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
```

```
                290                 295                 300
Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 267
<211> LENGTH: 321
<212> TYPE: DNA
<213> ORGANISM: Homo sapiens

<400> SEQUENCE: 267

```
cgtacggtgg ccgctccctc cgtgttcatc ttcccacctt ccgacgagca gctgaagtcc      60
ggcaccgctt ctgtcgtgtg cctgctgaac aacttctacc cccgcgaggc caaggtgcag     120
tggaaggtgg acaacgccct gcagtccggc aactcccagg aatccgtgac cgagcaggac     180
tccaaggaca gcacctactc cctgtcctcc accctgaccc tgtccaaggc cgactacgag     240
aagcacaagg tgtacgcctg cgaagtgacc caccagggcc tgtctagccc cgtgaccaag     300
tctttcaacc ggggcgagtg t                                              321
```

<210> SEQ ID NO 268
<211> LENGTH: 107
<212> TYPE: PRT
<213> ORGANISM: Homo sapiens

<400> SEQUENCE: 268

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 269
<211> LENGTH: 321
<212> TYPE: DNA
<213> ORGANISM: Homo sapiens

<400> SEQUENCE: 269

```
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggag     180
agcaaggaca gcacctacag cctcagcagc accctgacgc tgagcaaagc agactacgag     240
aaacacaaag tctacgccgg cgaagtcacc catcagggcc tgagctcgcc cgtcacaaag     300
agcttcaaca ggggagagtg t                                              321
```

<210> SEQ ID NO 270

<211> LENGTH: 107
<212> TYPE: PRT
<213> ORGANISM: Homo sapiens

<400> SEQUENCE: 270

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Gly Glu Val Thr His Gln Gly Leu Ser Ser
                85                  90                  95

Pro Val Thr Lys Ser Phe Asn Arg Gly Glu Cys
            100                 105

<210> SEQ ID NO 271
<211> LENGTH: 321
<212> TYPE: DNA
<213> ORGANISM: Homo sapiens

<400> SEQUENCE: 271
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
cggaaggtgg ataacgccct ccaatcgggt aactcccagg agagtgtcac agagcaggag     180
agcaaggaca gcacctacag cctcagcagc accctgacgc tgagcaaagc agactacgag     240
aaacacaaag tctacgcctg cgaagtcacc catcagggcc tgagctcgcc cgtcacaaag     300
agcttcaaca ggggagagtg t                                                321

<210> SEQ ID NO 272
<211> LENGTH: 107
<212> TYPE: PRT
<213> ORGANISM: Homo sapiens

<400> SEQUENCE: 272

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Arg Lys Val Asp Asn Ala Leu Gln
        35                  40                  45

Ser Gly Asn Ser Gln Glu Ser Val Thr Glu Gln Glu Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 273
<211> LENGTH: 321

```
<212> TYPE: DNA
<213> ORGANISM: Homo sapiens

<400> SEQUENCE: 273
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcagc accctgacgc tgagcaaagc agactacgag     240
aaacacaaac tctacgcctg cgaagtcacc catcagggcc tgagctcgcc cgtcacaaag     300
agcttcaaca ggggagagtg t                                                321

<210> SEQ ID NO 274
<211> LENGTH: 107
<212> TYPE: PRT
<213> ORGANISM: Homo sapiens

<400> SEQUENCE: 274

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Leu Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 275
<211> LENGTH: 321
<212> TYPE: DNA
<213> ORGANISM: Homo sapiens

<400> SEQUENCE: 275
cgaactgtgg ctgcaccatc tgtcttcatc ttcccgccat ctgatgagca gttgaaatct      60
ggaactgcct ctgttgtgtg cctgctgaat aacttctatc ccagagaggc caaagtacag     120
tggaaggtgg ataacgccct ccaatcgggt aactcccagg agagtgtcac agagcaggac     180
agcaaggaca gcacctacag cctcagcaac accctgacgc tgagcaaagc agactacgag     240
aaacacaaag tctacgcctg cgaagtcacc catcagggcc tgagctcgcc cgtcacaaag     300
agcttcaaca ggggagagtg c                                                321

<210> SEQ ID NO 276
<211> LENGTH: 107
<212> TYPE: PRT
<213> ORGANISM: Homo sapiens

<400> SEQUENCE: 276

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30
```

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
 50                  55                  60

Thr Tyr Ser Leu Ser Asn Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
             100                 105

<210> SEQ ID NO 277
<211> LENGTH: 312
<212> TYPE: DNA
<213> ORGANISM: Homo sapiens

<400> SEQUENCE: 277
cccaaggcca accccacggt cactctgttc ccgccctcct ctgaggagct ccaagccaac    60
aaggccacac tagtgtgtct gatcagtgac ttctacccgg gagctgtgac agtggcttgg   120
aaggcagatg gcagccccgt caaggcggga gtggagacga ccaaaccctc aaacagagc    180 aacaacaagt acgcggccag cagctacctg agcctgacgc cgagcagtg gaagtcccac    240 agaagctaca gctgccaggt cacgcatgaa gggagcaccg tggagaagac agtggcccct   300
acagaatgtt ca                                                        312

<210> SEQ ID NO 278
<211> LENGTH: 104
<212> TYPE: PRT
<213> ORGANISM: Homo sapiens

<400> SEQUENCE: 278

Pro Lys Ala Asn Pro Thr Val Thr Leu Phe Pro Pro Ser Ser Glu Glu
 1                5                  10                  15

Leu Gln Ala Asn Lys Ala Thr Leu Val Cys Leu Ile Ser Asp Phe Tyr
             20                  25                  30

Pro Gly Ala Val Thr Val Ala Trp Lys Ala Asp Gly Ser Pro Val Lys
         35                  40                  45

Ala Gly Val Glu Thr Thr Lys Pro Ser Lys Gln Ser Asn Asn Lys Tyr
 50                  55                  60

Ala Ala Ser Ser Tyr Leu Ser Leu Thr Pro Glu Gln Trp Lys Ser His
 65                  70                  75                  80

Arg Ser Tyr Ser Cys Gln Val Thr His Glu Gly Ser Thr Val Glu Lys
                 85                  90                  95

Thr Val Ala Pro Thr Glu Cys Ser
             100

<210> SEQ ID NO 279
<211> LENGTH: 318
<212> TYPE: DNA
<213> ORGANISM: Homo sapiens

<400> SEQUENCE: 279
ggtcagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca acaagtacgc ggccagcagc tacctgagcc tgacgcccga gcagtggaag    240
tcccacagaa gctacagctg ccaggtcacg catgaaggga gcaccgtgga agacagtg     300 gcccctacag aatgttca                                                  318

<210> SEQ ID NO 280
<211> LENGTH: 106
<212> TYPE: PRT
<213> ORGANISM: Homo sapiens

<400> SEQUENCE: 280

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 281
<211> LENGTH: 318
<212> TYPE: DNA
<213> ORGANISM: Homo sapiens

<400> SEQUENCE: 281
ggtcagccca aggccaaccc cactgtcact ctgttcccgc cctcctctga ggagctccaa    60
gccaacaagg ccacactagt gtgtctgatc agtgacttct acccgggagc tgtgacagtg   120
gcctggaagg cagatggcag ccccgtcaag gcgggagtgg agaccaccaa accctccaaa   180
cagagcaaca acaagtacgc ggccagcagc tacctgagcc tgacgcccga gcagtggaag    240
tcccacagaa gctacagctg ccaggtcacg catgaaggga gcaccgtgga agacagtg     300 gcccctacag aatgttca                                                  318

<210> SEQ ID NO 282
<211> LENGTH: 318
<212> TYPE: PRT
<213> ORGANISM: Homo sapiens

<400> SEQUENCE: 282

Gly Gly Cys Cys Ala Gly Cys Cys Thr Ala Gly Gly Cys Cys Gly
1               5                   10                  15

Cys Thr Cys Cys Thr Cys Thr Cys Gly Thr Gly Ala Cys Cys Thr
            20                  25                  30

Gly Thr Thr Cys Cys Cys Cys Cys Ala Thr Cys Cys Thr Cys Cys
        35                  40                  45

Gly Ala Gly Gly Ala Ala Cys Thr Cys Ala Gly Gly Cys Thr Ala
    50                  55                  60

Ala Cys Ala Ala Gly Gly Cys Cys Ala Cys Cys Thr Cys Gly Thr
65                  70                  75                  80

Gly Thr Gly Cys Cys Thr Gly Ala Thr Cys Ala Gly Cys Gly Ala Cys

```
                85                  90                  95
Thr Thr Cys Thr Ala Cys Cys Thr Gly Gly Cys Gly Cys Cys Gly
               100                 105                 110

Thr Gly Ala Cys Cys Gly Thr Gly Gly Cys Cys Thr Gly Ala Ala
               115                 120                 125

Gly Gly Cys Thr Gly Ala Thr Ala Gly Cys Thr Cys Thr Cys Thr
               130                 135                 140

Gly Thr Gly Ala Ala Gly Gly Cys Cys Gly Cys Gly Thr Gly Gly
145                 150                 155                 160

Ala Ala Ala Cys Cys Ala Cys Cys Ala Cys Cys Cys Thr Thr Cys
                    165                 170                 175

Cys Ala Ala Gly Cys Ala Gly Thr Cys Cys Ala Ala Cys Ala Ala
                180                 185                 190

Cys Ala Ala Thr Ala Cys Gly Cys Gly Cys Cys Thr Cys Cys Thr
                    195                 200                 205

Cys Cys Thr Ala Cys Cys Thr Gly Thr Cys Cys Cys Thr Gly Ala Cys
                210                 215                 220

Cys Cys Cys Thr Gly Ala Gly Cys Ala Gly Thr Gly Gly Ala Ala Gly
225                 230                 235                 240

Thr Cys Cys Cys Ala Cys Cys Gly Gly Thr Cys Cys Thr Ala Cys Ala
                    245                 250                 255

Gly Cys Thr Gly Cys Cys Ala Ala Gly Thr Gly Ala Cys Cys Cys Ala
                260                 265                 270

Cys Gly Ala Gly Gly Gly Cys Thr Cys Cys Ala Cys Cys Gly Thr Gly
                275                 280                 285

Gly Ala Ala Ala Gly Ala Cys Cys Gly Thr Cys Gly Cys Thr Cys
                290                 295                 300

Cys Thr Ala Cys Cys Gly Ala Gly Thr Gly Cys Thr Cys Cys
305                 310                 315

<210> SEQ ID NO 283
<211> LENGTH: 318
<212> TYPE: DNA
<213> ORGANISM: Homo sapiens

<400> SEQUENCE: 283
ggccagccta aagctgcccc cagcgtcacc ctgtttcctc cctccagcga ggagctccag      60
gccaacaagg ccaccctcgt gtgcctgatc tccgacttct atccgggcgc tgtgaccgtg     120
gcttggaaag ccgactccag ccctgtcaaa gccggcgtgg agaccaccac accctccaag     180
cagtccaaca acaagtacgc cgcctccagc tatctctccc tgaccccctga gcagtggaag     240 tcccaccggt cctactcctg tcaggtgacc cacgagggct ccaccgtgga aagaccgtc      300 gcccccaccg agtgctcc                                                   318

<210> SEQ ID NO 284
<211> LENGTH: 106
<212> TYPE: PRT
<213> ORGANISM: Homo sapiens

<400> SEQUENCE: 284

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
```

```
            35                  40                  45
Val Lys Ala Gly Val Glu Thr Thr Lys Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 285
<211> LENGTH: 318
<212> TYPE: DNA
<213> ORGANISM: Homo sapiens

<400> SEQUENCE: 285

```
ggtcagccca aggctgcccc ctcggtcact ctgttcccgc cctcctctga ggagcttcaa     60
gccaacaagg ccacactggt gtgtctcata agtgacttct acccgggagc cgtgacagtg    120
gcctggaagg cagatagcag ccccgtcaag gcgggagtgg agaccaccac accctccaaa    180
caaagcaaca acaagtacgc ggccagcagc tatctgagcc tgacgcctga gcagtggaag    240
tcccacagaa gctacagctg ccaggtcacg catgaaggga gcaccgtgga agacagtg      300
gcccctacag aatgttca                                                  318
```

<210> SEQ ID NO 286
<211> LENGTH: 106
<212> TYPE: PRT
<213> ORGANISM: Homo sapiens

<400> SEQUENCE: 286

```
Gly Gln Pro Lys Ala Ala Pro Ser Val Thr Leu Phe Pro Pro Ser Ser
  1               5                  10                  15

Glu Glu Leu Gln Ala Asn Lys Ala Thr Leu Val Cys Leu Ile Ser Asp
             20                  25                  30

Phe Tyr Pro Gly Ala Val Thr Val Ala Trp Lys Ala Asp Ser Ser Pro
         35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                 85                  90                  95

Glu Lys Thr Val Ala Pro Thr Glu Cys Ser
            100                 105
```

<210> SEQ ID NO 287
<211> LENGTH: 312
<212> TYPE: DNA
<213> ORGANISM: Homo sapiens

<400> SEQUENCE: 287

```
cccaaggctg cccctcggt cactctgttc ccaccctcct ctgaggagct tcaagccaac      60
aaggccacac tggtgtgtct cataagtgac ttctacccgg gagccgtgac agttgcctgg    120
aaggcagata gcagccccgt caaggcgggg gtggagacca ccacccctc caaacaaagc     180
aacaacaagt acgcggccag cagctacctg agcctgacgc tgagcagtg gaagtcccac     240
```

```
aaaagctaca gctgccaggt cacgcatgaa gggagcaccg tggagaagac agttgcccct    300
acggaatgtt ca                                                       312
```

<210> SEQ ID NO 288
<211> LENGTH: 104
<212> TYPE: PRT
<213> ORGANISM: Homo sapiens
<400> SEQUENCE: 288

```
Pro Lys Ala Ala Pro Ser Val Thr Leu Phe Pro Pro Ser Ser Glu Glu
1               5                   10                  15

Leu Gln Ala Asn Lys Ala Thr Leu Val Cys Leu Ile Ser Asp Phe Tyr
            20                  25                  30

Pro Gly Ala Val Thr Val Ala Trp Lys Ala Asp Ser Ser Pro Val Lys
        35                  40                  45

Ala Gly Val Glu Thr Thr Thr Pro Ser Lys Gln Ser Asn Asn Lys Tyr
    50                  55                  60

Ala Ala Ser Ser Tyr Leu Ser Leu Thr Pro Glu Gln Trp Lys Ser His
65                  70                  75                  80

Lys Ser Tyr Ser Cys Gln Val Thr His Glu Gly Ser Thr Val Glu Lys
                85                  90                  95

Thr Val Ala Pro Thr Glu Cys Ser
            100
```

<210> SEQ ID NO 289
<211> LENGTH: 318
<212> TYPE: DNA
<213> ORGANISM: Homo sapiens
<400> SEQUENCE: 289

```
ggtcagccca aggctgcccc ctcggtcact ctgttcccac cctcctctga ggagcttcaa    60
gccaacaagg ccacactggt gtgtctcata agtgacttct acccgggggcc agtgacagtt   120 gcctggaagg cagatagcag ccccgtcaag gcggggggtgg agaccaccac accctccaaa   180
caaagcaaca caagtacgc ggccagcagc tacctgagcc tgacgcctga gcagtggaag    240
tcccacaaaa gctacagctg ccaggtcacg catgaaggga gcaccgtgga agacagtg     300 gcccctacgg aatgttca                                                 318
```

<210> SEQ ID NO 290
<211> LENGTH: 106
<212> TYPE: PRT
<213> ORGANISM: Homo sapiens
<400> SEQUENCE: 290

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95
```

```
Glu Lys Thr Val Ala Pro Thr Glu Cys Ser
        100                 105
```

<210> SEQ ID NO 291
<211> LENGTH: 318
<212> TYPE: DNA
<213> ORGANISM: Homo sapiens

<400> SEQUENCE: 291

```
ggtcagccca aggctgcccc ctcggtcact ctgttcccac cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tacctgagcc tgacgcctga gcagtggaag      240
tcccacaaaa gctacagctg ccaggtcacg catgaaggga gcaccgtgga agacagtg       300 gcccctacag aatgttca                                                    318
```

<210> SEQ ID NO 292
<211> LENGTH: 106
<212> TYPE: PRT
<213> ORGANISM: Homo sapiens

<400> SEQUENCE: 292

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Lys Ser Tyr Ser Cys Gln Val Thr His Glu Gly Ser Thr Val
                85                  90                  95

Glu Lys Thr Val Ala Pro Thr Glu Cys Ser
        100                 105
```

<210> SEQ ID NO 293
<211> LENGTH: 318
<212> TYPE: DNA
<213> ORGANISM: Homo sapiens

<400> SEQUENCE: 293

```
ggtcagccca aggctgcccc ctcggtcact ctgttcccgc cctcctctga ggagcttcaa      60
gccaacaagg ccacactggt gtgtctcata agtgacttct acccgggagc cgtgacagtg     120
gcctggaagg cagatagcag ccccgtcaag gcgggagtgg agaccaccac accctccaaa     180
caaagcaaca caagtacgc ggccagcagc tacctgagcc tgacgcctga gcagtggaag      240
tcccacagaa gctacagctg ccaggtcacg catgaaggga gcaccgtgga agacagtg       300 gcccctacag aatgttca                                                    318
```

<210> SEQ ID NO 294
<211> LENGTH: 106
<212> TYPE: PRT
<213> ORGANISM: Homo sapiens

<400> SEQUENCE: 294

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 295
<211> LENGTH: 318
<212> TYPE: DNA
<213> ORGANISM: Homo sapiens

<400> SEQUENCE: 295

```
ggtcagccca aggctgcccc atcggtcact ctgttcccgc cctcctctga ggagcttcaa    60
gccaacaagg ccacactggt gtgcctgatc agtgacttct acccgggagc tgtgaaagtg   120
gcctggaagg cagatggcag ccccgtcaac acgggagtgg agaccaccac ccctccaaa    180
cagagcaaca caagtacgc ggccagcagc tacctgagcc tgacgcctga gcagtggaag   240
tcccacagaa gctacagctg ccaggtcacg catgaaggga gcaccgtgga agacagtg    300
gcccctgcag aatgttca                                                 318
```

<210> SEQ ID NO 296
<211> LENGTH: 106
<212> TYPE: PRT
<213> ORGANISM: Homo sapiens

<400> SEQUENCE: 296

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Lys Val Ala Trp Lys Ala Asp Gly Ser Pro
        35                  40                  45

Val Asn Thr Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Ala Glu Cys Ser
            100                 105
```

<210> SEQ ID NO 297
<211> LENGTH: 318
<212> TYPE: DNA
<213> ORGANISM: Homo sapiens

<400> SEQUENCE: 297

```
ggtcagccca aggctgcccc atcggtcact ctgttcccac cctcctctga ggagcttcaa    60
gccaacaagg ccacactggt gtgtctcgta agtgacttct acccgggagc cgtgacagtg   120
gcctggaagg cagatggcag ccccgtcaag gtgggagtgg agaccaccaa accctccaaa   180
caaagcaaca acaagtatgc ggccagcagc tacctgagcc tgacgcccga gcagtggaag   240
tcccacagaa gctacagctg ccgggtcacg catgaaggga gcaccgtgga aagacagtg    300 gcccctgcag aatgctct                                                 318
```

```
<210> SEQ ID NO 298
<211> LENGTH: 106
<212> TYPE: PRT
<213> ORGANISM: Homo sapiens

<400> SEQUENCE: 298
```

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Val Ser Asp
            20                  25                  30

Phe Tyr Pro Gly Ala Val Thr Val Ala Trp Lys Ala Asp Gly Ser Pro
        35                  40                  45

Val Lys Val Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Arg Val Thr His Glu Gly Ser Thr Val
                85                  90                  95

Glu Lys Thr Val Ala Pro Ala Glu Cys Ser
            100                 105
```

```
<210> SEQ ID NO 299
<211> LENGTH: 720
<212> TYPE: DNA
<213> ORGANISM: Homo sapiens

<400> SEQUENCE: 299
atggaggaga gtgtcgtacg gccctcagtg tttgtggtgg atggacagac cgacatccca    60
ttcacgaggc tgggacgaag ccaccggaga cagtcgtgca gtgtggcccg ggtgggtctg   120
ggtctcttgc tgttgctgat gggggctggg ctggccgtcc aaggctggtt cctcctgcag   180
ctgcactggc gtctaggaga gatggtcacc cgcctgcctg acggacctgc aggctcctgg   240
gagcagctga tacaagagcg aaggtctcac gaggtcaacc cagcagcgca tctcacaggg   300
gccaactcca gcttgaccgg cagcgggggg ccgctgttat gggagactca gctgggcctg   360
gccttcctga ggggcctcag ctaccacgat ggggcccttg tggtcaccaa agctggctac   420
tactacatct actccaaggt gcagctgggc ggtgtgggct gcccgctggg cctggccagc   480
accatcaccc acggcctcta caagcgcaca cccgctacc ccgaggagct ggagctgttg   540
gtcagccagc agtcaccctg cggacgggcc accagcagct cccgggtctg gtgggacagc   600
agcttcctgg gtggtgtggt acacctggag gctggggagg aggtggtcgt ccgtgtgctg   660
gatgaacgcc tggttcgact gcgtgatggt acccggtctt acttcggggc tttcatggtg   720
```

```
<210> SEQ ID NO 300
<211> LENGTH: 240
<212> TYPE: PRT
<213> ORGANISM: Homo sapiens
```

<400> SEQUENCE: 300

| Met | Glu | Glu | Ser | Val | Val | Arg | Pro | Ser | Val | Phe | Val | Val | Asp | Gly | Gln |
|---|---|---|---|---|---|---|---|---|---|---|---|---|---|---|---|
| 1 | | | | 5 | | | | | 10 | | | | | 15 | |

Thr Asp Ile Pro Phe Thr Arg Leu Gly Arg Ser His Arg Arg Gln Ser
          20                25              30

Cys Ser Val Ala Arg Val Gly Leu Gly Leu Leu Leu Leu Met Gly
       35               40              45

Ala Gly Leu Ala Val Gln Gly Trp Phe Leu Leu Gln Leu His Trp Arg
50               55                   60

Leu Gly Glu Met Val Thr Arg Leu Pro Asp Gly Pro Ala Gly Ser Trp
65               70              75            80

Glu Gln Leu Ile Gln Glu Arg Arg Ser His Glu Val Asn Pro Ala Ala
          85                90              95

His Leu Thr Gly Ala Asn Ser Ser Leu Thr Gly Ser Gly Gly Pro Leu
        100              105            110

Leu Trp Glu Thr Gln Leu Gly Leu Ala Phe Leu Arg Gly Leu Ser Tyr
        115              120            125

His Asp Gly Ala Leu Val Val Thr Lys Ala Gly Tyr Tyr Tyr Ile Tyr
        130              135            140

Ser Lys Val Gln Leu Gly Gly Val Gly Cys Pro Leu Gly Leu Ala Ser
145              150              155           160

Thr Ile Thr His Gly Leu Tyr Lys Arg Thr Pro Arg Tyr Pro Glu Glu
        165              170            175

Leu Glu Leu Leu Val Ser Gln Gln Ser Pro Cys Gly Arg Ala Thr Ser
        180              185            190

Ser Ser Arg Val Trp Trp Asp Ser Ser Phe Leu Gly Gly Val Val His
        195              200            205

Leu Glu Ala Gly Glu Glu Val Val Arg Val Leu Asp Glu Arg Leu
        210              215            220

Val Arg Leu Arg Asp Gly Thr Arg Ser Tyr Phe Gly Ala Phe Met Val
225              230              235           240

<210> SEQ ID NO 301
<211> LENGTH: 720
<212> TYPE: DNA
<213> ORGANISM: Homo sapiens

<400> SEQUENCE: 301

| atggaggaga | gtgtcgtacg | gccctcagtg | tttgtggtgg | atggacagac | cgacatccca | 60 |
| ttcacgaggc | tgggacgaag | ccaccggaga | cagtcgtgca | gtgtggcccg | ggtgggtctg | 120 |
| ggtctcttgc | tgttgctgat | gggggctggg | ctggccgtcc | aaggctggtt | cctcctgcag | 180 |
| ctgcactggc | gtctaggaga | gatggtcacc | cgcctgcctg | acggacctgc | aggctcctgg | 240 |
| gagcagctga | tacaagagcg | aaggtctcac | gaggtcaacc | cagcagcgca | tctcacaggg | 300 |
| gccaactcca | gcttgaccgg | cagcgggggg | ccgctgttat | gggagactca | gctgggcctg | 360 |
| gccttcctga | ggggcctcag | ctaccacgat | ggggcccttg | tggtcaccaa | agctggctac | 420 |
| tactacatct | actccaaggt | gcagctgggc | ggtgtgggct | gcccgctggg | cctggccagc | 480 |
| accatcaccc | acggcctcta | caagcgcaca | ccccgctacc | cgaggagct | ggagctgttg | 540 |
| gtcagccagc | agtcaccctg | cggacgggcc | accagcagct | cccgggtctg | gtgggacagc | 600 |
| agcttcctgg | gtggtgtggt | acacctggag | gctggggaga | aggtggtcgt | ccgtgtgctg | 660 |
| gatgaacgcc | tggttcgact | gcgtgatggt | acccggtctt | acttcggggc | tttcatggtg | 720 |

<210> SEQ ID NO 302
<211> LENGTH: 240
<212> TYPE: PRT
<213> ORGANISM: Homo sapiens

<400> SEQUENCE: 302

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 303
<211> LENGTH: 720
<212> TYPE: DNA
<213> ORGANISM: Homo sapiens
<220> FEATURE:
<223> OTHER INFORMATION: LIGHT-214E

<400> SEQUENCE: 303
atggaagagt ccgtcgtgcg gccctccgtg ttcgtggtgg atggccagac cgacatcccc      60
ttcaccagac tgggccggtc ccacagacgg cagtcttgct ctgtggctag agtgggcctg     120
ggcctcctgc tgctgctgat gggagctgga ctggctgtgc agggctggtt tctgctgcag    180
ctgcattggc ggctgggcga gatggtcacc aggctgcctg atggccctgc tggctcttgg    240
gagcagctga tccaggaacg cgcggtccac gaagtgaatc ctgccgctca tctgaccggc    300
gccaactctt ccctgaccgg atctggtgga cccctgctgt gggagactca gctgggcctg    360
gctttcctgc ggggcctgtc ttaccatgat ggcgccctgg tcgtgaccaa ggccggctac    420
tactacatct actccaaggt gcagctgggc ggcgtgggct gtcctctggg actggcttct    480

```
accatcaccc acggcctgta caagcggacc cccagatacc ccgaggaact ggaactgctg      540
gtgtcccagc agtccccttg tggcagagcc acctcctcca gcagagtgtg gtgggactcc      600
tctttcctgg gcggggtggt gcatctggaa gccggcgaag aggtggtcgt gcgggtgctg      660
gatgagagac tcgtgcggct gagggacggc accagaagct acttcggcgc ctttatggtg      720
```

<210> SEQ ID NO 304
<211> LENGTH: 240
<212> TYPE: PRT
<213> ORGANISM: Homo sapiens
<220> FEATURE:
<223> OTHER INFORMATION: LIGHT-214E

<400> SEQUENCE: 304

```
Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Glu Val Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240
```

<210> SEQ ID NO 305
<211> LENGTH: 720
<212> TYPE: DNA
<213> ORGANISM: Homo sapiens
<220> FEATURE:
<223> OTHER INFORMATION: LIGHT-214K

<400> SEQUENCE: 305

```
atggaagagt ccgtcgtgcg gccctccgtg ttcgtggtgg atggccagac cgacatcccc      60
ttcaccagac tgggccggtc ccacagacgg cagtcttgct ctgtggctag agtgggcctg     120
ggcctcctgc tgctgctgat gggagctgga ctggctgtgc agggctggtt tctgctgcag     180
```

| | |
|---|---|
| ctgcattggc ggctgggcga gatggtcacc aggctgcctg atggccctgc tggctcttgg | 240 |
| gagcagctga tccaggaacg gcggtcccac gaagtgaatc ctgccgctca tctgaccggc | 300 |
| gccaactctt ccctgaccgg atctggtgga cccctgctgt gggagactca gctgggcctg | 360 |
| gctttcctgc ggggcctgtc ttaccatgat ggcgccctgg tcgtgaccaa ggccggctac | 420 |
| tactacatct actccaaggt gcagctgggc ggcgtgggct gtcctctggg actggcttct | 480 |
| accatcaccc acggcctgta caagcggacc cccagatacc ccgaggaact ggaactgctg | 540 |
| gtgtcccagc agtccccttg tggcagagcc acctcctcca gcagagtgtg gtgggactcc | 600 |
| tctttcctgg gcggggtggt gcatctggaa gccggcgaaa aggtggtcgt gcgggtgctg | 660 |
| gatgagagac tcgtgcggct gagggacggc accagaagct acttcggcgc ctttatggtg | 720 |

<210> SEQ ID NO 306
<211> LENGTH: 240
<212> TYPE: PRT
<213> ORGANISM: Homo sapiens
<220> FEATURE:
<223> OTHER INFORMATION: LIGHT-214K

<400> SEQUENCE: 306

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Val Gly Leu Gly Leu Leu Leu Leu Leu Met Gly
        35                  40                  45

Ala Gly Leu Ala Val Gln Gly Trp Phe Leu Leu Gln Leu His Trp Arg
    50                  55                  60

Leu Gly Glu Met Val Thr Arg Leu Pro Asp Gly Pro Ala Gly Ser Trp
65                  70                  75                  80

Glu Gln Leu Ile Gln Glu Arg Arg Ser His Glu Val Asn Pro Ala Ala
                85                  90                  95

His Leu Thr Gly Ala Asn Ser Ser Leu Thr Gly Ser Gly Gly Pro Leu
            100                 105                 110

Leu Trp Glu Thr Gln Leu Gly Leu Ala Phe Leu Arg Gly Leu Ser Tyr
        115                 120                 125

His Asp Gly Ala Leu Val Val Thr Lys Ala Gly Tyr Tyr Tyr Ile Tyr
    130                 135                 140

Ser Lys Val Gln Leu Gly Gly Val Gly Cys Pro Leu Gly Leu Ala Ser
145                 150                 155                 160

Thr Ile Thr His Gly Leu Tyr Lys Arg Thr Pro Arg Tyr Pro Glu Glu
                165                 170                 175

Leu Glu Leu Leu Val Ser Gln Gln Ser Pro Cys Gly Arg Ala Thr Ser
            180                 185                 190

Ser Ser Arg Val Trp Trp Asp Ser Ser Phe Leu Gly Gly Val Val His
        195                 200                 205

Leu Glu Ala Gly Glu Lys Val Val Arg Val Leu Asp Glu Arg Leu
    210                 215                 220

Val Arg Leu Arg Asp Gly Thr Arg Ser Tyr Phe Gly Ala Phe Met Val
225                 230                 235                 240

<210> SEQ ID NO 307
<211> LENGTH: 633
<212> TYPE: DNA
<213> ORGANISM: Homo sapiens
<220> FEATURE:

<223> OTHER INFORMATION: LIGHT-214E

<400> SEQUENCE: 307

```
atgggctggt cctgcatcat cctgttcctg gtggccaccg ctaccggcgt gcattccatg      60
gactacaagg acgacgacga caagggcgga ggatccggag gaggctccgg aggcggatcc     120
attgagggca gggatggacc tgccggatcc tgggagcagc tgatccagga gaggcggtcc     180
cacgaagtga atcccgccgc tcacctgacc ggagccaata gctccctcac aggatccggc     240
ggacctctgc tgtgggaaac ccaactggga ctcgccttcc tgaggggcct ctcctaccac     300
gatggcgctc tggtcgtgac caaggccggc tactactaca tctactccaa ggtgcagctg     360
ggcggagtgg gatgtcctct gggactggcc agcaccatca cccatggcct ctacaagagg     420
acccctaggt atcctgagga actggagctg ctggtgagcc agcagtcccc ttgcggaagg     480
gctaccagct cctccagggt gtggtgggat tcctccttcc tgggaggagt cgtgcacctg     540
gaggctggcg aggaggtcgt ggtgagggtg ctggacgaga ggctggtgcg gctcagggat     600
ggcacaaggt cctacttcgg cgccttcatg gtg                                  633
```

<210> SEQ ID NO 308
<211> LENGTH: 211
<212> TYPE: PRT
<213> ORGANISM: Homo sapiens
<220> FEATURE:
<223> OTHER INFORMATION: LIGHT-214E

<400> SEQUENCE: 308

```
Met Gly Trp Ser Cys Ile Ile Leu Phe Leu Val Ala Thr Ala Thr Gly
 1               5                  10                  15

Val His Ser Met Asp Tyr Lys Asp Asp Asp Lys Gly Gly Gly Ser
             20                  25                  30

Gly Gly Gly Ser Gly Gly Gly Ser Ile Glu Gly Arg Asp Gly Pro Ala
         35                  40                  45

Gly Ser Trp Glu Gln Leu Ile Gln Glu Arg Arg Ser His Glu Val Asn
     50                  55                  60

Pro Ala Ala His Leu Thr Gly Ala Asn Ser Ser Leu Thr Gly Ser Gly
 65                  70                  75                  80

Gly Pro Leu Leu Trp Glu Thr Gln Leu Gly Leu Ala Phe Leu Arg Gly
                 85                  90                  95

Leu Ser Tyr His Asp Gly Ala Leu Val Val Thr Lys Ala Gly Tyr Tyr
            100                 105                 110

Tyr Ile Tyr Ser Lys Val Gln Leu Gly Gly Val Gly Cys Pro Leu Gly
        115                 120                 125

Leu Ala Ser Thr Ile Thr His Gly Leu Tyr Lys Arg Thr Pro Arg Tyr
    130                 135                 140

Pro Glu Glu Leu Glu Leu Leu Val Ser Gln Gln Ser Pro Cys Gly Arg
145                 150                 155                 160

Ala Thr Ser Ser Ser Arg Val Trp Trp Asp Ser Ser Phe Leu Gly Gly
                165                 170                 175

Val Val His Leu Glu Ala Gly Glu Glu Val Val Val Arg Val Leu Asp
            180                 185                 190

Glu Arg Leu Val Arg Leu Arg Asp Gly Thr Arg Ser Tyr Phe Gly Ala
        195                 200                 205

Phe Met Val
    210
```

<210> SEQ ID NO 309
<211> LENGTH: 633
<212> TYPE: DNA
<213> ORGANISM: Homo sapiens
<220> FEATURE:
<223> OTHER INFORMATION: LIGHT-214K

<400> SEQUENCE: 309

```
atgggctggt cctgcatcat cctgttcctg gtggccaccg ctaccggcgt gcattccatg    60
gactacaagg acgacgacga caagggcgga ggatccggag gaggctccgg aggcggatcc   120
attgagggca gggatggacc tgccggatcc tgggagcagc tgatccagga gaggcggtcc   180
cacgaagtga atcccgccgc tcacctgacc ggagccaata gctccctcac aggatccggc   240
ggacctctgc tgtgggaaac ccaactggga ctcgccttcc tgaggggcct ctcctaccac   300
gatggcgctc tggtcgtgac caaggccggc tactactaca tctactccaa ggtgcagctg   360
ggcggagtgg gatgtcctct gggactggcc agcaccatca cccatggcct ctacaagagg   420
acccctaggt atcctgagga actggagctg ctggtgagcc agcagtcccc ttgcggaagg   480
gctaccagct cctccagggt gtggtgggat cctccttcc tgggaggagt cgtgcacctg    540
gaggctggcg agaaggtcgt ggtgagggtg ctggacgaga ggctggtgcg gctcagggat   600
ggcacaaggt cctacttcgg cgccttcatg gtg                                633
```

<210> SEQ ID NO 310
<211> LENGTH: 211
<212> TYPE: PRT
<213> ORGANISM: Homo sapiens
<220> FEATURE:
<223> OTHER INFORMATION: LIGHT-214K

<400> SEQUENCE: 310

```
Met Gly Trp Ser Cys Ile Ile Leu Phe Leu Val Ala Thr Ala Thr Gly
  1               5                  10                  15

Val His Ser Met Asp Tyr Lys Asp Asp Asp Lys Gly Gly Gly Ser
             20                  25                  30

Gly Gly Gly Ser Gly Gly Gly Ser Ile Glu Gly Arg Asp Gly Pro Ala
         35                  40                  45

Gly Ser Trp Glu Gln Leu Ile Gln Glu Arg Arg Ser His Glu Val Asn
     50                  55                  60

Pro Ala Ala His Leu Thr Gly Ala Asn Ser Ser Leu Thr Gly Ser Gly
 65                  70                  75                  80

Gly Pro Leu Leu Trp Glu Thr Gln Leu Gly Leu Ala Phe Leu Arg Gly
                 85                  90                  95

Leu Ser Tyr His Asp Gly Ala Leu Val Val Thr Lys Ala Gly Tyr Tyr
            100                 105                 110

Tyr Ile Tyr Ser Lys Val Gln Leu Gly Gly Val Gly Cys Pro Leu Gly
        115                 120                 125

Leu Ala Ser Thr Ile Thr His Gly Leu Tyr Lys Arg Thr Pro Arg Tyr
    130                 135                 140

Pro Glu Glu Leu Glu Leu Leu Val Ser Gln Gln Ser Pro Cys Gly Arg
145                 150                 155                 160

Ala Thr Ser Ser Ser Arg Val Trp Trp Asp Ser Ser Phe Leu Gly Gly
                165                 170                 175

Val Val His Leu Glu Ala Gly Glu Lys Val Val Val Arg Val Leu Asp
            180                 185                 190

Glu Arg Leu Val Arg Leu Arg Asp Gly Thr Arg Ser Tyr Phe Gly Ala
        195                 200                 205
```

Phe Met Val
    210

<210> SEQ ID NO 311
<211> LENGTH: 349
<212> TYPE: DNA
<213> ORGANISM: Homo sapiens

<400> SEQUENCE: 311
caggtgctgc tggtgcagtc tggggctgag gtaaagaagc ctggggcctc agtgaaggtc      60
tcctgcaagg cttctggata caccttcacc cattttgata tcaactgggt gcgacaggcc     120
actggacaag ggcttgagtg gatgggatgg atgaaccctg acagtgataa cacagactat     180
gcacaggagt tccagggcag agtcaccatg accagggaca cctccataag cacagcctac     240
atggagctga gcagcctgag atctgaggac acggccgtgt attactgtgc gagggggggg     300
actaccctag actactgggg ccagggaacc ctggtcaccg tctcctcag                 349

<210> SEQ ID NO 312
<211> LENGTH: 116
<212> TYPE: PRT
<213> ORGANISM: Homo sapiens

<400> SEQUENCE: 312

Gln Val Leu Leu Val Gln Ser Gly Ala Glu Val Lys Lys Pro Gly Ala
1               5                   10                  15

Ser Val Lys Val Ser Cys Lys Ala Ser Gly Tyr Thr Phe Thr His Phe
            20                  25                  30

Asp Ile Asn Trp Val Arg Gln Ala Thr Gly Gln Gly Leu Glu Trp Met
        35                  40                  45

Gly Trp Met Asn Pro Asp Ser Asp Asn Thr Asp Tyr Ala Gln Glu Phe
    50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Gly Gly Thr Thr Leu Asp Tyr Trp Gly Gln Gly Thr Leu Val
            100                 105                 110

Thr Val Ser Ser
        115

<210> SEQ ID NO 313
<211> LENGTH: 325
<212> TYPE: DNA
<213> ORGANISM: Homo sapiens

<400> SEQUENCE: 313
tcctatgagc tgacacagcc accctcggtg tcagtgtccc caggacaaac ggccaggatc      60
acctgctctg gagatgcatt gccaaaaaaa tatgcttatt ggtaccagca gaagtcaggc     120
caggcccctg tactggtcat ctatgaggac agcaaacgac cctccgggat ccctgagaga     180
ttctctggct ccagctcagg gacaatggcc accttgacta tcagtggggc ccaggtggag     240
gatgaagctg actactactg ttactcaaca gacagcagtg ataatcatgt gatattcggc     300
ggagggacca agctgaccgt cctag                                           325

<210> SEQ ID NO 314
<211> LENGTH: 108

```
<212> TYPE: PRT
<213> ORGANISM: Homo sapiens

<400> SEQUENCE: 314

Ser Tyr Glu Leu Thr Gln Pro Pro Ser Val Ser Val Ser Pro Gly Gln
1               5                   10                  15

Thr Ala Arg Ile Thr Cys Ser Gly Asp Ala Leu Pro Lys Lys Tyr Ala
            20                  25                  30

Tyr Trp Tyr Gln Gln Lys Ser Gly Gln Ala Pro Val Leu Val Ile Tyr
        35                  40                  45

Glu Asp Ser Lys Arg Pro Ser Gly Ile Pro Glu Arg Phe Ser Gly Ser
    50                  55                  60

Ser Ser Gly Thr Met Ala Thr Leu Thr Ile Ser Gly Ala Gln Val Glu
65                  70                  75                  80

Asp Glu Ala Asp Tyr Tyr Cys Tyr Ser Thr Asp Ser Ser Asp Asn His
                85                  90                  95

Val Ile Phe Gly Gly Gly Thr Lys Leu Thr Val Leu
            100                 105

<210> SEQ ID NO 315
<211> LENGTH: 24
<212> TYPE: DNA
<213> ORGANISM: Homo sapiens

<400> SEQUENCE: 315 ggatacaccct tcacccattt tgat                                     24

<210> SEQ ID NO 316
<211> LENGTH: 15
<212> TYPE: DNA
<213> ORGANISM: Homo sapiens

<400> SEQUENCE: 316
cattttgata tcaac                                                15

<210> SEQ ID NO 317
<211> LENGTH: 24
<212> TYPE: DNA
<213> ORGANISM: Homo sapiens

<400> SEQUENCE: 317
atgaaccctg acagtgataa caca                                      24

<210> SEQ ID NO 318
<211> LENGTH: 51
<212> TYPE: DNA
<213> ORGANISM: Homo sapiens

<400> SEQUENCE: 318
tggatgaacc ctgacagtga taacacagac tatgcacagg agttccaggg c         51

<210> SEQ ID NO 319
<211> LENGTH: 27
<212> TYPE: DNA
<213> ORGANISM: Homo sapiens

<400> SEQUENCE: 319
gcgagagggg ggactaccct agactac                                   27

<210> SEQ ID NO 320
<211> LENGTH: 21
```

```
<212> TYPE: DNA
<213> ORGANISM: Homo sapiens

<400> SEQUENCE: 320 gggggacta ccctagacta c                                           21

<210> SEQ ID NO 321
<211> LENGTH: 18
<212> TYPE: DNA
<213> ORGANISM: Homo sapiens

<400> SEQUENCE: 321
gcattgccaa aaaaatat                                              18

<210> SEQ ID NO 322
<211> LENGTH: 33
<212> TYPE: DNA
<213> ORGANISM: Homo sapiens

<400> SEQUENCE: 322
tctggagatg cattgccaaa aaaatatgct tat                             33

<210> SEQ ID NO 323

<400> SEQUENCE: 323

000

<210> SEQ ID NO 324
<211> LENGTH: 21
<212> TYPE: DNA
<213> ORGANISM: Homo sapiens

<400> SEQUENCE: 324
gaggacagca aacgaccctc c                                          21

<210> SEQ ID NO 325
<211> LENGTH: 33
<212> TYPE: DNA
<213> ORGANISM: Homo sapiens

<400> SEQUENCE: 325
tactcaacag acagcagtga taatcatgtg ata                             33

<210> SEQ ID NO 326
<211> LENGTH: 33
<212> TYPE: DNA
<213> ORGANISM: Homo sapiens

<400> SEQUENCE: 326
tactcaacag acagcagtga taatcatgtg ata                             33

<210> SEQ ID NO 327
<211> LENGTH: 8
<212> TYPE: PRT
<213> ORGANISM: Homo sapiens

<400> SEQUENCE: 327

Gly Tyr Thr Phe Thr His Phe Asp
1               5

<210> SEQ ID NO 328
<211> LENGTH: 5
<212> TYPE: PRT
```

```
<213> ORGANISM: Homo sapiens

<400> SEQUENCE: 328

His Phe Asp Ile Asn
1               5

<210> SEQ ID NO 329
<211> LENGTH: 8
<212> TYPE: PRT
<213> ORGANISM: Homo sapiens

<400> SEQUENCE: 329

Met Asn Pro Asp Ser Asp Asn Thr
1               5

<210> SEQ ID NO 330
<211> LENGTH: 17
<212> TYPE: PRT
<213> ORGANISM: Homo sapiens

<400> SEQUENCE: 330

Trp Met Asn Pro Asp Ser Asp Asn Thr Asp Tyr Ala Gln Glu Phe Gln
1               5                   10                  15

Gly

<210> SEQ ID NO 331
<211> LENGTH: 9
<212> TYPE: PRT
<213> ORGANISM: Homo sapiens

<400> SEQUENCE: 331

Ala Arg Gly Gly Thr Thr Leu Asp Tyr
1               5

<210> SEQ ID NO 332
<211> LENGTH: 7
<212> TYPE: PRT
<213> ORGANISM: Homo sapiens

<400> SEQUENCE: 332

Gly Gly Thr Thr Leu Asp Tyr
1               5

<210> SEQ ID NO 333
<211> LENGTH: 6
<212> TYPE: PRT
<213> ORGANISM: Homo sapiens

<400> SEQUENCE: 333

Ala Leu Pro Lys Lys Tyr
1               5

<210> SEQ ID NO 334
<211> LENGTH: 11
<212> TYPE: PRT
<213> ORGANISM: Homo sapiens

<400> SEQUENCE: 334

Ser Gly Asp Ala Leu Pro Lys Lys Tyr Ala Tyr
1               5                   10

<210> SEQ ID NO 335

<400> SEQUENCE: 335
```

000

<210> SEQ ID NO 336
<211> LENGTH: 7
<212> TYPE: PRT
<213> ORGANISM: Homo sapiens

<400> SEQUENCE: 336

Glu Asp Ser Lys Arg Pro Ser
1               5

<210> SEQ ID NO 337
<211> LENGTH: 11
<212> TYPE: PRT
<213> ORGANISM: Homo sapiens

<400> SEQUENCE: 337

Tyr Ser Thr Asp Ser Ser Asp Asn His Val Ile
1               5                   10

<210> SEQ ID NO 338
<211> LENGTH: 11
<212> TYPE: PRT
<213> ORGANISM: Homo sapiens

<400> SEQUENCE: 338

Tyr Ser Thr Asp Ser Ser Asp Asn His Val Ile
1               5                   10

<210> SEQ ID NO 339
<211> LENGTH: 349
<212> TYPE: DNA
<213> ORGANISM: Homo sapiens

<400> SEQUENCE: 339
caggtgcagt tggtggagtc tgggggaggc ttggtcaagc ctggagggtc cctgagactc       60
tcctgtgcag cctctggatt caccttcagt gactactaca tgagctggat ccgccaggct      120
ccagggaagg gactggagtg gtttcatac attagtagaa gtagtttcat atactactca       180
gagtctgtga agggccgatt caccatctcc aggacaacg ccaagaactc actgtatctg       240
caaatgaaca gcctgagagc cgaggacacg gccgtgtatt actgtgcgcg atgggagcta      300
tccccttttg actactgggg ccagggaacc ctggtcaccg tctcctcag                 349

<210> SEQ ID NO 340
<211> LENGTH: 116
<212> TYPE: PRT
<213> ORGANISM: Homo sapiens

<400> SEQUENCE: 340

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Ser Ser Phe Ile Tyr Tyr Ser Glu Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
            85                  90                  95

Arg Trp Glu Leu Ser Pro Phe Asp Tyr Trp Gly Gln Gly Thr Leu Val
        100                 105                 110

Thr Val Ser Ser
        115

<210> SEQ ID NO 341
<211> LENGTH: 322
<212> TYPE: DNA
<213> ORGANISM: Homo sapiens

<400> SEQUENCE: 341
gacatccaga tgacccagtc tccatcctca ctgtctgcat ctgtaggaga cagagtcacc      60
atcacttgtc gggcgagtca gggcattagc aattatttag cctggtttca gcagaaacca     120
gggaaagccc ctaagtccct gatctatgct gcatccagtt tgcaaagtgg ggtcccatca     180
aagttcagcg gcagtggatc tgggacagat tcactctca ccatcagcag cctgcagcct     240
gaagattttg caacttattt ctgccaacag tataatactt acccattcac tttcggccct     300
gggaccaaag tggatatcaa ac                                              322

<210> SEQ ID NO 342
<211> LENGTH: 107
<212> TYPE: PRT
<213> ORGANISM: Homo sapiens

<400> SEQUENCE: 342

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Thr Tyr Pro Phe
                85                  90                  95

Thr Phe Gly Pro Gly Thr Lys Val Asp Ile Lys
            100                 105

<210> SEQ ID NO 343
<211> LENGTH: 24
<212> TYPE: DNA
<213> ORGANISM: Homo sapiens

<400> SEQUENCE: 343
ggattcacct tcagtgacta ctac                                            24

<210> SEQ ID NO 344
<211> LENGTH: 15
<212> TYPE: DNA
<213> ORGANISM: Homo sapiens

<400> SEQUENCE: 344
gactactaca tgagc                                                      15

```
<210> SEQ ID NO 345
<211> LENGTH: 21
<212> TYPE: DNA
<213> ORGANISM: Homo sapiens

<400> SEQUENCE: 345
attagtagaa gtagtttcat a                                          21

<210> SEQ ID NO 346
<211> LENGTH: 48
<212> TYPE: DNA
<213> ORGANISM: Homo sapiens

<400> SEQUENCE: 346
tacattagta gaagtagttt catatactac tcagagtctg tgaagggc             48

<210> SEQ ID NO 347
<211> LENGTH: 30
<212> TYPE: DNA
<213> ORGANISM: Homo sapiens

<400> SEQUENCE: 347
gcgcgatggg agctatcccc ttttgactac                                 30

<210> SEQ ID NO 348
<211> LENGTH: 24
<212> TYPE: DNA
<213> ORGANISM: Homo sapiens

<400> SEQUENCE: 348
tgggagctat cccctttga ctac                                        24

<210> SEQ ID NO 349
<211> LENGTH: 18
<212> TYPE: DNA
<213> ORGANISM: Homo sapiens

<400> SEQUENCE: 349
cagggcatta gcaattat                                              18

<210> SEQ ID NO 350
<211> LENGTH: 33
<212> TYPE: DNA
<213> ORGANISM: Homo sapiens

<400> SEQUENCE: 350
cgggcgagtc agggcattag caattattta gcc                             33

<210> SEQ ID NO 351

<400> SEQUENCE: 351

000

<210> SEQ ID NO 352
<211> LENGTH: 21
<212> TYPE: DNA
<213> ORGANISM: Homo sapiens

<400> SEQUENCE: 352
gctgcatcca gtttgcaaag t                                          21

<210> SEQ ID NO 353
<211> LENGTH: 27
```

```
<212> TYPE: DNA
<213> ORGANISM: Homo sapiens

<400> SEQUENCE: 353
caacagtata atacttaccc attcact                                             27

<210> SEQ ID NO 354
<211> LENGTH: 27
<212> TYPE: DNA
<213> ORGANISM: Homo sapiens

<400> SEQUENCE: 354
caacagtata atacttaccc attcact                                             27

<210> SEQ ID NO 355
<211> LENGTH: 8
<212> TYPE: PRT
<213> ORGANISM: Homo sapiens

<400> SEQUENCE: 355

Gly Phe Thr Phe Ser Asp Tyr Tyr
1               5

<210> SEQ ID NO 356
<211> LENGTH: 5
<212> TYPE: PRT
<213> ORGANISM: Homo sapiens

<400> SEQUENCE: 356

Asp Tyr Tyr Met Ser
1               5

<210> SEQ ID NO 357
<211> LENGTH: 7
<212> TYPE: PRT
<213> ORGANISM: Homo sapiens

<400> SEQUENCE: 357

Ile Ser Arg Ser Ser Phe Ile
1               5

<210> SEQ ID NO 358
<211> LENGTH: 16
<212> TYPE: PRT
<213> ORGANISM: Homo sapiens

<400> SEQUENCE: 358

Tyr Ile Ser Arg Ser Ser Phe Ile Tyr Tyr Ser Glu Ser Val Lys Gly
1               5                   10                  15

<210> SEQ ID NO 359
<211> LENGTH: 10
<212> TYPE: PRT
<213> ORGANISM: Homo sapiens

<400> SEQUENCE: 359

Ala Arg Trp Glu Leu Ser Pro Phe Asp Tyr
1               5                   10

<210> SEQ ID NO 360
<211> LENGTH: 8
<212> TYPE: PRT
<213> ORGANISM: Homo sapiens

<400> SEQUENCE: 360
```

Trp Glu Leu Ser Pro Phe Asp Tyr
1               5

<210> SEQ ID NO 361
<211> LENGTH: 6
<212> TYPE: PRT
<213> ORGANISM: Homo sapiens

<400> SEQUENCE: 361

Gln Gly Ile Ser Asn Tyr
1               5

<210> SEQ ID NO 362
<211> LENGTH: 11
<212> TYPE: PRT
<213> ORGANISM: Homo sapiens

<400> SEQUENCE: 362

Arg Ala Ser Gln Gly Ile Ser Asn Tyr Leu Ala
1               5                   10

<210> SEQ ID NO 363

<400> SEQUENCE: 363

000

<210> SEQ ID NO 364
<211> LENGTH: 7
<212> TYPE: PRT
<213> ORGANISM: Homo sapiens

<400> SEQUENCE: 364

Ala Ala Ser Ser Leu Gln Ser
1               5

<210> SEQ ID NO 365
<211> LENGTH: 9
<212> TYPE: PRT
<213> ORGANISM: Homo sapiens

<400> SEQUENCE: 365

Gln Gln Tyr Asn Thr Tyr Pro Phe Thr
1               5

<210> SEQ ID NO 366
<211> LENGTH: 9
<212> TYPE: PRT
<213> ORGANISM: Homo sapiens

<400> SEQUENCE: 366

Gln Gln Tyr Asn Thr Tyr Pro Phe Thr
1               5

<210> SEQ ID NO 367
<211> LENGTH: 352
<212> TYPE: DNA
<213> ORGANISM: Homo sapiens

<400> SEQUENCE: 367
caggttcagc tggtgcaatc tggagctgag gtgcagaagc ctggggcctc agtgatggtc     60
tcctgcaagg cttctggtta caccttacc tattatggta tcagctgggt gcgacaggcc    120
cctggacaag ggcttgagtg gatgggatgg atcagcgcta acagtggtaa cacaaactat    180

```
gcacagaagt tccagggcag agtcaccatg accacagaca catccacgaa cacagcctac    240
atggaactaa ggagcctgag aactgacgac acggccgttt attactgtgc gaaaggggg     300 gtcgcagtcc ttgagtattg gggccaggga accctggtca ccgtctcctc ag            352
```

<210> SEQ ID NO 368
<211> LENGTH: 117
<212> TYPE: PRT
<213> ORGANISM: Homo sapiens

<400> SEQUENCE: 368

```
Gln Val Gln Leu Val Gln Ser Gly Ala Glu Val Gln Lys Pro Gly Ala
1               5                   10                  15

Ser Val Met Val Ser Cys Lys Ala Ser Gly Tyr Thr Phe Thr Tyr Tyr
            20                  25                  30

Gly Ile Ser Trp Val Arg Gln Ala Pro Gly Gln Gly Leu Glu Trp Met
        35                  40                  45

Gly Trp Ile Ser Ala Asn Ser Gly Asn Thr Asn Tyr Ala Gln Lys Phe
    50                  55                  60

Gln Gly Arg Val Thr Met Thr Thr Asp Thr Ser Thr Asn Thr Ala Tyr
65                  70                  75                  80

Met Glu Leu Arg Ser Leu Arg Thr Asp Asp Thr Ala Val Tyr Tyr Cys
                85                  90                  95

Ala Lys Gly Gly Val Ala Val Leu Glu Tyr Trp Gly Gln Gly Thr Leu
            100                 105                 110

Val Thr Val Ser Ser
        115
```

<210> SEQ ID NO 369
<211> LENGTH: 322
<212> TYPE: DNA
<213> ORGANISM: Homo sapiens

<400> SEQUENCE: 369

```
gacatccagt tgacccagtc tccatccttc ctgtctgcat ctgtaggaga cagagtcacc    60
atcacttgct gggccagtca gggcattagc agttatttag cctggtatca gcaaaaacca   120
gggaaagccc ctaacctcct gatctatgtt gcatccactt tgcaaagtgg ggtcccatca   180
aggttcagcg gcagtggatc tgggacagaa ttcactctca caatcagcag cctgcagcct   240
gaagattttg caacttatta ctgtcaacag cttaagattt acccactcac tttcggcgga   300
gggaccaagg tggagatcaa ac                                             322
```

<210> SEQ ID NO 370
<211> LENGTH: 107
<212> TYPE: PRT
<213> ORGANISM: Homo sapiens

<400> SEQUENCE: 370

```
Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Ser Ser Tyr
            20                  25                  30

Leu Ala Trp Tyr Gln Gln Lys Pro Gly Lys Ala Pro Asn Leu Leu Ile
        35                  40                  45

Tyr Val Ala Ser Thr Leu Gln Ser Gly Val Pro Ser Arg Phe Ser Gly
    50                  55                  60
```

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Lys Ile Tyr Pro Leu
                 85                  90                  95

Thr Phe Gly Gly Gly Thr Lys Val Glu Ile Lys
            100                 105

<210> SEQ ID NO 371
<211> LENGTH: 24
<212> TYPE: DNA
<213> ORGANISM: Homo sapiens

<400> SEQUENCE: 371
ggttacacct ttacctatta tggt                                                24

<210> SEQ ID NO 372
<211> LENGTH: 15
<212> TYPE: DNA
<213> ORGANISM: Homo sapiens

<400> SEQUENCE: 372
tattatggta tcagc                                                          15

<210> SEQ ID NO 373
<211> LENGTH: 24
<212> TYPE: DNA
<213> ORGANISM: Homo sapiens

<400> SEQUENCE: 373
atcagcgcta acagtggtaa caca                                                24

<210> SEQ ID NO 374
<211> LENGTH: 51
<212> TYPE: DNA
<213> ORGANISM: Homo sapiens

<400> SEQUENCE: 374
tggatcagcg ctaacagtgg taacacaaac tatgcacaga gttccaggg c                   51

<210> SEQ ID NO 375
<211> LENGTH: 30
<212> TYPE: DNA
<213> ORGANISM: Homo sapiens

<400> SEQUENCE: 375
gcgaaagggg gggtcgcagt ccttgagtat                                          30

<210> SEQ ID NO 376
<211> LENGTH: 24
<212> TYPE: DNA
<213> ORGANISM: Homo sapiens

<400> SEQUENCE: 376
gggggggtcg cagtccttga gtat                                                24

<210> SEQ ID NO 377
<211> LENGTH: 18
<212> TYPE: DNA
<213> ORGANISM: Homo sapiens

<400> SEQUENCE: 377
cagggcatta gcagttat                                                       18

<210> SEQ ID NO 378
<211> LENGTH: 33
<212> TYPE: DNA
<213> ORGANISM: Homo sapiens

<400> SEQUENCE: 378
tgggccagtc agggcattag cagttattta gcc        33

<210> SEQ ID NO 379

<400> SEQUENCE: 379

000

<210> SEQ ID NO 380
<211> LENGTH: 21
<212> TYPE: DNA
<213> ORGANISM: Homo sapiens

<400> SEQUENCE: 380
gttgcatcca ctttgcaaag t        21

<210> SEQ ID NO 381
<211> LENGTH: 27
<212> TYPE: DNA
<213> ORGANISM: Homo sapiens

<400> SEQUENCE: 381
caacagctta agatttaccc actcact        27

<210> SEQ ID NO 382
<211> LENGTH: 27
<212> TYPE: DNA
<213> ORGANISM: Homo sapiens

<400> SEQUENCE: 382
caacagctta agatttaccc actcact        27

<210> SEQ ID NO 383
<211> LENGTH: 8
<212> TYPE: PRT
<213> ORGANISM: Homo sapiens

<400> SEQUENCE: 383

Gly Tyr Thr Phe Thr Tyr Tyr Gly
1               5

<210> SEQ ID NO 384
<211> LENGTH: 5
<212> TYPE: PRT
<213> ORGANISM: Homo sapiens

<400> SEQUENCE: 384

Tyr Tyr Gly Ile Ser
1               5

<210> SEQ ID NO 385
<211> LENGTH: 8
<212> TYPE: PRT
<213> ORGANISM: Homo sapiens

<400> SEQUENCE: 385

Ile Ser Ala Asn Ser Gly Asn Thr
1               5

<210> SEQ ID NO 386
<211> LENGTH: 17
<212> TYPE: PRT
<213> ORGANISM: Homo sapiens

<400> SEQUENCE: 386

Trp Ile Ser Ala Asn Ser Gly Asn Thr Asn Tyr Ala Gln Lys Phe Gln
1               5                   10                  15
Gly

<210> SEQ ID NO 387
<211> LENGTH: 10
<212> TYPE: PRT
<213> ORGANISM: Homo sapiens

<400> SEQUENCE: 387

Ala Lys Gly Gly Val Ala Val Leu Glu Tyr
1               5                   10

<210> SEQ ID NO 388
<211> LENGTH: 8
<212> TYPE: PRT
<213> ORGANISM: Homo sapiens

<400> SEQUENCE: 388

Gly Gly Val Ala Val Leu Glu Tyr
1               5

<210> SEQ ID NO 389
<211> LENGTH: 6
<212> TYPE: PRT
<213> ORGANISM: Homo sapiens

<400> SEQUENCE: 389

Gln Gly Ile Ser Ser Tyr
1               5

<210> SEQ ID NO 390
<211> LENGTH: 11
<212> TYPE: PRT
<213> ORGANISM: Homo sapiens

<400> SEQUENCE: 390

Trp Ala Ser Gln Gly Ile Ser Ser Tyr Leu Ala
1               5                   10

<210> SEQ ID NO 391

<400> SEQUENCE: 391

000

<210> SEQ ID NO 392
<211> LENGTH: 7
<212> TYPE: PRT
<213> ORGANISM: Homo sapiens

<400> SEQUENCE: 392

Val Ala Ser Thr Leu Gln Ser
1               5

<210> SEQ ID NO 393
<211> LENGTH: 9

<212> TYPE: PRT
<213> ORGANISM: Homo sapiens

<400> SEQUENCE: 393

Gln Gln Leu Lys Ile Tyr Pro Leu Thr
1               5

<210> SEQ ID NO 394
<211> LENGTH: 9
<212> TYPE: PRT
<213> ORGANISM: Homo sapiens

<400> SEQUENCE: 394

Gln Gln Leu Lys Ile Tyr Pro Leu Thr
1               5

<210> SEQ ID NO 395
<211> LENGTH: 363
<212> TYPE: DNA
<213> ORGANISM: Homo sapiens

<400> SEQUENCE: 395
caggtgcagc tggtggagtc tgggggaggc ttggtcaagc ctggagggtc cctgagactc      60
tcctgtgcag cctctggatt caccttcagt gactactaca tgaactggat ccgccaggct     120
ccagggaagg gsctggagtg gattgcagac attagtagtc gtgacaatac catttactac     180
gcagactctg tgaagggccg attcaccatc tccagggaca acgccaagaa ctcactgtat     240
ctgcaaatga acagtctgag agccgaggac acggccgtgt attactgtgc gagagagagg     300
gggttcgggg actacttcgg tatggacgtc tggggccaag ggaccacggt caccgtctcc     360
tca                                                                    363

<210> SEQ ID NO 396
<211> LENGTH: 121
<212> TYPE: PRT
<213> ORGANISM: Homo sapiens

<400> SEQUENCE: 396

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Ile
        35                  40                  45

Ala Asp Ile Ser Ser Arg Asp Asn Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Gly Phe Gly Asp Tyr Phe Gly Met Asp Val Trp Gly
            100                 105                 110

Gln Gly Thr Thr Val Thr Val Ser Ser
        115                 120

<210> SEQ ID NO 397
<211> LENGTH: 322
<212> TYPE: DNA
<213> ORGANISM: Homo sapiens

<400> SEQUENCE: 397

```
gccatccagt tgacccagtc tccatcctcc ctgtctgcat ctgtaggaga cagagtcacc    60
atcgcttgcc gggcaagtca ggacattagc agtgctttag cctggttccg gcagacacca   120
gggaaaactc ctaagctcct gatctatgat gcctccagtt tggaaagtgg agtcccatca   180
aggttcctcg gcagtggatc tgggacagat ttcactctca ccatcagcag cctgcagcct   240
gaagattttg caatttatta ctgtcaacag tttaacactt accctctcac tttcggcgga   300
gggaccaagg tggagatcaa ac                                             322
```

<210> SEQ ID NO 398
<211> LENGTH: 107
<212> TYPE: PRT
<213> ORGANISM: Homo sapiens

<400> SEQUENCE: 398

```
Ala Ile Gln Leu Thr Gln Ser Pro Ser Ser Leu Ser Ala Ser Val Gly
1               5                   10                  15
Asp Arg Val Thr Ile Ala Cys Arg Ala Ser Gln Asp Ile Ser Ser Ala
            20                  25                  30
Leu Ala Trp Phe Arg Gln Thr Pro Gly Lys Thr Pro Lys Leu Leu Ile
        35                  40                  45
Tyr Asp Ala Ser Ser Leu Glu Ser Gly Val Pro Ser Arg Phe Leu Gly
    50                  55                  60
Ser Gly Ser Gly Thr Asp Phe Thr Leu Thr Ile Ser Ser Leu Gln Pro
65                  70                  75                  80
Glu Asp Phe Ala Ile Tyr Tyr Cys Gln Gln Phe Asn Thr Tyr Pro Leu
                85                  90                  95
Thr Phe Gly Gly Gly Thr Lys Val Glu Ile Lys
            100                 105
```

<210> SEQ ID NO 399
<211> LENGTH: 24
<212> TYPE: DNA
<213> ORGANISM: Homo sapiens

<400> SEQUENCE: 399

```
ggattcacct tcagtgacta ctac                                            24
```

<210> SEQ ID NO 400
<211> LENGTH: 15
<212> TYPE: DNA
<213> ORGANISM: Homo sapiens

<400> SEQUENCE: 400

```
gactactaca tgaac                                                      15
```

<210> SEQ ID NO 401
<211> LENGTH: 24
<212> TYPE: DNA
<213> ORGANISM: Homo sapiens

<400> SEQUENCE: 401

```
attagtagtc gtgacaatac catt                                            24
```

<210> SEQ ID NO 402
<211> LENGTH: 51
<212> TYPE: DNA
<213> ORGANISM: Homo sapiens

<400> SEQUENCE: 402
gacattagta gtcgtgacaa taccatttac tacgcagact ctgtgaaggg c         51

<210> SEQ ID NO 403
<211> LENGTH: 42
<212> TYPE: DNA
<213> ORGANISM: Homo sapiens

<400> SEQUENCE: 403
gcgagagaga gggggttcgg ggactacttc ggtatggacg tc                   42

<210> SEQ ID NO 404
<211> LENGTH: 36
<212> TYPE: DNA
<213> ORGANISM: Homo sapiens

<400> SEQUENCE: 404 gagaggggt tcggggacta cttcggtatg gacgtc                           36

<210> SEQ ID NO 405
<211> LENGTH: 18
<212> TYPE: DNA
<213> ORGANISM: Homo sapiens

<400> SEQUENCE: 405
caggacatta gcagtgct                                              18

<210> SEQ ID NO 406
<211> LENGTH: 33
<212> TYPE: DNA
<213> ORGANISM: Homo sapiens

<400> SEQUENCE: 406
cgggcaagtc aggacattag cagtgcttta gcc                             33

<210> SEQ ID NO 407

<400> SEQUENCE: 407

000

<210> SEQ ID NO 408
<211> LENGTH: 21
<212> TYPE: DNA
<213> ORGANISM: Homo sapiens

<400> SEQUENCE: 408
gatgcctcca gtttggaaag t                                          21

<210> SEQ ID NO 409
<211> LENGTH: 27
<212> TYPE: DNA
<213> ORGANISM: Homo sapiens

<400> SEQUENCE: 409
caacagttta acacttaccc tctcact                                    27

<210> SEQ ID NO 410
<211> LENGTH: 27
<212> TYPE: DNA
<213> ORGANISM: Homo sapiens

<400> SEQUENCE: 410
caacagttta acacttaccc tctcact 27

<210> SEQ ID NO 411
<211> LENGTH: 8
<212> TYPE: PRT
<213> ORGANISM: Homo sapiens

<400> SEQUENCE: 411

Gly Phe Thr Phe Ser Asp Tyr Tyr
1               5

<210> SEQ ID NO 412
<211> LENGTH: 5
<212> TYPE: PRT
<213> ORGANISM: Homo sapiens

<400> SEQUENCE: 412

Asp Tyr Tyr Met Asn
1               5

<210> SEQ ID NO 413
<211> LENGTH: 8
<212> TYPE: PRT
<213> ORGANISM: Homo sapiens

<400> SEQUENCE: 413

Ile Ser Ser Arg Asp Asn Thr Ile
1               5

<210> SEQ ID NO 414
<211> LENGTH: 17
<212> TYPE: PRT
<213> ORGANISM: Homo sapiens

<400> SEQUENCE: 414

Asp Ile Ser Ser Arg Asp Asn Thr Ile Tyr Tyr Ala Asp Ser Val Lys
1               5                   10                  15

Gly

<210> SEQ ID NO 415
<211> LENGTH: 14
<212> TYPE: PRT
<213> ORGANISM: Homo sapiens

<400> SEQUENCE: 415

Ala Arg Glu Arg Gly Phe Gly Asp Tyr Phe Gly Met Asp Val
1               5                   10

<210> SEQ ID NO 416
<211> LENGTH: 12
<212> TYPE: PRT
<213> ORGANISM: Homo sapiens

<400> SEQUENCE: 416

Glu Arg Gly Phe Gly Asp Tyr Phe Gly Met Asp Val
1               5                   10

<210> SEQ ID NO 417
<211> LENGTH: 6
<212> TYPE: PRT
<213> ORGANISM: Homo sapiens

<400> SEQUENCE: 417

Gln Asp Ile Ser Ser Ala

<210> SEQ ID NO 418
<211> LENGTH: 11
<212> TYPE: PRT
<213> ORGANISM: Homo sapiens

<400> SEQUENCE: 418

Arg Ala Ser Gln Asp Ile Ser Ser Ala Leu Ala
1               5                   10

<210> SEQ ID NO 419

<400> SEQUENCE: 419

000

<210> SEQ ID NO 420
<211> LENGTH: 7
<212> TYPE: PRT
<213> ORGANISM: Homo sapiens

<400> SEQUENCE: 420

Asp Ala Ser Ser Leu Glu Ser
1               5

<210> SEQ ID NO 421
<211> LENGTH: 9
<212> TYPE: PRT
<213> ORGANISM: Homo sapiens

<400> SEQUENCE: 421

Gln Gln Phe Asn Thr Tyr Pro Leu Thr
1               5

<210> SEQ ID NO 422
<211> LENGTH: 9
<212> TYPE: PRT
<213> ORGANISM: Homo sapiens

<400> SEQUENCE: 422

Gln Gln Phe Asn Thr Tyr Pro Leu Thr
1               5

<210> SEQ ID NO 423
<211> LENGTH: 192
<212> TYPE: PRT
<213> ORGANISM: Oryctolagus sp.

<400> SEQUENCE: 423

Asp Tyr Lys Asp Asp Asp Lys Gly Gly Gly Ser Gly Gly Gly Ser
1               5                   10                  15

Gly Gly Gly Ser Ile Glu Gly Arg Asp Gln Asp Thr Gly Ser Trp Glu
            20                  25                  30

Gln Leu Val Gln Ala Arg Arg Ser His Lys Ala Ser Pro Ala Ala His
        35                  40                  45

Leu Thr Gly Ala Asn Ser Ser Ser Met Gly Thr Gly Gly Pro Leu Leu
    50                  55                  60

Trp Glu Thr Gln Leu Gly Leu Ala Phe Leu Arg Gly Leu Gly Tyr His
65                  70                  75                  80

Asp Gly Ala Leu Val Thr Thr Gln Ala Gly Tyr Tyr Tyr Ile Tyr Ser
                85                  90                  95

```
Lys Val Gln Leu Gly Gly Val Gly Cys Pro Gln Gly Leu Ala Thr Asp
            100                 105                 110

Leu Pro Val Thr His Gly Leu Tyr Lys Arg Thr Thr Arg Tyr Pro Glu
        115                 120                 125

Glu Leu Glu Leu Leu Val Ser Arg Arg Ser Pro Cys Gly Arg Ala Ala
    130                 135                 140

Ser Ser Arg Val Trp Trp Asp Ser Ser Phe Leu Gly Gly Val Val His
145                 150                 155                 160

Leu Glu Ala Gly Glu Glu Val Val Arg Val Leu Glu Glu Gln Leu
                165                 170                 175

Val Arg Leu Arg Asp Gly Thr Arg Ser Tyr Phe Gly Ala Phe Met Val
            180                 185                 190

<210> SEQ ID NO 424
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 424

His His His His His His
1               5

<210> SEQ ID NO 425
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 425

Asp Tyr Lys Asp Asp Asp Asp Lys
1               5

<210> SEQ ID NO 426
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 426

Gly Gly Gly Ser Gly Gly Gly Ser Gly Gly Gly Ser
1               5                   10

<210> SEQ ID NO 427
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 427

Ile Glu Gly Arg
1
```

ANTI-LIGHT ANTIBODIES

CROSS-REFERENCE TO RELATED APPLICATIONS

This application is a 35 U.S.C. § 371 National Phase Entry Application of International Application No. PCT/GB2015/050054 filed Jan. 13, 2015, which designated the U.S., and which claims benefit of GB Application Nos. 1400597.9 filed Jan. 14, 2014 and 1413950.5 filed Aug. 6, 2014, the contents of each of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on May 16, 2017 is named Sequence_listing_069496-087650-US_SL.txt and is 158,993 bytes in size.

BACKGROUND

LIGHT, (lymphotoxin-like, exhibits inducible expression and competes with HSV glycoprotein D for HVEM, a receptor expressed by T lymphocytes) is one potential cytokine target that has been implicated in the processes of chronic inflammatory autoimmune diseases (Immunity. 1998 January; 8(1):21-30, "LIGHT, a new member of the TNF superfamily, and lymphotoxin alpha are ligands for herpesvirus entry mediator", Mauri D N et al). As a member of the TNF superfamily (TNFSF) of ligands, LIGHT is also known as TNFSF14 or CD258. LIGHT is expressed on the surface of T cells upon activation in a tightly regulated manner appearing within 4 hours, peaking by 12-24 hours and disappearing by 48 hours (J Biol Chem. 2002 Nov. 8; 277(45):42841-51. Epub 2002 Sep. 4, "Mechanisms regulating expression of the tumor necrosis factor-related LIGHT gene. Role of calcium-signaling pathway in the transcriptional control", Castellano R et al). However, LIGHT is also present at detectable levels constitutively on the surface of immature dendritic cells (J Immunol. 2000 Apr. 15; 164(8):4105-10, "LIGHT, a TNF-like molecule, costimulates T cell proliferation and is required for dendritic cell-mediated allogeneic T cell response", Tamada K et al) and on T cells and natural killer (NK) cells of the gut (J Immunol. 2005 Jan. 15; 174(2):646-53, "LIGHT is constitutively expressed on T and NK cells in the human gut and can be induced by CD2-mediated signalling", Cohavy O et al). LIGHT mediates its biologic effects by binding three TNF superfamily receptors including the lymphotoxin β receptor (LTβR) (Science. 1994 Apr. 29; 264(5159):707-10, "A lymphotoxin-beta-specific receptor", Crowe P D et al; J Immunol. 1997 Oct. 1; 159(7):3288-98, "Characterization of lymphotoxin-alpha beta complexes on the surface of mouse lymphocytes", Browning J L et al), the herpes virus entry mediator (HVEM) (Cell. 1996 Nov. 1; 87(3):427-36, "Herpes simplex virus-1 entry into cells mediated by a novel member of the TNF/NGF receptor family", Montgomery R I et al), and decoy receptor 3 (DcR3) (J Biol Chem. 1999 May 14; 274(20):13733-6, "A newly identified member of tumor necrosis factor receptor superfamily (TR6) suppresses LIGHT-mediated apoptosis", Yu K Y et al).

Mice treated with an inhibitory LTβR-Fc fusion protein reduced the inflammatory symptoms in the CD4+ CD45RBhigh T cell transfer model of colitis, a CD4+ T cell-mediated pathology (Gastroenterology. 1998 December; 115(6):1464-75, "Both the lymphotoxin and tumor necrosis factor pathways are involved in experimental murine models of colitis", Mackay F et al). Constitutive transgenic T cell specific expression of LIGHT also has been shown to lead to severe intestinal inflammation with autoimmune-like pathology resembling human inflammatory bowel disease (IBD) (J Immunol. 2005 Jun. 15; 174(12): 8173-82, "The critical role of LIGHT in promoting intestinal inflammation and Crohn's disease", Wang J et al; J Immunol. 2001 Dec. 1; 167(11):6330-7, "Constitutive expression of LIGHT on T cells leads to lymphocyte activation, inflammation, and tissue destruction", Shaikh R B et al; J Immunol. 2001 Nov. 1; 167(9):5099-105, "The critical role of LIGHT, a TNF family member, in T cell development", Wang J et al; J Clin Invest. 2004 March; 113(6):826-35, "Dysregulated LIGHT expression on T cells mediates intestinal inflammation and contributes to IgA nephropathy", Wang J et al). LIGHT-expressing lymphocytes can induce IBD-like symptoms (e.g., cytokine profiles of human Crohn's disease, fissuring ulcers, ileitis, and increases in colonic IFN-γ and TNF) when mesenteric lymph node cells from LIGHT transgenic animals are transferred to RAG−/− (J Immunol. 2005 Jun. 15; 174(12):8173-82, "The critical role of LIGHT in promoting intestinal inflammation and Crohn's disease", Wang J et al). In human disease, increases of LIGHT expression were observed in patients with active Crohn's disease (Cohavy et al 2005 supra; Wang et al 2005 supra; Wang et al 2004 supra; J Immunol. 2004 Jul. 1; 173(1):251-8, "LIGHT expression by mucosal T cells may regulate IFN-gamma expression in the intestine", Cohavy O et al). LIGHT has also been demonstrated to be elevated in gut T cells of IBD patients (Cohavy et al 2004 supra). Genetic evidence also supports a role for LIGHT in IBD (J Immunol. 2001 Nov. 1; 167(9):5122-8, "Genomic characterization of LIGHT reveals linkage to an immune response locus on chromosome 19p13.3 and distinct isoforms generated by alternate splicing or proteolysis", Granger S W et al; Am J Hum Genet. 2000 June; 66(6):1863-70. Epub 2000 Apr. 21, "Genomewide search in Canadian families with inflammatory bowel disease reveals two novel susceptibility loci", Rioux J D et al; Inflamm Bowel Dis. 2004 May; 10(3):173-81, "Inflammatory bowel disease is linked to 19p13 and associated with ICAM-12, Low J H et al; Gastroenterology. 2003 February; 124(2):521-36, "The genetics of inflammatory bowel disease", Bonen D K, Cho J H).

Human LIGHT (hLIGHT) has also been implicated in graft-versus-host disease (GvHD). For example, LIGHT has been shown to provide potent costimulatory activity for T cells, enhancing proliferation and the production of Th1 cytokines independent of the B7-CD28 pathway (see, e.g., Tamada et al 2000 supra). Blocking of LIGHT-HVEM costimulation by either anti-HVEM monoclonal antibodies, HVEM-Ig, or LTβR fusion protein inhibits allogeneic T cell responses (see, e.g., Tamada et al 2000 supra; J Immunol. 1998 Aug. 15; 161(4):1786-94, "Antibodies to TR2 (herpesvirus entry mediator), a new member of the TNF receptor superfamily, block T cell proliferation, expression of activation markers, and production of cytokines", Harrop J A et al). Furthermore, in vivo administration of LTβR-Ig or murine anti-LIGHT antibodies inhibits anti-host cytotoxic T lymphocyte (CTL) responses in a murine acute GvHD model (Nat Med. 2000 March; 6(3):283-9, "Modulation of T-cell-mediated immunity in tumor and graft-versus-host disease models through the LIGHT co-stimulatory pathway", Tamada K et al).

Inflammatory bowel diseases (IBDs)—mostly represented by Crohn's disease (CD) and ulcerative colitis (UC)—are a group of inflammatory disorders of the gastrointestinal tract characterized by an abnormal immune response to antigens of the intestinal content that leads to a persistent inflammatory state. Reference is made to World J Gastroenterol. 2010 Sep. 14; 16(34):4264-71, "Intestinal epithelial cells in inflammatory bowel diseases", Roda G et al. The pathogenesis of inflammatory bowel diseases (IBDs) seems to involve a primary defect in one or more of the elements responsible for the maintenance of intestinal homeostasis and oral tolerance. The most important element is represented by the intestinal barrier, a complex system formed mostly by intestinal epithelial cells (IECs). IECs have an active role in producing mucus and regulating its composition; they provide a physical barrier capable of controlling antigen traffic through the intestinal mucosa. At the same time, they are able to play the role of non-professional antigen presenting cells, by processing and presenting antigens directly to the cells of the intestinal immune system. On the other hand, immune cells regulate epithelial growth and differentiation, producing a continuous bi-directional cross-talk within the barrier. Several alterations of the barrier function have been identified in IBD, starting from mucus features up to its components, from epithelial junctions up to the Toll-like receptors, and altered immune responses. It remains to be understood whether these defects are primary causes of epithelial damage or secondary effects. The authors review the possible role of the epithelial barrier and particularly describe the role of IECs in the pathogenesis of IBD.

SUMMARY OF THE INVENTION

The invention provides anti-human LIGHT antibodies and fragments and novel medical applications for treating or preventing hLIGHT-mediated diseases or conditions in humans. To this end, the invention provides:—

An antibody or a fragment thereof, that specifically binds to 214E hLIGHT and competes for binding to said hLIGHT with an antibody selected from the group consisting of 1C02, 13H04 and 31A10.

The invention also provides related pharmaceutical compositions, kits, methods, nucleic acids, vectors, host cell and uses.

Further configurations of the invention are as follows.

In a First Configuration

An antibody or a fragment thereof that specifically binds to hLIGHT for treating or preventing a hLIGHT-mediated disease or condition in a human in a method wherein the antibody or fragment is administered to said human, wherein the antibody or fragment is for treating or preventing said hLIGHT-mediated disease or condition by decreasing one or more of
  a. the secretion of a cytokine selected from IL-2, TNF alpha and interferon gamma in the human;
  b. the proliferation of leukocytes of the human; and
  c. the binding of hLIGHT by human epithelial cells expressing a receptor for hLIGHT.

In a Second Configuration

An antibody or a fragment thereof, that specifically binds to 214E hLIGHT and competes for binding to said hLIGHT with an antibody selected from the group consisting of 31A10, 29C09, 14B09, 62C01, 13H04, 144F05, 42A02 and 117C06.

In a Third Configuration

Use of an antibody or a fragment thereof, that specifically binds to hLIGHT in the manufacture of a medicament for administration to a human, for treating or preventing a hLIGHT-mediated disease or condition in the human by decreasing one or more of
  a. the secretion of a cytokine selected from IL-2, TNF alpha and interferon gamma in the human;
  b. the proliferation of leukocytes of the human; and
  c. the binding of hLIGHT by human epithelial cells expressing a receptor for hLIGHT.

In a Fourth Configuration

A method of treating or preventing a hLIGHT-mediated disease or condition in a human by decreasing one, more or all of
  a. the secretion of a cytokine selected from IL-2, TNF alpha and interferon gamma in the human;
  b. the proliferation of leukocytes of the human; and
  c. the binding of hLIGHT by human epithelial cells expressing a receptor for hLIGHT;
wherein the method comprises administering to said human a therapeutically effective amount of an antibody or fragment that specifically binds to hLIGHT.

In a Fifth Configuration

An antibody or antibody fragment that comprises variable domains that
  i. specifically bind both 214E hLIGHT and 214K hLIGHT,
  ii. compete with an antibody comprising the variable regions of 01C02 for binding 214E hLIGHT and
  iii. do not compete with an antibody comprising the variable regions of an antibody selected from 01C06 and 18E04 for binding to 214E hLIGHT.

The invention also provides pharmaceutical compositions, kits, nucleic acids, vectors and hosts.

BRIEF DESCRIPTION OF THE DRAWINGS

FIG. 1 shows all 8 identified lead mAb candidates in an HT29 IL-8 cytokine release assay where recombinant hLIGHT-214E is added to the culture to induce IL-8 secretion by HT29 cells. This IL-8 secretion will be neutralized if antibodies to hLIGHT inhibit the binding of recombinant hLIGHT-214E to HT29 cells via hLIGHT receptors expressed on the cell surface. Briefly, HT29 cells, a human colorectal adenocarcinoma cell line, were plated and treated with hLIGHT which was pre-incubated with various concentrations of each of the 41 purified antibody hits. The 8 best clones were selected and are depicted in FIG. 1. Data from FIG. 1 is from a single experiment which is representative of at least two independent experiments.

FIG. 2 shows binding of all 8 lead clones at 0.64 µg/ml to CHO-S-hLIGHT 214E cells compared to secondary detection antibody only (shown as filled in grey histogram). The term "no antibody" in the figure specifies the use of no primary antibody used but not the lack of the secondary detection antibody. Data from FIG. 2 is derived from a single experiment. An isotype control (mouse IgG1/Kappa, Sigma M9269) was run alongside to demonstrate specificity (very last panel in the figure).

The lead 8 antibodies were tested for their ability to neutralize the binding of recombinant hLIGHT to its receptors, either human HVEM or human LTβR, in an HTRF assay as outlined in example 2. FIG. 3A shows the lead panel of antibodies neutralizing LTβR binding to recombinant hLIGHT-214E. FIG. 3B shows neutralization of HVEM binding to hLIGHT. Both FIGS. 3A and 3B are derived from a single experiment which is representative of at least three independent experiments. An isotype control mouse IgG1 antibody (Sigma M9269) was run in both assays (depicted as filled in circles).

FIG. 4A shows two additional hybridoma-derived lead mAb candidates in an HT29 IL-8 cytokine release assay where recombinant hLIGHT-214E is added to the culture to induce IL-8 secretion by HT29 cells. This IL-8 secretion will be neutralized if antibodies to hLIGHT inhibit the binding of recombinant hLIGHT-214E to HT29 cells via hLIGHT receptors expressed on the cell surface. Briefly, HT29 cells, a human colorectal adenocarcinoma cell line, were plated and treated with hLIGHT which was pre-incubated with various concentrations of each of the antibody hits purified from hybridoma supernatants.

FIG. 4B shows the two identified lead mAb candidates cloned from single B cells (BCT). In both cases, data is from a single experiment representative of at least two independent experiments.

FIG. 5 shows binding of two additional hybridoma-derived lead antibodies at 0.64 μg/ml to CHO-S-hLIGHT 214E cells compared to secondary detection antibody only (shown as filled in grey histogram). The term "no antibody" in the Figure specifies the use of no primary antibody used but not the lack of the secondary detection antibody. Data from FIG. 5 is derived from a single experiment. An isotype control (mouse IgG1/Kappa, Sigma M9269) was run alongside to demonstrate specificity (final panel in the Figure).

The two additional hybridoma-derived antibodies were tested for their ability to neutralize the binding of recombinant hLIGHT to its receptors, either human HVEM or human LTβR, in an HTRF assay as outlined in Example 2. FIG. 6A shows the lead panel of antibodies neutralizing LTβR binding to recombinant hLIGHT-214E. FIG. 6B shows neutralization of HVEM binding to hLIGHT. Both FIGS. 6A and 6B are derived from a single experiment which is representative of at least two independent experiments. An isotype control mouse IgG1 antibody (Sigma M9269) was run in both assays (depicted as filled circles).

FIG. 6C shows neutralization of LTβR binding to hLIGHT, and FIG. 6D shows neutralization of HVEM binding to hLIGHT by the lead BCT mAbs. Data are from a single experiment representative of two independent experiments. A non-binding IgG4(PE) isotype control generated in-house was run in both assays (depicted as filled circles).

FIG. 7 shows the binding of antibodies to recombinant human LIGHT-214E and rabbit LIGHT in an SPR assay. LIGHT antibodies were captured on an anti-human IgG sensor chip surface and then human and rabbit LIGHT proteins were passed over captured mAbs. Results are expressed as response units (RU) over time. Human LIGHT sensorgrams are in black; rabbit LIGHT sensorgrams are in light grey.

The final panel of four antibodies were tested for their ability to neutralize the binding of recombinant human LIGHT to its receptors, either human HVEM or human LTβR, in an HTRF assay as outlined in Example 13. FIG. 8A shows the lead panel of antibodies neutralizing HVEM binding to recombinant hLIGHT-214E. FIG. 8B shows neutralization of LTβR binding to hLIGHT-214E. Both FIGS. 8A and 8B are from a single experiment representative of two independent experiments. A non-binding IgG4 (PE) isotype control generated in-house was run in both assays.

FIG. 8C shows the lead panel of antibodies in an HT29 IL-8 release assay, where recombinant hLIGHT-214E is added to the culture to induce IL-8 secretion by HT29 cells. This IL-8 secretion will be neutralized if antibodies to hLIGHT inhibit the binding of recombinant hLIGHT-214E to HT29 cells via hLIGHT receptors expressed on the cell surface. Briefly, HT29 cells, a human colorectal adenocarcinoma cell line, were plated and treated with hLIGHT which was pre-incubated with various concentrations of each of the antibody hits purified from hybridoma supernatants. A non-binding IgG4(PE) isotype control generated in-house was also run.

DETAILED DESCRIPTION OF THE INVENTION

Figure 1:
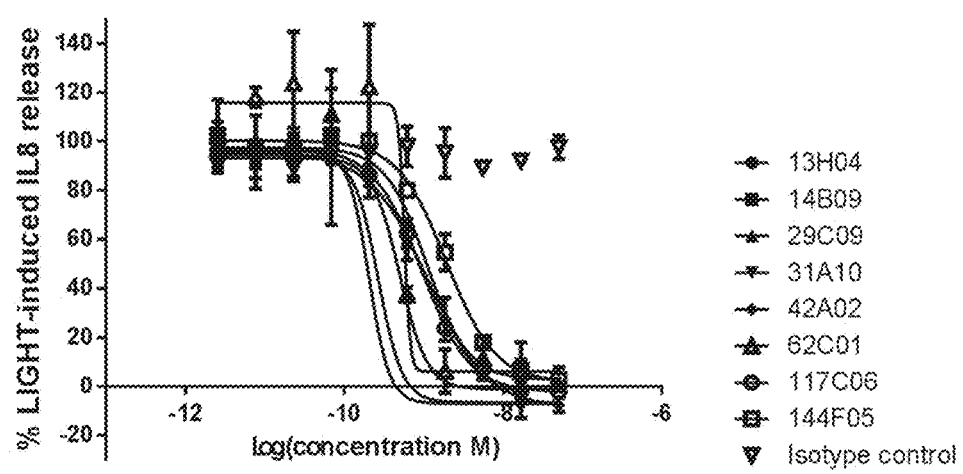
FIG. 1.

The invention provides the following aspects.

The invention is useful, for example, for treating or preventing an inflammatory bowel disease, eg, UC or CD, or for treating or preventing an airway inflammatory disease or condition. In an example this aspect is useful for treating or preventing asthma.

1. An antibody or a fragment thereof that specifically binds to hLIGHT for treating or preventing a hLIGHT-mediated disease or condition in a human in a method wherein the antibody or fragment is administered to said human, wherein the antibody or fragment is for treating or preventing said hLIGHT-mediated disease or condition by decreasing one or more of
   a. the secretion of a cytokine selected from IL-2 (interleukin-2), TNF alpha and interferon gamma in the human;
   b. the proliferation of leukocytes of the human; and
   c. the binding of hLIGHT by human epithelial cells expressing a receptor for hLIGHT.

The inventors, thus identified for the first time decreases of (a), (b) and (c) as ways of treating and/or preventing LIGHT-mediated disease and conditions in humans and they provide antibodies and antibody fragments for this purpose.

In an example, the decrease of (a), (b) or (c) or any other decrease disclosed herein is a decrease of at least 10 or 20% compared to the level in a human at risk of or suffering from the hLIGHT-mediated disease or condition. In an example, the latter is the human recited in aspect 1 prior to administration of the antibody or fragment; in another example the latter human is a different human. In an example, said decrease is at least 10, 20, 30, 40, 50 or 60%.

In an example, the antibody or fragment is capable of effecting a decrease of secretion of the relevant cytokine in an in vitro assay (as explained further below), and thus administration of such antibody or fragment to the human leads to decrease of (a).

In an example, the antibody or fragment is capable of effecting a decrease of the proliferation of leukocytes (eg, PBMCs) in an in vitro assay (as explained further below), and thus administration of such antibody or fragment to the human leads to decrease of (b).

In an example, the antibody or fragment is capable of effecting a decrease of the binding of hLIGHT by human epithelial cells expressing a receptor for hLIGHT in an in vitro assay (as explained further below), and thus administration of such antibody or fragment to the human leads to decrease of (c).

Additionally or alternatively, assessment of said decreases can be performed using samples from the treated human. For example, reference is made to J Clin Immunol. 2004 January; 24(1):74-85; "Increased expression of CCL20 in human inflammatory bowel disease"; Kaser A et al. This publication provides an example of a generally-applicable technique of using tissue biopsies and reading out decreased cytokine levels indicative of decreased cytokine secretion after treatment with an antibody in vivo. Similar methods can be used to determine decrease of the secretion of one or more cytokines in a human having received an antibody of the invention. The skilled person will be familiar with techniques for assessing cytokine levels in patients and patient samples, for example, by use of one or more of tissue biopsy, immunohistochemistry, immunofluorescence, tissue staining, cytokine mRNA quantification (eg, using PCR, such as Taqman™ PCR), cytokine protein detection and quantification (eg, using cytokine-specific tool antibody and quantification, such as by ELISA or another standard protein quantification technique). For example, where the disease or condition is one of the GI tract (eg, IBD), one can perform biopsy of relevant gut tissue from a patient that has received an antibody of the invention, followed by quantification of cytokine mRNA and/or cytokine protein (eg, using quantitative PCR). The result can be compared with a cytokine quantification in biopsied relevant tissue from the same patient prior to antibody administration or compared to another human patient suffering from the same disease or condition but receiving no anti-LIGHT treatment or no treatment for the disease or condition. In this way, the skilled person can determine that the antibody of the invention decreases secretion of the cytokine in the human recipient. Instead of assessing gut tissue levels, one can instead use a different tissue or sample from the human patient dependent upon the nature and location of the disease or condition. For example, where the disease or condition is one of the airways (eg, lung), it is possible to take a lung or other airway tissue sample for cytokine assessment. Alternatively, one can use a Bronchoalveolar lavage (BAL) sample, as will be apparent to the skilled person. In another example, for some disease or conditions one can assess the decrease in cytokine in a blood, serum or plasma sample taken from a human that has received an antibody of the invention, and then comparing to the level before receiving the antibody or comparing to the level in an untreated human, as discussed above.

As is known in the art, the term "leukocytes" includes, for example, one or more of lymphocytes, polymorphonuclear leukocyte and monocytes. As is also readily apparent to the skilled person the term "monocytes" includes, for example, peripheral blood mononuclear cells (PBMCs) or monocyte derived cells, eg, dendritic cells (DCs). See, for example, Immunobiology. 2013 November; 218(11):1392-401. doi: 10.1016/j.imbio.2013.07.005. Epub 2013 Jul. 25; "Leukoreduction system chambers are an efficient, valid, and economic source of functional monocyte-derived dendritic cells and lymphocytes", Pfeiffer I A et al.

The proliferation of leukocytes, eg, lamina propria lymphocytes (LPLs), can be assessed using tissue biopsy, staining and histology, as will be apparent to the skilled person. Hematoxylin and eosin stain (H&E stain or HE stain) is, for example, commonly used in histology to look for infiltrating lymphocytes a whole range of human tissue and is one of the principal stains in histology. It is the most widely used stain in medical diagnosis and is often the gold standard, and as such can be used to assess proliferation of leukocytes as per the invention. For example, GI tract tissue (eg, gut tissue) from a human that is suffering from or at risk of a hLIGHT-mediated disease or condition can be obtained, stained and assessed for the extent of infiltration of LPLs. Comparison can be made between such tissue from a human that has received an antibody of the invention compared to the extent of infiltration in tissue obtained from the same human prior to administration of antibody or from another human that has not received treatment and is at risk of or suffering from the disease or condition. For example, the comparison is between human gut tissues taken from the same (or different) humans suffering from IBD.

One can, for example, assess binding of hLIGHT by human epithelial cells expressing a receptor for hLIGHT using an in vitro receptor occupancy assay of biopsied relevant tissue from a human that has received an antibody of the invention. Comparison can be made with assayed tissue from the human prior to antibody administration or from another human that has not received treatment but is suffering from or at risk of the same disease or condition. Receptor occupancy assays are familiar to the skilled person.

The cell biology of the intestinal epithelium, its damage and relation to inflammatory bowel disease is reviewed in Deuring et al, "The cell biology of the intestinal epithelium and its relation to inflammatory bowel disease", The International Journal of Biochemistry & Cell Biology 45 (2013) 798-806. Inflammatory bowel disease (IBD) is a chronic inflammatory disorder affecting the gastrointestinal tract with an apparently ever-increasing incidence and tendency to more severe clinical phenotypes. The disease is characterised by an exaggerated immune response to the luminal flora, suggesting that deficiencies in barrier function of intestinal flora may be involved, and studies support this notion (Cucchiara et al., 2012; Jostins et al., 2012; Manichanh et al., 2012; Salzman et al., 2007, all cited in Deuring et al). IBD includes two main groups: Crohn's disease (CD) and ulcerative colitis (UC). CD patients can have inflammatory lesions in their entire gastrointestinal tract, whereas the inflammation in UC patients is restricted to the colon.

Reference is made to Hisamatsu et al ("Immune aspects of the pathogenesis of inflammatory bowel disease", Pharmacology & Therapeutics 137 (2013) 283-297) and the documents cited therein. Intestinal epithelial cells play a role as a barrier to prevent invasion by pathogens, and the influx of antigens. IECs produce mucins and trefoil factors which are important protective components of the mucus layer covering the surface of the intestinal lumen. IECs also produce several types of antimicrobial peptide such as defensins, which are a classical innate immune mechanism. Therefore, disruption of this barrier system may allow invasion by not only pathogenic micro-organisms, but also commensal bacteria and food antigens. IECs also act as sensors for pathogens through several innate immune receptors such as toll-like receptors (TLRs) and NODs, and produce cytokines and chemokines to recruit immune cells. TLR signaling pathways induce the production of pro-inflammatory cytokines and chemokines in IECs, and also affect epithelial integrity. Important findings regarding the role of cross-talk between IECs and immune cells have been reported. NF-κB signaling in IECs plays an important role in gut immune homeostasis (Nenci et al., 2007; Zaph et al., 2007). Nenchiet et al reported that mice lacking NEMO (also named IKKγ) in their IECs conditionally developed spontaneous colitis. In NEMO knockout mice, the number of apoptotic IECs was increased, resulting in deterioration of the integrity of the epithelial barrier. Furthermore, these mice exhibited decreased production of the antimicrobial defensin peptides produced by IECs. These changes led to translocation of enteric flora and recruitment of innate immune cells (Nenci et al., 2007). Gunther et al. demonstrated that caspase-8 in IECs plays a key role in protecting these cells from TNF-α-induced necroptotic cell death.

Granuloma formation is the one of the most important pathological characteristics of human Crohn's disease. Mizoguchi et al demonstrated that F4/80-positive immature CD11c+ dendritic cells (DCs) produce IL-23 and contribute to granuloma formation in a murine colitis model (Mizoguchi et al., 2007). A Th1 immune response is predominant in Crohn's disease. Indeed, CD4+ T cells in the LP of Crohn's disease expressed T-bet and produced large amounts of interferon (IFN)-γ (Matsuoka et al., 2004). Sakuraba et al demonstrated that DCs in the mesentric lymph nodes of patients with Crohn's disease strongly promoted a Th1 and Th17 immune response (Sakuraba et al., 2009). Mesentric lymph node DCs contribute to IBD pathogenesis, particularly that of Crohn's disease.

Reference is made to Nat Med. 2011 May; 17(5): 596-603. doi:10.1038/nm.2356, "The tumor necrosis factor family member LIGHT is a target for asthmatic airway remodelling", Taylor A Doherty et al and the documents cited therein. Individuals with chronic asthma show a progressive decline in lung function that is thought to be due to structural remodelling of the airways characterized by subepithelial fibrosis and smooth muscle hyperplasia. LIGHT was shown to be expressed on lung inflammatory cells after allergen exposure.

Role of Cytokines in Disease and Conditions

Reference is made to Muzes et al, *World J Gastroenterol* 2012 Nov. 7; 18(41): 5848-5861 ISSN 1007-9327 (print) ISSN 2219-2840 (online), "Changes of the cytokine profile in inflammatory bowel Diseases".

Cytokines are indispensable signals of the mucosa-associated immune system for maintaining normal gut homeostasis. An imbalance of their profile in favour of inflammation initiation may lead to disease states, such as that is observed in inflammatory bowel diseases (IBD), eg, Crohn's disease (CD) and ulcerative colitis (UC). The role of pro-inflammatory cytokines such as IL-1α, IL-1β, IL-2, -6, -8, -12, -17, -23, IFN-gamma, or TNF alpha in IBD is associated with the initiation and progression of UC and CD. CD is often described as a prototype of T-helper (Th) 1-mediated diseases because the primary inflammatory mediators are the Th1 cytokines such as interleukin (IL)-12, interferon (IFN)-γ, and tumour necrosis factor (TNF)-α.

Binding of TNF-like ligands to their receptors triggers intracellular pathways that are directly involved in cell proliferation, differentiation, and survival. Most members of the TNF/TNF-receptor protein superfamilies are expressed on immune cells and play a critical role in multiple components of the immune response. TNF-α is a master cytokine in the pathogenesis of IBD. It exerts its pleiotropic effects through the expression of adhesion molecules, fibroblast proliferation, procoagulant factors, as well as the initiation of cytotoxic, apoptotic and acute-phase responses. The source of TNF-α in IBD is partly the innate immune cells, such as macrophages or monocytes, and also differentiated Th1 cells. The serum levels of TNF-α correlate with the clinical activity of UC and CD[31]. It plays an orchestrating role in colonic inflammation in IBD. The role of TNF-α in CD has been widely investigated. Binding TNF-α to serum soluble TNF receptor 1 and 2 (sTNFR1 and 2) initiates pro-inflammatory signalling. The levels of sTNFR1 and 2 are elevated in CD.

Tumour necrosis factor-like factor (TL1A), another member of the TNF family, stimulates IFN-γ secretion by binding to death receptor 3 (DR3). DR3 is expressed by a high percentage of cells from mucosal biopsies of UC and CD, and an increase of IFN-γ level has been observed with disease activity in IBD patients. The TL1A/DR3 system is involved in the pathogenesis of CD. The macrophages of the lamina propria are a major producer of TL1A, which expression is markedly enhanced in CD. It has been found that TL1A and IL-23 synergistically promotes the production of IFN-γ by mucosal T cells. FN-Y: is produced by TH1 T-cells. Once inflammation is initiated, IFN-γ is produced and subsequently acts through various molecules and pathways of the immune system to intensify the inflammatory process. There is an overwhelming body of literature extensively documenting the proinflammatory nature of IFN-γ which has led to the mainstream opinion that IFN-γ is a prime proinflammatory cytokine in inflammation and autoimmune disease. Interferon-gamma is causatively involved in experimental inflammatory bowel disease in mice (Ito et al, *Clinical and Experimental Immunology* (2006), 146: 330-338). The study clearly demonstrated that IFN-γ-/- mice manifested attenuated colitis after stimulation with DSS, in terms of the degree of body weight loss, DAI, histological score and MPO activity. IFN-γ was increasingly produced in the colon of DSS-treated WT mice that showed severe IBD-like symptoms.

Interleukin-2 (IL-2) is produced by T-cells and is mostly important for T-cells to differentiate into effector T-cells. IL-2 is also important for T-cell proliferation. This is important for IBD because effector T-cells are thought to be a major cell type to cause damage in IBD.

IL-8 (interleukin-8; aka CXCL8) primarily mediates the activation and migration of neutrophils into tissue from peripheral blood and to sites of inflammation. The tissue level of IL-8 has been found to be higher in active UC compared to normal colonic tissue, and its serum concentration has been related to endoscopic and histological severity of UC. IL-8 is important for inflammatory settings and cancer (see, eg, "The Chemokine CXCL8 in Carcinogenesis and Drug Response", ISRN Oncol. 2013 Oct. 9; 2013: 859154; Gales D et al; and Future Oncol. 2010 January; 6(1):111-6. doi: 10.2217/fon.09.128; "CXCL8 and its cognate receptors in melanoma progression and metastasis", Singh S et al). In cancer particularly, IL-8 is thought to contribute also by supporting angiogenesis.

2. The antibody or fragment of aspect 1 for treating or preventing hLIGHT-mediated damage of epithelial cells in said human.

As explained herein, the pathogenesis of inflammatory bowel diseases (IBDs) seems to involve a primary defect in one or more of the elements responsible for the maintenance of intestinal homeostasis and oral tolerance. The most important element is represented by the intestinal barrier, a complex system formed mostly by intestinal epithelial cells (IECs). Thus, this aspect of the invention is useful for treating or preventing an inflammatory bowel disease, eg, UC or CD. This aspect is also useful for treating or preventing an airway inflammatory disease or condition. In an example this aspect is useful for treating or preventing asthma.

3. The antibody or fragment of aspect 1 or 2, wherein the antibody or fragment antagonises the binding of hLIGHT to a hLIGHT receptor selected from HVEM and LTβR.

In an example, the hLIGHT receptor is expressed by a human cell selected from an epithelial cell, a gastrointestinal cell, a colon cell, an intestinal cell, a lung epithelial cell or a synovial cell. This this aspect of the invention is useful for treating or preventing an inflammatory bowel disease, eg, UC or CD. This aspect is also useful for treating or preventing an airway inflammatory disease or condition. In an example this aspect is useful for treating or preventing asthma.

In another embodiment, the antibody or fragment antagonises the binding of hLIGHT to a hLIGHT receptor selected from FcβR and DcR3.

4. The antibody or fragment of any preceding aspect, wherein the leukocytes are selected from the group consisting of polymorphonuclear leukocytes, monocytes, peripheral blood mononuclear cells (PBMCs), lymphocytes, T-cells, dendritic cells (DC cells) and natural killer cells (NK cells).

5. The antibody or fragment of aspect 4, wherein the leukocytes comprise lamina propria lymphocytes (LPLs) and the disease or condition is a disease or condition of the gastrointestinal tract (GI tract).

6. The antibody or fragment of any preceding aspect, wherein the epithelial cells comprise cells selected from the group consisting of gastrointestinal cells, colon cells, intestinal cells and airway (eg, lung) epithelial cells.

7. The antibody or fragment of any preceding aspect, for treating or preventing said hLIGHT-mediated disease, condition or epithelial cell damage in said human by decreasing the proliferation of T-cells in said human.

In an example, the antibody or fragment is capable of effecting a decrease of the proliferation of T-cells in an in vitro assay (eg, in a DC cell/T-cell in vitro assay, for example as explained further below), and thus administration of such antibody or fragment to the human leads to decrease of the proliferation of T-cells in said human.

8. The antibody or fragment of any preceding aspect, for treating or preventing said hLIGHT-mediated disease, condition or epithelial cell damage in said human by antagonising the interaction between hLIGHT and leukocytes of the human, wherein the proliferation of leukocytes is decreased.

In an example, the antibody or fragment is capable of effecting a decrease of the proliferation of leukocytes (eg, mononuclear cells) in an in vitro assay (eg, in a MLR in vitro assay, for example as explained further below), and thus administration of such antibody or fragment to the human leads to decrease of the proliferation of leukocytes in said human.

9. The antibody or fragment of any preceding aspect, for treating or preventing said hLIGHT-mediated disease, condition or epithelial cell damage in said human by decreasing the proliferation of leukocytes of the human by antagonising the LIGHT/LIGHT receptor interaction mediated by T-cells in said human.

In an example, the antibody or fragment is capable of effecting a decrease of the proliferation of leukocytes (eg, mononuclear cells) in an in vitro assay wherein the antibody or fragment antagonises LIGHT/LIGHT receptor interaction mediated by T-cells in said assay, and thus administration of such antibody or fragment to the human leads to decrease of the proliferation of leukocytes in said human.

10. The antibody or fragment of any preceding aspect, for treating or preventing said hLIGHT-mediated disease, condition or epithelial cell damage in said human by decreasing the secretion of a cytokine selected from IL-2, TNF alpha and interferon gamma in the human.

In an example, the antibody or fragment is for treating or preventing said hLIGHT-mediated disease, condition or epithelial cell damage in said human by decreasing the secretion of (i) IL-2 and interferon gamma, (ii) IL-2 and TNF alpha or (iii) interferon gamma and TNF alpha in the human.

In an example, the antibody or fragment is capable of effecting a decrease of the secretion of a cytokine selected from IL-2, TNF alpha and interferon gamma in an in vitro assay (eg, in a MLR in vitro assay, for example as explained further below), and thus administration of such antibody or fragment to the human leads to decrease of the secretion of said selected cytokine(s) in said human.

11. The antibody or fragment of any preceding aspect, for treating or preventing said hLIGHT-mediated disease, condition or epithelial cell damage in said human by decreasing the secretion of IL-8 cytokine in the human.

In an example, the antibody or fragment is capable of effecting a decrease of the secretion of IL-8 in an in vitro assay (eg, in a MLR in vitro assay, for example as explained further below), and thus administration of such antibody or fragment to the human leads to decrease of the secretion of IL-8 in said human.

12. The antibody or fragment of aspect 10 or 11, for treating or preventing said disease, condition or epithelial cell damage by decreasing the secretion of said cytokine mediated by the interaction of dendritic cells (DC cells) with T-cells in the human.

In an example, the antibody or fragment is capable of effecting a decrease of said cytokine(s) secretion in a DC cell/T-cell in vitro assay (for example as explained further below), and thus administration of such antibody or fragment to the human leads to decrease of the secretion of said cytokine(s) in said human.

13. The antibody or fragment of any preceding aspect, wherein epithelial cell damage is a symptom or cause of said disease or condition in humans.

14. The antibody or fragment of any preceding aspect, wherein the human is suffering from or at risk of an inflammatory bowel disease (IBD), allogenic transplant rejection, graft-versus-host disease (GvHD) or airway inflammation and said method treats or prevents IBD, allogenic transplant rejection, GvHD or airway inflammation in the human.

In an example of any preceding aspect the human is suffering from or at risk of an inflammatory or autoimmune disease or condition or has been diagnosed as such.

15. The antibody or fragment of any preceding aspect, wherein the hLIGHT is 214E hLIGHT.

In an example, the antibody or fragment specifically binds 214E hLIGHT and the disease or condition in said human is mediated by 214E hLIGHT or 214K hLIGHT. In an embodiment, the disease or condition is mediated by hLIGHT comprising a mixture of 214E and 214K subunits, eg, two 214E subunits and one 21K subunit; or two 214K subunits and one 214E subunit. This is useful for treating a human that is heterozygous (one LIGHT allele being the 214E allele and the other the 214K allele).

16. The antibody or fragment of any preceding aspect, wherein the antibody or fragment specifically binds to 214K hLIGHT.

This is useful for treating 214K homozygous humans or heterozygous (214E & 214K) humans.

17. The antibody or fragment of any preceding aspect, wherein the human has been genotyped for a nucleotide sequence encoding 214E hLIGHT polypeptide.

In an example, the human is genotyped before administration of the antibody or fragment to the human.

18. The antibody or fragment of any preceding aspect, wherein the human has been phenotyped for a 214E hLIGHT polypeptide.

In an example, the human is phenotyped before administration of the antibody or fragment to the human.

19. An antibody or antibody fragment
   Wherein the antibody or fragment comprises variable domains that
      i. specifically bind both 214E hLIGHT and 214K hLIGHT,
      ii. compete with an antibody comprising the variable regions of 01C02 or 13H04 for binding 214E hLIGHT and
      iii. do not compete with an antibody comprising the variable regions of an antibody selected from 01C06 and 18E04 for binding to 214E hLIGHT; or
   Wherein the antibody or fragment comprises variable domains that
      iv. specifically bind both 214E hLIGHT and 214K hLIGHT,
      v. compete with an antibody comprising the variable regions of 31A10 for binding 214E hLIGHT and
      vi. compete with an antibody comprising the variable regions of an antibody selected from 01C06 and 18E04 for binding to 214E hLIGHT.

20. The antibody or fragment of aspect 19, wherein (ii), (iii), (v) and (vi) are determined using surface plasmon resonance (SPR).

21. The antibody or fragment of aspect 19 or 20, wherein (ii), (iii), (v) and (vi) are determined using the variable domains in a human IgG4 antibody format (optionally IgG4(PE)).

22. The antibody or fragment of aspect 19, 20 or 21, wherein the antibody is in a human IgG4 format (optionally IgG4(PE)).

23. The antibody or fragment of any one of aspects 19 to 22, comprising VH domains that comprise an amino acid sequence that is at least 95% identical to SEQ ID NO: 368.

24. The antibody or fragment of any one of aspects 19 to 23, comprising VL domains that comprise an amino acid sequence that is at least 95% identical to SEQ ID NO: 370.

25. The antibody or fragment of any one of aspects 19 to 24, comprising VH domains that comprise SEQ ID NO: 368.

26. The antibody or fragment of any one of aspects 19 to 25, comprising VL domains that comprise SEQ ID NO: 370.

27. An antibody or a fragment thereof, that specifically binds to 214E hLIGHT and competes for binding to said hLIGHT with an antibody selected from the group consisting of 1C02, 1C06, 18E04, 98C07, 31A10, 29C09, 14B09, 62C01, 144F05, 42A02 and 117C06. I an alternative, the group consists of 31A10, 29C09, 14B09, 62C01, 13H04, 144F05, 42A02 and 117C06. In an example, the selected antibody is 31A10. In an example, the selected antibody is 1C02. In an example, the selected antibody is 13H04. In an example, the selected antibody is 31A10.

In an example of any aspect, competition is determined by surface plasmon resonance (SPR), such techniques being readily apparent to the skilled person. SPR can be carried out using Biacore™, Proteon™ or another standard SPR technique. Such competition may be due, for example, to the antibodies/fragments binding to identical or overlapping epitopes of hLIGHT.

28. The antibody or fragment of any one of aspects 19 to 27, wherein the antibody or fragment is according to any one of aspects 1 to 18.

29. The antibody or fragment of any preceding aspect, comprising lambda light chain variable domains (optionally which are human).

In an example of any aspect of the present invention, the variable domains of the antibody or fragment are human or humanised. Additionally, optionally the antibody or fragment further comprises human or humanised constant regions (eg, human Fc and/or human CL).

In an example of any aspect of the present invention, the variable domains of the antibody or fragment are produced by a transgenic animal (eg, a rodent, mouse, rat, rabbit, chicken, sheep, Camelid or shark). In an example of any aspect of the present invention, the variable domains of the antibody or fragment are produced or identified by phage display, ribosome display or yeast display.

In an example of any aspect of the present invention, the antibody or fragment is recombinant.

In an example of any aspect of the present invention, the antibody or fragment is produced by a recombinant mammalian, bacterial, insect, plant or yeast cell. In an example, the mammalian cell is a CHO or HEK293 cell and the antibody or fragment comprises CHO or HEK293 cell glycosylation.

In an example of any aspect of the present invention, the antibody or fragment is isolated.

30. The antibody or fragment of any preceding aspect, wherein the antibody or fragment specifically binds to 214K hLIGHT and competes for binding to said 214K hLIGHT with an antibody selected from the group consisting of 1C02, 1C06, 18E04, 31A10, 29C09, 14B09, 13H04, 144F05 and 42A02. I an alternative, the group consists of 31A10, 29C09, 14B09, 13H04, 144F05 and 42A02. In an example, the selected antibody is 31A10. In an example, the selected antibody is 1C02. In an example, the selected antibody is 1C02. In an example, the selected antibody is 13H04. In an example, the selected antibody is 31A10.

31. The antibody or fragment of any one of aspects 1 to 29, wherein the antibody or fragment specifically binds to (i) a 214E hLIGHT and competes for binding to said 214E hLIGHT with an antibody selected from the group consisting of 1C02, 1C06, 18E04, 14B09, 13H04 and 42A02; and (ii) a 214K hLIGHT and competes for binding to said 214K hLIGHT with an antibody selected from the group consisting of 1C02, 1C06, 18E04, 14B09, 13H04 and 42A02. These antibodies or fragments bind to both E and K alleles and thus are universally useful for all humans (E/E homozygotes, K/K homozygotes and E/K heterozygotes). I an alternative, the group consists of 14B09, 13H04 and 42A02. In an example, the selected antibody is 1C02. In an example, the selected antibody is 13H04.

32. The antibody or fragment of any one of aspects 1 to 29, wherein the antibody or fragment specifically binds to (i)

a 214E hLIGHT and competes for binding to said 214E hLIGHT with an antibody selected from the group consisting of 31A10, 29C09 and 144F05; and (ii) a 214K hLIGHT and competes for binding to said 214K hLIGHT with an antibody selected from the group consisting of 31A10, 29C09 and 144F05. These antibodies or fragments bind to both E and K alleles and thus are universally useful for treating, genotyping or diagnosing all humans (E/E homozygotes, K/K homozygotes and E/K heterozygotes). In an example, the selected antibody is 31A10.

33. The antibody or fragment of any one of aspects 1 to 29, wherein (i) the antibody or fragment specifically binds to 214E hLIGHT and competes for binding to said 214E hLIGHT with 98C07, 62C01 or 117C06; and (ii) the antibody or fragment does not specifically bind to a 214K hLIGHT. Antibodies or fragments that bind to E allele but not K are useful for treating, diagnosing or genotyping humans that are E/E homozygotes and E/K heterozygotes. Genotyping to distinguish such humans from K/K homozygotes is possible with these antibodies and fragments. In an example, the selected antibody is 98C07.

34. The antibody or fragment of any preceding aspect, comprising a VH domain which comprises a HCDR1 sequence selected from the group consisting of the HCDR1 of:
   a. 31A10, and wherein the antibody or fragment competes with 31A10 for binding to said hLIGHT;
   b. 29C09, and wherein the antibody or fragment competes with 29C09 for binding to said hLIGHT;
   c. 14B09, and wherein the antibody or fragment competes with 14B09 for binding to said hLIGHT;
   d. 62C01, and wherein the antibody or fragment competes with 62C01 for binding to said hLIGHT;
   e. 13H04, and wherein the antibody or fragment competes with 13H04 for binding to said hLIGHT;
   f. 144F05, and wherein the antibody or fragment competes with 144F05 for binding to said hLIGHT;
   g. 42A02, and wherein the antibody or fragment competes with 42A02 for binding to said hLIGHT;
   h. 117C06, and wherein the antibody or fragment competes with 117C06 for binding to said hLIGHT;
   i. 1C02, and wherein the antibody or fragment competes with 1C02 for binding to said hLIGHT;
   j. 1C06, and wherein the antibody or fragment competes with 1C06 for binding to said hLIGHT;
   k. 18E04, and wherein the antibody or fragment competes with 18E04 for binding to said hLIGHT; and
   l. 98C07, and wherein the antibody or fragment competes with 98C07 for binding to said hLIGHT.
   In an example the HCDR1 sequence selected from the group consisting of the HCDR1 of:
      i. 1C02, and wherein the antibody or fragment competes with 1C02 for binding to said hLIGHT;
      ii. 13H04, and wherein the antibody or fragment competes with 13H04 for binding to said hLIGHT; and
   m. 31A10, and wherein the antibody or fragment competes with 31A10 for binding to said hLIGHT.

35. The antibody or fragment of any preceding aspect, comprising a VH domain which comprises a HCDR2 sequence selected from the group consisting of the HCDR2 of:
   a. 31A10, and wherein the antibody or fragment competes with 31A10 for binding to said hLIGHT;
   b. 29C09, and wherein the antibody or fragment competes with 29C09 for binding to said hLIGHT;
   c. 14B09, and wherein the antibody or fragment competes with 14B09 for binding to said hLIGHT;
   d. 62C01, and wherein the antibody or fragment competes with 62C01 for binding to said hLIGHT;
   e. 13H04, and wherein the antibody or fragment competes with 13H04 for binding to said hLIGHT;
   f. 144F05, and wherein the antibody or fragment competes with 144F05 for binding to said hLIGHT;
   g. 42A02, and wherein the antibody or fragment competes with 42A02 for binding to said hLIGHT;
   h. 117C06, and wherein the antibody or fragment competes with 117C06 for binding to said hLIGHT;
   i. 1C02, and wherein the antibody or fragment competes with 1C02 for binding to said hLIGHT;
   j. 1C06, and wherein the antibody or fragment competes with 1C06 for binding to said hLIGHT;
   k. 18E04, and wherein the antibody or fragment competes with 18E04 for binding to said hLIGHT; and
   l. 98C07, and wherein the antibody or fragment competes with 98C07 for binding to said hLIGHT.
   In an example the HCDR2 sequence selected from the group consisting of the HCDR2 of:
      i. 1C02, and wherein the antibody or fragment competes with 1C02 for binding to said hLIGHT;
      ii. 13H04, and wherein the antibody or fragment competes with 13H04 for binding to said hLIGHT; and
      iii. 31A10, and wherein the antibody or fragment competes with 31A10 for binding to said hLIGHT.

36. The antibody or fragment of any preceding aspect, comprising a VH domain which comprises a HCDR3 sequence selected from the group consisting of the HCDR3 of:
   a. 31A10, and wherein the antibody or fragment competes with 31A10 for binding to said hLIGHT;
   b. 29C09, and wherein the antibody or fragment competes with 29C09 for binding to said hLIGHT;
   c. 14B09, and wherein the antibody or fragment competes with 14B09 for binding to said hLIGHT;
   d. 62C01, and wherein the antibody or fragment competes with 62C01 for binding to said hLIGHT;
   e. 13H04, and wherein the antibody or fragment competes with 13H04 for binding to said hLIGHT;
   f. 144F05, and wherein the antibody or fragment competes with 144F05 for binding to said hLIGHT;
   g. 42A02, and wherein the antibody or fragment competes with 42A02 for binding to said hLIGHT;
   h. 117C06, and wherein the antibody or fragment competes with 117C06 for binding to said hLIGHT;
   i. 1C02, and wherein the antibody or fragment competes with 1C02 for binding to said hLIGHT;
   j. 1C06, and wherein the antibody or fragment competes with 1C06 for binding to said hLIGHT;
   k. 18E04, and wherein the antibody or fragment competes with 18E04 for binding to said hLIGHT; and
   l. 98C07, and wherein the antibody or fragment competes with 98C07 for binding to said hLIGHT.
   In an example the HCDR3 sequence selected from the group consisting of the HCDR3 of:
      i. 1C02, and wherein the antibody or fragment competes with 1C02 for binding to said hLIGHT;
      ii. 13H04, and wherein the antibody or fragment competes with 13H04 for binding to said hLIGHT; and
      iii. 31A10, and wherein the antibody or fragment competes with 31A10 for binding to said hLIGHT.

37. The antibody or fragment of any preceding aspect, comprising a VH domain which comprises (i) the CDR1 and 2, (ii) CDR1 and 3, (iii) CDR2 and 3 or (iv) CDR1, 2 and 3 sequences:
   a. The CDR1, 2 and 3 sequences recited in (a) of aspects 34-36, and wherein the antibody or fragment competes with 31A10 for binding to said hLIGHT;
   b. The CDR1, 2 and 3 sequences recited in (b) of aspects 34-36, and wherein the antibody or fragment competes with 29C09 for binding to said hLIGHT;
   c. The CDR1, 2 and 3 sequences recited in (c) of aspects 34-36, and wherein the antibody or fragment competes with 14B09 for binding to said hLIGHT;
   d. The CDR1, 2 and 3 sequences recited in (d) of aspects 34-36, and wherein the antibody or fragment competes with 62C01 for binding to said hLIGHT;
   e. The CDR1, 2 and 3 sequences recited in (e) of aspects 34-36, and wherein the antibody or fragment competes with 13H04 for binding to said hLIGHT;
   f. The CDR1, 2 and 3 sequences recited in (f) of aspects 34-36, and wherein the antibody or fragment competes with 144F05 for binding to said hLIGHT;
   g. The CDR1, 2 and 3 sequences recited in (g) of aspects 34-36, and wherein the antibody or fragment competes with 42A02 for binding to said hLIGHT;
   h. The CDR1, 2 and 3 sequences recited in (h) of aspects 34-36, and wherein the antibody or fragment competes with 117C06 for binding to said hLIGHT;
   i. The CDR1, 2 and 3 sequences recited in (i) of aspects 34-36, and wherein the antibody or fragment competes with 1C02 for binding to said hLIGHT;
   j. The CDR1, 2 and 3 sequences recited in (j) of aspects 34-36, and wherein the antibody or fragment competes with 1C06 for binding to said hLIGHT;
   k. The CDR1, 2 and 3 sequences recited in (k) of aspects 34-36, and wherein the antibody or fragment competes with 18E04 for binding to said hLIGHT; or
   l. The CDR1, 2 and 3 sequences recited in (I) of aspects 34-36, and wherein the antibody or fragment competes with 98C07 for binding to said hLIGHT.
38. The antibody or fragment of any preceding aspect, comprising a VH domain which comprises an amino acid sequence selected from the group consisting of SEQ ID NOs: 2, 30, 58, 86, 114, 142, 170, 198 and 226; or from the group consisting of SEQ ID NOs: 368, 312, 340, 396, 2, 58, 86, 114, 142, 170, 198 and 266. In an alternative, the group consists of SEQ ID NOs: 2, 58, 86, 114, 142, 170, 198 and 266.

In an aspect, the invention provides an anti-hLIGHT antibody or fragment (optionally according to any other aspect recited herein) comprising a VH domain which comprises an amino acid sequence selected from the group consisting of SEQ ID NOs: 2, 30, 58, 86, 114, 142, 170, 198, 226; or from the group consisting of SEQ ID NOs: 2, 58, 86, 114, 142, 170, 198, 226.

In another example of the invention, the antibody or fragment comprises a VH domain amino acid sequence set out in the sequence listing below. Additionally or alternatively, the antibody or fragment comprises a HCDR1 domain amino acid sequence set out in the sequence listing below. Additionally or alternatively, the antibody or fragment comprises a HCDR2 domain amino acid sequence set out in the sequence listing below. Additionally or alternatively, the antibody or fragment comprises a HCDR3 domain amino acid sequence set out in the sequence listing below.

In an example of the invention, the antibody or fragment comprises a VL domain amino acid sequence set out in the sequence listing below. Additionally or alternatively, the antibody or fragment comprises a LCDR1 domain amino acid sequence set out in the sequence listing below. Additionally or alternatively, the antibody or fragment comprises a LCDR2 domain amino acid sequence set out in the sequence listing below. Additionally or alternatively, the antibody or fragment comprises a LCDR3 domain amino acid sequence set out in the sequence listing below.

In an example of any aspect herein, the antibody or fragment comprises a heavy chain comprising a constant region selected from the group consisting of SEQ ID NOs: 254, 256, 258, 260, 264 and 266 and optionally a VH domain as recited in aspect 30. In an example, the antibody or fragment comprises two copies of such a heavy chain. In another example, the heavy chain comprise a rodent, rat, mouse, human, rabbit, chicken, Camelid, sheep, bovine, non-human primate or shark constant region (eg, Fc).

In an example of any aspect herein, the antibody or fragment comprises a heavy chain comprising a gamma (eg, human gamma) constant region, eg, a human gamma1 constant region.

In an example of any aspect herein, the antibody or fragment is chimaeric, eg, it comprises human variable domains and non-human (eg, rodent, mouse or rat) constant regions.

39. The antibody or fragment of any one of aspects 34 to 38, comprising first and second copies of said VH domain.
40. The antibody or fragment of any preceding aspect, comprising a VL domain which comprises a LCDR1 sequence selected from the group consisting of the LCDR1 of:
   a. 31A10, and wherein the antibody or fragment competes with 31A10 for binding to said hLIGHT;
   b. 29C09, and wherein the antibody or fragment competes with 29C09 for binding to said hLIGHT;
   c. 14B09, and wherein the antibody or fragment competes with 14B09 for binding to said hLIGHT;
   d. 62C01, and wherein the antibody or fragment competes with 62C01 for binding to said hLIGHT;
   e. 13H04, and wherein the antibody or fragment competes with 13H04 for binding to said hLIGHT;
   f. 144F05, and wherein the antibody or fragment competes with 144F05 for binding to said hLIGHT;
   g. 42A02, and wherein the antibody or fragment competes with 42A02 for binding to said hLIGHT;
   h. 117C06, and wherein the antibody or fragment competes with 117C06 for binding to said hLIGHT
   i. 1C02, and wherein the antibody or fragment competes with 1C02 for binding to said hLIGHT;
   j. 1C06, and wherein the antibody or fragment competes with 1C06 for binding to said hLIGHT;
   k. 18E04, and wherein the antibody or fragment competes with 18E04 for binding to said hLIGHT; and
   l. 98C07, and wherein the antibody or fragment competes with 98C07 for binding to said hLIGHT.
   In an example the LCDR1 sequence selected from the group consisting of the LCDR1 of:
      i. 1C02, and wherein the antibody or fragment competes with 1C02 for binding to said hLIGHT;
      ii. 13H04, and wherein the antibody or fragment competes with 13H04 for binding to said hLIGHT; and iii. 31A10, and wherein the antibody or fragment competes with 31A10 for binding to said hLIGHT.
41. The antibody or fragment of any preceding aspect, comprising a VL domain which comprises a LCDR2 sequence selected from the group consisting of the LCDR2 of:
  a. 31A10, and wherein the antibody or fragment competes with 31A10 for binding to said hLIGHT;
  b. 29C09, and wherein the antibody or fragment competes with 29C09 for binding to said hLIGHT;
  c. 14B09, and wherein the antibody or fragment competes with 14B09 for binding to said hLIGHT;
  d. 62C01, and wherein the antibody or fragment competes with 62C01 for binding to said hLIGHT;
  e. 13H04, and wherein the antibody or fragment competes with 13H04 for binding to said hLIGHT;
  f. 144F05, and wherein the antibody or fragment competes with 144F05 for binding to said hLIGHT;
  g. 42A02, and wherein the antibody or fragment competes with 42A02 for binding to said hLIGHT;
  h. 117C06, and wherein the antibody or fragment competes with 117C06 for binding to said hLIGHT;
  i. 1C02, and wherein the antibody or fragment competes with 1C02 for binding to said hLIGHT;
  j. 1C06, and wherein the antibody or fragment competes with 1C06 for binding to said hLIGHT;
  k. 18E04, and wherein the antibody or fragment competes with 18E04 for binding to said hLIGHT; and
  l. 98C07, and wherein the antibody or fragment competes with 98C07 for binding to said hLIGHT.
    In an example the LCDR2 sequence selected from the group consisting of the LCDR2 of:
      i. 1C02, and wherein the antibody or fragment competes with 1C02 for binding to said hLIGHT;
      ii. 13H04, and wherein the antibody or fragment competes with 13H04 for binding to said hLIGHT; and
      iii. 31A10, and wherein the antibody or fragment competes with 31A10 for binding to said hLIGHT.
42. The antibody or fragment of any preceding aspect, comprising a VL domain which comprises a LCDR3 sequence selected from the group consisting of the LCDR3 of:
  a. 31A10, and wherein the antibody or fragment competes with 31A10 for binding to said hLIGHT;
  b. 29C09, and wherein the antibody or fragment competes with 29C09 for binding to said hLIGHT;
  c. 14B09, and wherein the antibody or fragment competes with 14B09 for binding to said hLIGHT;
  d. 62C01, and wherein the antibody or fragment competes with 62C01 for binding to said hLIGHT;
  e. 13H04, and wherein the antibody or fragment competes with 13H04 for binding to said hLIGHT;
  f. 144F05, and wherein the antibody or fragment competes with 144F05 for binding to said hLIGHT;
  g. 42A02, and wherein the antibody or fragment competes with 42A02 for binding to said hLIGHT;
  h. 117C06, and wherein the antibody or fragment competes with 117C06 for binding to said hLIGHT;
  i. 1C02, and wherein the antibody or fragment competes with 1C02 for binding to said hLIGHT;
  j. 1C06, and wherein the antibody or fragment competes with 1C06 for binding to said hLIGHT;
  k. 18E04, and wherein the antibody or fragment competes with 18E04 for binding to said hLIGHT; and
  l. 98C07, and wherein the antibody or fragment competes with 98C07 for binding to said hLIGHT.
    In an example the LCDR3 sequence selected from the group consisting of the LCDR3 of:
      i. 1C02, and wherein the antibody or fragment competes with 1C02 for binding to said hLIGHT;
      ii. 13H04, and wherein the antibody or fragment competes with 13H04 for binding to said hLIGHT; and
      iii. 31A10, and wherein the antibody or fragment competes with 31A10 for binding to said hLIGHT.
      In an alternative of (ii), the LCDR3 is the LCDR3 of 13H04 (SEQ ID NO: 163 or 168), with the exception that an amino acid other than Cys is present at the first position of the CDR. For example, there is a conservative substitution of the Cys by another amino acid. For example, a Ser is present in the first position instead of a Cys. In an example, the antibody or fragment of the invention comprises a VL domain of 13H04 but with said change at the first position of the LCDR3.
43. The antibody or fragment of any preceding aspect, comprising a VL domain which comprises (i) the CDR1 and 2, (ii) CDR1 and 3, (iii) CDR2 and 3 or (iv) CDR1, 2 and 3 sequences:
  a. The CDR1, 2 and 3 sequences recited in (a) of aspects 40-42, and wherein the antibody or fragment competes with 31A10 for binding to said hLIGHT;
  b. The CDR1, 2 and 3 sequences recited in (b) of aspects 40-42, and wherein the antibody or fragment competes with 29C09 for binding to said hLIGHT;
  c. The CDR1, 2 and 3 sequences recited in (c) of aspects 40-42, and wherein the antibody or fragment competes with 14B09 for binding to said hLIGHT;
  d. The CDR1, 2 and 3 sequences recited in (d) of aspects 40-42, and wherein the antibody or fragment competes with 62C01 for binding to said hLIGHT;
  e. The CDR1, 2 and 3 sequences recited in (e) of aspects 40-42, and wherein the antibody or fragment competes with 13H04 for binding to said hLIGHT;
  f. The CDR1, 2 and 3 sequences recited in (g) of aspects 40-42, and wherein the antibody or fragment competes with 144F05 for binding to said hLIGHT;
  g. The CDR1, 2 and 3 sequences recited in (i) of aspects 40-42, and wherein the antibody or fragment competes with 42A02 for binding to said hLIGHT;
  h. The CDR1, 2 and 3 sequences recited in (j) of aspects 40-42, and wherein the antibody or fragment competes with 117C06 for binding to said hLIGHT;
  i. The CDR1, 2 and 3 sequences recited in (i) of aspects 40-42, and wherein the antibody or fragment competes with 1C02 for binding to said hLIGHT;
  j. The CDR1, 2 and 3 sequences recited in (j) of aspects 40-42, and wherein the antibody or fragment competes with 1C06 for binding to said hLIGHT;
  k. The CDR1, 2 and 3 sequences recited in (k) of aspects 40-42, and wherein the antibody or fragment competes with 18E04 for binding to said hLIGHT; or
  l. The CDR1, 2 and 3 sequences recited in (l) of aspects 40-42, and wherein the antibody or fragment competes with 98C07 for binding to said hLIGHT.
44. The antibody or fragment of any one of aspects 40 to 43, comprising a VL domain which comprises an amino acid sequence selected from the group consisting of SEQ ID NOs: 370, 314, 342, 398, 16, 72, 100, 128, 156, 184, 212 and 240. In an alternative, the group consists of SEQ ID NOs: 16, 72, 100, 128, 156, 184, 212 and 240.

In an aspect of the invention, there is provided an anti-hLIGHT antibody or fragment (optionally according to any other aspect herein), comprising a VL domain which comprises an amino acid sequence selected from the group consisting of SEQ ID NOs: 16, 44, 72, 100, 128, 156, 184, 212 and 240; or from the group consisting of SEQ ID NOs: 16, 72, 100, 128, 156, 184, 212 and 240.

In an example of any aspect herein, the antibody or fragment comprises a light chain (eg, lambda light chain) comprising a constant region selected from the group consisting of SEQ ID NOs: 268, 270, 272, 274, 276, 278, 280, 284, 286, 288, 290, 292, 294, 296 and 298 and optionally a VL domain (eg, lambda VL) as recited in aspect 36. In an example, the antibody or fragment comprises two copies of such a light chain (optionally also two copies of the heavy chain described above). In another example, the light chain comprise a rodent, rat, mouse, human, rabbit, chicken, Camelid, sheep, bovine, non-human primate or shark constant region.

In an example, the antibody or fragment comprises a lambda light chain comprising a constant region selected from the group consisting of SEQ ID NOs: 278, 280, 284, 286, 288, 290, 292, 294, 296 and 298 and optionally a lambda VL domain.

In an example, the VL domains of the antibody or fragment are lambda light chain variable domains.

45. The antibody or fragment of any one of aspects 32 to 36, comprising first and second copies of said VL domain.

46. The antibody or fragment of any preceding aspect, wherein the antibody or fragment competes with mAb664 for binding to 214E hLIGHT.

The antibody mAb664 is a mouse IgG1 anti-LIGHT antibody available from R&D Systems (catalogue number mAB664, clone name 115520).

47. The antibody or fragment of any preceding aspect, wherein the hLIGHT is human cell surface-expressed hLIGHT, eg, on epithelial cells (eg, any type of epithelial cell disclosed herein).

48. The antibody or fragment of any preceding aspect, wherein the antibody or fragment decreases the proliferation of human PBMCs or T-cells in the presence of hLIGHT in an in vitro mixed lymphocyte reaction (MLR) assay by at least 20, 30, 40, 50 or 60% compared to the proliferation of human PBMCs or T-cells in the presence of hLIGHT in an in vitro control MLR assay in the absence of an antibody that is specific for hLIGHT. An illustration of a suitable assay is provided in the examples below.

49. The antibody or fragment of aspect 48, wherein the hLIGHT in the assay is surface-expressed on human dendritic cells (DC cells). An illustration of a suitable assay is provided in the examples below.

50. The antibody or fragment of any preceding aspect, wherein the antibody or fragment decreases IL-8 secretion from human epithelial cells (eg, human colon cells) expressing a receptor for 214E hLIGHT. In an example the cells express HVEM or LTβR. In an example, the antibody or fragment decreases IL-8 secretion by HT-29 cells (ATCC® HTB-38) in vitro.

51. The antibody or fragment of any preceding aspect, wherein the antibody or fragment decreases IL-8 secretion from human HT-29 cells expressing 214E hLIGHT in vitro.

52. The antibody or fragment of aspect 51, wherein the antibody or fragment decreases IL-8 secretion by at least 20, 30, 40, 50 or 60% compared to the IL-8 production by HT-29 cells expressing 214E hLIGHT in a HT-29 in vitro control assay in the absence of an antibody that is specific for hLIGHT.

53. The antibody or fragment of aspect 52, wherein the antibody or fragment completely inhibits IL-8 secretion in a HT-29 in vitro assay.

54. The antibody or fragment of any preceding aspect, wherein the antibody or fragment decreases cytokine secretion mediated by the interaction of human dendritic cells (DC cells) with human T-cells, wherein the cytokine is selected from one, two, more or all of interferon gamma, IL-8, TNF alpha and IL-2 (eg, IL-2 and/or interferon gamma). This can be assessed, for example, using a MLR in vitro assay (eg, a DC/T-cell MLR in vitro assay). An illustration of a suitable assay is provided in the examples below.

In an example, the DC cells are mismatched to the T-cells, eg, MHC mis-matched, as is possible for example when the DC cells are from a human that is different from the T-cell human source. In an example, the DC cells are produced by in vitro induction of human monocytes with GMCSF and IL-4.

55. The antibody or fragment of any preceding aspect, wherein the antibody or fragment decreases interferon gamma secretion by at least 20, 30, 40, 50 or 60% compared to the production of interferon gamma mediated by the interaction of human dendritic cells (DC cells) with human T-cells in the absence of an antibody that is specific for hLIGHT.

56. The antibody or fragment of any preceding aspect, wherein the antibody or fragment decreases TNF alpha secretion by at least 20, 30, 40, 50 or 60% compared to the production of TNF alpha mediated by the interaction of human dendritic cells (DC cells) with human T-cells in the absence of an antibody that is specific for hLIGHT.

57. The antibody or fragment of any preceding aspect, wherein the antibody or fragment decreases IL-2 secretion by at least 10, 20, 30, 40, 50 or 60% compared to the production of IL-2 mediated by the interaction of human dendritic cells (DC cells) with human T-cells in the absence of an antibody that is specific for hLIGHT.

58. The antibody or fragment of any preceding aspect, wherein the antibody or fragment decreases cytokine secretion in a human peripheral blood mononuclear cell (PBMC) mixed lymphocyte (MLR) assay, wherein the cytokine is selected from one, two, more or all of interferon gamma, IL-8, TNF alpha and IL-2 (eg, IL-2 and/or interferon gamma).

59. The antibody or fragment of any preceding aspect, wherein the antibody or fragment decreases interferon gamma secretion by at least 20, 30, 40, 50 or 60% compared to the production of interferon gamma in a human PBMC MLR assay in the absence of an antibody that is specific for hLIGHT.

60. The antibody or fragment of any preceding aspect, wherein the antibody or fragment decreases TNF alpha secretion by at least 20, 30, 40, 50 or 60% compared to the production of TNF alpha in a human PBMC MLR assay in the absence of an antibody that is specific for hLIGHT.

61. The antibody or fragment of any preceding aspect, wherein the antibody or fragment decreases IL-2 secretion by at least 10, 20, 30, 40, 50 or 60% compared to the production of IL-2 in a human PBMC MLR assay in the absence of an antibody that is specific for hLIGHT.

62. The antibody or fragment of any one of aspects 54 to 61, wherein the cells are primary cells.

A "primary cell" refers to a cell in a human or such a cell that has been taken from the patient for binding to the antibody or fragment of the invention in vitro (as may be useful, for example, in a method of diagnosis of LIGHT status or disease/condition status in the human). Primary cells as used herein are not cells of human cell lines, which typically have undergone many cultures in vitro. The ability of the antibody or fragment of the invention to specifically inhibit hLIGHT binding to receptor (eg, HVEM or LTβR) in this embodiment is advantageous since it provides a direct indication of the utility for addressing cells in human patients suffering or at risk of a hLIGHT-mediated disease or condition.

63. The antibody or fragment of any preceding aspect, wherein the antibody or fragment inhibits binding of 214E hLIGHT to a human HVEM and/or human lymphotoxin β receptor with an IC50 of $1 \times 10^{-8}$ or less in a HTRF (homogenous time resolved fluorescence) assay. In an example, the IC50 is in the range from $1 \times 10^{-8}$ to $1 \times 10^{-11}$ or in the range from $1 \times 10^{-9}$ to $1 \times 10^{-10}$.

64. A pharmaceutical composition comprising an antibody or fragment of any preceding aspect and a diluent, excipient or carrier; and optionally further comprising an anti-inflammatory drug.

65. A kit comprising an antibody or fragment of any one of aspects 1 to 63 and means for genotyping a human as positive or negative for a nucleotide sequence encoding 214E hLIGHT polypeptide and/or means for phenotyping a human as positive or negative for a 214E hLIGHT polypeptide. In an example, the means for genotyping comprises a nucleic acid that hybridises under stringent conditions to at least 10, 15 or 20 contiguous nucleotides of 214E hLIGHT, wherein the nucleotides comprise 214E and the nucleic acid does not hybridise under the same conditions to at least respectively 10, 15 or 20 contiguous nucleotides of 214K hLIGHT, wherein the nucleotides comprise 214K. In an example, the means for phenotyping comprises an antibody or fragment (eg, one of the invention) that specifically binds to 214E LIGHT, but not 214K LIGHT.

Hybridisation under stringent conditions will be apparent to the skilled person, eg, conditions of 5×SSC, 5×Denhardt's reagent, and 0.5% SDS at 65° C. In an example, stringent conditions comprise hybridization to filter-bound DNA in 6× sodium chloride/sodium citrate (SSC) at about 45° C. followed by one or more washes in 0.2×SSC/0.1% SDS at about 50-65° C.; or may be highly stringent conditions (e.g., hybridization to filter-bound nucleic acid in 6×SSC at about 45° C. followed by one or more washes in 0.1×SSC/0.2% SDS at about 68° C.), or other stringent hybridization conditions which are known to those of skill in the art (see, for example, Ausubel, F. M. et al., eds., 1989, Current Protocols in Molecular Biology, Vol. I, Green Publishing Associates, Inc. and John Wiley & Sons, Inc., New York at pages 6.3.1-6.3.6 and 2.10.3).

66. A kit comprising an antibody or fragment of any one of aspects 1 to 63 and means for genotyping a human as positive or negative for a nucleotide sequence encoding 214K hLIGHT polypeptide and/or means for phenotyping a human as positive or negative for a 214K hLIGHT polypeptide. In an example, the means for genotyping comprises a nucleic acid that hybridises under stringent conditions to at least 10, 15 or 20 contiguous nucleotides of 214K hLIGHT, wherein the nucleotides comprise 214K and the nucleic acid does not hybridise under the same conditions to at least respectively 10, 15 or 20 contiguous nucleotides of 214E hLIGHT, wherein the nucleotides comprise 214E. In an example, the means for phenotyping comprises an antibody or fragment (eg, one of the invention) that specifically binds to 214K LIGHT, but not 214E LIGHT.

The invention also provides a pharmaceutical composition or kit for treating and/or preventing a LIGHT-mediated condition or disease, the composition or kit comprising an antibody or fragment of the invention (and optionally an anti-inflammatory drug) optionally in combination with a label or instructions for use to treat and/or prevent said disease or condition in a human; optionally wherein the label or instructions comprise a marketing authorisation number (eg, an FDA or EMA authorisation number); optionally wherein the kit comprises an IV or injection device that comprises the antibody or fragment.

67. A nucleic acid that encodes the HCDR3 of an antibody recited in any one of aspects 1 to 63.

68. The nucleic acid of aspect 67 comprising a nucleotide sequence that is at least 80, 85, 90, 95, 96, 97, 98 or 99% identical or is 100% identical to a sequence selected from SEQ ID NOs: 375, 376, 319, 320, 347, 348, 403, 404, 7, 13, 63, 69, 91, 97, 119, 125, 147, 153, 175, 181, 203, 209, 231 and 237; or selected from SEQ ID NOs: 375, 376, 319, 320, 347, 348, 403, 404, 7, 13, 63, 69, 91, 97, 119, 125, 147, 153, 175, 181, 203, 209, 231 and 237. In an example, the nucleotide sequence is at least 80, 85, 90, 95, 96, 97, 98 or 99% identical or is 100% identical to a sequence selected from SEQ ID NOs: 7, 13, 35, 41, 63, 69, 91, 97, 119, 125, 147, 153, 175, 181, 203, 209, 231 and 237; or selected from SEQ ID NOs: 7, 13, 63, 69, 91, 97, 119, 125, 147, 153, 175, 181, 203, 209, 231 and 237.

In an aspect, the invention provides a nucleic acid comprising a nucleotide sequence that encodes a VH domain of an anti-hLIGHT antibody, wherein the nucleotide sequence comprises a HCDR3 sequence that is at least 80, 85, 90, 95, 96, 97, 98 or 99% identical or is 100% identical to a sequence selected from SEQ ID NOs: 7, 13, 35, 41, 63, 69, 91, 97, 119, 125, 147, 153, 175, 181, 203, 209, 231 and 237; or is selected from SEQ ID NOs: 7, 13, 63, 69, 91, 97, 119, 125, 147, 153, 175, 181, 203, 209, 231 and 237. Optionally, the antibody is according to any other aspect herein.

In another embodiment, there is provided the nucleic acid of aspect 59 comprising a nucleotide sequence that is 100% identical to a sequence selected from SEQ ID NOs: 7, 13, 35, 41, 63, 69, 91, 97, 119, 125, 147, 153, 175, 181, 203, 209, 231 and 237; or selected from SEQ ID NOs: 7, 13, 63, 69, 91, 97, 119, 125, 147, 153, 175, 181, 203, 209, 231 and 237, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Amino acid substitutions include alterations in which an amino acid is replaced with a different naturally-occurring amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid.

Additionally or alternatively, there is provided the nucleic acid of aspect 59 comprising a nucleotide sequence that is 100% identical to a sequence selected from SEQ ID NOs: 7, 13, 35, 41, 63, 69, 91, 97, 119, 125, 147, 153, 175, 181, 203, 209, 231 and 237; or selected from SEQ ID NOs: 7, 13, 63, 69, 91, 97, 119, 125, 147, 153, 175, 181, 203, 209, 231 and 237, except for 1, 2, 3, 4, 5, 6 or 7 synonymous nucleotide substitutions and no, 1, 2 or 3 nucleotide substitutions that produce conservative amino acid changes in the corresponding protein sequence.

69. A nucleic acid that encodes the HCDR2 of an antibody recited in any one of aspects 1 to 63; optionally wherein the nucleic acid is according to aspect 67 or 68.

70. The nucleic acid of aspect 69 comprising a nucleotide sequence that is at least 80, 85, 90, 95, 96, 97, 98 or 99% identical to or is 100% identical to a sequence selected from SEQ ID NOs: 373, 374, 317, 318, 345, 346, 401, 402, 5, 11, 61, 67, 89, 95, 117, 123, 145, 151, 173, 179, 201, 207, 229 and 235; or selected from SEQ ID NOs: 373, 374, 317, 318, 345, 346, 401, 402, 5, 11, 61, 67, 89, 95, 117, 123, 145, 151, 173, 179, 201, 207, 229 and 235. In an example, the nucleotide sequence is at least 80, 85, 90, 95, 96, 97, 98 or 99% identical or is 100% identical to a sequence selected from SEQ ID NOs: 5, 11, 33, 39, 61, 67, 89, 95, 117, 123, 145, 151, 173, 179, 201, 207, 229 and 235; or is selected from SEQ ID NOs: 5, 11, 61, 67, 89, 95, 117, 123, 145, 151, 173, 179, 201, 207, 229 and 235

In an aspect, the invention provides a nucleic acid comprising a nucleotide sequence that encodes a VH domain of an anti-hLIGHT antibody, wherein the nucleotide sequence comprises a HCDR2 sequence that is at least 80, 85, 90, 95, 96, 97, 98 or 99% identical or is 100% identical to a sequence selected from SEQ ID NOs: 5, 11, 33, 39, 61, 67, 89, 95, 117, 123, 145, 151, 173, 179, 201, 207, 229 and 235; or selected from SEQ ID NOs: 5, 11, 61, 67, 89, 95, 117, 123, 145, 151, 173, 179, 201, 207, 229 and 235. Optionally, the antibody is according to any other aspect herein.

In another embodiment, there is provided the nucleic acid of aspect 61 comprising a nucleotide sequence that is 100% identical to a sequence selected from SEQ ID NOs: 5, 11, 33, 39, 61, 67, 89, 95, 117, 123, 145, 151, 173, 179, 201, 207, 229 and 235; or selected from SEQ ID NOs: 5, 11, 61, 67, 89, 95, 117, 123, 145, 151, 173, 179, 201, 207, 229 and 235, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Additionally or alternatively, there is provided the nucleic acid of aspect 61 comprising a nucleotide sequence that is 100% identical to a sequence selected from SEQ ID NOs: 5, 11, 33, 39, 61, 67, 89, 95, 117, 123, 145, 151, 173, 179, 201, 207, 229 and 235; or selected from SEQ ID NOs: 5, 11, 61, 67, 89, 95, 117, 123, 145, 151, 173, 179, 201, 207, 229 and 235, except for 1, 2, 3, 4, 5, 6 or 7 synonymous nucleotide substitutions and no, 1, 2 or 3 nucleotide substitutions that produce conservative amino acid changes in the corresponding protein sequence.

71. A nucleic acid that encodes the HCDR1 of an antibody recited in any one of aspects 1 to 63; optionally wherein the nucleic acid is according to any one of aspects 67 to 70.

72. The nucleic acid of aspect 63 comprising a nucleotide sequence that is at least 80, 85, 90, 95, 96, 97, 98 or 99% identical to or is 100% identical to a sequence selected from SEQ ID NOs: 371, 372, 315, 316, 343, 344, 399, 400, 3, 9, 59, 65, 87, 93, 115, 121, 143, 149, 171, 177, 199, 205, 227 and 233; or selected from SEQ ID NOs: 371, 372, 315, 316, 343, 344, 399, 400, 3, 9, 59, 65, 87, 93, 115, 121, 143, 149, 171, 177, 199, 205, 227 and 233. In an example, the nucleotide sequence is at least 80, 85, 90, 95, 96, 97, 98 or 99% identical to or is 100% identical to a sequence selected from SEQ ID NOs: 3, 9, 31, 37, 59, 65, 87, 93, 115, 121, 143, 149, 171, 177, 199, 205, 227 and 233; or is selected from SEQ ID NOs: 3, 9, 59, 65, 87, 93, 115, 121, 143, 149, 171, 177, 199, 205, 227 and 233

In an aspect, the invention provides a nucleic acid comprising a nucleotide sequence that encodes a VH domain of an anti-hLIGHT antibody, wherein the nucleotide sequence comprises a HCDR1 sequence that is at least 80, 85, 90, 95, 96, 97, 98 or 99% identical or is 100% identical to a sequence selected from SEQ ID NOs: 3, 9, 31, 37, 59, 65, 87, 93, 115, 121, 143, 149, 171, 177, 199, 205, 227 and 233; or selected from SEQ ID NOs: 3, 9, 59, 65, 87, 93, 115, 121, 143, 149, 171, 177, 199, 205, 227 and 233. Optionally, the antibody is according to any other aspect herein.

In another embodiment, there is provided the nucleic acid of aspect 63 comprising a nucleotide sequence that is 100% identical to a sequence selected from SEQ ID NOs: SEQ ID NOs: 3, 9, 31, 37, 59, 65, 87, 93, 115, 121, 143, 149, 171, 177, 199, 205, 227 and 233; or selected from SEQ ID NOs: 3, 9, 59, 65, 87, 93, 115, 121, 143, 149, 171, 177, 199, 205, 227 and 233, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Additionally or alternatively, there is provided the nucleic acid of aspect 63 comprising a nucleotide sequence that is 100% identical to a sequence selected from SEQ ID NOs: SEQ ID NOs: 3, 9, 31, 37, 59, 65, 87, 93, 115, 121, 143, 149, 171, 177, 199, 205, 227 and 233; or selected from SEQ ID NOs: 3, 9, 59, 65, 87, 93, 115, 121, 143, 149, 171, 177, 199, 205, 227 and 233, except for 1, 2, 3, 4, 5, 6 or 7 synonymous nucleotide substitutions and no, 1, 2 or 3 nucleotide substitutions that produce conservative amino acid changes in the corresponding protein sequence.

73. A nucleic acid that encodes a VH domain and/or a VL domain of an antibody recited in any one of aspects 1 to 63.

74. The nucleic acid of aspect 65 comprising a nucleotide sequence that is at least 80, 85, 90, 95, 96, 97, 98 or 99% identical to or is 100% identical to a sequence selected from the group consisting of SEQ ID NOs: 367, 311, 339, 395, 1, 29, 57, 85, 113, 141, 169, 197 and 225; or from the group consisting of SEQ ID NOs: 367, 311, 339, 395, 1, 57, 85, 113, 141, 169, 197 and 225. In an example, the nucleotide sequence is at least 80, 85, 90, 95, 96, 97, 98 or 99% identical to or is 100% identical to a sequence selected from the group consisting of SEQ ID NOs: 1, 29, 57, 85, 113, 141, 169, 197 and 225; or from the group consisting of SEQ ID NOs: 1, 57, 85, 113, 141, 169, 197 and 225.

In another embodiment, there is provided the nucleic acid of aspect 65 comprising a nucleotide sequence that is 100% identical to a sequence selected from the group consisting of SEQ ID NOs: 1, 29, 57, 85, 113, 141, 169, 197 and 225; or from the group consisting of SEQ ID NOs: 1, 57, 85, 113, 141, 169, 197 and 225, except for 1, 2 or 3 nucleotide substitutions, wherein each substitution produces no amino acid change or produces a conservative amino acid change (i.e., the nucleotide substitution is a synonymous substitution) in the corresponding protein sequence. The skilled person will be familiar with conservative amino acid changes.

Additionally or alternatively, there is provided the nucleic acid of aspect 65 comprising a nucleotide sequence that is 100% identical to a sequence selected from the group consisting of SEQ ID NOs: 1, 29, 57, 85, 113, 141, 169, 197 and 225; or from the group consisting of SEQ ID NOs: 1, 57, 85, 113, 141, 169, 197 and 225, except for 1, 2, 3, 4, 5, 6 or 7 synonymous nucleotide substitutions and no, 1, 2 or 3 nucleotide substitutions that produce conservative amino acid changes in the corresponding protein sequence.

75. The nucleic acid of aspect 65 or 66 comprising a nucleotide sequence that is at least 80, 85, 90, 95, 96, 97, 98 or 99% identical to or is 100% identical to a sequence selected from SEQ ID NOs: 369, 313, 341, 397, 15, 43, 71, 99, 127, 155, 183, 211 and 239; or from the group consisting of SEQ ID NOs: 369, 313, 341, 397, 15, 71, 99, 127, 155, 183, 211 and 239. In an example, the nucleotide sequence is at least 80, 85, 90, 95, 96, 97, 98 or 99% identical to or is 100% identical to a sequence selected from SEQ ID NOs: 15, 43, 71, 99, 127, 155, 183, 211 and 239; or from the group consisting of SEQ ID NOs: 15, 71, 99, 127, 155, 183, 211 and 239.

In another embodiment, there is provided the nucleic acid of aspect 65 or 66 comprising a nucleotide sequence that is 100% identical to a sequence selected from SEQ ID NOs: 15, 43, 71, 99, 127, 155, 183, 211 and 239; or from the group consisting of SEQ ID NOs: 15, 71, 99, 127, 155, 183, 211 and 239, except for 1, 2 or 3 nucleotide substitutions, wherein each substitution produces no amino acid change or produces a conservative amino acid change (i.e., the nucleotide substitution is a synonymous substitution) in the corresponding protein sequence.

The skilled person will be familiar with conservative amino acid changes.

Additionally or alternatively, there is provided the nucleic acid of aspect 65 or 66 comprising a nucleotide sequence that is 100% identical to a sequence selected from SEQ ID NOs: 15, 43, 71, 99, 127, 155, 183, 211 and 239; or from the group consisting of SEQ ID NOs: 15, 71, 99, 127, 155, 183, 211 and 239, except for 1, 2, 3, 4, 5, 6 or 7 synonymous nucleotide substitutions and no, 1, 2 or 3 nucleotide substitutions that produce conservative amino acid changes in the corresponding protein sequence.

76. A nucleic acid that encodes a heavy chain or a LIGHT chain of an antibody recited in any one of aspects 1 to 63.

77. The nucleic acid of aspect 76, comprising a nucleotide sequence as recited in any one of aspects 67 to 75.

78. A vector comprising the nucleic acid of any one of aspects 67 to 77; optionally wherein the vector is a CHO or HEK293 vector. In an example, the vector is a yeast vector, eg, a *Saccharomyces* or *Pichia* vector.

79. A host comprising the nucleic acid of any one of aspects 67 to 77 or the vector of aspect 70. In an example, the host is a mammalian (eg, human, eg, CHO or HEK293) cell line or a yeast or bacterial cell line.

80. Use of an antibody or a fragment thereof, that specifically binds to hLIGHT in the manufacture of a medicament for administration to a human, for treating or preventing a hLIGHT-mediated disease or condition in the human by decreasing one or more of
   m. the secretion of a cytokine selected from IL-2, TNF alpha and interferon gamma in the human;
   n. the proliferation of leukocytes of the human; and
   o. the binding of hLIGHT by human epithelial cells expressing a receptor for hLIGHT.
   The features of any of the previous aspects, examples or embodiments optionally apply mutatis mutandis to this use.

81. A method of treating or preventing a hLIGHT-mediated disease or condition in a human by decreasing one, more or all of:
   p. the secretion of a cytokine selected from IL-2, TNF alpha and interferon gamma in the human;
   q. the proliferation of leukocytes of the human; and
   r. the binding of hLIGHT by human epithelial cells expressing a receptor for hLIGHT;
   wherein the method comprises administering to said human a therapeutically effective amount of an antibody or fragment that specifically binds to hLIGHT.
   The features of any of the previous aspects, examples or embodiments optionally apply mutatis mutandis to this method.
   The method of the invention treats or prevents said disease or condition in the human. A "therapeutically effective amount" of the antibody or fragment is that amount (administered in one or several doses, which may be spaced in time, eg, substantially monthly administration) that is effective to bring about said treatment or prevention. This will be readily apparent to the skilled person and may vary according to the particular human patient and disease or condition being addressed.

82. The method or use of aspect 80 or 81, for treating or preventing said hLIGHT-mediated disease, condition or epithelial cell damage in said human by decreasing the proliferation of T-cells in said human.

83. The method or use of any one of aspects 80 to 82, for treating or preventing said hLIGHT-mediated disease, condition or epithelial cell damage in said human by antagonising the interaction between hLIGHT and leukocytes of the human, wherein the proliferation of leukocytes is decreased.

84. The method or use of any one of aspects 80 to 83, for treating or preventing said hLIGHT-mediated disease, condition or epithelial cell damage in said human by decreasing the proliferation of leukocytes of the human by antagonising the LIGHT/LIGHT receptor interaction mediated by T-cells in said human.

85. The method or use of any one of aspects 80 to 84, for treating or preventing said hLIGHT-mediated disease, condition or epithelial cell damage in said human by decreasing the secretion of IL-8 cytokine in the human.

86. The method of aspect 85, for treating or preventing said disease, condition or epithelial cell damage by decreasing the secretion of said IL-8 mediated by the interaction of dendritic cells (DC cells) with T-cells in the human.
87. The method or use of any one of aspects 80 to 86, wherein epithelial cell damage is a symptom or cause of said disease or condition in humans.
88. The method or use of any one of aspects 80 to 87, wherein the human is suffering from or at risk of an inflammatory bowel disease (IBD), allogenic transplant rejection or graft-versus-host disease (GvHD) and said method treats or prevents IBD, allogenic transplant rejection or GvHD in the human.
89. The method or use of any one of aspects 80 to 88, wherein the hLIGHT is 214E hLIGHT.
90. The method or use of any one of aspects 80 to 89, wherein the human has been genotyped as positive for a nucleotide sequence encoding 214E hLIGHT polypeptide.
Optionally, the method comprises carrying out the genotyping before administration of the antibody or fragment to the patient.
91. The method or use of any one of aspects 80 to 90, wherein the human has been phenotyped as positive for a 214E hLIGHT polypeptide.
Optionally, the method comprises carrying out the phenotyping before administration of the antibody or fragment to the patient.
92. The method or use of any one of aspects 80 to 91, wherein the method or use comprises genotyping the human as positive for a nucleotide sequence encoding 214E hLIGHT polypeptide.
Optionally, the method comprises carrying out the genotyping before administration of the antibody or fragment to the patient.
93. The method or use of any one of aspects 80 to 92, wherein the method or use comprises phenotyping the human as positive for a 214E hLIGHT polypeptide.
Optionally, the method comprises carrying out the phenotyping before administration of the antibody or fragment to the patient.
94. The method or use of any one of aspects 80 to 93, wherein the antibody or fragment is according to any one of aspects 1 to 63 or any example, configuration or embodiment described herein.
In an example of the antibody or fragment of the invention, the antibody or fragment specifically binds rabbit LIGHT protein (SEQ ID NO: 423) and human LIGHT protein (SEQ ID NO: 308), wherein binding affinity to human LIGHT extracellular protein is at least the affinity of binding to rabbit LIGHT extracellular protein, eg, 1-2 times the affinity of binding to rabbit LIGHT extracellular protein. Illustrative antibodies are shown in the Examples below. This feature is useful for pharmaceutical developing and testing in rabbit models of disease involving LIGHT.
95. The antibody, fragment, composition, kit, method or use of any preceding aspect, for treating or preventing an inflammatory or autoimmune disease or condition in a human or for reducing or preventing angiogenesis in a human.
96. The antibody, fragment, composition, kit, method or use of any preceding aspect, wherein the disease or condition is selected from the group consisting of an inflammatory bowel disease (IBD), Crohn's disease, rheumatoid arthritis, psoriasis, bronchiolitis, gingivitis, transplant rejection, allogenic transplant rejection, graft-versus-host disease (GvHD), asthma, adult respiratory distress syndrome (ARDS), septic shock, ulcerative colitis, Sjogren's syndrome and airway inflammation.

In an example, the disease or condition is a LIGHT-mediated disease or condition disclosed in EP1958637 or EP2034832.

In an example, the disease or condition is an inflammatory or autoimmune disease or condition.

As used herein, inflammatory disease or condition refers to pathological states resulting in inflammation, for example caused by neutrophil chemotaxis. Examples of such disorders include inflammatory skin diseases including psoriasis; responses associated with inflammatory bowel disease (such as Crohn's disease and ulcerative colitis); ischemic reperfusion; adult respiratory distress syndrome; dermatitis; meningitis; encephalitis; uveitis; autoimmune diseases such as rheumatoid arthritis, Sjogren's syndrome, vasculitis; diseases involving leukocyte diapedesis; central nervous system (CNS) inflammatory disorder, multiple organ injury syndrome secondary to septicemia or trauma; alcoholic hepatitis, bacterial pneumonia, antigen-antibody complex mediated diseases; inflammations of the lung, including pleurisy, alveolitis, vasculitis, pneumonia, chronic bronchitis, bronchiectasis, and cystic fibrosis; etc. The preferred indications are bacterial pneumonia and inflammatory bowel disease such as ulcerative colitis. The invention is thus in an example provided for treating or preventing any one or more of such conditions.

In an example, the disease or condition is schizophrenia.
In an example, the disease or condition is cancer.
As explained in the examples, the inventors devised a set of criteria that is particularly useful of identifying antibodies and fragments of the invention, these criteria being:—
(a) The ability of the antibody or fragment to bind cell-surface hLIGHT on CHO-S cells and/or bind recombinant hLIGHT in a HTRF assay;
(b) The ability of the antibody or fragment to neutralise human HVEM and/or LTβR in a receptor neutralisation HTRF assay and/or a flow cytometry receptor neutralisation assay; and
(c) The ability of the antibody or fragment to specifically bind both human and cynomolgus monkey LIGHT (useful so that the PK, PD, efficacy and other parameters of the antibody or fragment can be assessed in the cyno model as a surrogate for humans).

Thus, in an example of the invention the antibody or fragment meets criteria (a), (b) and (c).

In an example, criterion (a) is set so that the antibody or fragment shows <70% receptor binding to CHO-S LIGHT-214E cells by FACS.

In an example, criterion (a) is set so that the antibody or fragment shows <90% of receptor binding to LIGHT in the HTRF assay.

In an example, criterion (a) is set so that the antibody or fragment shows at least a 20% effect in the HTRF assay.

In an example, HVEM-Fc and/or LTβR-Fc is used in criterion (b).

In an embodiment, assaying or testing of an antibody or fragment of the invention is carried out at or substantially at pH7 (eg, for in vitro tests and assays) and at or substantially at rtp.

Optionally, the antibody or fragment specifically binds hLIGHT (eg, 214E hLIGHT) with an affinity (apparent affinity, Kd) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, eg, in the range of 1 mM to 1 pM (eg, 1 mM to 100 pM; 10 nM to 100 pM; 1 nM to 10 pM; or 100 pM to 1 pM) as determined by SPR, eg, under SPR conditions disclosed herein). Additionally or alternatively, the antibody or fragment specifically binds cynomolgus monkey LIGHT (eg, 214E cyno LIGHT) with an affinity (apparent affinity, Kd) of less than 1 microM, 1000 nM to 100 nM, 100 nM to 10 nM, 10 nM to 1 nM, 1000 pM to 500 pM, 500 pM to 200 pM, less than 200 pM, 200 pM to 150 pM, 200 pM to 100 pM, 100 pM to 10 pM, 10 pM to 1 pM, eg, in the range of 1 mM to 1 pM (eg, 1 mM to 100 pM; 10 nM to 100 pM; 1 nM to 10 pM; or 100 pM to 1 pM) as determined by SPR, eg, under SPR conditions disclosed herein). Such binding measurements can be made using a variety of binding assays known in the art, eg, using surface plasmon resonance (SPR), such as by Biacore™ or using the ProteOn XPR36™ (Bio-Rad®), or using KinExA® (Sapidyne Instruments, Inc).

In an example, the antibody or fragment can bind both 214E and 214K hLIGHT with similar apparent affinity (eg, with apparent affinities (Kd) that are no more than 2 fold different from each other). In another example, the antibody or fragment can bind 214E hLIGHT, but binds to 214K hLIGHT with an apparent affinity (Kd) that is ≥20 fold less than the apparent affinity for 214E hLIGHT or it does not bind to 214K hLIGHT (eg, as determined by SPR, eg, an SPR condition disclosed herein).

In an example, the antibody or fragment binds 214E and 21K hLIGHT, wherein the antibody or fragment binding to 214K hLIGHT is with a Kd (determined by SPR) that is at least 60, 70, 80, 90 or 95% of the Kd for binding to 21E hLIGHT.

LIGHT binding ability, specificity and affinity (Kd, $K_{off}$ and/or $K_{on}$) can be determined by any routine method in the art, eg, by surface plasmon resonance (SPR). The term "Kd", as used herein, is intended to refer to the equilibrium dissociation constant of a particular antibody-antigen interaction.

In one embodiment, the surface plasmon resonance (SPR) is carried out at 25° C. In another embodiment, the SPR is carried out at 37° C.

In one embodiment, the SPR is carried out at physiological pH, such as about pH7 or at pH7.6 (eg, using Hepes buffered saline at pH7.6 (also referred to as HBS-EP)).

In one embodiment, the SPR is carried out at a physiological salt level, eg, 150 mM NaCl.

In one embodiment, the SPR is carried out at a detergent level of no greater than 0.05% by volume, eg, in the presence of P20 (polysorbate 20; eg, Tween-20™) at 0.05% and EDTA at 3 mM.

In one example, the SPR is carried out at 25° C. or 37° C. in a buffer at pH7.6, 150 mM NaCl, 0.05% detergent (eg, P20) and 3 mM EDTA. The buffer can contain 10 mM Hepes. In one example, the SPR is carried out at 25° C. or 37° C. in HBS-EP. HBS-EP is available from Teknova Inc (California; catalogue number H8022).

In an example, the affinity of the antibody or fragment is determined using SPR by
1. Coupling anti-mouse (or other relevant human, rat or non-human vertebrate antibody constant region species-matched) IgG (eg, Biacore™ BR-1008-38) to a biosensor chip (eg, GLM chip) such as by primary amine coupling;
2. Exposing the anti-mouse IgG (or other matched species antibody) to a test IgG antibody to capture test antibody on the chip;
3. Passing the test antigen over the chip's capture surface at 1024 nM, 256 nM, 64 nM, 16 nM, 4 nM with a 0 nM (i.e. buffer alone); and
4. And determining the affinity of binding of test antibody to test antigen using surface plasmon resonance, eg, under an SPR condition discussed above (eg, at 25° C. in physiological buffer). SPR can be carried out using any standard SPR apparatus, such as by Biacore™ or using the ProteOn XPR36™ (Bio-Rad®).

Regeneration of the capture surface can be carried out with 10 mM glycine at pH1.7. This removes the captured antibody and allows the surface to be used for another interaction. The binding data can be fitted to 1:1 model inherent using standard techniques, eg, using a model inherent to the ProteOn XPR36™ analysis software.

In an example, the antibody or fragment of the invention is contained in a medical container, eg, a vial, syringe, IV container or an injection device (eg, an intraocular or intravitreal injection device). In an example, the antibody or fragment is in vitro, eg, in a sterile container. In an example, the invention provides a kit comprising the antibody or fragment of the invention, packaging and instructions for use in treating or preventing or diagnosing in a human a disease or condition mediated by the LIGHT. In an example, the instructions indicate that the human should be genotyped for a LIGHT variant sequence of the invention before administering the antibody or fragment to the human. In an example, the instructions indicate that the human should be phenotyped for a LIGHT variant of the invention before administering the antibody or fragment to the human. In an example, the human is of Chinese (eg, Han or CHS) ethnicity and the instructions are in Chinese (eg, Mandarin).

In an example the binding site(s) of the antibody or fragment are selected from a plurality (eg, library) of binding sites. For example, the plurality of binding sites comprises or consists of a plurality of 4-chain antibodies or fragments thereof, eg, dAbs, Fabs or scFvs. Suitable methods for producing pluralities of binding sites for screening include phage display (producing a phage display library of antibody binding sites), ribosome display (producing a ribosome display library of antibody binding sites), yeast display (producing a yeast display library of antibody binding sites), or immunisation of a non-human vertebrate (eg, a rodent, eg, a mouse or rat, eg, a Velocimouse™ Kymouse™, Xenomouse™, Aliva Mouse™, HuMab Mouse™, Omnimouse™, Omnirat™ or MeMo Mouse™) with LIGHT or a LLIGHT epitope and isolation of a repertoire of antibody-producing cells (eg, a B-cell, plasma cell or plasmablast repertoire) and/or a repertoire of isolated antibodies, fragments or binding sites.

The term "epitope" is a region of an antigen that is bound by an antibody or fragment. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

The term "isolated" with reference to any aspect of the invention, eg, an antibody or fragment, means that a subject antibody or fragment etc. (1) is free of at least some other proteins with which it would normally be found, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is operably associated (by covalent or noncovalent interaction) with a polypeptide with which it is not associated in nature, or (6) does not occur in nature. Typically, an "isolated" antibody, fragment, etc. constitutes at least about 5%, at least about 10%, at least about 25%, or at least about 50% of a given sample. Genomic DNA, cDNA, mRNA or other RNA, of synthetic origin, or any combination thereof can encode such an isolated antibody, fragment, etc. Preferably, the isolated antibody, fragment, etc. is substantially free from proteins or polypeptides or other contaminants that are found in its natural environment that would interfere with its therapeutic, diagnostic, prophylactic, research or other use.

For example, an "isolated" antibody is one that has been identified, separated and/or recovered from a component of its production environment (eg, naturally or recombinantly). Preferably, the isolated polypeptide is free of association with all other components from its production environment, eg, so that the antibody has been isolated to an FDA-approvable or approved standard. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant cells since at least one component of the antibody's natural environment will not be present. Ordinarily, however, an isolated polypeptide or antibody will be prepared by at least one purification step.

Immunoconjugates

The invention encompasses the antibody or fragment conjugated to a therapeutic moiety ("immunoconjugate"), such as a cytotoxin, a chemotherapeutic drug, an immunosuppressant or a radioisotope. Cytotoxin agents include any agent that is detrimental to cells. Examples of suitable cytotoxin agents and chemotherapeutic agents for forming immunoconjugates are known in the art, see for example, WO 05/103081, which is incorporated by reference herein in its entirety.

Bispecifics

The antibodies and fragments of the present invention may be monospecific, bispecific, or multispecific. Multispecific mAbs may be specific for different epitopes of one target polypeptide or may contain antigen-binding domains specific for more than one target polypeptide. See, e.g., Tutt et al. (1991) J. Immunol. 147:60-69. The human anti-hLIGHT antibodies or fragments can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment, to produce a bispecific or a multispecific antibody with a second binding specificity.

An exemplary bi-specific antibody format that can be used in the context of the present invention involves the use of a first immunoglobulin (Ig) CH3 domain and a second Ig CH3 domain, wherein the first and second Ig CH3 domains differ from one another by at least one amino acid, and wherein at least one amino acid difference reduces binding of the bispecific antibody to Protein A as compared to a bi-specific antibody lacking the amino acid difference. In one embodiment, the first Ig CH3 domain binds Protein A and the second Ig CH3 domain contains a mutation that reduces or abolishes Protein A binding such as an H95R modification (by IMGT exon numbering; H435R by EU numbering). The second CH3 may further comprise a Y96F modification (by IMGT; Y436F by EU). Further modifications that may be found within the second CH3 include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q and V422I by EU) in the case of IgG4 antibodies. Variations on the bi-specific antibody format described above are contemplated within the scope of the present invention.

In certain embodiments, the antibody or LIGHT binding fragment thereof comprises less than six CDRs. In some embodiments, the antibody or antigen binding fragment thereof comprises or consists of one, two, three, four, or five CDRs selected from the group consisting of HCDR1, HCDR2, HCDR3, LCDR1, LCDR2, and LCDR3. In specific embodiments, the antibody or antigen binding fragment thereof comprises or consists of one, two, three, four, or five CDRs selected from the group consisting of the HCDR1, HCDR2, HCDR3, LCDR1, LCDR2, and LCDR3 sequences in the sequence listing.

In specific embodiments, an antibody of the invention is a fully human antibody, a monoclonal antibody, a recombinant antibody, an antagonist antibody, an hLIGHT-neutralising antibody or any combination thereof or the invention provides an hLIGHT binding fragment thereof. In an example, the antibody is a chimaeric antibody comprising human variable domains and non-human (eg, mouse or rat or rabbit) constant domains. In particular embodiments, the antibody is a fully human antibody, such as a fully human monoclonal antibody, or antigen binding fragment thereof, that specifically binds to hLIGHT. In preferred embodiments, the antibody is an antagonist antibody. In preferred embodiments, the antibody is a neutralising antibody.

In an example, the antibody or fragment is a lambda-type antibody or fragment (i.e., whose variable domains are lambda variable domains). Optionally, the antibody or fragment also comprises lambda constant domains.

In certain embodiments, the antibody competes (e.g., in a dose dependent manner) with HVEM, LTβR, DcR3, or a fusion protein thereof (e.g., Fc:HVEM, Fc: LTβR or Fc:DcR3), for binding to hLIGHT, such as a cell surface-expressed hLIGHT or soluble hLIGHT. Exemplary competitive blocking tests are provided in the Examples herein.

In another aspect, provided herein are isolated nucleic acids encoding antibodies that specifically bind to a hLIGHT polypeptide (e.g., a cell surface-expressed or soluble hLIGHT), a hLIGHT polypeptide fragment, or a hLIGHT epitope. In certain embodiments, the nucleic acid encodes a VH chain, VL chain, VH domain, VL domain, HCDR1, HCDR2, HCDR3, LCDR1, LCDR2, and LCDR3 as disclosed in the sequence listing.

In another aspect, provided herein are vectors and host cells comprising nucleic acids encoding antibodies or fragments of the invention.

In certain embodiments, the antibody specifically binds to one or more single nucleotide polymorphism (SNP) variants of hLIGHT, such as hLIGHT comprising SNP 214E (referred to herein as "214E hLIGHT") and/or hLIGHT comprising SNP 214K (referred to herein as "214K hLIGHT"). In an example, the 214E hLIGHT comprises SNP 32S. In an example, the 214E hLIGHT comprises SNP 32L. In an example, the 214K hLIGHT comprises SNP 32S. In an example, the 214K hLIGHT comprises SNP 32L. LIGHT is a trimer of 3 monomer LIGHT polypeptides. Humans that are homozygous for SNP 214E produce subunit monomers that have the 214E SNP and thus hLIGHT (trimer) in these humans only comprises E at position 214 of its constituent subunits. Humans that are heterozygous for SNP 214K and 214E have the possibility to produce hLIGHT (trimer) that comprises a mixture of subunits differing at position 214. In an example of any aspect of the invention, the hLIGHT is a 214E hLIGHT that comprises a trimer of monomers, wherein each monomer comprises 214E (referred to herein as "214E hLIGHT trimer"). In another example of any aspect of the invention, the hLIGHT is a 214K hLIGHT that comprises a trimer of monomers, wherein each monomer comprises 214K (referred to herein as "214K hLIGHT trimer").

In an aspect, provided herein is a method for decreasing (eg, by at least 20, 30, 40 50 or 60%) or completely inhibiting binding of hLIGHT to one, more or all of HVEM, LTβR and DcR3 in a subject (e.g., a human subject), comprising administering to the subject an effective amount of an antibody or fragment thereof of the invention that specifically binds to 214E hLIGHT and/or 214K hLIGHT (e.g., a cell surface-expressed or soluble hLIGHT).

In an aspect, provided herein is a method of treating or preventing a hLIGHT-mediated disease or condition in a subject (eg, a human subject), the method comprising administering to the subject an effective amount of an antibody or fragment thereof of the invention that specifically binds to 214E hLIGHT and/or 214K hLIGHT (e.g., a cell surface-expressed or soluble hLIGHT), wherein the disease or condition is treated or prevented by the antibody or fragment. In an example, the method comprises decreasing or inhibiting a hLIGHT biological activity, such as secretion of one, more or all of IL-2, IL-8, TNF alpha and interferon gamma, in the subject. In an example, the biological activity is selected from the secretion of one, more or all of IL-2, TNF alpha and interferon gamma. In an example, the biological activity is selected from the secretion of one, more or all of IL-8, CCL20 and RANTES.

In an aspect, provided herein is a method of decreasing or inhibiting a hLIGHT biological activity, such as secretion of one, more or all of IL-2, IL-8, TNF alpha and interferon gamma, in a subject (e.g., a human subject), the method comprising administering to the subject an effective amount of an antibody or fragment thereof of the invention that specifically binds to 214E hLIGHT and/or 214K hLIGHT (e.g., a cell surface-expressed or soluble hLIGHT), wherein hLIGHT biological activity is decreased by the antibody or fragment. In an example, the biological activity is selected from the secretion of one, more or all of IL-2, TNF alpha and interferon gamma. In an example, the biological activity is selected from the secretion of one, more or all of IL-8, CCL20 and RANTES.

The term "about" or "approximately" means within 20%, preferably within 10%, and more preferably within 5% (or 1% or less) of a given value or range.

As used herein, "administer" or "administration" refers to the act of injecting or otherwise physically delivering a substance as it exists outside the body (e.g., an anti-hLIGHT antibody provided herein) into a patient, such as by mucosal, intradermal, intravenous, intramuscular delivery and/or any other method of physical delivery described herein or known in the art. When a disease, or a symptom thereof, is being treated, administration of the substance typically occurs after the onset of the disease or symptoms thereof. When a disease, or symptoms thereof, are being prevented, administration of the substance typically occurs before the onset of the disease or symptoms thereof.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences (e.g., amino acid sequences or nucleic acid sequences) can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264 2268, modified as in Karlin and Altschul, 1993, Proc. Natl. Acad. Sci. U.S.A. 90:5873 5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score 50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389 3402. Alternatively, PSI BLAST can be used to perform an iterated search which detects distant relationships between molecules (Id.). When utilizing BLAST, Gapped BLAST, and PSI Blast programs, the default parameters of the respective programs (e.g., of XBLAST and NBLAST) can be used (see, e.g., National Center for Biotechnology Information (NCBI) on the worldwide web, ncbi.nlm.nih.gov). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, an "antagonist" or "inhibitor" of hLIGHT refers to a ligand (eg, antibody or fragment) that is capable of inhibiting or otherwise decreasing one or more of the biological activities of hLIGHT, such as in a cell expressing hLIGHT or in a cell expressing a hLIGHT ligand, such as a hLIGHT receptor. For example, in certain embodiments, antibodies of the invention are antagonist antibodies that inhibit or otherwise decrease secretion of CCL20, IL-8 and/or RANTES from a cell having a cell surface-expressed hLIGHT receptor (e.g., HVEM, LTβR and/or DcR3) when said antibody is contacted with said cell. In some embodiments, an antagonist of hLIGHT (e.g., an antagonistic antibody of the invention) may, for example, act by inhibiting or otherwise decreasing the activation and/or cell signaling pathways of the cell expressing a hLIGHT receptor, thereby inhibiting a hLIGHT-mediated biological activity of the cell the relative to the hLIGHT-mediated biological activity in the absence of antagonist. In certain embodiments the antibodies provided herein are fully human, antagonistic anti-hLIGHT antibodies, preferably fully human, monoclonal, antagonistic anti-hLIGHT antibodies.

The term "antibody" and "immunoglobulin" or "Ig" may be used interchangeably herein. An antibody or a fragment thereof that specifically binds to a hLIGHT antigen may be cross-reactive with related antigens. Preferably, an antibody or a fragment thereof that specifically binds to a hLIGHT antigen does not cross-react with other antigens. An antibody or a fragment thereof that specifically binds to a hLIGHT antigen can be identified, for example, by immunoassays, BIAcore™, or other techniques known to those of skill in the art. An antibody or a fragment thereof binds specifically to a hLIGHT antigen when it binds to a hLIGHT antigen with higher affinity than to any cross-reactive antigen as determined using experimental techniques, such as radioimmunoassays (RIA) and enzyme-linked immunosorbent assays (ELISAs). Typically a specific or selective reaction will be at least twice background signal or noise and more typically more than 10 times background. See, e.g., Paul, ed., 1989, Fundamental Immunology Second Edition, Raven Press, New York at pages 332-336 for a discussion regarding antibody specificity.

Antibodies of the invention include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies of the present invention include immunoglobulin molecules and immunologically active portions of immunoglobulin molecules, i.e., antigen binding domains or molecules that contain an antigen-binding site that specifically binds to a hLIGHT antigen (e.g., one or more complementarity determining regions (CDRs) of an anti-hLIGHT antibody). The antibodies of the invention can be of any type (e.g., IgG, IgE, IgM, IgD, IgA and IgY), any class (e.g., IgG1, IgG2, IgG3, IgG4, IgA1 and IgA2), or any subclass (e.g., IgG2a and IgG2b) of immunoglobulin molecule. In preferred embodiments, the hLIGHT antibodies are fully human, such as fully human monoclonal hLIGHT antibodies. In certain embodiments, antibodies of the invention are IgG antibodies, or a class (e.g., human IgG1 or IgG4) or subclass thereof.

The term "antigen binding domain," "antigen binding region," "antigen binding fragment," and similar terms refer to that portion of an antibody which comprises the amino acid residues that interact with an antigen and confer on the binding agent its specificity and affinity for the antigen (e.g., the complementarity determining regions (CDR)). The antigen binding region can be derived from any animal species, such as rodents (e.g., rabbit, rat or hamster) and humans. Preferably, the antigen binding region will be of human origin.

As used herein, the term "composition" is intended to encompass a product containing the specified ingredients (e.g., an antibody of the invention) in, optionally, the specified amounts, as well as any product which results, directly or indirectly, from combination of the specified ingredients in, optionally, the specified amounts.

The term "constant region" or "constant domain" refers to a carboxy terminal portion of the LIGHT and heavy chain which is not directly involved in binding of the antibody to antigen but exhibits various effector function, such as interaction with the Fc receptor. The terms refer to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the LIGHT chain.

In the context of a polypeptide, the term "derivative" as used herein refers to a polypeptide that comprises an amino acid sequence of a hLIGHT polypeptide, a fragment of a hLIGHT polypeptide, or an antibody that specifically binds to a hLIGHT polypeptide which has been altered by the introduction of amino acid residue substitutions, deletions or additions. The term "derivative" as used herein also refers to a hLIGHT polypeptide, a fragment of a hLIGHT polypeptide, or an antibody that specifically binds to a hLIGHT polypeptide which has been chemically modified, e.g., by the covalent attachment of any type of molecule to the polypeptide. For example, but not by way of limitation, a hLIGHT polypeptide, a fragment of a hLIGHT polypeptide, or a hLIGHT antibody may be chemically modified, e.g., by glycosylation, acetylation, pegylation, phosphorylation, amidation, derivatization by known protecting/blocking groups, proteolytic cleavage, linkage to a cellular ligand or other protein, etc. The derivatives are modified in a manner that is different from naturally occurring or starting peptide or polypeptides, either in the type or location of the molecules attached. Derivatives further include deletion of one or more chemical groups which are naturally present on the peptide or polypeptide. A derivative of a hLIGHT polypeptide, a fragment of a hLIGHT polypeptide, or a hLIGHT antibody may be chemically modified by chemical modifications using techniques known to those of skill in the art, including, but not limited to specific chemical cleavage, acetylation, formulation, metabolic synthesis of tunicamycin, etc. Further, a derivative of a hLIGHT polypeptide, a fragment of a hLIGHT polypeptide, or a hLIGHT antibody may contain one or more non-classical amino acids. A polypeptide derivative possesses a similar or identical function as a hLIGHT polypeptide, a fragment of a hLIGHT polypeptide, or a hLIGHT antibody described herein.

The term "effective amount" as used herein refers to the amount of a therapy (e.g., an antibody or pharmaceutical composition provided herein) which is sufficient to reduce and/or ameliorate the severity and/or duration of a given disease and/or a symptom related thereto. This term also encompasses an amount necessary for the reduction or amelioration of the advancement or progression of a given disease, reduction or amelioration of the recurrence, development or onset of a given disease, and/or to improve or enhance the prophylactic or therapeutic effect(s) of another therapy (e.g., a therapy other than anti-hLIGHT antibody provided herein). In some embodiments, the effective amount of an antibody of the invention is from about 0.1 mg/kg (mg of antibody per kg weight of the subject) to about 100 mg/kg. In certain embodiments, an effective amount of an antibody provided therein is about 0.1 mg/kg, about 0.5 mg/kg, about 1 mg/kg, 3 mg/kg, 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 60 mg/kg, about 70 mg/kg, about 80 mg/kg about 90 mg/kg or about 100 mg/kg (or a range therein). In some embodiments, "effective amount" as used herein also refers to the amount of an antibody of the invention to achieve a specified result (e.g., inhibition of a hLIGHT biological activity of a cell, such as inhibition of secretion of CCL20, IL-8 or RANTES from the cell).

The term "epitope" as used herein refers to a localized region on the surface of an antigen, such as hLIGHT polypeptide or hLIGHT polypeptide fragment, that is capable of being bound to one or more antigen binding regions of an antibody, and that has antigenic or immunogenic activity in an animal, preferably a mammal, and most preferably in a human, that is capable of eliciting an immune response. An epitope having immunogenic activity is a portion of a polypeptide that elicits a antibody response in an animal. An epitope having antigenic activity is a portion of a polypeptide to which an antibody specifically binds as determined by any method well known in the art, for example, by the immunoassays described herein. Antigenic epitopes need not necessarily be immunogenic. Epitopes usually consist of chemically active surface groupings of molecules such as amino acids or sugar side chains and have specific three dimensional structural characteristics as well as specific charge characteristics. A region of a polypeptide contributing to an epitope may be contiguous amino acids of the polypeptide or the epitope may come together from two or more non-contiguous regions of the polypeptide The epitope may or may not be a three-dimensional surface feature of the antigen. In certain embodiments, a hLIGHT epitope is a three-dimensional surface feature of a hLIGHT polypeptide (e.g., in a trimeric form of a hLIGHT polypeptide). In other embodiments, a hLIGHT epitope is linear feature of a hLIGHT polypeptide (e.g., in a trimeric form or monomeric form of the hLIGHT polypeptide). Antibodies provided herein may specifically bind to an epitope of the monomeric (denatured) form of hLIGHT, an epitope of the trimeric (native) form of hLIGHT, or both the monomeric (denatured) form and the trimeric (native) form of hLIGHT. In specific embodiments, the antibodies provided herein specifically bind to an epitope of the trimeric form of hLIGHT but do not specifically bind the monomeric form of hLIGHT.

The term "excipients" as used herein refers to inert substances which are commonly used as a diluent, vehicle, preservatives, binders, or stabilizing agent for drugs and includes, but not limited to, proteins (e.g., serum albumin, etc.), amino acids (e.g., aspartic acid, glutamic acid, lysine, arginine, glycine, histidine, etc.), fatty acids and phospholipids (e.g., alkyl sulfonates, caprylate, etc.), surfactants (e.g., SDS, polysorbate, nonionic surfactant, etc.), saccharides (e.g., sucrose, maltose, trehalose, etc.) and polyols (e.g., mannitol, sorbitol, etc.). See, also, Remington's Pharmaceutical Sciences (1990) Mack Publishing Co., Easton, Pa., which is hereby incorporated by reference in its entirety.

In the context of a peptide or polypeptide, the term "fragment" as used herein refers to a peptide or polypeptide that comprises less than the full length amino acid sequence. Such a fragment may arise, for example, from a truncation at the amino terminus, a truncation at the carboxy terminus, and/or an internal deletion of a residue(s) from the amino acid sequence. Fragments may, for example, result from alternative RNA splicing or from in vivo protease activity. In certain embodiments, hLIGHT fragments include polypeptides comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least contiguous 100 amino acid residues, at least 125 contiguous amino acid residues, at least 150 contiguous amino acid residues, at least 175 contiguous amino acid residues, at least 200 contiguous amino acid residues, or at least 250 contiguous amino acid residues of the amino acid sequence of a hLIGHT polypeptide or an antibody that specifically binds to a hLIGHT polypeptide. In a specific embodiment, a fragment of a hLIGHT polypeptide or an antibody that specifically binds to a hLIGHT antigen retains at least 1, at least 2, or at least 3 functions of the polypeptide or antibody.

The terms "fully human antibody" or "human antibody" are used interchangeably herein and refer to an antibody that comprises a human variable region and, most preferably a human constant region. In specific embodiments, the terms refer to an antibody that comprises a variable region and constant region of human origin. "Fully human" anti-hLIGHT antibodies, in certain embodiments, can also encompass antibodies which bind hLIGHT polypeptides and are encoded by nucleic acid sequences which are naturally occurring somatic variants of human germline immunoglobulin nucleic acid sequence. In a specific embodiment, the anti-hLIGHT antibodies provided herein are fully human antibodies. The term "fully human antibody" includes antibodies having variable and constant regions corresponding to human germline immunoglobulin sequences as described by Kabat et al. (See Kabat et al. (1991) Sequences of Proteins of Immunological Interest, Fifth Edition, U.S. Department of Health and Human Services, NIH Publication No. 91-3242). Exemplary methods of producing fully human antibodies are provided, e.g., in the Examples herein, but any method known in the art may be used.

The phrase "recombinant human antibody" includes human antibodies that are prepared, expressed, created or isolated by recombinant means, such as antibodies expressed using a recombinant expression vector transfected into a host cell, antibodies isolated from a recombinant, combinatorial human antibody library, antibodies isolated from an animal (e.g., a mouse or cow) that is transgenic and/or transchromosomal for human immunoglobulin genes (see e.g., Taylor, L. D. et al. (1992) Nucl. Acids Res. 20:6287-6295) or antibodies prepared, expressed, created or isolated by any other means that involves splicing of human immunoglobulin gene sequences to other DNA sequences. Such recombinant human antibodies can have variable and constant regions derived from human germline immunoglobulin sequences (See Kabat, E. A. et al. (1991) Sequences of Proteins of Immunological Interest, Fifth Edition, U.S. Department of Health and Human Services, NIH Publication No. 91-3242). In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "fusion protein" as used herein refers to a polypeptide that comprises an amino acid sequence of an antibody and an amino acid sequence of a heterologous polypeptide or protein (i.e., a polypeptide or protein not normally a part of the antibody (e.g., a non-anti-hLIGHT antigen antibody)). The term "fusion" when used in relation to hLIGHT or to a anti-hLIGHT antibody refers to the joining of a peptide or polypeptide, or fragment, variant and/or derivative thereof, with a heterologous peptide or polypeptide. Preferably, the fusion protein retains the biological activity of the hLIGHT or anti-hLIGHT antibody. In certain embodiments, the fusion protein comprises a hLIGHT antibody VH domain, VL domain, VH CDR (one, two or three VH CDRs), and/or VL CDR (one, two or three VL CDRs), wherein the fusion protein specifically binds to a hLIGHT epitope.

The term "heavy chain" when used in reference to an antibody refers to five distinct types, called alpha (α), delta (δ), epsilon (ε), gamma (γ) and mu (μ), based on the amino acid sequence of the heavy chain constant domain. These distinct types of heavy chains are well known and give rise to five classes of antibodies, IgA, IgD, IgE, IgG and IgM, respectively, including four subclasses of IgG, namely IgG1, IgG1, IgG3 and IgG4. Preferably the heavy chain is a human heavy chain.

The term "host" as used herein refers to an animal, preferably a mammal, and most preferably a human.

The term "host cell" as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

The term "immunomodulatory agent" and variations thereof including, but not limited to, immunomodulatory agents, as used herein refer to an agent that modulates a host's immune system. In certain embodiments, an immunomodulatory agent is an immunosuppressant agent. In certain other embodiments, an immunomodulatory agent is an immunostimulatory agent. In accordance with the invention, an immunomodulatory agent used in the combination therapies of the invention does not include an anti-hLIGHT antibody or antigen-binding fragment. Immunomodulatory agents include, but are not limited to, small molecules, peptides, polypeptides, proteins, fusion proteins, antibodies, inorganic molecules, mimetic agents, and organic molecules.

As used herein, the term "in combination" in the context of the administration of other therapies refers to the use of more than one therapy. The use of the term "in combination" does not restrict the order in which therapies are administered to a subject with an infection. A first therapy can be administered before (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks), concurrently, or after (e.g., 1 minute, 45 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks) the administration of a second therapy to a subject which had, has, or is susceptible to a hLIGHT-mediated disease. Any additional therapy can be administered in any order with the other additional therapies. In certain embodiments, the antibodies of the invention can be administered in combination with one or more therapies (e.g., therapies that are not the antibodies of the invention that are currently administered to prevent, treat, manage, and/or ameliorate a hLIGHT-mediated disease. Non-limiting examples of therapies that can be administered in combination with an antibody of the invention include analgesic agents, anesthetic agents, antibiotics, or immunomodulatory agents or any other agent listed in the U.S. Pharmacopoeia and/or Physician's Desk Reference.

An "isolated" or "purified" antibody is for example substantially free of cellular material or other contaminating proteins from the cell or tissue source from which the antibody is derived, or substantially free of chemical precursors or other chemicals when chemically synthesized. The language "substantially free of cellular material" includes preparations of an antibody in which the antibody is separated from cellular components of the cells from which it is isolated or recombinantly produced. Thus, an antibody that is substantially free of cellular material includes preparations of antibody having less than about 30%, 20%, 10%, or 5% (by dry weight) of heterologous protein (also referred to herein as a "contaminating protein"). When the antibody is recombinantly produced, it is also preferably substantially free of culture medium, i.e., culture medium represents less than about 20%, 10%, or 5% of the volume of the protein preparation. When the antibody is produced by chemical synthesis, it is preferably substantially free of chemical precursors or other chemicals, i.e., it is separated from chemical precursors or other chemicals which are involved in the synthesis of the protein. Accordingly such preparations of the antibody have less than about 30%, 20%, 10%, 5% (by dry weight) of chemical precursors or compounds other than the antibody of interest. In a preferred embodiment, antibodies of the invention are isolated or purified.

An "isolated" nucleic acid molecule is one which is separated from other nucleic acid molecules which are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a specific embodiment, a nucleic acid molecule(s) encoding an antibody of the invention is isolated or purified.

The term "human LIGHT," "hLIGHT" or "hLIGHT polypeptide" and similar terms refers to the polypeptides ("polypeptides," "peptides" and "proteins" are used interchangeably herein) comprising the amino acid sequence in the sequence listing and related polypeptides, including SNP variants thereof. Related polypeptides include allelic variants (e.g., SNP variants); splice variants; fragments; derivatives; substitution, deletion, and insertion variants; fusion polypeptides; and interspecies homologs, preferably, which retain hLIGHT activity and/or are sufficient to generate an anti-hLIGHT immune response. Exemplary non-synonymous SNP variants include, but are not limited to, hLIGHT polypeptides comprising 214E-32S (a glutamic acid at position 214 and serine at position 32 of a hLIGHT polypeptide (e.g., the hLIGHT polypeptide depicted in SEQ ID NO:52)), 214K-32S, 214E-32L and 214E-32L. Also encompassed are soluble forms of hLIGHT which are sufficient to generate an anti-hLIGHT immunological response. As those skilled in the art will appreciate, an anti-hLIGHT antibody of the invention can bind to a hLIGHT polypeptide, polypeptide fragment, antigen, and/or epitope, as an epitope is part of the larger antigen, which is part of the larger polypeptide fragment, which, in turn, is part of the larger polypeptide hLIGHT can exist in a trimeric (native) or monomeric (denatured) form.

The terms "Kabat numbering," and like terms are recognized in the art and refer to a system of numbering amino acid residues which are more variable (i.e. hypervariable) than other amino acid residues in the heavy and LIGHT chain variable regions of an antibody, or an antigen binding portion thereof (Kabat et al. (1971) Ann. NY Acad. Sci. 190:382-391 and, Kabat et al. (1991) Sequences of Proteins of Immunological Interest, Fifth Edition, U.S. Department of Health and Human Services, NIH Publication No. 91-3242). For the heavy chain variable region, the hypervariable region typically ranges from amino acid positions 31 to 35 for CDR1, amino acid positions 50 to 65 for CDR2, and amino acid positions 95 to 102 for CDR3. For the LIGHT chain variable region, the hypervariable region typically ranges from amino acid positions 24 to 34 for CDR1, amino acid positions 50 to 56 for CDR2, and amino acid positions 89 to 97 for CDR3.

The term "LIGHT chain" when used in reference to an antibody refers to two distinct types, called kappa (κ) of lambda (λ) based on the amino acid sequence of the constant domains. LIGHT chain amino acid sequences are well known in the art. In preferred embodiments, the LIGHT chain is a human LIGHT chain.

The term "monoclonal antibody" refers to an antibody obtained from a population of homogenous or substantially homogeneous antibodies, and each monoclonal antibody will typically recognize a single epitope on the antigen. In preferred embodiments, a "monoclonal antibody," as used herein, is an antibody produced by a single hybridoma or other cell, wherein the antibody specifically binds to only a hLIGHT epitope as determined, e.g., by ELISA or other antigen-binding or competitive binding assay known in the art or in the Examples provided herein. The term "monoclonal" is not limited to any particular method for making the antibody. For example, monoclonal antibodies of the invention may be made by the hybridoma method as described in Kohler et al.; Nature, 256:495 (1975) or may be isolated from phage libraries using the techniques as described herein, for example. Other methods for the preparation of clonal cell lines and of monoclonal antibodies expressed thereby are well known in the art (see, for example, Chapter 11 in: Short Protocols in Molecular Biology, (2002) 5th Ed., Ausubel et al., eds., John Wiley and Sons, New York). Other exemplary methods of producing other monoclonal antibodies are provided in the Examples herein.

The term "naturally occurring" or "native" when used in connection with biological materials such as nucleic acid molecules, polypeptides, host cells, and the like, refers to those which are found in nature and not manipulated by a human being.

The term "pharmaceutically acceptable" as used herein means being approved by a regulatory agency of the Federal or a state government, or listed in the U.S. Pharmacopeia, European Pharmacopeia or other generally recognized Pharmacopeia for use in animals, and more particularly in humans.

"Polyclonal antibodies" as used herein refers to an antibody population generated in an immunogenic response to a protein having many epitopes and thus includes a variety of different antibodies directed to the same and to different epitopes within the protein. Methods for producing polyclonal antibodies are known in the art (See, e.g., see, for example, Chapter 11 in: Short Protocols in Molecular Biology, (2002) 5th Ed., Ausubel et al., eds., John Wiley and Sons, New York).

As used herein, the term "polynucleotide," "nucleotide," nucleic acid" "nucleic acid molecule" and other similar terms are used interchangeable and include DNA, RNA, mRNA and the like.

As used herein, the terms "prevent," "preventing," and "prevention" refer to the total or partial inhibition of the development, recurrence, onset or spread of a hLIGHT-mediated disease and/or symptom related thereto, resulting from the administration of a therapy or combination of therapies provided herein (e.g., a combination of prophylactic or therapeutic agents, such as an antibody of the invention).

As used herein, the term "prophylactic agent" refers to any agent that can totally or partially inhibit the development, recurrence, onset or spread of a hLIGHT-mediated disease and/or symptom related thereto in a subject. In certain embodiments, the term "prophylactic agent" refers to an antibody of the invention. In certain other embodiments, the term "prophylactic agent" refers to an agent other than an antibody of the invention. Preferably, a prophylactic agent is an agent which is known to be useful to or has been or is currently being used to prevent a hLIGHT-mediated disease and/or a symptom related thereto or impede the onset, development, progression and/or severity of a hLIGHT-mediated disease and/or a symptom related thereto. In specific embodiments, the prophylactic agent is a fully human anti-hLIGHT antibody, such as a fully human anti-hLIGHT monoclonal antibody.

A region of a hLIGHT contributing to an epitope may be contiguous amino acids of the polypeptide or the epitope may come together from two or more non-contiguous regions of the polypeptide The epitope may or may not be a three-dimensional surface feature of the antigen. A localized region on the surface of a hLIGHT antigen that is capable of eliciting an immune response is a hLIGHT epitope. The epitope may or may not be a three-dimensional surface feature of the antigen.

A "hLIGHT-mediated disease" and "hLIGHT-mediated condition" are used interchangeably and refer to any disease or condition that is completely or partially caused by or is the result of hLIGHT. In certain embodiments, hLIGHT is aberrantly (e.g., highly) expressed on the surface of a cell. In some embodiments, hLIGHT may be aberrantly upregulated on a particular cell type. In other embodiments, normal, aberrant or excessive cell signaling is caused by binding of hLIGHT to a hLIGHT ligand. In certain embodiments, the hLIGHT ligand is a hLIGHT receptor (e.g., HVEM, LTβR, or DCR3), for example, that is expressed on the surface of a cell, such as a colonic epithelial cell. In certain embodiments, the hLIGHT-mediated disease is an inflammatory bowel disease (IBD), such as Crohn's disease (CD) or ulcerative colitis (UC). In other embodiments, the hLIGHT-mediated disease is graft-versus-host disease (GVHD).

The terms "hLIGHT receptor" or "hLIGHT binding receptor" are used interchangeably herein and refer to a receptor polypeptide that binds to hLIGHT. In specific embodiments, the hLIGHT receptor is HVEM, FcβR or DcR3. In some embodiments, the hLIGHT receptor is expressed on the surface of a cell, such as a colonic epithelial cell.

As used herein, the terms "subject" and "patient" are used interchangeably. As used herein, a subject is preferably a mammal such as a non-primate (e.g., cows, pigs, horses, cats, dogs, rats, etc.) or a primate (e.g., monkey and human), most preferably a human. In one embodiment, the subject is a mammal, preferably a human, having a hLIGHT-mediated disease. In another embodiment, the subject is a mammal, preferably a human, at risk of developing a hLIGHT-mediated disease.

As used herein "substantially all" refers to refers to at least about 60%, at least about 70%, at least about 75%, at least about 80%, at least about 85%, at least about 90%, at least about 95%, at least about 98%, at least about 99%, or about 100%.

The term "substantially free of surfactant" as used herein refers to a formulation of an antibody that specifically binds to a hLIGHT antigen, said formulation containing less than 0.0005%, less than 0.0003%, or less than 0.0001% of surfactants and/or less than 0.0005%, less than 0.0003%, or less than 0.0001% of surfactants.

The term "substantially free of salt" as used herein refers to a formulation of an antibody that specifically binds to a hLIGHT antigen, said formulation containing less than 0.0005%, less than 0.0003%, or less than 0.0001% of inorganic salts.

The term "surfactant" as used herein refers to organic substances having amphipathic structures; namely, they are composed of groups of opposing solubility tendencies, typically an oil-soluble hydrocarbon chain and a water-soluble ionic group. Surfactants can be classified, depending on the charge of the surface-active moiety, into anionic, cationic, and nonionic surfactants. Surfactants are often used as wetting, emulsifying, solubilizing, and dispersing agents for various pharmaceutical compositions and preparations of biological materials.

As used herein, the term "tag" refers to any type of moiety that is attached to, e.g., a polypeptide and/or a polynucleotide that encodes a hLIGHT or hLIGHT antibody or antigen binding fragment thereof. For example, a polynucleotide that encodes a hLIGHT, hLIGHT antibody or antigen binding fragment thereof can contain one or more additional tag-encoding nucleotide sequences that encode a, e.g., a detectable moiety or a moiety that aids in affinity purification. When translated, the tag and the antibody can be in the form of a fusion protein. The term "detectable" or "detection" with reference to a tag refers to any tag that is capable of being visualized or wherein the presence of the tag is otherwise able to be determined and/or measured (e.g., by quantitation). A non-limiting example of a detectable tag is a fluorescent tag.

As used herein, the term "therapeutic agent" refers to any agent that can be used in the treatment, management or amelioration of a hLIGHT-mediated disease and/or a symptom related thereto. In certain embodiments, the term "therapeutic agent" refers to an antibody of the invention. In certain other embodiments, the term "therapeutic agent" refers to an agent other than an antibody of the invention. Preferably, a therapeutic agent is an agent which is known to be useful for, or has been or is currently being used for the treatment, management or amelioration of a hLIGHT-mediated disease or one or more symptoms related thereto. In specific embodiments, the therapeutic agent is a fully human anti-hLIGHT antibody, such as a fully human anti-hLIGHT monoclonal antibody.

The combination of therapies (e.g., use of prophylactic or therapeutic agents) which is more effective than the additive effects of any two or more single therapy. For example, a synergistic effect of a combination of prophylactic and/or therapeutic agents permits the use of lower dosages of one or more of the agents and/or less frequent administration of said agents to a subject with a hLIGHT-mediated disease. The ability to utilize lower dosages of prophylactic or therapeutic therapies and/or to administer said therapies less frequently reduces the toxicity associated with the administration of said therapies to a subject without reducing the efficacy of said therapies in the prevention, management, treatment or amelioration of a hLIGHT-mediated disease. In addition, a synergistic effect can result in improved efficacy of therapies in the prevention, or in the management, treatment or amelioration of a hLIGHT-mediated disease. Finally, synergistic effect of a combination of therapies (e.g., prophylactic or therapeutic agents) may avoid or reduce adverse or unwanted side effects associated with the use of any single therapy.

As used herein, the term "therapy" refers to any protocol, method and/or agent that can be used in the prevention, management, treatment and/or amelioration of a hLIGHT-mediated disease (e.g., IBD or GVHD). In certain embodiments, the terms "therapies" and "therapy" refer to a biological therapy, supportive therapy, and/or other therapies useful in the prevention, management, treatment and/or amelioration of a hLIGHT-mediated disease known to one of skill in the art such as medical personnel.

As used herein, the terms "treat," "treatment" and "treating" refer to the reduction or amelioration of the progression, severity, and/or duration of a hLIGHT-mediated disease (e.g., IBD or GVHD) resulting from the administration of one or more therapies (including, but not limited to, the administration of one or more prophylactic or therapeutic agents, such as an antibody of the invention). In specific embodiments, such terms refer to the reduction or inhibition of the binding of hLIGHT to HVEM, the reduction or inhibition of the binding of hLIGHT to LTβR, the reduction or inhibition of the binding of hLIGHT to DcR3, the reduction or inhibition of the production or secretion of CCL20 from a cell expressing a hLIGHT receptor of a subject, the reduction or inhibition of the production or secretion of IL-8 from a cell expressing a hLIGHT receptor of a subject, the reduction or inhibition of the production or secretion of RANTES from a cell expressing a hLIGHT receptor of a subject, and/or the inhibition or reduction of one or more symptoms associated with a hLIGHT-mediated disease, such as an IBD or GVHD. In specific embodiments, a prophylactic agent is a fully human anti-hLIGHT antibody, such as a fully human anti-hLIGHT monoclonal antibody.

The term "variable region" or "variable domain" refers to a portion of the LIGHT and heavy chains, typically about the amino-terminal 120 to 130 amino acids in the heavy chain and about 100 to 110 amino acids in the LIGHT chain, which differ extensively in sequence among antibodies and are used in the binding and specificity of each particular antibody for its particular antigen. The variability in sequence is concentrated in those regions called complimentarily determining regions (CDRs) while the more highly conserved regions in the variable domain are called framework regions (FR). The CDRs of the LIGHT and heavy chains are primarily responsible for the interaction of the antibody with antigen. Numbering of amino acid positions used herein is according to the EU Index, as in Kabat et al. (1991) Sequences of proteins of immunological interest. (U.S. Department of Health and Human Services, Washington, D.C.) 5th ed. ("Kabat et al."). In preferred embodiments, the variable region is a human variable region.

Antibodies

Antibodies of the invention include, but are not limited to, synthetic antibodies, monoclonal antibodies, recombinantly produced antibodies, multispecific antibodies (including bi-specific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above.

In particular, antibodies provided herein include immunoglobulin molecules and immunologically active portions of immunoglobulin molecules, i.e., molecules that contain an antigen binding site that specifically binds to a hLIGHT antigen. The immunoglobulin molecules provided herein can be of any type (e.g., IgG, IgE, IgM, IgD, IgA and IgY), class (e.g., IgG1, IgG2, IgG3, IgG4, IgA1 and IgA2) or subclass of immunoglobulin molecule. In a specific embodiment, an antibody provided herein is an IgG antibody, preferably an IgG1 or IgG4.

Variants and derivatives of antibodies include antibody fragments that retain the ability to specifically bind to an epitope. Preferred fragments include Fab fragments (an antibody fragment that contains the antigen-binding domain and comprises a LIGHT chain and part of a heavy chain bridged by a disulfide bond); Fab' (an antibody fragment containing a single anti-binding domain comprising an Fab and an additional portion of the heavy chain through the hinge region); F(ab')2 (two Fab' molecules joined by inter-chain disulfide bonds in the hinge regions of the heavy chains; the Fab' molecules may be directed toward the same or different epitopes); a bispecific Fab (a Fab molecule having two antigen binding domains, each of which may be directed to a different epitope); a single chain Fab chain comprising a variable region, also known as, a sFv (the variable, antigen-binding determinative region of a single LIGHT and heavy chain of an antibody linked together by a chain of 10-25 amino acids); a disulfide-linked Fv, or dsFv (the variable, antigen-binding determinative region of a single LIGHT and heavy chain of an antibody linked together by a disulfide bond); a camelized VH (the variable, antigen-binding determinative region of a single heavy chain of an antibody in which some amino acids at the VH interface are those found in the heavy chain of naturally occurring camel antibodies); a bispecific sFv (a sFv or a dsFv molecule having two antigen-binding domains, each of which may be directed to a different epitope); a diabody (a dimerized sFv formed when the VH domain of a first sFv assembles with the VL domain of a second sFv and the VL domain of the first sFv assembles with the VH domain of the second sFv; the two antigen-binding regions of the diabody may be directed towards the same or different epitopes); and a triabody (a trimerized sFv, formed in a manner similar to a diabody, but in which three antigen-binding domains are created in a single complex; the three antigen binding domains may be directed towards the same or different epitopes). Derivatives of antibodies also include one or more CDR sequences of an antibody combining site. The CDR sequences may be linked together on a scaffold when two or more CDR sequences are present. In certain embodiments, the antibody to be used with the invention comprises a single-chain Fv ("scFv"). scFvs are antibody fragments comprising the VH and VL domains of an antibody, wherein these domains are present in a single polypeptide chain. Generally, the scFv polypeptide further comprises a polypeptide linker between the VH and VL domains which enables the scFv to form the desired structure for antigen binding. For a review of scFvs see Pluckthun in The Pharmacology of Monoclonal Antibodies, vol. 113, Rosenburg and Moore eds. Springer-Verlag, New York, pp. 269-315 (1994).

The antibodies of the invention may be from any animal origin including birds and mammals (e.g., human, murine, donkey, sheep, rabbit, goat, guinea pig, camel, horse, or chicken). In certain embodiments, the antibodies of the invention are human or humanized monoclonal antibodies. As used herein, "human" antibodies include antibodies having the amino acid sequence of a human immunoglobulin and include antibodies isolated from human immunoglobulin libraries or from mice that express antibodies from human genes.

In preferred embodiments, the antibodies of the invention are fully human antibodies, such as fully human antibodies that specifically bind a hLIGHT polypeptide, a hLIGHT polypeptide fragment, or a hLIGHT epitope. Such fully human antibodies would be advantageous over fully mouse (or other full or partial non-human species antibodies), humanized antibodies, or chimeric antibodies to minimize the development of unwanted or unneeded side effects, such as immune responses directed toward non-fully human antibodies (e.g., anti-hLIGHT antibodies derived from other species) when administered to the subject.

The antibodies of the present invention may be monospecific, bispecific, trispecific or of greater multispecificity. Multispecific antibodies may be specific for different epitopes of a hLIGHT polypeptide or may be specific for both a hLIGHT polypeptide as well as for a heterologous epitope, such as a heterologous polypeptide or solid support material. In preferred embodiments, the antibodies provided herein are monospecific for a given epitope of a hLIGHT polypeptide and do not specifically bind to other epitopes.

Also provided herein is a B-cell (eg, an immortalised B-cell) or a hybridoma that produces an anti-hLIGHT antibody or fragment described herein.

In certain embodiments, an isolated antibody is provided herein that specifically binds to a hLIGHT epitope wherein the binding to the hLIGHT epitope by the antibody is competitively blocked (e.g., in a dose-dependent manner) by: an antibody or fragment of the invention. The antibody may or may not be a fully human antibody. In preferred embodiments, the antibody is a fully human monoclonal anti-hLIGHT antibody, and even more preferably a fully human, monoclonal, antagonist anti-hLIGHT antibody. Exemplary competitive blocking tests that can be used are provided in the Examples herein.

In some embodiments, the antibody or fragment of the invention competes (e.g., in a dose-dependent manner) with HVEM, LTβR and/or DcR3 (or fusion protein(s) thereof) for binding to cell surface-expressed hLIGHT. In other embodiments, the antibody or fragment of the invention competes (e.g., in a dose-dependent manner) with HVEM, LTβR and/or DcR3 (or fusion protein(s) thereof) for binding to soluble hLIGHT. Exemplary competitive binding assays that can be used are provided in the Examples herein. In one embodiment, the antibody or fragment partially or completely inhibits binding of HVEM, LTβR and/or DcR3 to cell surface-expressed hLIGHT, such as hLIGHT. In another embodiment, the antibody partially or completely inhibits binding of HVEM, LTβR and/or DcR3 to soluble hLIGHT.

In some embodiments, the antibody or fragment partially or completely inhibits the secretion of CCL20, IL-8, and/or RANTES from a cell having cell surface-expressed hLIGHT ligand, such as a hLIGHT receptor (e.g., HVEM, LTβR and/or DcR3). In certain embodiments, the cell expressing the hLIGHT receptor is a colonic epithelial cell.

Preferably, the antibodies of the invention are fully human, monoclonal antibodies, such as fully human, monoclonal antagonist antibodies, that specifically bind to hLIGHT.

In some embodiments, the antibody or fragment provided herein binds to a hLIGHT epitope that is a three-dimensional surface feature of a hLIGHT polypeptide (e.g., in a trimeric form of a hLIGHT polypeptide). A region of a hLIGHT polypeptide contributing to an epitope may be contiguous amino acids of the polypeptide or the epitope may come together from two or more non-contiguous regions of the polypeptide A hLIGHT epitope may be present in (a) the trimeric form ("a trimeric hLIGHT epitope") of hLIGHT, (b) the monomeric form ("a monomeric hLIGHT epitope") of hLIGHT, (c) both the trimeric and monomeric form of hLIGHT, (d) the trimeric form, but not the monomeric form of hLIGHT, or (e) the monomeric form, but not the trimeric form of hLIGHT.

For example, in some embodiments, the epitope is only present or available for binding in the trimeric (native) form, but is not present or available for binding in the monomeric (denatured) form by an anti-hLIGHT antibody. In other embodiments, the hLIGHT epitope is linear feature of the hLIGHT polypeptide (e.g., in a trimeric form or monomeric form of the hLIGHT polypeptide). Antibodies provided herein may specifically bind to (a) an epitope of the monomeric form of hLIGHT, (b) an epitope of the trimeric form of hLIGHT, (c) an epitope of the monomeric but not the trimeric form of hLIGHT, (d) an epitope of the trimeric but not the monomeric form of hLIGHT, or (e) both the monomeric form and the trimeric form of hLIGHT. In preferred embodiments, the antibodies provided herein specifically bind to an epitope of the trimeric form of hLIGHT but do not specifically bind to an epitope the monomeric form of hLIGHT.

The present invention also provides antibodies that specifically bind to a hLIGHT epitope, the antibodies comprising derivatives of the VH domains, VH CDRs, VL domains, and VL CDRs described herein that specifically bind to a hLIGHT antigen. The present invention also provides antibodies comprising derivatives of antibodies disclosed in the Examples, wherein said antibodies specifically bind to a hLIGHT epitope. Standard techniques known to those of skill in the art can be used to introduce mutations in the nucleotide sequence encoding a molecule of the invention, including, for example, site-directed mutagenesis and PCR-mediated mutagenesis which results in amino acid substitutions. Preferably, the derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original molecule. In a preferred embodiment, the derivatives have conservative amino acid substitutions are made at one or more predicted non-essential amino acid residues. Alternatively, mutations can be introduced randomly along all or part of the coding sequence, such as by saturation mutagenesis, and the resultant mutants can be screened for biological activity to identify mutants that retain activity. Following mutagenesis, the encoded protein can be expressed and the activity of the protein can be determined.

In another embodiment, an antibody that specifically binds to a hLIGHT epitope comprises a variable domain amino acid sequence that is at least 35%, at least 40%, at least 45%, at least 50%, at least 55%, at least 60%, at least 65%, at least 70%, at least 75%, at least 80%, at least 85%, at least 90%, at least 95%, or at least 99% identical to a variable domain amino acid sequence of the sequence listing.

In specific embodiments, the antibody is a fully human anti-human antibody, such as a fully human monoclonal antibody. Fully human antibodies may be produced by any method known in the art. Exemplary methods include immunization with a hLIGHT antigen (any hLIGHT polypeptide capable of eliciting an immune response, and optionally conjugated to a carrier) of transgenic animals (e.g., mice) that are capable of producing a repertoire of human antibodies in the absence of endogenous immunoglobulin production; see, e.g., Jakobovits et al., (1993) Proc. Natl. Acad. Sci., 90:2551; Jakobovits et al., (1993) Nature, 362:255 258 (1993); Bruggermann et al., (1993) Year in Immunol., 7:33. Other methods of producing fully human anti-hLIGHT antibodies can be found in the Examples provided herein.

Alternatively, fully human antibodies may be generated through the in vitro screening of phage display antibody libraries; see e.g., Hoogenboom et al., J. Mol. Biol., 227:381 (1991); Marks et al., J. Mol. Biol., 222:581 (1991), incorporated herein by reference. Various antibody-containing phage display libraries have been described and may be readily prepared by one skilled in the art. Libraries may contain a diversity of human antibody sequences, such as human Fab, Fv, and scFv fragments, that may be screened against an appropriate target.

The antibodies and fragments of the invention include antibodies and fragments that are chemically modified, i.e., by the covalent attachment of any type of molecule to the antibody. For example, but not by way of limitation, the antibody derivatives include antibodies that have been chemically modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formulation, metabolic synthesis of tunicamycin, etc. Additionally, the antibody may contain one or more non-classical amino acids.

The present invention also provides antibodies that specifically bind to a hLIGHT antigen which comprise a framework region known to those of skill in the art (e.g., a human or non-human fragment). The framework region may, for example, be naturally occurring or consensus framework regions. Most preferably, the framework region of an antibody of the invention is human (see, e.g., Chothia et al., 1998, J. Mol. Biol. 278:457-479 for a listing of human framework regions, which is incorporated by reference herein in its entirety). See also Kabat et al. (1991) Sequences of Proteins of Immunological Interest (U.S. Department of Health and Human Services, Washington, D.C.) 5th ed.

In a specific embodiment, the present invention provides for antibodies that specifically bind to a hLIGHT antigen, said antibodies comprising the amino acid sequence of one or more of the CDRs in the sequence listing and human framework regions with one or more amino acid substitutions at one, two, three or more of the following residues: (a) rare framework residues that differ between the murine antibody framework (i.e., donor antibody framework) and the human antibody framework (i.e., acceptor antibody framework); (b) Vernier zone residues when differing between donor antibody framework and acceptor antibody framework; (c) interchain packing residues at the VH/VL interface that differ between the donor antibody framework and the acceptor antibody framework; (d) canonical residues which differ between the donor antibody framework and the acceptor antibody framework sequences, particularly the framework regions crucial for the definition of the canonical class of the murine antibody CDR loops; (e) residues that are adjacent to a CDR; (g) residues capable of interacting with the antigen; (h) residues capable of interacting with the CDR; and (i) contact residues between the VH domain and the VL domain. In certain embodiments, antibodies that specifically bind to a hLIGHT antigen comprising the human framework regions with one or more amino acid substitutions at one, two, three or more of the above-identified residues are antagonistic hLIGHT antibodies.

The present invention encompasses antibodies that specifically bind to a hLIGHT antigen, said antibodies comprising the amino acid sequence of the VH domain and/or VL domain in the sequence listing but having mutations (e.g., one or more amino acid substitutions) in the framework regions. In certain embodiments, antibodies that specifically bind to a hLIGHT antigen comprise the amino acid sequence of the VH domain and/or VL domain or an antigen-binding fragment thereof of an antibody disclosed in the Examples with one or more amino acid residue substitutions in the framework regions of the VH and/or VL domains.

In some embodiments, antibodies provided herein decrease or inhibit binding of hLIGHT to HVEM, LTβR and/or DcR3, and/or decrease or inhibit a hLIGHT biological activity, such as secretion of CCL20, IL8 and/or RANTES, in subject (e.g., a human subject). In certain embodiments, antibodies provided herein, such as a human monoclonal anti-hLIGHT antibody, decreases or inhibits binding of a soluble or cell-surface expressed hLIGHT to HVEM or LTβR, and/or decreases or inhibits secretion of CCL20 and/or RANTES after contact with a soluble or cell-surface expressed hLIGHT, in a subject. In some embodiments, the hLIGHT is a SNP variant of hLIGHT, such as 214E-32S, 214K-32S, 214E-32L or 214K-32L. Blocking activity of an antibody provided herein of hLIGHT binding to HVEM, LTβR and/or DCR3 can be detected using an assay as described in the Examples. Inhibition of biological activity of cells expressing a hLIGHT receptor by a hLIGHT antibody provided herein can be detected using an assay as described in the Examples.

The present invention also provides for fusion proteins comprising an antibody provided herein that specifically binds to a hLIGHT antigen and a heterologous polypeptide. In some embodiments, the heterologous polypeptide to which the antibody is fused is useful for targeting the antibody to cells having cell surface-expressed hLIGHT.

Antibody Conjugates and Fusion Proteins

The following discussion on conjugates and fusion proteins also applies to fragments so that disclosure mentioning antibodies can also apply mutatis mutandis to fragments of the invention.

In some embodiments, antibodies of the invention are conjugated or recombinantly fused to a diagnostic, detectable or therapeutic agent or any other molecule. The conjugated or recombinantly fused antibodies can be useful, e.g., for monitoring or prognosing the onset, development, progression and/or severity of a hLIGHT-mediated disease as part of a clinical testing procedure, such as determining the efficacy of a particular therapy.

Such diagnosis and detection can accomplished, for example, by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Sn; and positron emitting metals using various positron emission tomographies, and non-radioactive paramagnetic metal ions.

The present invention further encompasses uses of the antibodies of the invention conjugated or recombinantly fused to a therapeutic moiety (or one or more therapeutic moieties). The antibody may be conjugated or recombinantly fused to a therapeutic moiety, such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Therapeutic moieties include, but are not limited to, antimetabolites (e.g., methotrexate, 6-mercaptopurine, 6-thioguanine, cytarabine, 5-fluorouracil decarbazine); alkylating agents (e.g., mechlorethamine, thioepa chlorambucil, melphalan, carmustine (BCNU) and lomustine (CCNU), cyclothosphamide, busulfan, dibromomannitol, streptozotocin, mitomycin C, and cisdichlorodiamine platinum (II) (DDP), and cisplatin); anthracyclines (e.g., daunorubicin (formerly daunomycin) and doxorubicin); antibiotics (e.g., d actinomycin (formerly actinomycin), bleomycin, mithramycin, and anthramycin (AMC)); Auristatin molecules (e.g., auristatin PHE, bryostatin 1, and solastatin 10; see Woyke et al., Antimicrob. Agents Chemother. 46:3802-8 (2002), Woyke et al., Antimicrob. Agents Chemother. 45:3580-4 (2001), Mohammad et al., Anticancer Drugs 12:735-40 (2001), Wall et al., Biochem. Biophys. Res. Commun 266: 76-80 (1999), Mohammad et al., Int. J. Oncol. 15:367-72 (1999), all of which are incorporated herein by reference); hormones (e.g., glucocorticoids, progestins, androgens, and estrogens), DNA-repair enzyme inhibitors (e.g., etoposide or topotecan), kinase inhibitors (e.g., compound ST1571, imatinib mesylate (Kantarjian et al., Clin Cancer Res. 8(7): 2167-76 (2002)); cytotoxic agents (e.g., paclitaxel, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucorticoids, procaine, tetracaine, lidocaine, propranolol, and puromycin and analogs or homologs thereof and those compounds disclosed in U.S. Pat. Nos. 6,245,759, 6,399,633, 6,383,790, 6,335,156, 6,271,242, 6,242,196, 6,218,410, 6,218,372, 6,057,300, 6,034,053, 5,985,877, 5,958,769, 5,925,376, 5,922,844, 5,911,995, 5,872,223, 5,863,904, 5,840,745, 5,728,868, 5,648,239, 5,587,459); farnesyl transferase inhibitors (e.g., R115777, BMS-214662, and those disclosed by, for example, U.S. Pat. Nos. 6,458,935, 6,451,812, 6,440,974, 6,436,960, 6,432,959, 6,420,387, 6,414,145, 6,410,541, 6,410,539, 6,403,581, 6,399,615, 6,387,905, 6,372,747, 6,369,034, 6,362,188, 6,342,765, 6,342,487, 6,300,501, 6,268,363, 6,265,422, 6,248,756, 6,239,140, 6,232,338, 6,228,865, 6,228,856, 6,225,322, 6,218,406, 6,211,193, 6,187,786, 6,169,096, 6,159,984, 6,143,766, 6,133,303, 6,127,366, 6,124,465, 6,124,295, 6,103,723, 6,093,737, 6,090,948, 6,080,870, 6,077,853, 6,071,935, 6,066,738, 6,063,930, 6,054,466, 6,051,582, 6,051,574, and 6,040,305); topoisomerase inhibitors (e.g., camptothecin; irinotecan; SN-38; topotecan; 9-aminocamptothecin; GG-211 (GI 147211); DX-8951f; IST-622; rubitecan; pyrazoloacridine; XR-5000; saintopin; UCE6; UCE1022; TAN-1518A; TAN 1518B; KT6006; KT6528; ED-110; NB-506; ED-110; NB-506; and rebeccamycin); bulgarein; DNA minor groove binders such as Hoescht dye 33342 and Hoechst dye 33258; nitidine; fagaronine; epiberberine; coralyne; beta-lapachone; BC-4-1; bisphosphonates (e.g., alendronate, cimadronte, clodronate, tiludronate, etidronate, ibandronate, neridronate, olpandronate, risedronate, piridronate, pamidronate, zolendronate) HMG-CoA reductase inhibitors, (e.g., lovastatin, simvastatin, atorvastatin, pravastatin, fluvastatin, statin, cerivastatin, lescol, lupitor, rosuvastatin and atorvastatin); antisense oligonucleotides (e.g., those disclosed in the U.S. Pat. Nos. 6,277,832, 5,998,596, 5,885,834, 5,734,033, and 5,618,709); adenosine deaminase inhibitors (e.g., Fludarabine phosphate and 2-Chlorodeoxyadenosine); ibritumomab tiuxetan (Zevalin®); tositumomab (Bexxar®)) and pharmaceutically acceptable salts, solvates, clathrates, and prodrugs thereof.

Further, an antibody of the invention may be conjugated or recombinantly fused to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *pseudomonas* exotoxin, cholera toxin, or diphtheria toxin; a protein such as tumor necrosis factor, γ-interferon, α-interferon, nerve growth factor, platelet derived growth factor, tissue plasminogen activator, an apoptotic agent, e.g., TNF-γ, TNF-γ, AIM I (see, International Publication No. WO 97/33899), AIM II (see, International Publication No. WO 97/34911), Fas Ligand (Takahashi et al., 1994, J. Immunol., 6:1567-1574), and VEGF (see, International Publication No. WO 99/23105), an anti-angiogenic agent, e.g., angiostatin, endostatin or a component of the coagulation pathway (e.g., tissue factor); or, a biological response modifier such as, for example, a lymphokine (e.g., interferon gamma, interleukin-1 ("IL-"), interleukin-2 ("IL-2"), interleukin-5 ("IL-5"), interleukin-6 ("IL-6"), interleukin-7 ("IL-7"), interleukin 9 ("IL-9"), interleukin-10 ("IL-10"), interleukin-12 ("IL-12"), interleukin-15 ("IL-15"), interleukin-23 ("IL-23"), granulocyte macrophage colony stimulating factor ("GM-CSF"), and granulocyte colony stimulating factor ("G-CSF")), or a growth factor (e.g., growth hormone ("GH")), or a coagulation agent (e.g., calcium, vitamin K, tissue factors, such as but not limited to, Hageman factor (factor XII), high-molecular-weight kininogen (HMWK), prekallikrein (PK), coagulation proteins-factors II (prothrombin), factor V, XIIa, VIII, XIIIa, XI, XIa, IX, IXa, X, phospholipid, and fibrin monomer).

The present invention encompasses antibodies of the invention recombinantly fused or chemically conjugated (covalent or non-covalent conjugations) to a heterologous protein or polypeptide (or fragment thereof, preferably to a polypeptide of about 10, about 20, about 30, about 40, about 50, about 60, about 70, about 80, about 90 or about 100 amino acids) to generate fusion proteins. In particular, the invention provides fusion proteins comprising an antigen-binding fragment of an antibody of the invention (e.g., a Fab fragment, Fd fragment, Fv fragment, F(ab)2 fragment, a VH domain, a VH CDR, a VL domain or a VL CDR) and a heterologous protein, polypeptide, or peptide. In one embodiment, the heterologous protein, polypeptide, or peptide that the antibody is fused to is useful for targeting the antibody to a particular cell type, such as a cell that expresses hLIGHT or an hLIGHT receptor. For example, an antibody that specifically binds to a cell surface receptor expressed by a particular cell type (e.g., an immune cell) may be fused or conjugated to a modified antibody of the invention.

A conjugated or fusion protein of the invention comprises any antibody of the invention described herein and a heterologous polypeptide. In one embodiment, a conjugated or fusion protein of the invention comprises the variable domains of an antibody disclosed in the Examples and a heterologous polypeptide.

In addition, an antibody of the invention can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, Clin Cancer Res. 4(10):2483-90; Peterson et al., 1999, Bioconjug. Chem. 10(4):553-7; and Zimmerman et al., 1999, Nucl. Med. Biol. 26(8):943-50, each incorporated by reference in their entireties.

Moreover, antibodies of the invention can be fused to marker sequences, such as a peptide to facilitate purification. In preferred embodiments, the marker amino acid sequence is a hexa-histidine peptide (SEQ ID NO: 424), such as the tag provided in a pQE vector (QIAGEN, Inc.), among others, many of which are commercially available. As described in Gentz et al., 1989, Proc. Natl. Acad. Sci. USA 86:821-824, for instance, hexa-histidine (SEQ ID NO: 424) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "FLAG" tag.

Methods for fusing or conjugating therapeutic moieties (including polypeptides) to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al.

(eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), Thorpe et al., 1982, Immunol. Rev. 62:119-58; U.S. Pat. Nos. 5,336,603, 5,622,929, 5,359,046, 5,349,053, 5,447,851, 5,723,125, 5,783,181, 5,908,626, 5,844,095, and 5,112,946; EP 307,434; EP 367, 166; EP 394,827; PCT publications WO 91/06570, WO 96/04388, WO 96/22024, WO 97/34631, and WO 99/04813; Ashkenazi et al., Proc. Natl. Acad. Sci. USA, 88: 10535-10539, 1991; Traunecker et al., Nature, 331:84-86, 1988; Zheng et al., J. Immunol., 154:5590-5600, 1995; Vil et al., Proc. Natl. Acad. Sci. USA, 89:11337-11341, 1992, which are incorporated herein by reference in their entireties.

Fusion proteins may be generated, for example, through the techniques of gene-shuffling, motif-shuffling, exon-shuffling, and/or codon-shuffling (collectively referred to as "DNA shuffling"). DNA shuffling may be employed to alter the activities of antibodies of the invention (e.g., antibodies with higher affinities and lower dissociation rates). See, generally, U.S. Pat. Nos. 5,605,793, 5,811,238, 5,830,721, 5,834,252, and 5,837,458; Patten et al., 1997, Curr. Opinion Biotechnol. 8:724-33; Harayama, 1998, Trends Biotechnol. 16(2):76-82; Hansson et al., 1999, J. Mol. Biol. 287:265-76; and Lorenzo and Blasco, 1998, Biotechniques 24(2):308-313 (each of these patents and publications are hereby incorporated by reference in its entirety). Antibodies, or the encoded antibodies, may be altered by being subjected to random mutagenesis by error-prone PCR, random nucleotide insertion or other methods prior to recombination. A polynucleotide encoding an antibody of the invention may be recombined with one or more components, motifs, sections, parts, domains, fragments, etc. of one or more heterologous molecules.

An antibody of the invention can also be conjugated to a second antibody to form an antibody heteroconjugate as described in U.S. Pat. No. 4,676,980, which is incorporated herein by reference in its entirety.

The therapeutic moiety or drug conjugated or recombinantly fused to an antibody of the invention that specifically binds to a hLIGHT antigen should be chosen to achieve the desired prophylactic or therapeutic effect(s). In certain embodiments, the antibody is a modified antibody. A clinician or other medical personnel should consider the following when deciding on which therapeutic moiety or drug to conjugate or recombinantly fuse to an antibody of the invention: the nature of the disease, the severity of the disease, and the condition of the subject.

Antibodies of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Pharmaceutical Compositions

The following discussion on compositions also applies to fragments so that disclosure mentioning antibodies can also apply mutatis mutandis to fragments of the invention.

Therapeutic formulations containing one or more antibodies of the invention provided herein can be prepared for storage by mixing the antibody having the desired degree of purity with optional physiologically acceptable carriers, excipients or stabilizers (Remington's Pharmaceutical Sciences (1990) Mack Publishing Co., Easton, Pa.), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The antibodies of the invention provided herein can also, for example, be formulated in liposomes. Liposomes containing the molecule of interest are prepared by methods known in the art, such as described in Epstein et al. (1985) Proc. Natl. Acad. Sci. USA 82:3688; Hwang et al. (1980) Proc. Natl. Acad. Sci. USA 77:4030; and U.S. Pat. Nos. 4,485,045 and 4,544,545. Liposomes with enhanced circulation time are disclosed in U.S. Pat. No. 5,013,556.

Particularly useful immunoliposomes can be generated by the reverse phase evaporation method with a lipid composition containing phosphatidylcholine, cholesterol and PEG-derivatized phosphatidylethanolamine (PEG-PE). Liposomes are extruded through filters of defined pore size to yield liposomes with the desired diameter. Fab' fragments of an antibody provided herein can be conjugated to the liposomes as described in Martin et al. (1982) J. Biol. Chem. 257:286-288 via a disulfide interchange reaction. A chemotherapeutic agent (such as Doxorubicin) is optionally contained within the liposome; See Gabizon et al., (1989) J. National Cancer Inst. 81(19):1484.

Formulations, such as those described herein, can also contain more than one active compound as necessary for the particular indication being treated. In certain embodiments, formulations comprise an antibody of the invention and one or more active compounds with complementary activities that do not adversely affect each other. Such molecules are suitably present in combination in amounts that are effective for the purpose intended. For example, an antibody of the invention can be combined with one or more other therapeutic agents. Such combined therapy can be administered to the patient serially or simultaneously or in sequence.

An antibody of the invention can also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (1990) Mack Publishing Co., Easton, Pa.

The formulations to be used for in vivo administration can be sterile. This is readily accomplished by filtration through, e.g., sterile filtration membranes.

Sustained-release preparations can also be prepared. Suitable examples of sustained-release preparations include semipermeable matrices of solid hydrophobic polymers containing the antagonist, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The pharmaceutical compositions provided herein contain therapeutically effective amounts of one or more of the antibodies of the invention provided herein, and optionally one or more additional prophylactic of therapeutic agents, in a pharmaceutically acceptable carrier. Such pharmaceutical compositions are useful in the prevention, treatment, management or amelioration of a hLIGHT-mediated disease, such as an inflammatory bowel disease, or one or more of the symptoms thereof.

Pharmaceutical carriers suitable for administration of the compounds provided herein include any such carriers known to those skilled in the art to be suitable for the particular mode of administration.

In addition, the antibodies of the invention may be formulated as the sole pharmaceutically active ingredient in the composition or may be combined with other active ingredients (such as one or more other prophylactic or therapeutic agents).

The compositions can contain one or more antibodies of the invention. In one embodiment, the antibodies are formulated into suitable pharmaceutical preparations, such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. In one embodiment, the antibodies described above are formulated into pharmaceutical compositions using techniques and procedures well known in the art (see, e.g., Ansel (1985) Introduction to Pharmaceutical Dosage Forms, 4th Ed., p. 126).

In the compositions, effective concentrations of one or more antibodies or derivatives thereof is (are) mixed with a suitable pharmaceutical carrier. The concentrations of the compounds in the compositions are effective for delivery of an amount, upon administration, that treats, prevents, or ameliorates a hLIGHT-mediated disease or symptom thereof.

In one embodiment, the compositions are formulated for single dosage administration. To formulate a composition, the weight fraction of compound is dissolved, suspended, dispersed or otherwise mixed in a selected carrier at an effective concentration such that the treated condition is relieved, prevented, or one or more symptoms are ameliorated.

An antibody of the invention is included in the pharmaceutically acceptable carrier in an effective amount sufficient to exert a therapeutically useful effect in the absence of undesirable side effects on the patient treated. The therapeutically effective concentration can be determined empirically by testing the compounds in in vitro and in vivo systems using routine methods and then extrapolated therefrom for dosages for humans.

The concentration of antibody in the pharmaceutical composition will depend on, e.g., the physicochemical characteristics of the antibody, the dosage schedule, and amount administered as well as other factors known to those of skill in the art.

In one embodiment, a therapeutically effective dosage produces a serum concentration of antibody of from about 0.1 ng/ml to about 50-100 µg/ml. The pharmaceutical compositions, in another embodiment, provide a dosage of from about 0.001 mg to about 2000 mg of antibody per kilogram of body weight per day. Pharmaceutical dosage unit forms can be prepared to provide from about 0.01 mg, 0.1 mg or 1 mg to about 500 mg, 1000 mg or 2000 mg, and in one embodiment from about 10 mg to about 500 mg of the antibody and/or a combination of other optional essential ingredients per dosage unit form.

The antibody can be administered at once, or may be divided into a number of smaller doses to be administered at intervals of time. It is understood that the precise dosage and duration of treatment is a function of the disease being treated and can be determined empirically using known testing protocols or by extrapolation from in vivo or in vitro test data. It is to be noted that concentrations and dosage values can also vary with the severity of the condition to be alleviated. It is to be further understood that for any particular subject, specific dosage regimens can be adjusted over time according to the individual need and the professional judgment of the person administering or supervising the administration of the compositions, and that the concentration ranges set forth herein are exemplary only and are not intended to limit the scope or practice of the claimed compositions.

Upon mixing or addition of the antibody, the resulting mixture can be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The antibody is, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the antibody sufficient to produce the desired therapeutic effect, in association with the required pharmaceutical carrier, vehicle or diluent. Examples of unit-dose forms include ampoules and syringes and individually packaged tablets or capsules. Unit-dose forms can be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

In preferred embodiments, one or more anti-hLIGHT antibodies of the invention are in a liquid pharmaceutical formulation. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered can also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences (1990) Mack Publishing Co., Easton, Pa.

Dosage forms or compositions containing antibody in the range of 0.005% to 100% with the balance made up from non-toxic carrier can be prepared. Methods for preparation of these compositions are known to those skilled in the art.

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules can be hard or soft gelatin capsules, while granules and powders can be provided in non-effervescent or effervescent form with the combination of other ingredients known to those skilled in the art.

In certain embodiments, the formulations are solid dosage forms. In certain embodiments, the formulations are capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an emetic coating; and a film coating. Examples of binders include microcrystalline cellulose, gum tragacanth, glucose solution, acacia mucilage, gelatin solution, molasses, polyinylpyrrolidine, povidone, crospovidones, sucrose and starch paste. Lubricants include talc, starch, magnesium or calcium stearate, lycopodium and stearic acid. Diluents include, for example, lactose, sucrose, starch, kaolin, salt, mannitol and dicalcium phosphate. Glidants include, but are not limited to, colloidal silicon dioxide. Disintegrating agents include croscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

The antibodies of the invention can be provided in a composition that protects it from the acidic environment of the stomach. For example, the composition can be formulated in an enteric coating that maintains its integrity in the stomach and releases the active compound in the intestine. The composition can also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The antibody can also be mixed with other active materials which do not impair the desired action, or with materials that supplement the desired action, such as antacids, H2 blockers, and diuretics. The active ingredient is an antibody or pharmaceutically acceptable derivative thereof as described herein. Higher concentrations, up to about 98% by weight of the active ingredient may be included.

In all embodiments, tablets and capsules formulations can be coated as known by those of skill in the art in order to modify or sustain dissolution of the active ingredient. Thus, for example, they may be coated with a conventional enterically digestible coating, such as phenylsalicylate, waxes and cellulose acetate phthalate.

In preferred embodiments, the formulations are liquid dosage forms. Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is, in one embodiment, encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, can be diluted with a sufficient quantity of a pharmaceutically acceptable liquid carrier, e.g., water, to be easily measured for administration.

Alternatively, liquid or semi-solid oral formulations can be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in one embodiment, is characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the pharmaceutical compositions to be administered can also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The antibody diffuses through the outer polymeric membrane in a release rate controlling step. The amount of antibody contained in such parenteral compositions is highly dependent on the specific nature thereof, as well as the activity of the compound and the needs of the subject.

Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations can be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (TWEEN® 80). A sequestering or chelating agent of metal ions includes EDTA. Pharmaceutical carriers also include ethyl alcohol, polyethylene glycol and propylene glycol for water miscible vehicles; and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations can be packaged in an ampoule, a vial or a syringe with a needle. All preparations for parenteral administration can be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In one embodiment, a therapeutically effective dosage is formulated to contain a concentration of at least about 0.1% w/w up to about 90% w/w or more, in certain embodiments more than 1% w/w of the active compound to the treated tissue(s).

The antibody can be suspended in micronized or other suitable form. The form of the resulting mixture depends upon a number of factors, including the intended mode of administration and the solubility of the compound in the selected carrier or vehicle. The effective concentration is sufficient for ameliorating the symptoms of the condition and may be empirically determined.

In other embodiments, the pharmaceutical formulations are lyophilized powders, which can be reconstituted for administration as solutions, emulsions and other mixtures. They may also be reconstituted and formulated as solids or gels.

The lyophilized powder is prepared by dissolving a antibody provided herein, or a pharmaceutically acceptable derivative thereof, in a suitable solvent. In some embodiments, the lyophilized powder is sterile. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, in one embodiment, about neutral pH. Subsequent sterile filtration of the solution followed by lyophilization under standard conditions known to those of skill in the art provides the desired formulation. In one embodiment, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture can be a solution, suspension, emulsions or the like and can be formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The antibodies of the invention can be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflations, alone or in combination with an inert carrier such as lactose. In such a case, the particles of the formulation will, in one embodiment, have diameters of less than 50 microns, in one embodiment less than 10 microns.

The compounds can be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433, and 5,860,957.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (*theobroma* oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm.

Tablets and capsules for rectal administration can be manufactured using the same pharmaceutically acceptable substance and by the same methods as for formulations for oral administration.

The antibodies and other compositions provided herein may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874. In some embodiments, the anti-hLIGHT antibodies of the invention are targeted (or otherwise administered) to the colon, such as in a patient having or at risk of having an IBD.

In one embodiment, liposomal suspensions, including tissue-targeted liposomes, such as tumor-targeted liposomes, may also be suitable as pharmaceutically acceptable carriers. These can be prepared according to methods known to those skilled in the art. For example, liposome formulations can be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

Methods of Administration and Dosing

The present invention further provides for compositions comprising one or more antibodies or fragments of the invention for use in the prevention, management, treatment and/or amelioration of a hLIGHT-mediated disease (or symptom thereof). Discussion in respect of antibodies also applies mutatis mutandis to fragments of the invention.

In certain embodiments, provided herein are compositions comprising one or more antibodies of the invention for use in the prevention, management, treatment and/or amelioration of a hLIGHT-mediated disease, such as IBD (e.g., ulcerative colitis or Crohn's disease), or a symptom thereof. IBD symptoms may range from mild to severe and generally depend upon the part of the intestinal tract involved. Exemplary symptoms of IBD include abdominal cramps and pain, bloody diarrhea, severe urgency to have a bowel movement, fever, loss of appetite, weight loss, anemia, fatigue, and/or sores on lower legs, ankles, calves, thighs, and arms. Exemplary intestinal complications of IBD include profuse bleeding from the ulcers, perforation or rupture of the bowel, strictures and obstruction, fistulae (abnormal passage) and perianal disease, toxic megacolon (e.g., acute nonobstructive dilation of the colon), and/or malignancy (e.g., cancer of the colon or small intestine). Exemplary extraintestinal complications of IBD include arthritis, skin conditions, inflammation of the eye, liver and kidney disorders, and/or bone loss. Any combination of these symptoms may be prevented, managed, treated, and/or ameliorated using the compositions and methods provided herein.

In certain embodiments, provided herein are compositions comprising one or more antibodies of the invention for use in the prevention, management, treatment and/or amelioration of an hLIGHT-mediated disease, such as GVHD, or a symptom thereof. GVHD generally occurs following allogeneic or matched unrelated bone marrow transplants (BMT).

In some embodiments, the GVHD is acute GVHD. The symptoms of acute GVHD can happen quickly and can be mild or severe. In certain instances, acute GVHD develops within about three months after transplant, such as when blood counts recover after transplant. It certain instances, the acute GVHD affects the skin, gastrointestinal (GI) tract and/or liver. For example, in some patients, acute skin GVHD begins with a rash, for example, on the palms of the patient's hands, soles of the feet, or shoulders. However, the rash can become widespread, and may be itchy and painful and/or might blister and peel. Acute liver GVHD may affect normal functions of the liver, such as liver enzymes, and may in turn, cause jaundice. Acute liver GVHD may also cause the patient's abdomen to become swollen and painful if the liver becomes enlarged. Finally, symptoms of acute gut GVHD (or GVHD of the digestive system) can include diarrhea, mucus or blood in the stool, cramping or abdominal pain, indigestion, nausea and/or loss of appetite. Other general symptoms of acute GVHD can include anemia. low grade fever, and/or being more prone to infections. Any combination of these symptoms of acute GVHD may be prevented, managed, treated, and/or ameliorated using the compositions and methods provided herein.

In other embodiments, the GVHD is chronic GVHD. Chronic GVHD can occur from about three months to about a year or longer after transplant. Chronic GVHD can be mild or severe, and generally includes symptoms similar to those of acute GVHD. Chronic GVHD can affect the skin and digestive system, including the liver but can also involve other organs and the immune system (e.g., making the patient more prone to infections) and/or connective tissues. Symptoms of chronic skin GVHD include a rash, dry skin, tight skin, itchy skin, darkening of the color of the skin, thickening of the skin, and/or may affect hair (e.g., hair loss, turning gray) or nails (e.g., hard or brittle nails). Chronic gut GVHD can affect the digestive system, mouth, esophagus, lining of the stomach, and/or lining of the bowel, and symptoms can include diarrhea, dry or sore mouth, painful swallowing, low nutrient absorption by the stomach, bloating, stomach cramps. Chronic liver GVHD can cause damage and scarring of the liver (cirrhosis). Chronic GVHD of the eyes can affect the glands that make tears, causing eyes to become dry, burning and painful or difficult to tolerate bright LIGHT. Chronic lung GVHD can cause shortness of breath, wheezing, persistent cough, and/or being more prone to chest infections. Chronic GVHD affects tendons (e.g., inflammation) that connect muscle to bone causing difficulty straightening or bending your arms and legs. Any combination of these symptoms of chronic GVHD may be prevented, managed, treated, and/or ameliorated using the compositions and methods provided herein.

In a specific embodiment, a composition for use in the prevention, management, treatment and/or amelioration of a hLIGHT-mediated disease comprises the LIGHT bindins sites of an antibody of the invention, eg, an antibody disclosed in the Examples.

In another embodiment, a composition for use in the prevention, management, treatment and/or amelioration of a hLIGHT-mediated disease comprises one or more antibodies comprising one or more VH domains having an amino acid sequence of any one of the VH domains in the sequence. In another embodiment, a composition for use in the prevention, management, treatment and/or amelioration of a hLIGHT-mediated disease comprises one or more antibodies comprising one or more VH CDR1s having an amino acid sequence of any one of the VH CDR1s in the sequence listing. In another embodiment, a composition for use in the prevention, management, treatment and/or amelioration of a hLIGHT-mediated disease comprises one or more antibodies comprising one or more VH CDR2s having an amino acid sequence of any one of the VH CDR2s in the sequence listing. In a preferred embodiment, a composition for use in the prevention, management, treatment and/or amelioration of a hLIGHT-mediated disease comprises one or more antibodies comprising one or more VH CDR3s having an amino acid sequence of any one of the VH CDR3s in the sequence listing.

In another embodiment, a composition for use in the prevention, management, treatment and/or amelioration of a hLIGHT-mediated disease comprises one or more antibodies comprising one or more VL domains having an amino acid sequence of any one of the VL domains in the sequence listing. In another embodiment, a composition for use in the prevention, management, treatment and/or amelioration of a hLIGHT-mediated disease comprises one or more antibodies comprising one or more VL CDR1s having an amino acid sequence of any one of the VL CDR1s in the sequence listing. In another embodiment, a composition for use in the prevention, management, treatment and/or amelioration of a hLIGHT-mediated disease comprises one or more antibodies comprising one or more VL CDR2s having an amino acid sequence of any one of the VL CDR2s in the sequence listing. In a preferred embodiment, a composition for use in the prevention, management, treatment and/or amelioration of a hLIGHT-mediated disease comprises one or more antibodies comprising one or more VL CDR3s having an amino acid sequence of any one of the VL CDR3s in the sequence listing.

In another embodiment, a composition for use in the prevention, management, treatment and/or amelioration of a hLIGHT-mediated disease comprises one or more antibodies comprising one or more VH domains having an amino acid sequence of any one of the VH domains in the sequence listing, and one or more VL domains having an amino acid sequence of any one of the VL domains in the sequence listing.

In another embodiment, a composition for use in the prevention, management, treatment and/or amelioration of a hLIGHT-mediated disease comprises one or more antibodies comprising one or more VH CDR1s having an amino acid sequence of any one of the VH CDR1s in the sequence listing, and one or more VL CDR1s having an amino acid sequence of any one of the VL CDR1s in the sequence listing. In another embodiment, a composition for use in the prevention, management, treatment and/or amelioration of a hLIGHT-mediated disease comprises one or more antibodies comprising one or more VH CDR1s having an amino acid sequence of any one of the VH CDR1s in the sequence listing, and one or more VL CDR2s having an amino acid sequence of any one of the VL CDR2s in the sequence listing. In another embodiment, a composition for use in the prevention, management, treatment and/or amelioration of a hLIGHT-mediated disease comprises one or more antibodies comprising one or more VH CDR1s having an amino acid sequence of any one of the VH CDR1s in the sequence listing, and one or more VL CDR3s having an amino acid sequence of any one of the VL CDR3s having an amino acid sequence of any one of the VL CDR3s in the sequence listing.

As discussed in more detail elsewhere herein, a composition of the invention may be used either alone or in combination with other compounds or compositions. Moreover, the antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclotides, or toxins. See, e.g., PCT publications WO 92/08495; WO 91/14438; WO 89/12624; U.S. Pat. No. 5,314,995; and EP 396,387.

In some embodiments, provided herein are methods for decreasing or inhibiting binding of hLIGHT to HVEM, LTβR and/or DcR3 in a subject (e.g., a human subject), comprising administering to the subject an effective amount of an antibody that specifically binds to a hLIGHT polypeptide (e.g., a cell surface-expressed or soluble hLIGHT). In one embodiment, the hLIGHT is a SNP variant of hLIGHT, such as 214E-32S, 214K-32S, 214E-32L or 214K-32L. In some embodiments, a hLIGHT biological activity, such as secretion of CCL20, IL8 and/or RANTES or another cytokine disclosed herein, is also decreased in the subject.

In certain embodiments, provided herein are methods for decreasing or inhibiting a hLIGHT biological activity, such as secretion of CCL20, IL8 and/or RANTES or other cytoline, in a subject (e.g., a human subject), comprising administering to the subject an effective amount of an antibody that specifically binds to a hLIGHT polypeptide (e.g., a cell surface-expressed hLIGHT), wherein hLIGHT biological activity is decreased by the antibody. In some embodiments, the hLIGHT is a SNP variant of hLIGHT, such as 214E-32S, 214K-32S, 214E-32L or 214K-32L.

In other embodiments, provided herein are methods for decreasing or inhibiting binding of hLIGHT to HVEM, LTβR and/or DcR3 in a cell having cell surface-expressed hLIGHT, contacting the cell with an effective amount of an antibody that specifically binds to a hLIGHT polypeptide (e.g., a cell surface-expressed or soluble hLIGHT), such as a hLIGHT polypeptide, a hLIGHT polypeptide fragment, or a hLIGHT epitope. In certain embodiments, the hLIGHT is a SNP variant of hLIGHT, such as 214E-32S, 214K-32S, 214E-32L or 214K-32L. In some embodiments, a hLIGHT biological activity, such as secretion of CCL20, IL8 and/or RANTES or other cytokine disclosed herein, is also decreased in the cell.

In certain embodiments, provided herein are methods for decreasing or inhibiting a hLIGHT biological activity, such as secretion of CCL20, IL8 and/or RANTES or other cytokine disclosed herein, in a cell having a cell surface-expressed hLIGHT receptor (such as, HVEM, LTβR and/or Dc3R), contacting the cell with an effective amount of an antibody that specifically binds to a hLIGHT polypeptide (e.g., a cell surface-expressed or soluble hLIGHT) wherein hLIGHT biological activity is decreased by the antibody. In some embodiments, the hLIGHT is a SNP variant of hLIGHT, such as 214E-32S, 214K-32S, 214E-32L or 214K-32L.

Antibodies of the present invention may be used, for example, to purify, detect, and target hLIGHT antigens, in both in vitro and in vivo diagnostic and therapeutic methods. For example, the modified antibodies have use in immunoassays for qualitatively and quantitatively measuring levels of hLIGHT in biological samples. See, e.g., Harlow et al., Antibodies: A Laboratory Manual, (Cold Spring Harbor Laboratory Press, 2nd ed. 1988) (incorporated by reference herein in its entirety).

The invention also provides methods of preventing, managing, treating and/or ameliorating a hLIGHT-mediated disease by administrating to a subject of an effective amount of an antibody, or pharmaceutical composition comprising an antibody of the invention. In one aspect, an antibody is substantially purified (i.e., substantially free from substances that limit its effect or produce undesired side-effects). In preferred embodiments, the antibody is a fully human monoclonal antibody, such as a fully human monoclonal antagonist antibody. The subject administered a therapy is preferably a mammal such as non-primate (e.g., cows, pigs, horses, cats, dogs, rats etc.) or a primate (e.g., a monkey, such as a cynomolgous monkey, or a human). In a preferred embodiment, the subject is a human. In another preferred embodiment, the subject is a human infant or a human infant born prematurely. In another embodiment, the subject is a human with a hLIGHT-mediated disease.

Various delivery systems are known and can be used to administer a prophylactic or therapeutic agent (e.g., an antibody of the invention), including, but not limited to, encapsulation in liposomes, microparticles, microcapsules, recombinant cells capable of expressing the antibody, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent (e.g., an antibody of the invention), or pharmaceutical composition include, but are not limited to, parenteral administration (e.g., intradermal, intramuscular, intraperitoneal, intravenous and subcutaneous), epidural, and mucosal (e.g., intranasal and oral routes). In a specific embodiment, a prophylactic or therapeutic agent (e.g., an antibody of the present invention), or a pharmaceutical composition is administered intranasally, intramuscularly, intravenously, or subcutaneously. The prophylactic or therapeutic agents, or compositions may be administered by any convenient route, for example by infusion or bolus injection, by absorption through epithelial or mucocutaneous linings (e.g., oral mucosa, intranasal mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety.

In a specific embodiment, it may be desirable to administer a prophylactic or therapeutic agent, or a pharmaceutical composition of the invention locally to the area in need of treatment. This may be achieved by, for example, and not by way of limitation, local infusion, by topical administration (e.g., by intranasal spray), by injection, or by means of an implant, said implant being of a porous, non-porous, or gelatinous material, including membranes, such as sialastic membranes, or fibers. Preferably, when administering an antibody of the invention, care must be taken to use materials to which the antibody does not absorb.

In another embodiment, a prophylactic or therapeutic agent, or a composition of the invention can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

In another embodiment, a prophylactic or therapeutic agent, or a composition of the invention can be delivered in a controlled release or sustained release system. In one embodiment, a pump may be used to achieve controlled or sustained release (see Langer, supra; Sefton, 1987, CRC Crit. Ref. Biomed. Eng. 14:20; Buchwald et al., 1980, Surgery 88:507; Saudek et al., 1989, N. Engl. J. Med. 321:574). In another embodiment, polymeric materials can be used to achieve controlled or sustained release of a prophylactic or therapeutic agent (e.g., an antibodies of the invention) or a composition of the invention (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J., Macromol. Sci. Rev. Macromol. Chem. 23:61; see also Levy et al., 1985, Science 228:190; During et al., 1989, Ann. Neurol. 25:351; Howard et al., 1989, J. Neurosurg. 7 1:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the nasal passages or lungs, thus requiring only a fraction of the systemic dose (see, e.g., Goodson, in Medical Applications of Controlled Release, supra, vol. 2, pp. 115-138 (1984)). Controlled release systems are discussed in the review by Langer (1990, Science 249:1527-1533). Any technique known to one of skill in the art can be used to produce sustained release formulations comprising one or more antibodies of the invention. See, e.g., U.S. Pat. No. 4,526,938, PCT publication WO 91/05548, PCT publication WO 96/20698, Ning et al., 1996, "Intratumoral Radioimmunotherapy of a Human Colon Cancer Xenograft Using a Sustained-Release Gel," Radiotherapy & Oncology 39:179-189, Song et al., 1995, "Antibody Mediated Lung Targeting of Long-Circulating Emulsions," PDA Journal of Pharmaceutical Science & Technology 50:372-397, Cleek et al., 1997, "Biodegradable Polymeric Carriers for a bFGF Antibody for Cardiovascular Application," Pro. Int'l. Symp. Control. Rel. Bioact. Mater. 24:853-854, and Lam et al., 1997, "Microencapsulation of Recombinant Humanized Monoclonal Antibody for Local Delivery," Proc. Int'l. Symp. Control Rel. Bioact. Mater. 24:759-760, each of which is incorporated herein by reference in their entirety.

In a specific embodiment, where the composition of the invention is a nucleic acid encoding a prophylactic or therapeutic agent (e.g., an antibody of the invention), the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell surface receptors or transfecting agents, or by administering it in linkage to a homeobox-like peptide which is known to enter the nucleus (see, e.g., Joliot et al., 1991, Proc. Natl. Acad. Sci. USA 88:1864-1868), etc. Alternatively, a nucleic acid can be introduced intracellularly and incorporated within host cell DNA for expression by homologous recombination.

In a specific embodiment, a composition of the invention comprises one, two or more antibodies or fragments of the invention. In another embodiment, a composition of the invention comprises one, two or more antibodies or fragments of the invention and a prophylactic or therapeutic agent other than an antibody of the invention. Preferably, the agents are known to be useful for or have been or are currently used for the prevention, management, treatment and/or amelioration of a hLIGHT-mediated disease. In addition to prophylactic or therapeutic agents, the compositions of the invention may also comprise a carrier.

The compositions of the invention include bulk drug compositions useful in the manufacture of pharmaceutical compositions (e.g., compositions that are suitable for administration to a subject or patient) that can be used in the preparation of unit dosage forms. In a preferred embodiment, a composition of the invention is a pharmaceutical composition. Such compositions comprise a prophylactically or therapeutically effective amount of one or more prophylactic or therapeutic agents (e.g., an antibody of the invention or other prophylactic or therapeutic agent), and a pharmaceutically acceptable carrier. Preferably, the pharmaceutical compositions are formulated to be suitable for the route of administration to a subject.

In a specific embodiment, the term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences (1990) Mack Publishing Co., Easton, Pa. Such compositions will contain a prophylactically or therapeutically effective amount of the antibody, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection. Such compositions, however, may be administered by a route other than intravenous.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The invention also provides that an antibody of the invention is packaged in a hermetically sealed container such as an ampoule or sachette indicating the quantity of antibody. In one embodiment, the antibody is supplied as a dry sterilized lyophilized powder or water free concentrate in a hermetically sealed container and can be reconstituted, e.g., with water or saline to the appropriate concentration for administration to a subject. Preferably, the antibody is supplied as a dry sterile lyophilized powder in a hermetically sealed container at a unit dosage of at least 0.1 mg, at least 0.5 mg, at least 1 mg, at least 2 mg, or at least 3 mg, and more preferably at least 5 mg, at least 10 mg, at least 15 mg, at least 25 mg, at least 30 mg, at least 35 mg, at least 45 mg, at least 50 mg, at least 60 mg, at least 75 mg, at least 80 mg, at least 85 mg, at least 90 mg, at least 95 mg, or at least 100 mg. The lyophilized antibody can be stored at between 2 and 8° C. in its original container and the antibody can be administered within 12 hours, preferably within 6 hours, within 5 hours, within 3 hours, or within 1 hour after being reconstituted. In an alternative embodiment, an antibody is supplied in liquid form in a hermetically sealed container indicating the quantity and concentration of the antibody. Preferably, the liquid form of the antibody is supplied in a hermetically sealed container at least 0.1 mg/ml, at least 0.5 mg/ml, or at least 1 mg/ml, and more preferably at least 5 mg/ml, at least 10 mg/ml, at least 15 mg/ml, at least 25 mg/ml, at least 30 mg/ml, at least 40 mg/ml, at least 50 mg/ml, at least 60 mg/ml, at least 70 mg/ml, at least 80 mg/ml, at least 90 mg/ml, or at least 100 mg/ml.

The compositions of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of a prophylactic or therapeutic agent (e.g., an antibody of the invention), or a composition of the invention that will be effective in the prevention, management, treatment and/or amelioration of a hLIGHT-mediated disease can be determined by standard clinical techniques.

Accordingly, a dosage of an antibody or a composition that results in a serum titer of from about 0.1 µg/ml to about 450 µg/ml, and in some embodiments at least 0.1 µg/ml, at least 0.2 µg/ml, at least 0.4 µg/ml, at least 0.5 µg/ml, at least 0.6 µg/ml, at least 0.8 µg/ml, at least 1 µg/ml, at least 1.5 µg/ml, and preferably at least 2 µg/ml, at least 5 µg/ml, at least 10 µg/ml, at least 15 µg/ml, at least 20 µg/ml, at least 25 µg/ml, at least 30 µg/ml, at least 35 µg/ml, at least 40 µg/ml, at least 50 g/ml, at least 75 µg/ml, at least 100 µg/ml, at least 125 µg/ml, at least 150 µg/ml, at least 200 µg/ml, at least 250 µg/ml, at least 300 µg/ml, at least 350 µg/ml, at least 400 µg/ml, or at least 450 µg/ml can be administered to a human for the prevention, management, treatment and/or amelioration of a hLIGHT-mediated disease. In addition, in vitro assays may optionally be employed to help identify optimal dosage ranges. The precise dose to be employed in the formulation will also depend on the route of administration, and the seriousness of a hLIGHT-mediated disease, and should be decided according to the judgment of the practitioner and each patient's circumstances.

Effective doses may be extrapolated from dose-response curves derived from in vitro or animal model test systems.

For the antibodies of the invention, the dosage administered to a patient is typically 0.1 mg/kg to 100 mg/kg of the patient's body weight. In some embodiments, the dosage administered to the patient is about 1 mg/kg to about 75 mg/kg of the patient's body weight. Preferably, the dosage administered to a patient is between 1 mg/kg and 20 mg/kg of the patient's body weight, more preferably 1 mg/kg to 5 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of the antibodies of the invention may be reduced by enhancing uptake and tissue penetration of the antibodies by modifications such as, for example, lipidation.

In one embodiment, approximately 100 mg/kg or less, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less of an antibody or fragment the invention is administered 5 times, 4 times, 3 times, 2 times or, preferably, 1 time to manage a hLIGHT-mediated disease. In some embodiments, an antibody of the invention is administered about 1-12 times, wherein the doses may be administered as necessary, e.g., weekly, biweekly, monthly, bimonthly, trimonthly, etc., as determined by a physician. In some embodiments, a lower dose (e.g., 1-15 mg/kg) can be administered more frequently (e.g., 3-6 times). In other embodiments, a higher dose (e.g., 25-100 mg/kg) can be administered less frequently (e.g., 1-3 times). However, as will be apparent to those in the art, other dosing amounts and schedules are easily determinable and within the scope of the invention.

In a specific embodiment, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, approximately 0.1 mg/kg or less of an antibody or fragment the invention in a sustained release formulation is administered to a subject, preferably a human, to prevent, manage, treat and/or ameliorate a hLIGHT-mediated disease. In another specific embodiment, an approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 0.1 mg/kg or less bolus of an antibody the invention not in a sustained release formulation is administered to a subject, preferably a human, to prevent, manage, treat and/or ameliorate a hLIGHT-mediated disease, and after a certain period of time, approximately 100 mg/kg, approximately 75 mg/kg or less, approximately 50 mg/kg or less, approximately 25 mg/kg or less, approximately 10 mg/kg or less, approximately 5 mg/kg or less, approximately 1 mg/kg or less, approximately 0.5 mg/kg or less, or approximately 5 mg/kg or less of an antibody of the invention in a sustained release is administered to said subject (e.g., intranasally or intramuscularly) two, three or four times (preferably one time). In accordance with this embodiment, a certain period of time can be 1 to 5 days, a week, two weeks, or a month.

In some embodiments, a single dose of an antibody or fragment of the invention is administered to a patient to prevent, manage, treat and/or ameliorate a hLIGHT-mediated disease two, three, four, five, six, seven, eight, nine, ten, eleven, twelve times, thirteen, fourteen, fifteen, sixteen, seventeen, eighteen, nineteen, twenty, twenty-one, twenty-two, twenty-three, twenty-four, twenty five, or twenty six at bi-weekly (e.g., about 14 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In another embodiment, a single dose of an antibody of the invention is administered to patient to prevent, manage, treat and/or ameliorate a hLIGHT-mediated disease two, three, four, five, six, seven, eight, nine, ten, eleven, or twelve times at about monthly (e.g., about 30 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each dose monthly dose may or may not be identical).

In one embodiment, a single dose of an antibody or fragment of the invention is administered to a patient to prevent, manage, treat and/or ameliorate a hLIGHT-mediated disease two, three, four, five, or six times at about bi-monthly (e.g., about 60 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each bi-monthly dose may or may not be identical).

In some embodiments, a single dose of an antibody or fragment of the invention is administered to a patient to prevent, manage, treat and/or ameliorate a hLIGHT-mediated disease two, three, or four times at about tri-monthly (e.g., about 120 day) intervals over the course of a year, wherein the dose is selected from the group consisting of about 0.1 mg/kg, about 0.5 mg/kg, about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, about 100 mg/kg, or a combination thereof (i.e., each tri-monthly dose may or may not be identical).

In certain embodiments, the route of administration for a dose of an antibody or fragment of the invention to a patient is intranasal, intramuscular, intravenous, or a combination thereof, but other routes described herein are also acceptable. Each dose may or may not be administered by an identical route of administration. In some embodiments, an antibody or fragment of the invention may be administered via multiple routes of administration simultaneously or subsequently to other doses of the same or a different antibody or fragment of the invention.

In certain embodiments, antibodies or fragments of the invention are administered prophylactically or therapeutically to a subject. Antibodies or fragments of the invention can be prophylactically or therapeutically administered to a subject so as to prevent, lessen or ameliorate a hLIGHT-mediated disease or symptom thereof.

Gene Therapy

In a specific embodiment, nucleic acids or nucleotide sequences of the invention are administered to prevent, manage, treat and/or ameliorate a hLIGHT-mediated disease by way of gene therapy. Gene therapy refers to therapy performed by the administration to a subject of an expressed or expressible nucleic acid. In an embodiment of the invention, the nucleic acids produce their encoded antibody, and the antibody mediates a prophylactic or therapeutic effect.

Any of the methods for gene therapy available in the art can be used according to the present invention.

Diagnostic Use of Antibodies

Although antibodies are mentioned in respect of diagnostic uses, this disclosure is to be read as also applying mutatis mutandis to the fragments of the invention.

Labeled antibodies or of the invention and derivatives and analogs thereof, which specifically bind to a hLIGHT antigen can be used for diagnostic purposes to detect, diagnose, or monitor a hLIGHT-mediated disease. The invention provides methods for the detection of a hLIGHT-mediated disease comprising: (a) assaying the expression of a hLIGHT antigen in cells or a tissue sample of a subject using one or more antibodies of the invention that specifically bind to the hLIGHT antigen; and (b) comparing the level of the hLIGHT antigen with a control level, e.g., levels in normal tissue samples (e.g., from a patient not having a hLIGHT-mediated disease, or from the same patient before disease onset), whereby an increase in the assayed level of hLIGHT antigen compared to the control level of the hLIGHT antigen is indicative of a hLIGHT-mediated disease.

The invention provides a diagnostic assay for diagnosing a hLIGHT-mediated disease comprising: (a) assaying for the level of a hLIGHT antigen in cells or a tissue sample of an individual using one or more antibodies of the invention that specifically bind to a hLIGHT antigen; and (b) comparing the level of the hLIGHT antigen with a control level, e.g., levels in normal tissue samples, whereby an increase in the assayed hLIGHT antigen level compared to the control level of the hLIGHT antigen is indicative of a hLIGHT-mediated disease. A more definitive diagnosis of a hLIGHT-mediated disease may allow health professionals to employ preventative measures or aggressive treatment earlier thereby preventing the development or further progression of the hLIGHT-mediated disease.

Antibodies of the invention can be used to assay hLIGHT antigen levels in a biological sample using classical immunohistological methods as described herein or as known to those of skill in the art (e.g., see Jalkanen et al., 1985, J. Cell. Biol. 101:976-985; and Jalkanen et al., 1987, J. Cell. Biol. 105:3087-3096). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I) carbon (14C), sulfur (35S), tritium (3H), indium (121I n), and technetium (99Tc); luminescent labels, such as luminol; and fluorescent labels, such as fluorescein and rhodamine, and biotin.

One aspect of the invention is the detection and diagnosis of a hLIGHT-mediated disease in a human. In one embodiment, diagnosis comprises: a) administering (for example, parenterally, subcutaneously, or intraperitoneally) to a subject an effective amount of a labeled antibody that specifically binds to a hLIGHT antigen; b) waiting for a time interval following the administering for permitting the labeled antibody to preferentially concentrate at sites in the subject where the hLIGHT antigen is expressed (and for unbound labeled molecule to be cleared to background level); c) determining background level; and d) detecting the labeled antibody in the subject, such that detection of labeled antibody above the background level indicates that the subject has a hLIGHT-mediated disease. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99Tc. The labeled antibody will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled antibody to preferentially concentrate at sites in the subject and for unbound labeled antibody to be cleared to background level is 6 to 48 hours or 6 to 24 hours or 6 to 12 hours. In another embodiment the time interval following administration is 5 to 20 days or 5 to 10 days.

In one embodiment, monitoring of a hLIGHT-mediated disease is carried out by repeating the method for diagnosing the a hLIGHT-mediated disease, for example, one month after initial diagnosis, six months after initial diagnosis, one year after initial diagnosis, etc.

Presence of the labeled molecule can be detected in the subject using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patient using positron emission-tomography. In yet another embodiment, the molecule is labeled with a paramagnetic label and is detected in a patient using magnetic resonance imaging (MRI).

Methods of Producing Antibodies

Antibodies and fragments of the invention that specifically bind to an antigen (LIGHT) can be produced by any method known in the art for the synthesis of antibodies, in particular, by chemical synthesis or preferably, by recombinant expression techniques. The practice of the invention employs, unless otherwise indicated, conventional techniques in molecular biology, microbiology, genetic analysis, recombinant DNA, organic chemistry, biochemistry, PCR, oligonucleotide synthesis and modification, nucleic acid hybridization, and related fields within the skill of the art. These techniques are described in the references cited herein and are fully explained in the literature. See, e.g., Maniatis et al. (1982) Molecular Cloning: A Laboratory Manual, Cold Spring Harbor Laboratory Press; Sambrook et al. (1989), Molecular Cloning: A Laboratory Manual, Second Edition, Cold Spring Harbor Laboratory Press; Sambrook et al. (2001) Molecular Cloning: A Laboratory Manual, Cold Spring Harbor Laboratory Press, Cold Spring Harbor, N.Y.; Ausubel et al., Current Protocols in Molecular Biology, John Wiley & Sons (1987 and annual updates); Current Protocols in Immunology, John Wiley & Sons (1987 and annual updates) Gait (ed.) (1984) Oligonucleotide Synthesis: A Practical Approach, IRL Press; Eckstein (ed.) (1991) Oligonucleotides and Analogues: A Practical Approach, IRL Press; Birren et al. (eds.) (1999) Genome Analysis: A Laboratory Manual, Cold Spring Harbor Laboratory Press.

Polyclonal antibodies that specifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling et al., in: Monoclonal Antibodies and T-Cell Hybridomas 563 681 (Elsevier, N.Y., 1981) (said references incorporated by reference in their entireties). The term "monoclonal antibody" as used herein is not limited to antibodies produced through hybridoma technology. Other exemplary methods of producing monoclonal antibodies are discussed elsewhere herein, such as e.g., use of the KM Mouse™. Additional exemplary methods of producing monoclonal antibodies are provided in the Examples herein.

Methods for producing and screening for specific antibodies using hybridoma technology are routine and well known in the art. Briefly, mice can be immunized with a hLIGHT antigen and once an immune response is detected, e.g., antibodies specific for hLIGHT antigen are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilptrack et al., 1997 Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting a modified antibody of the invention wherein, preferably, the hybridoma is generated by fusing splenocytes isolated from a mouse immunized with a hLIGHT antigen with myeloma cells and then screening the hybridomas resulting from the fusion for hybridoma clones that secrete an antibody able to bind to a hLIGHT antigen.

Antibody fragments which recognize specific hLIGHT antigens may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the LIGHT chain constant region and the CH1 domain of the heavy chain. Further, the antibodies of the present invention can also be generated using various phage display methods known in the art.

For example, antibodies can also be generated using various phage display methods. In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in PCT publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. The VH and VL domains may also cloned into one vector expressing the necessary constant regions. The heavy chain conversion vectors and LIGHT chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO 98/16654, WO 96/34096, WO 96/33735, and WO 91/10741; each of which is incorporated herein by reference in its entirety.

In preferred embodiments, human antibodies are produced. Human antibodies and/or fully human antibodies can be produced using any method known in the art, including the Examples provided herein. For example, transgenic mice which are incapable of expressing functional endogenous immunoglobulins, but which can express human immunoglobulin genes. For example, the human heavy and LIGHT chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and LIGHT chain genes. The mouse heavy and LIGHT chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., PCT publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. Other methods are detailed in the Examples herein. In addition, companies such as Abgenix, Inc. (Freemont, Calif.) and Genpharm (San Jose, Calif.) can be engaged to provide human antibodies directed against a selected antigen using technology similar to that described above.

A chimeric antibody is a molecule in which different portions of the antibody are derived from different immunoglobulin molecules. Methods for producing chimeric antibodies are known in the art. See, e.g., Morrison, 1985, Science 229:1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab')2, Fabc, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the LIGHT chain as well as at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. Examples of VL and VH constant domains that can be used in certain embodiments of the invention include, but are not limited to, C-kappa and C-gamma-1 (nG1m) described in Johnson et al. (1997) J. Infect. Dis. 176, 1215-1224 and those described in U.S. Pat. No. 5,824,307. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most preferably greater than 95%. Humanized antibodies can be produced using variety of techniques known in the art, including but not limited to, CDR-grafting (European Patent No. EP 239,400; International publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5): 489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., J. Immunol. 169: 1119 25 (2002), Caldas et al., Protein Eng. 13(5):353-60 (2000), Morea et al., Methods 20(3):267 79 (2000), Baca et al., J. Biol. Chem. 272(16):10678-84 (1997), Roguska et al., Protein Eng. 9(10):895 904 (1996), Couto et al., Cancer Res. 55 (23 Supp):5973s-5977s (1995), Couto et al., Cancer Res. 55(8):1717-22 (1995), Sandhu J S, Gene 150(2):409-10 (1994), and Pedersen et al., J. Mol. Biol. 235(3):959-73 (1994). See also U.S. Patent Pub. No. US 2005/0042664 A1 (Feb. 24, 2005), which is incorporated by reference herein in its entirety. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Reichmann et al., 1988, Nature 332:323, which are incorporated herein by reference in their entireties.) Single domain antibodies, for example, antibodies lacking the LIGHT chains, can be produced by methods well-known in the art. See Riechmann et al., 1999, J. Immunol. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that specifically bind to a hLIGHT antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8):2429-2438).

Kits

The invention also provides a pharmaceutical or diagnostic pack or kit comprising one or more containers filled with one or more of the ingredients of the pharmaceutical compositions of the invention, such as one or more antibodies or fragments provided herein. Optionally associated with such container(s) can be a notice in the form prescribed by a governmental agency regulating the manufacture, use or sale of pharmaceuticals or biological products, which notice reflects approval by the agency of manufacture, use or sale for human administration, eg, an authorisation number.

The present invention provides kits that can be used in the above methods. In one embodiment, a kit comprises an antibody of the invention, preferably a purified antibody, in one or more containers. In a specific embodiment, the kits of the present invention contain a substantially isolated hLIGHT antigen as a control. Preferably, the kits of the present invention further comprise a control antibody which does not react with the hLIGHT antigen. In another specific embodiment, the kits of the present invention contain a means for detecting the binding of a modified antibody to a hLIGHT antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized hLIGHT antigen. The hLIGHT antigen provided in the kit may also be attached to a solid support. In a more specific embodiment the detecting means of the above described kit includes a solid support to which hLIGHT antigen is attached. Such a kit may also include a non-attached reporter-labeled antihuman antibody. In this embodiment, binding of the antibody to the hLIGHT antigen can be detected by binding of the said reporter-labeled antibody.

"Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the blood brain barrier (BBB)). Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered "conservative substitutions" if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, J. Mol Biol, 1999, 217, 721-739 and Taylor et al, J. Theor. Biol. 119 (1986); 205-218 and S. French and B. Robson, J. Mol. Evol. 19 (1983) 171. Accordingly, one can select conservative amino acid substitutions suitable for amino acids on the exterior of a protein or peptide (i.e.

amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

As used herein an "antibody" refers to IgG, IgM, IgA, IgD or IgE molecules or antigen-specific antibody fragments thereof (including, but not limited to, a Fab, F(ab')$_2$, Fv, disulphide linked Fv, scFv, single domain antibody, closed conformation multispecific antibody, disulphide-linked scfv, diabody), whether derived from any species that naturally produces an antibody, or created by recombinant DNA technology; whether isolated from serum, B-cells, hybridomas, transfectomas, yeast or bacteria. Antibodies can be humanized using routine technology.

As described herein, an "antigen" is a molecule that is bound by a binding site on an antibody agent. Typically, antigens are bound by antibody ligands and are capable of raising an antibody response in vivo. An antigen can be a polypeptide, protein, nucleic acid or other molecule or portion thereof. The term "antigenic determinant" refers to an epitope on the antigen recognized by an antigen-binding molecule, and more particularly, by the antigen-binding site of said molecule.

As used herein, the term "antibody fragment" refers to a polypeptide that includes at least one immunoglobulin variable domain or immunoglobulin variable domain sequence and which specifically binds a given antigen. An antibody fragment can comprise an antibody or a polypeptide comprising an antigen-binding domain of an antibody. In some embodiments, an antibody fragment can comprise a monoclonal antibody or a polypeptide comprising an antigen-binding domain of a monoclonal antibody. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody fragment" encompasses antigen-binding fragments of antibodies (e.g., single chain antibodies, Fab and sFab fragments, F(ab')2, Fd fragments, Fv fragments, scFv, and domain antibodies (dAb) fragments (see, e.g. de Wildt et al., Eur J. Immunol. 1996; 26(3):629-39; which is incorporated by reference herein in its entirety)) as well as complete antibodies. An antibody can have the structural features of IgA, IgG, IgE, IgD, IgM (as well as subtypes and combinations thereof). Antibodies can be from any source, including mouse, rabbit, pig, rat, and primate (human and non-human primate) and primatized antibodies. Antibodies also include midibodies, humanized antibodies, chimeric antibodies, and the like.

As used herein, "antibody variable domain" refers to the portions of the light and heavy chains of antibody molecules that include amino acid sequences of Complementarity Determining Regions (CDRs; ie., CDR1, CDR2, and CDR3), and Framework Regions (FRs). VH refers to the variable domain of the heavy chain. VL refers to the variable domain of the light chain. According to the methods used in this invention, the amino acid positions assigned to CDRs and FRs may be defined according to Kabat (Sequences of Proteins of Immunological Interest (National Institutes of Health, Bethesda, Md., 1987 and 1991)) or according to IMGT nomenclature.

As used herein, the term "antibody binding site" refers to a polypeptide or domain that comprises one or more CDRs of an antibody and is capable of binding an antigen. For example, the polypeptide comprises a CDR3 (eg, HCDR3). For example the polypeptide comprises CDRs 1 and 2 (eg, HCDR1 and 2) or CDRs 1-3 of a variable domain of an antibody (eg, HCDRs1-3). In an example, the antibody binding site is provided by a single variable domain (eg, a VH or VL domain). In another example, the binding site comprises a VH/VL pair or two or more of such pairs.

As used herein, "genotyping" refers to a process of determining the specific allelic composition of a cell and/or subject at one or more position within the genome, e.g. by determining the nucleic acid sequence at that position. Genotyping refers to a nucleic acid analysis and/or analysis at the nucleic acid level. As used herein, "phenotyping" refers a process of determining the identity and/or composition of an expression product of a cell and/or subject, e.g. by determining the polypeptide sequence of an expression product. Phenotyping refers to a protein analysis and/or analysis at the protein level.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder. The term "treating" includes reducing or alleviating at least one adverse effect or symptom of a condition, disease or disorder. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment). For treatment to be effective a complete cure is not contemplated. The method can in certain aspects include cure as well.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

Multiple compositions can be administered separately or simultaneously. Separate administration refers to the two compositions being administered at different times, e.g. at least 10, 20, 30, or 10-60 minutes apart, or 1, 2, 3, 4, 5, 6, 7, 8, 9, 10, 12 hours apart. One can also administer compositions at 24 hours apart, or even longer apart. Alternatively, two or more compositions can be administered simultaneously, e.g. less than 10 or less than 5 minutes apart. Compositions administered simultaneously can, in some aspects, be administered as a mixture, with or without similar or different time release mechanism for each of the components.

As used herein, "authorization number" or "marketing authorization number" refers to a number issued by a regulatory agency upon that agency determining that a particular medical product and/or composition may be marketed and/or offered for sale in the area under the agency's jurisdiction. As used herein "regulatory agency" refers to one of the agencies responsible for evaluating, e.g, the safety and efficacy of a medical product and/or composition and controlling the sales/marketing of such products and/or compositions in a given area. The Food and Drug Administration (FDA) in the US and the European Medicines Agency (EPA) in Europe are but two examples of such regulatory agencies. Other non-limiting examples can include SDA, MPA, MHPRA, IMA, ANMAT, Hong Kong Department of Health-Drug Office, CDSCO, Medsafe, and KFDA.

As used herein, "injection device" refers to a device that is designed for carrying out injections, an injection including the steps of temporarily fluidically coupling the injection device to a person's tissue, typically the subcutaneous tissue. An injection further includes administering an amount of liquid drug into the tissue and decoupling or removing the injection device from the tissue. In some embodiments, an injection device can be an intravenous device or IV device, which is a type of injection device used when the target tissue is the blood within the circulatory system, e.g., the blood in a vein. A common, but non-limiting example of an injection device is a needle and syringe.

As used herein, a "buffer" refers to a chemical agent that is able to absorb a certain quantity of acid or base without undergoing a strong variation in pH.

As used herein, "packaging" refers to how the components are organized and/or restrained into a unit fit for distribution and/or use. Packaging can include, e.g., boxes, bags, syringes, ampoules, vials, tubes, clamshell packaging, barriers and/or containers to maintain sterility, labeling, etc.

As used herein, "instructions" refers to a display of written, printed or graphic matter on the immediate container of an article, for example the written material displayed on a vial containing a pharmaceutically active agent, or details on the composition and use of a product of interest included in a kit containing a composition of interest. Instructions set forth the method of the treatment as contemplated to be administered or performed.

As used herein the term "comprising" or "comprises" is used in reference to antibodies, fragments, uses, compositions, methods, and respective component(s) thereof, that are essential to the method or composition, yet open to the inclusion of unspecified elements, whether essential or not.

The term "consisting of" refers to antibodies, fragments, uses, compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (4 ed.), Cold Spring Harbor Laboratory Press, Cold Spring Harbor, N.Y., USA (2012); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

It will be understood that particular configurations, aspects, examples, clauses and embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference. The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

EXAMPLES

Example 1

Antigen Preparation, Immunization Procedures, and Hybridoma Generation

The following example provides a detailed description of the generation and identification of a panel of anti-human LIGHT monoclonal antibodies using the Kyouse™ system (see, eg, WO2011004192). To this end, genetically engineered mice containing a large number of human immunoglobulin genes were immunized with soluble recombinant human LIGHT or surface expressed human LIGHT displayed on mouse embryonic fibroblast (MEF) cells. Various immunization regimes, including conventional intraperitoneal injections as well as a rapid immunisation at multiple sites regime were set up, boosting animals over several weeks (see detailed methods below). At the end of each regime, secondary lymphoid tissue such as the spleen, and in some cases, the lymph nodes were removed. Tissues were prepared into a single cell suspension and fused with SP2/0 cells to generate a stable hybridoma cell line.

Materials and Methods

Cloning Expression and Purification of Recombinant Cynomolgus and Human LIGHT (214E and 214K Alleles):

cDNA encoding the extracellular domain of human (214E hLIGHT—wherein all subunits had the 214E) and cynomologus (*Macaca fascicularis*) LIGHT was cloned into a pREP4 expression plasmid (Invitrogen) using standard restriction enzyme digestion and ligation. The alternative human form (214K hLIGHT—wherein all subunits had the 214K) was created using the 214E LIGHT pREP4 vector as a template and the 214K mutation was introduced by site directed mutagenesis. The constructs also contained a FLAG peptide motif to aid purification. Constructs were sequenced to ensure their correct sequence composition.

Human LIGHT-214E (ie, 214E hLIGHT), LIGHT-214K (ie, 214K hLIGHT) as well as cynomolgus monkey LIGHT were expressed transiently to produce recombinant protein using Invitrogen's FreeStyle™ CHO-S suspension adapted cell line. Plasmids were transfected into the cells using PEI (polyethylenimine MW 40000) and left to overgrow for a period of 13 days before harvesting the supernatant for purification. Cells were fed during the overgrow process with ActiCHO™ Feeds A and B from GE Healthcare to help boost productivity and promote longevity of the cells. During the overgrow process samples were taken regularly to monitor cell growth and viability.

FLAG-tagged LIGHT proteins were purified in a two-step process; firstly the clarified tissue culture supernatants from the CHO-S expression were purified using M2 anti-FLAG affinity chromatography. The eluted fractions containing the LIGHT protein were then subjected to size exclusion chromatography and assessed for purity by SDS-PAGE analysis and quantified by spectrophotometer reading at OD280 nm.

Generation of Stably Transfected MEF and CHO-S Cells Expressing 214E and 214K Human LIGHT:

The full length 214E and 214K human LIGHT sequences were codon optimized for mammalian expression and cloned into an expression vector under the CMV promoter flanked by 3' and 5' piggyBac specific terminal repeat sequences facilitating stable integration into the cell genome (see: "A hyperactive piggyBac transposase for mammalian applications"; Yusa K, Zhou L, Li M A, Bradley A, Craig N L. Proc Natl Acad Sci USA. 2011 Jan. 25). Furthermore, the expression vector contained either a puromycin or neomycin selection cassette to facilitate stable cell line generation. The hLIGHT expression plasmid was co-transfected with a plasmid encoding piggyBac transposase into an in-house derived mouse embryonic fibroblast (MEF) cell line (embryos used to generate this line were obtained from a 129S5 crossed to C57BL6 female mouse) and CHO-S cells using the FreeStyle Max transfection reagent (Invitrogen) according to manufacturer instructions. 24 hours after transfection, the media was supplemented with G418 or neomycin and grown for at least 2 weeks to select a stable cell line with media being exchanged every 3-4 days. The expression of hLIGHT was assessed by flow cytometry using an anti-human LIGHT-PE conjugated antibody (eBioscience, 12-2589-42). Complete MEF media was made up of Dulbecco's Modified Eagle's Medium (Gibco) supplemented with 10% v/v fetal bovine serum (Gibco). Complete CHO-S media was made up of CD-CHO media supplemented with 8 mM Glutamax (Gibco).

Preparation of MEF Cells for Mouse Immunizations:

Cell culture medium was removed and cells washed once with 1×PBS. Cells were treated for 5 minutes with trypsin to loosen cells from tissue culture surface. Cells were collected and trypsin neutralized by the addition of complete media containing 10% v/v fetal bovine serum (FCS). Cells were then centrifuged at 300×g for 10 minutes and washed with 25 ml of 1×PBS. Cells were counted and resuspended at the appropriate concentration in 1×PBS.

Immunization Procedure:

Transgenic Kymice™ were immunized with 214E hLIGHT in either soluble form, expressed by CHO-S cells, or membrane bound form, expressed by stably transfected MEF cells. Mice were divided into four groups according to immunization procedure and immunised as follows: Group one were given 1×10E07 MEF-214E hLIGHT cells only (resuspended in 1×PBS with no adjuvant); Group two were given 1×10E07 MEF-214E hLIGHT cells emulsified in Sigma Adjuvant System (Sigma S6322); Group three received an alternating regime of 1×10E07 MEF-214E hLIGHT cells and 214E hLIGHT protein emulsified in Sigma adjuvant, where the initial antigen priming was given as MEF cells intraperitoneally followed by an alternating regime of protein (decreasing amounts starting with 15 µg protein followed by 5 µg protein) and MEF cells. For the final boosts cells were injected intraperitoneally as well as protein, which was given intravenously. Group four received 214E hLIGHT protein emulsified in Sigma Adjuvant System (25 µg were used as prime, followed by 15, 10 and 5 µg for the following boosts).

When immunizing with cells, the adjuvant was mixed with cells at a 1:1 v/v ratio and gently mixed by pipetting before injecting intraperitoneally. When immunizing with protein, the adjuvant was mixed with protein at a 1:1 v/v ratio and vortexed repeatedly. All mice were bled before being primed and then boosted every three weeks. At least 3 serial bleeds spaced apart at least 2 weeks were collected and analysed for hLIGHT specific IgG titre using an ELISA or flow cytometry based assay. Titre data was used to select mice for fusion and hybridoma generation. Final boosts were administered three days prior to tissue collection. Spleen tissues were taken and subjected to hybridoma fusion. Antibody clones 31A10 and 62C01 were isolated from mice immunized with a combination of MEF-214E hLIGHT cells and recombinant protein (214E hLIGHT) from group three.

Rapid Immunisation at Multiple Sites:

Transgenic Kymice™ were pre-bled before being immunized with equal mixtures of recombinantly expressed 214E hLIGHT and hLIGHT-214K emulsified in Sigma Adjuvant System (Sigma S6322). For all immunizations, mice were anaesthetised using Isoflurane and all injections were administered subcutaneously at six sites on the ventral side of the mouse (reference: "Rapid Development of Affinity Matured Monoclonal Antibodies Using RIMMS"; Kilpatrick et al. Hybridoma, 1997). Mice were returned to their home cage and recovery monitored. Mice were boosted seven times every three to four days over a total of 25 days. Spleen and lymph node tissues were taken two days after the last boost and used for hybridoma fusion. The terminal bleed was collected and analysed for hLIGHT specific IgG titers using a standard ELISA protocol. Antibody clones 42A02, 29C09, 14B09, 13H04, 117C06, and 144F05 were all isolated from this experiment using a RIMMS immunization regime.

Determination of Serum Titers by FACS Using CHO-S Expressed hLIGHT:

CHO-S cells expressing 214E hLIGHT or 214K hLIGHT or untransfected CHO-S cells, diluted in FACS buffer (PBS+ 1% w/v BSA+0.1% w/v NaN3) were distributed to a 96 well V-bottom plate (Greiner) at a density of 1×10E05 cells per well. Cells were washed with 150 µl of PBS and centrifuged at 300×g for 3 min. Supernatant was aspirated and 150 µl of PBS added. This wash step was repeated. A titration of mouse serum was prepared, diluting samples in FACS buffer. 50 µl/well of this titration was then added to the cell plate. To determine the change in activity level due to immunization, serum from each animal prior to immunization was diluted to 1 in 100 in FACS buffer and 50 µl/well added to the cells. A suitable reference antibody (antiLIGHT antibody, R&D system, MAB664) or mouse IgG1 control antibody (Sigma) were diluted in FACS buffer (between 1-9 µg/ml) and 50 µl added to cells. Cells were incubated at 4° C. for 30 minutes. Cells were washed twice with 150 µl of PBS, centrifuging after each wash step and aspirating supernatant (centrifuged at 300×g for 3 minutes). To detect antibody binding, APC goat-anti-mouse IgG (Jackson ImmunoResearch) was diluted 1 in 500 in FACS buffer and 50 µl was added to the cells. Cells were incubated 30 minutes at 4° C. in dark. Cells were washed twice with 150 µl of PBS centrifuging after each wash step and aspirating supernatant (centrifuged at 300×g for 3 minutes). To fix cells 100 µl 2% v/v paraformaldehyde was added and cells incubated for 30 minutes at 4° C., cells were pelleted by centrifugation at 300×g and the plates resuspended in 50 µl of FACS buffer. APC signal intensity (geomean) was measured by flow cytometry using a BD FACS Array instrument.

Determination of Serum Titers by ELISA Using Recombinant hLIGHT:

Titers in mouse serum samples were determined using a reverse LIGHT ELISA protocol. Anti-mouse IgG capture antibody (Southern Biotech) (4 µg/ml diluted in PBS, 50 al/well) was adsorbed to 96 well low auto-fluorescent, high protein binding plates (Costar) overnight at 4° C. Excess IgG was removed by washing with PBS-Tween (0.1% v/v) and the wells were blocked with 1% w/v bovine serum albumin (BSA, Sigma) in PBS for 1 hr at RT, after which plates were washed as described previously. A titration of mouse serum was prepared, diluting samples in reagent diluent (0.1% w/v BSA/PBS). 50 µl/well of this titration was then added to ELISA plates. To determine the change in activity level due to immunization, serum from each animal prior to immunization was diluted to 1 in 100 in reagent diluent and 50 µl/well added to the ELISA plate. As a positive control for biotinylated LIGHT binding an anti-LIGHT antibody (R&D systems) diluted to 1 µg/ml was added to plates at 50 µl. Mouse IgG1 isotype control (Sigma) was included as a negative control and was diluted to 1 µg/ml in reagent diluent and 50 µL/well added to ELISA plate. In some instances serum sample from a mouse immunized with a non-relevant antigen was diluted 1 in 1000 and 50 µl/well was added to the ELISA plate. The plates were incubated at room temperature for at least 1 hour. Following incubation, plates were washed as before to remove unbound proteins. Biotinylated LIGHT (100 ng/ml in reagent diluent; 50 µl/well) was then added to the plates and incubated at RT for 1 hr. Unbound biotinylated LIGHT was removed by washing with PBS-Tween (0.1% v/v), while the remaining biotinylated LIGHT was detected by streptavidin-Europium3+ conjugate (DELFIA® detection, PerkinElmer) diluted in DELFIA® assay buffer (Perkin Elmer) or streptavidin-HRP diluted in reagent diluent.

In the case of streptavidin-HRP, the plates were washed as described before and 50 µL of TMB (Sigma) was added to the plate. Then the reaction was stopped by adding 50 µL of 1M sulfuric acid (Fluka analytical). The OD at 450 nm was measured on an Envision plate reader (PerkinElmer).

In case of streptavidin-Europium3, the plates were washed with TBS (Tris buffered saline)-Tween (0.1% v/v) and 200 µL/well of DELFIA Enhancement solution (Perkin Elmer) was added to the plate. The time-resolved fluorescence was measured at 615 nm on an Envision plate reader (PerkinElmer). Fluorescence data was plotted as Europium counts.

Murine Tissue Isolation and Preparation:

Spleens were excised from immunised mice and washed in 1×PBS and kept on ice until further processing. Where used, axillary, inguinal as well as mesenteric lymph nodes were removed and placed in sterile 1×PBS on ice until further processing. Tissues were prepared in buffer containing 1×PBS (Invitrogen) and 3% heat-inactivated FBS (Invitrogen). Splenocytes were dispersed by mashing the tissue through a 45 µm strainer (BD Falcon) and rinsing with 30 ml 3% FBS/PBS buffer before centrifugation at 700 g for 10 minutes at 4° C. To remove red blood cells, the pelleted splenocytes were resuspended in 4 ml of Red Blood Cell Lysis Buffer (Sigma). After 4 minutes of incubation, the lysis reaction was stopped by addition of 3% FBS/1×PBS buffer. Cell clumps were filtered out with a 45 µm strainer. The remaining splenocytes were pelleted for further procedures. For the KM050 experiment, the lymph nodes were dispersed by mashing the tissue through a 45 µm strainer (BD Falcon) and rinsing with 30 ml 3% FBS/PBS buffer before centrifugation at 700 g for 10 minutes at 4° C. Lymph nodes did not undergo red blood cell lysis. The remaining lymph node cells were pelleted for further procedures.

Hybridoma Fusion:

Following final boost spleens or lymph nodes were taken and B-cells subjected to a positive selection method using the MACS® Separation system. Briefly, where lymph nodes were used those cells were pooled with the splenocytes from the corresponding mice after red blood cell lysis and total cell number determined. Cells were resuspended in 80 µl 3% FBS/PBS buffer per 1×10E07 cells, before adding the anti-mouse IgG1 plus anti-mouse IgG2a+b MicroBeads (Miltenyi Biotec) and incubated for 15 minutes at 4° C. The cells/MicroBeads mixture was then applied to a pre-wetted LS column placed in a magnetic MACS Separator and washed with 3% FBS/PBS buffer. IgG positive cells were collected in the labelled, column-bound fraction in 3% FBS/PBS buffer.

Enriched B-cells were treated with CpG overnight (final concentration 25 µM) and the following day washed once in BSA fusion buffer (0.3M D-Sorbitol, 0.11 mM calcium acetate hydrate, 0.5 mM magnesium acetate tetrahydrate and 0.1% BSA (v/w), adjusted to pH7.2). Washed cells resuspended in 200 µl of BSA fusion buffer and cell count determined. SP2/0 cells treated in the same way, but washed twice instead of once with BSA fusion buffer. B-cells fused at a ratio of 3:1 with SP2/0 myeloma cells by electrofusion using a BTX ECM 2001 Electro Cell Manipulator (Harvard Apparatus). Each fusion was left overnight in recovery medium (Dulbecco's Modified Eagle's Medium—high glucose (no phenol red, no L-G) containing OPI (Sigma), L-Glutamax (Gibco), 20% FBS (Gibco, batch-tested for hybridoma) and 2-mercaptoethanol, resuspended in 1 part recovery medium and 9 parts semi-solid medium (ClonaCell-HY Hybridoma Selection Medium D, Stemcell Technologies) and then seeded onto 10 cm petri dishes. Visible colonies were picked 12 days later into 96-well plates and cultured for another 2-3 days prior to screening.

Monocloning of Hybridoma Wells:

Hybridomas found to be polyclonal were monocloned using the following procedure. Cells taken from an existing colony growing in one well of a 24 well plate were counted using Trypan Blue exclusion on the Cedex cell counter and seeded at a final concentration of 400 viable cells/ml in 1 part Hybridoma Maintenance Medium (Advanced DMEM (Gibco, cat#12491) L-Glutamax (Gibco, cat#35050), 20% FBS (Gibco, batch-tested for hybridoma), HT supplement (Gibco, cat#41065), Penicillin-Streptomycin and 2-mercaptoethanol) to 9 parts semi-solid medium (ClonaCell-HY Hybridoma Selection Medium D, Cat#0.804, Stemcell Technologies) onto 10 cm petri dishes. Visible colonies were picked 12 days later into 96 well plates and cultured for another 2-3 days prior to screening. A maximum of 4×96 well plates were picked per parental colony and screened for hLIGHT binding and receptor neutralization. The best monocloned hybridoma clone was taken forward. Antibodies 31A10 and 144F05 were monocloned using this procedure.

Example 2

Hybridoma Supernatant Screening

After generation of hybridoma clones, the hybridoma supernatant was assessed in a sequential primary and secondary screen and appropriate hybridoma clones selected based on criteria of antibody binding to hLIGHT and receptor neutralization activity. Using this screening cascade, 25163 hybridoma clones were tested and 540 identified as primary hits. Thereafter, 41 hybridoma clones were confirmed by using secondary screening criteria (see details in materials and methods) (Table 1).

TABLE 1

Clone Number Focusing By Screening

| Experiment ID | Number of hybridoma screened | Number of primary hits cherry picked | Number of secondary hits confirmed | Number of Lead Candidate mAbs |
|---|---|---|---|---|
| KM044-2 | 11,249 | 147 | 10 | 2 |
| KM050 | 13,914 | 393 | 31 | 6 |

Among the 41 clones identified by secondary screen, eight clones were selected by the inventors to be part of the antibody lead panel dependent upon desired selection criteria devised by the inventors (see details in Example 3).

For the primary screen, the inventors devised the following selection criteria: wells containing hybridoma clones were selected if antibodies present in the supernatant could bind to natively displayed 214E hLIGHT expressed on the cell surface. This assay was set up by plating CHO-S cells expressing hLIGHT on the cell surface, followed by incubation with hybridoma supernatant, followed by a fluorescent detection antibody. The presence of an anti-LIGHT antibody in the supernatant was read-out using a plate reader capable of reading the appropriate fluorescence. Furthermore, the inventors assessed hybridoma supernatant for binding to recombinantly expressed human LIGHT-214E using an HTRF (Homogeneous Time Resolved Fluorescence) assay. Clones meeting certain selection criteria (see further detailed description below), using data from the above mentioned two primary screen assays, were then cherry-picked and moved on to a secondary screen where the ability of each antibody to neutralize 214E hLIGHT binding to both receptors LTβR and HVEM was determined. The inventors decided to assess this using a receptor neutralization HTRF assay and a flow cytometry-based receptor neutralization assay. Lastly, the inventors decided to analyse hybridoma supernatant by SPR to evaluate apparent affinity of the antibodies to recombinant trimeric human LIGHT (ie, recombinant 214E hLIGHT and 214K hLIGHT) as well as cross-reactivity to cynomolgus monkey LIGHT.

Antibodies were defined as a secondary hit when antibodies in hybridoma supernatant bound to h LIGHT-214E, but not necessarily 214K hLIGHT, with high apparent affinity as well as cross-reacted with recombinant cynomolgus monkey LIGHT. Additionally antibodies in the supernatant had to at least neutralize one of LIGHT's receptors, i.e.: LTβR or HVEM, in at least one of the two assays tested (i.e.: HTRF or flow cytometry based assay).

Materials and Methods

Primary Screen—Binding to Cell Expressed Human LIGHT-214E:

Supernatants collected from hybridoma cells were tested to assess the ability of secreted antibodies to bind to 214E hLIGHT expressed on the surface of CHO-S cells. To determine CHO-S 214E hLIGHT binding, cells were plated in black walled clear bottom tissue culture treated 384-well plates (Costar) at 2×E04/well in F12 media (GIBCO) supplemented with 10% v/v FBS (GIBCO) and cultured overnight. Culture media was removed from 384-well assay plates. At least 40 µl of hybridoma supernatant or positive control anti-human LIGHT reference antibody (at a final concentration of 1 µg/ml) or isotype IgG1 control antibody (referred to in some instances as Cm7, Sigma M9269, at a final concentration of 1 µg/ml) diluted in hybridoma maintaining media (HMM) were added to each well. HMM was made up of Advanced DMEM (Gibco) supplemented with 1× Glutamax (Gibco), 20% v/v FBS (Gibco), 0.05 mM 3-Mercaptoethanol, 1×HT supplement (Gibco), and 1× penicillin/streptomycin (Gibco). Plates were incubated for 1 hour at 4° C. Culture media was aspirated and 50 µl of goat anti-mouse Alexa Fluor 790 (Jackson ImmunoResearch 115-655-071) at 1000 ng/mL supplemented with 0.2 µM DRAQ5 (Biostatus) diluted in FACS Buffer (PBS+1% w/v BSA+0.1% v/v NaN3) were added. Plates were again incubated for 1 hour at 4° C. Supernatant was aspirated and 25 µl of 4% v/v paraformaldehyde added and plates were incubated 15 minutes at room temperature. Plates were washed twice with 100 µl PBS and then the wash buffer was completely removed. Fluorescence intensity was read by scanning plates using an Odyssey Infrared Imaging System (LI-COR®). Anti-mouse binding (800 nm channel) was normalised to cell number (700 nm channel) according to LI-COR® recommended algorithm. Percent effect was calculated as detailed below (Equation 1). Total binding was defined using reference antibody at a final assay concentration of 1 µg/ml. Non specific binding was defined using mouse IgG1 isotype control (Sigma) at a final assay concentration of 1 µg/ml. For clones derived from KM044-2 a selection criteria of greater than or equal to 3.0 percent response was applied to define a well as a hit. Alternatively, for clones derived from KM050, a selection criteria of greater than or equal to 5.0 percent response was applied to define a well as a hit (see Table 1).

Equation 1

Calculation of Percentage Effect from Primary Screen $(LI-COR)$ and $HTRF$ (Using 800% Resp values $(LI-COR)$ or 665/620 nm ratio (see equation 2) $(HTRF)$ $$\text{Percent effect} = \frac{(\text{sample well} - \text{non specific binding}) \times 100}{(\text{total binding} - \text{non specfic binding})}$$

Non specific binding = values from wells containing isotype control mouse $IgG1$ Total Binding = values from wells containing reference antibody Primary Screen: Binding to Recombinant Human LIGHT-214E:

In parallel to screening for binding to CHO-S expressed LIGHT-214E, supernatants collected from hybridoma wells were also tested to assess the ability of secreted antibodies to bind to 214E hLIGHT expressed as a recombinant protein (produced in-house, see details in Example 1). Binding of secreted antibodies to recombinant 214E hLIGHT were identified by HTRF® (Homogeneous Time-Resolved Fluorescence, Cisbio) assay format using biotinylated 214E hLIGHT. 5 al of hybridoma supernatant was transferred to a white 384 well low volume non binding surface polystyrene plate (Greiner). 5 µl of 20 nM biotinylated 214E hLIGHT diluted in HTRF buffer (PBS (Sigma)+0.53M KF (Sigma)+0.1% w/v BSA (Sigma) was pre-incubated with 5 µl of hybridoma supernatant or 5 µl of reference antibody or mouse IgG1 isotype control diluted to 5 nM working concentration for 1 hr at room temperature. 10 µl of combined detection reagents Streptavidin D2 (Cisbio) diluted 1:200 in HTRF assay buffer for final dilution 1:400 and goat anti-mouse IgG (Southern Biotech) labelled with europium cryptate (Cisbio) diluted 1:200 in HTRF assay buffer for final dilution 1:400 were added. The plate was left to incubate in dark for 2 hours prior to reading time resolved fluorescence at 620 nm and 665 nm emission wavelengths using an EnVision plate reader (Perkin Elmer). More details of the HTRF® assay technology can be found in Mathis (1995) Clinical Chemistry 41(9), 1391-1397. Data were analysed by calculating 665/620 ratio and percent effect for each sample according to equation 2 and equation 1 respectively.

Calculation of 665/620 ratio     Equation 2

665/620 ratio=(sample 665/620 nm value)×10000

For clones derived from KM044-2 and KM050 a selection criteria of greater than or equal to 20 percent effect was applied by the inventors to define a well as a hit from recombinant 214E hLIGHT binding as described in Table 1.

Secondary Screen: Binding to Cell Expressed and Recombinant Human LIGHT-214E

To determine whether wells selected using the primary screen selection criteria had the required characteristics set by the inventors, a number of assays were performed. Hybridoma clones selected as hits from primary screening were cultured for 3 days and the supernatants collected from hybridoma cells were tested to assess whether the secreted antibodies that bind to CHO-S expressed 214E hLIGHT, may also bind to CHO-S expressed 214K hLIGHT (a), in some case bind to untransfected CHO-S cells (b), and whether they neutralise recombinant LTβR-Fc or HVEM-Fc binding to CHO-S 214E hLIGHT and (c) ability to neutralise LTβR Fc or HVEM Fc binding to recombinant biotinylated 214E hLIGHT (d).

Binding to CHO-S Expressed hLIGHT and Receptor Neutralisation (Assays a, b, and c):

CHO-S cells expressing 214E hLIGHT or 214K hLIGHT or untransfected CHO-S cells, diluted in FACS buffer (PBS+1% w/v BSA+0.1% w/v NaN3) were distributed to a 96 well V-bottom plate (Greiner) at a density of 1×10E05 cells per well. Cells were washed with 150 µl of PBS and centrifuged at 300×g for 3 min. Supernatant was aspirated and 150 µl of PBS added. This wash step was repeated.

25 µl of hybridoma supernatant or purified antibody from hybridoma supernatant diluted in FACS buffer was added to the washed cells and incubated for 10-15 minutes. Reference Antibody or mouse IgG1 control antibody (Sigma, M9269) were diluted in FACS buffer to 50 lag/mL and 25 µl added to cells. 25 µl of human HVEM huFc (R&D Systems, 356-HV-100/CF) diluted to 720 ng/mL or human LTβR huFc (R&D Systems, 629-LR-100/CF) diluted to 1300 ng/mL in FACS buffer were then added to wells. Cells were incubated at 4° C. for 30 minutes.

Cells were washed twice with 150 µl of PBS centrifuging after each wash step and aspirating supernatant (centrifuged at 300×g for 3 minutes).

To detect antibody and receptor binding 50 µl of Goat anti-human IgG-PE (Jackson ImmunoResearch) and APC anti-mouse IgG (Jackson ImmunoResearch) diluted 1 in 500 in FACS buffer was added to the cells. Cells were incubated 30 minutes at 4° C. in dark.

Cells were washed twice with 150 µl of PBS centrifuging after each wash step and aspirating supernatant (centrifuged at 300×g for 3 minutes).

To fix cells 100 µl 2% v/v paraformaldehyde was added and cells incubated for 30 minutes at 4° C., cells were pelleted by centrifugation 300×g and the plates and resuspended in 50 µl of FACS buffer. PE and APC signal intensity (geomean) was measured by flow cytometry using a BD FACS Array instrument.

% receptor binding was calculated using equations 3. Binding to CHO expressed LIGHT were defined as geomean >2 times non specific binding geomean (average of IgG1 isotype control+receptor control wells).

Percentage of receptor binding (FACS)     Equation 3

Based on geomean fluorescence

% of Receptor binding =

$$\frac{\text{sample value} - \text{non specific binding}}{\text{total binding} - \text{non specific binding}} \times 100$$

Non-specific binding = No antibody, no receptor

Total binding = receptor (LTβR or HVEM) only binding (no inhibitor) + isotype control at 1 µg/ml

Secondary Screen—HTRF Ligand/Receptor Neutralisation (Assay d):

The following methods were carried out. 5 µL of Flag-tagged LIGHT (in-house) at 2.5 nM final concentration (10 nM working concentration) diluted in HTRF buffer with 5 µl of supernatants collected from hybridoma wells were pre-incubated for 1 hour at room temperature. To wells used to define total binding, 5 µl of LIGHT (10 nM working, 2.5 nM final) and 5 µl of hybridoma maintaining media (HMM)) were added. To wells used to define non specific binding (receptor only) 10 µl of HMM was added. Or, in some cases, non specific binding defined as 5 µl of reference antibody diluted to 1200 nM in HMM and 5 µl of LIGHT (10 nM working, 2.5 nM final). Total and non specific binding wells were pre-incubated for 1 hour at RT in the same plate as wells containing supernatants collected from hybridoma wells.

LIGHT receptor was diluted in HTRF assay buffer and added to all wells, 5 µl/well of HVEM-Fc or LTβR-Fc (R&D systems) at 1.2 nM for HVEM (0.3 nM final) and 0.4 nM for LTβR (0.1 nM final).

In order to detect binding, 5 µl of combined detection reagent were added to all wells. Anti-flag D2 (Cisbio) was diluted to 20 nM (5 nM final) in HTRF assay buffer and anti-human Fc K (Cisbio) was diluted 1:100 in HTRF assay buffer (for final dilution 1:400).

Plates were left to incubate in dark for 3 hours prior to reading time resolved fluorescence at 620 nm and 665 nm emission wavelengths using an EnVision plate reader (Perkin Elmer). More details of the HTRF® assay technology can be found in Mathis (1995) Clinical Chemistry 41(9), 1391-1397. Data were analysed by calculating 665/620 ratio (2) and percentage of receptor for each sample according to equation 4 and equation 5 respectively.

$$665/620 \text{ ratio (2)} = \text{sample } 665/620 \text{ nm value} \quad \text{Equation 4}$$

Percentage of receptor binding (HTRF)    Equation 5
Based on calculation of 665/620 ratio (2) (equation 4)
% of Receptor binding =
$$\frac{\text{sample value} - \text{non specific binding}}{\text{total binding} - \text{non specific binding}} \times 100$$
Non specific binding = receptor and reference
    antibody at 300 nM final concentration
Total binding = receptor (HVEM or LTβR)
    and LIGHT (no inhibitor)

Hit Criteria Selection from Secondary Screening:

A panel of hits were selected based on binding and neutralisation assays. Hits in CHO-S LIGHT-214E assay were defined by the inventors as <70% receptor binding to CHO-S LIGHT-214E cells by FACS. Hits in flag LIGHT/HVEM-Fc or flag LIGHT/LTβR Fc HTRF neutralisation assays were defined as clones with <90% of receptor binding to LIGHT. Binding to CHO-S LIGHT-214E and in some cases to CHO-LIGHT 214K were defined as >2*background (mouse IgG1 binding) geomean. Data is summarised in Table 1. Apparent affinity measurements by SPR were also considered.

Example 3

Antibody Lead Characterization

Figure 2:
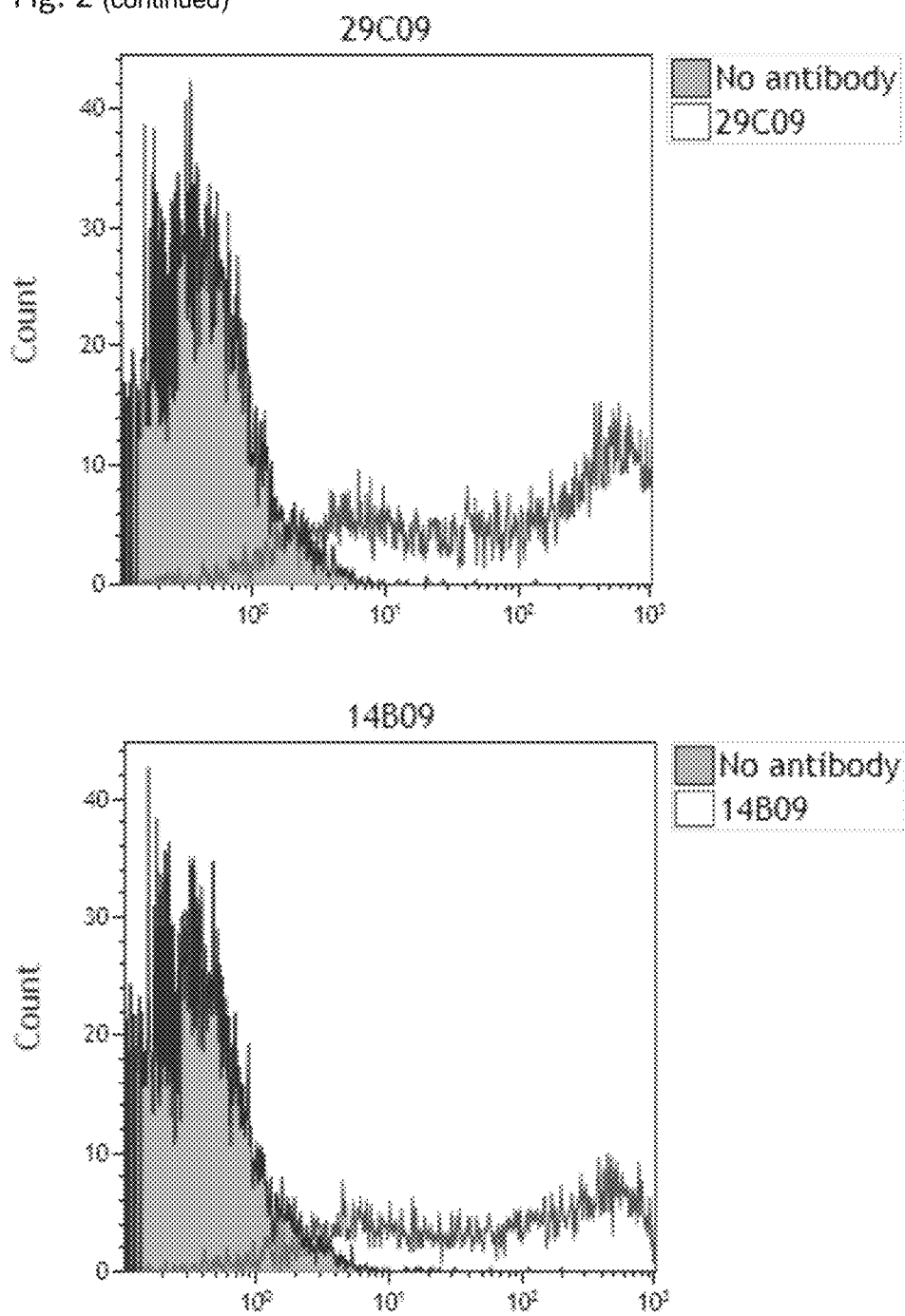
FIG. 2.
Figure 2:
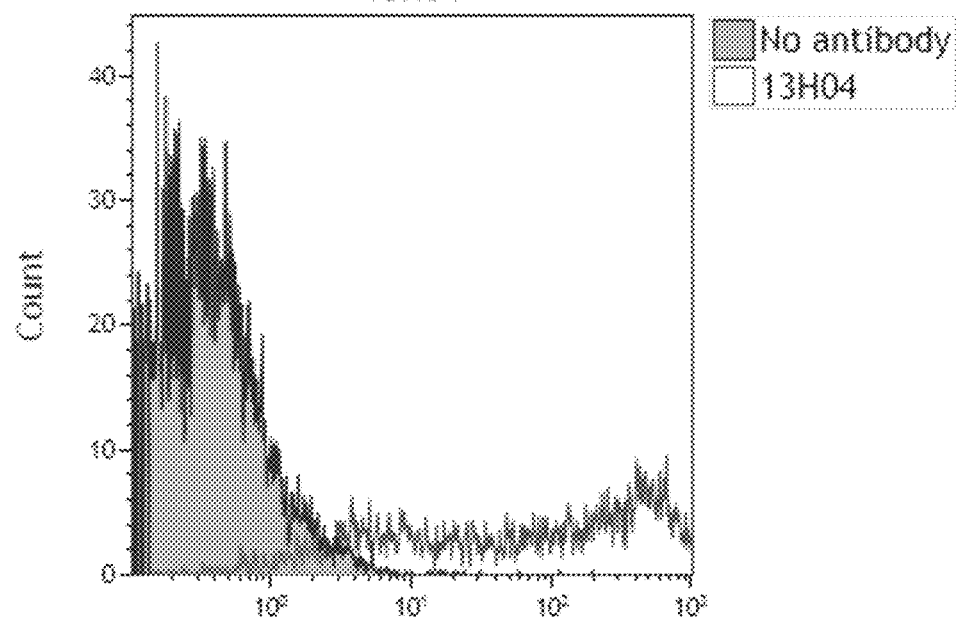
Figure 2:
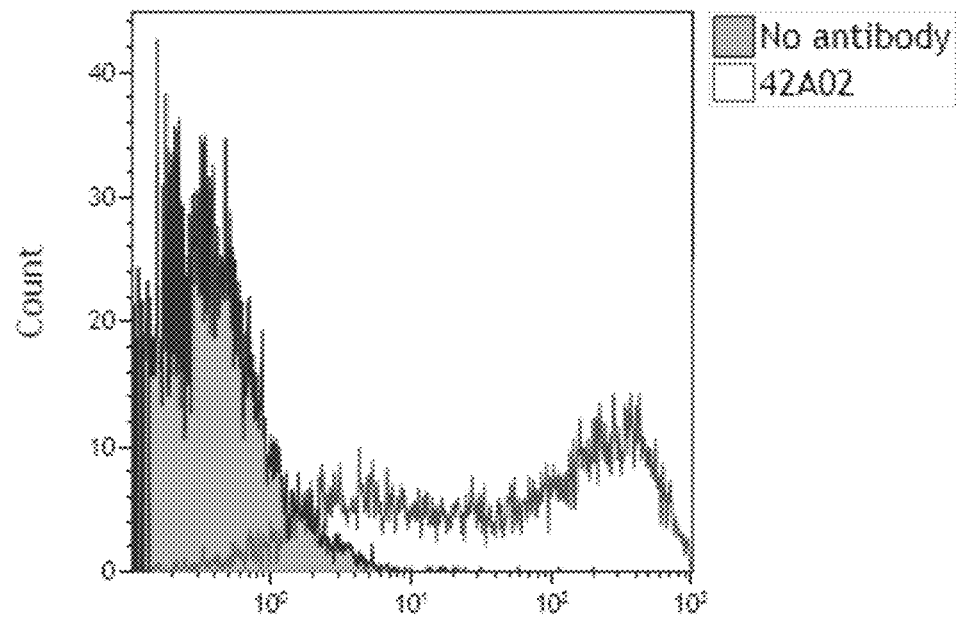
Figure 2:
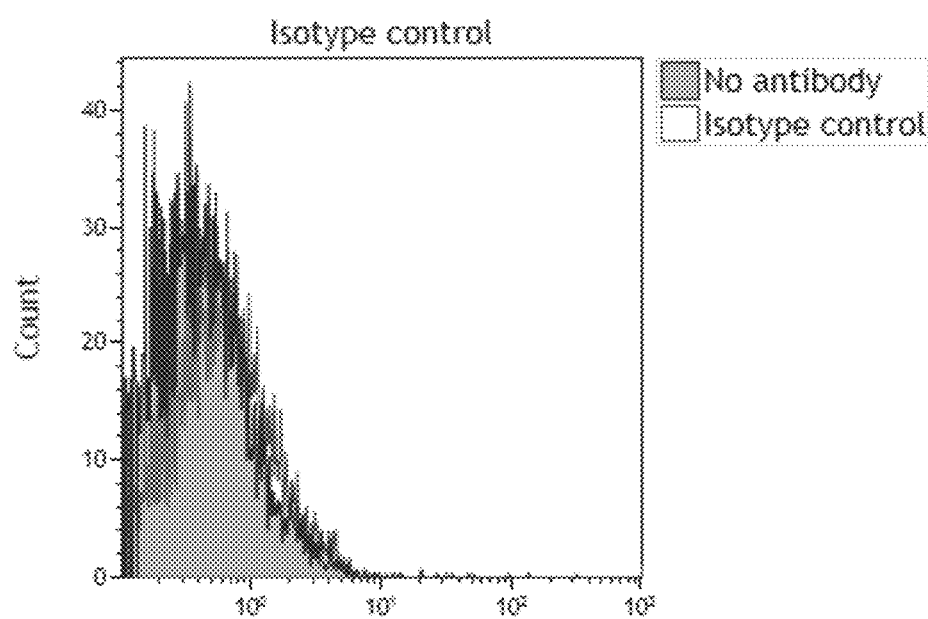
Figure 3A:
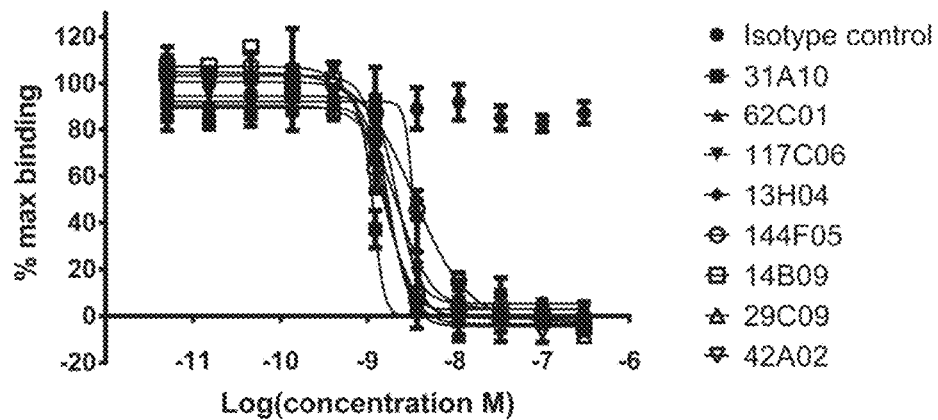
FIGS. 3A-3B.
Figure 3B:
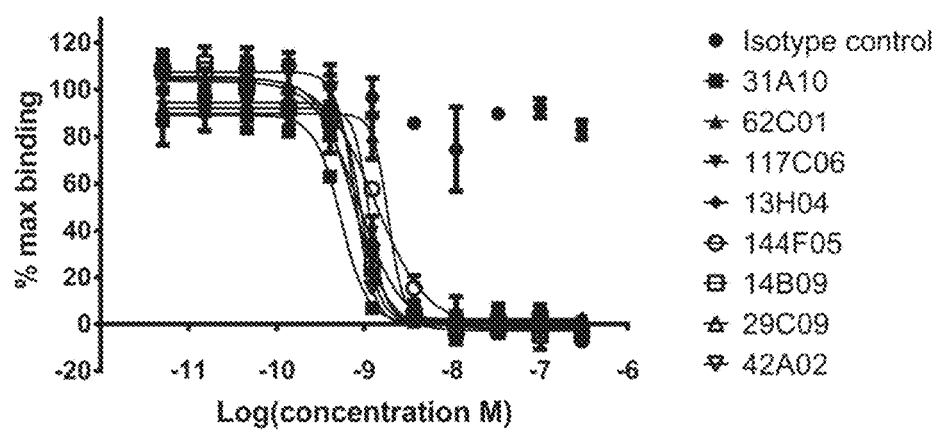

After the identification of 41 hybridoma clones in the secondary screen, selected wells were expanded and murine/human chimeric antibodies purified using a standard Protein G based affinity chromatography purification (see method below). The antibodies were subjected to various assays to assess their ability to block hLIGHT binding to its receptors HVEM and LTβR, as well as the ability of each antibody to bind to human as well as cynomolgus monkey LIGHT with high apparent affinity. To decipher which antibodies were the best among the selected 41, all clones were tested using an in vitro cytokine release assay, where recombinant human LIGHT-214E is added to the culture to induce IL-8 secretion by HT29 cells. More specifically in this assay, HT29 cells, a human colorectal adenocarcinoma cell line, were plated and treated with hLIGHT which was pre-incubated with various concentrations of each of the 41 purified antibody hits. The best 8 neutralizers were selected and a titration of these selected antibodies is depicted in FIG. 1. Data from FIG. 1 is from a single experiment which is representative of at least two independent experiments. Furthermore, all 8 selected leads were tested to bind to natively expressed hLIGHT-214E as expressed on the cell surface of CHO-S cells as determined by flow cytometry. FIG. 2 shows binding of all lead clones at 0.64 μg/ml to CHO-S-hLIGHT 214E cells compared to secondary detection antibody only. In FIG. 2 the term "no antibody" specifies the use of no primary antibody used but not the lack of the secondary detection antibody. Data from FIG. 2 is derived from a single experiment. An isotype control (mouse IgG1/Kappa, Sigma M9269) was run alongside to demonstrate specificity. Furthermore, the lead 8 antibodies were tested for their ability to neutralize the binding of recombinant hLIGHT to its receptors, either human HVEM or human LTβR, in an HTRF assay as outlined in Example 2. FIG. 3A shows the lead panel of antibodies neutralizing LTβR binding to recombinant 214E hLIGHT. FIG. 3B shows neutralization of HVEM binding to hLIGHT. Both FIGS. 3A and 3B are derived from a single experiment which is representative of at least three independent experiments. An isotype control mouse IgG1 antibody (Sigma M9269) was run in both assays. All 8 lead antibodies were again subjected to SPR analysis evaluating the apparent affinity to hLIGHT as well as the level of cross-reactivity to cynomolgus monkey LIGHT. Additionally, cross-reactivity to mouse LIGHT was determined but shown to be very poor or completely absent for the lead panel of antibodies presented here. A summary of the 8 identified lead candidate antibodies can be seen in Table 2.

TABLE 2 mAb Lead Summary

| Clone Information | | Binding- SPR | | | | Binding-Flow Cytometry | Receptor Neutralization | | | |
|---|---|---|---|---|---|---|---|---|---|---|
| | | Human LIGHT | Human LIGHT | Cynomolgus | Murine | Human LIGHT | HT29 IL-8 release, | HVEM HTRF, | LTβR HTRF, | |
| Experiment ID | Clone ID | in nM (214E) | in nM (214K) | LIGHT in nM | LIGHT in nM | in nM (214E) | IC50 in M †† | IC50 in M † | IC50 in M † | Kappa/Lambda |
| KM044-2 | 31A10 | CNROR* | 0.349 | CNROR* | weak binding | yes | 2.17E-10‡ | 6.62E-10 | 1.45E-09 | κ |
| KM044-2 | 62C01 | 1.02 | 23.6 | 1.64 | weak binding | yes | 5.78E-10 | 1.60E-09 | 2.66E-09 | κ |
| KM050 | 29C09 | 0.311 | 0.605 | 2.28 | no binding | yes | 3.30E-10 | 9.22E-10 | 1.55E-09 | λ |
| KM050 | 14B09 | 0.492 | 3.37 | 0.156 | no binding | yes | 1.31E-09 | 8.95E-10 | 1.57E-09 | λ |
| KM050 | 13H04 | 0.881 | 1.57 | 0.561 | no binding | yes | 1.33E-09‡ | 1.09E-09 | 1.97E-09 | λ |
| KM050 | 42A02 | 0.062 | 0.161 | 0.084 | no binding | yes | 9.17E-10 | 8.98E-10 | 1.65E-09 | λ |
| KM050 | 117C06 | 1.03 | no binding | 2.82 | no binding | yes | 1.42E-09 | 1.28E-09 | 2.53E-09 | κ |
| KM050 | 144F05 | 3.25 | 5.78 | 2.89 | no binding | yes | 2.75E-09 | 1.34E-09 | 3.32E-09 | κ |

*CNROR = cannot resolve off-rate
† Numbers in this column represent an average of at least 3 independent experiments
†† Numbers in this column (except for 13H04 and 31A10) represent an average of 3 independent experiments
‡Number in this box (Clone 13H04 and 31A10) represents an average of 2 independent experiments Materials and Methods:

Purification of Antibodies from Hybridoma Supernatant:

Antibodies were purified using Protein G affinity chromatography. Antibodies were eluted from the Protein G media using IgG Elute reagent (Pierce) and the eluted antibodies were buffer swapped into PBS prior to use.

Antibody purity was assessed by SDS-PAGE analysis and quantified by spectrophotometer reading at OD280 nm.

Inhibition of LIGHT Induced IL8 Release from HT29 Cells:

HT29 cells (American Type Culture Collection, ATCC #HTB-38) colorectal adenocarcinoma of epithelial morphology (Fogh J. and Trempe G Human tumor cells in vitro. New York: Plenum Press; 1975) were maintained in McCoys 5a medium (GIBCO)+10% v/v FBS (GIBCO). Cells were split between 1:4 and 1:12 from 100% confluency for routine culture. 100 µl of HT29 cells at 1×10E06/ml in culture media were dispensed in a 96-well clear plate (Costar) (1×10E05 cells/well). A titration of inhibitor was used in order to establish the clone potency as measured by IC50 values in the assay. Antibodies were titrated in culture media from at 50 nM final (200 nM working concentration). 150 µl of titration of inhibitor was added to 150 µl of recombinant 214E hLIGHT (in house expressed) (10 ng/mL final so 40 ng/mL working concentration) diluted in culture media. The inhibitor titration and hLIGHT were pre-incubated together for 30 minutes at 37° C. in 96 well sterile U-bottom clear plate (Costar). 100 µl of hLIGHT+ inhibitor titration was added to the cells in duplicate or 100 µl of control (culture media or LTα1β2 (R&D Systems, 678-LY-010/CF) at 0.5 µg/mL final or LIGHT only at 10 ng/mL final or culture media only). Cells were then cultured overnight (16-18 h) in a humidified atmosphere at 37° C. and 5% CO2. Following the incubation period conditioned supernatant from the HT29 cells was removed and levels of IL8 determined by IL-8 ELISA (R&D systems).

IL-8 levels in supernatants were determined using human IL-8 Duoset ELISA kit (R & D) Systems). IL-8 capture antibody (4 µg/ml diluted in PBS, 50 al/well) was adsorbed to 96 well low auto-fluorescent, high protein binding plates (Costar) overnight at 4° C. Excess IgG was removed by washing with PBS-Tween and the wells were blocked with 1% bovine serum albumin (BSA) in PBS for 1 hour at room temperature, after which plates were washed as described previously. 50 al/well of conditioned culture media was then added IL-8 standards (from 2000 pg/ml, 1:2 dilution) were also added to ELISA plates as an ELISA control and the plates were incubated at room temperature for at least 1 hour.

Following incubation, plates were washed as before to remove unbound proteins. Biotinylated IL-8 detection Ab (20 ng/ml in reagent diluent (0.1% BSA/PBS); 50 µl/well) was then added to the plates and incubated at RT for 1 h. Unbound detection antibody was removed by washing with PBS-Tween (0.1% v/v), while the remaining biotinylated antibody was detected by streptavidin-Europium3+conjugate (DELFIA® detection, PerkinElmer). Time-resolved fluorescence was measured at 615 nm on an Envision plate reader (PerkinElmer). Fluorescence data was plotted as Europium counts. Inhibitor data was normalized to percentage of maximal IL-8 release using the Europium counts from LIGHT stimulation in the absence of inhibitor control (max control) and no LIGHT control (media control) as Equation 6. IC50 values were determined using GraphPad Prism software by curve fitting using a four-parameter logistic equation (Equation 7).

$$\% \text{ LIGHT} - \text{induced } IL8 \text{ release} \qquad \text{Equation 6}$$

$$\% \text{ LIGHT} - \text{induced } IL8 \text{ release} = \frac{(\text{sample} - \text{media})}{(\text{max} - \text{media})} \times 100$$

Max = LIGHT only (no inhibitor)

Media = culture media only (no LIGHT)

Four Parameter Logistic Calculation  Equation 7

$$Y = \text{Bottom} + (\text{Top} - \text{Bottom})/(1 + 10^{\wedge}((\text{Log IC50} - X) * \text{HillSlope}))$$

X = logarithm of concentration.

Y = specific binding (equation 6)

Top and Bottom = Plateus in same units as Y (specific binding)

Log IC50 in same units as X. Y starts at Bottom and goes to Top with a sigmoid shape. Specific binding decreases as X increases Binding of Antibodies Purified from Hybridoma Supernatant to CHO-S Expressed hLIGHT Binding of antibodies purified from hybridoma supernatant was carried out as described herein.

HTRF Ligand/Receptor Neutralisation:

The following methods were carried out with a titration of inhibitor in order to establish the clone potency as measured by IC50 values in the assay. 5 µl of Flag-tagged hLIGHT (in-house) diluted to 2.5 nM final concentration (10 nM working concentration) in HTRF buffer with 5 µl of a titration of antibody purified from hybridoma supernatant diluted in HTRF assay buffer from 300 nM final (1200 nM working concentration) was pre-incubated for 1 hour at room temperature. To wells used to define total binding, 5 µl of LIGHT (10 nM working, 2.5 nM final) and 5 µl of hybridoma maintaining media (HMM,)) were added. To wells used to define non specific binding (receptor only) 10 µl of HMM was added. Total and non specific binding wells were pre-incubated for 1 hr at RT in the same plate as wells containing titration of inhibitor.

LIGHT receptor was diluted in HTRF assay buffer and added to all wells, 5 µl/well of HVEM-Fc or LTβR-Fc (R&D systems) at 1.2 nM for HVEM (0.3 nM final) and 0.4 nM for LTβR (0.1 nM final).

In order to detect binding, 5 µl of combined detection reagent were added to all wells. Anti-flag D2 (Cisbio) was diluted to 20 nM (5 nM final) in HTRF assay buffer and anti-human Fc K (Cisbio) was diluted 1:100 in HTRF assay buffer (for final dilution 1:400).

Plate were left to incubate in the dark for 3 hours prior to reading time resolved fluorescence at 620 nm and 665 nm emission wavelengths using an EnVision plate reader (Perkin Elmer). More details of the HTRF® assay technology can be found in Mathis (1995) Clinical Chemistry 41(9), 1391-1397. Data were analysed by calculating % Delta F values and % of receptor for each sample according to equation 8 and equation 9 respectively.

Calculation of % DeltaF  Equation 8

$$\% \text{ delta } F = \frac{(\text{sample } 665/620 \text{ nm ratio value}) - (\text{non-specific control } 665/620 \text{ nm ratio value})}{\text{non-specific control } 665/620 \text{ nm ratio}} \times 100$$

Non-specific control = receptor only

-continued

Percentage of receptor binding (HTRF)     Equation 9
Based on calculation of DeltaF (Equation 8)

$$\% \text{ of Receptor binding} = \frac{\text{sample value}}{\text{total binding}} \times 100$$

Total binding =
   receptor (HVEM or LTβR) and LIGHT (no inhibitor)

Surface Plasmon Resonance Analysis:

SPR analysis was carried out using the ProteOn™ XPR36 Array System (BioRad). Anti-mouse IgG (GE Healthcare BR-1008-38) was immobilised on a GLC biosensor surface using amine coupling, the surface was then blocked using 1M ethanolamine. Test antibodies were captured on this surface and recombinant hLIGHT (214E, 214K and cynomologus variants) were used at a single concentration of 256 nM, binding sensorgrams were double referenced using a buffer injection (i.e. 0 nM) to remove baseline drift and injection artefacts. Apparent affinities for the LIGHT-antibody interaction were determined using the 1:1 model inherent to the ProteOn XPR36 analysis software. The assay was run using HBS-EP (Teknova) as running buffer and carried out at 25° C.

Example 4

Antibody Binding Characterization Study

Antibody cross-blocking experiments using SPR demonstrated that the isolated antibodies fall into 3 distinct epitope categories. Antibody clones 31A10, 29C09, and 144F05 bind to epitope category 1 and can recognize both hLIGHT allele variants (214E & 214K) with similar apparent affinity. Antibody clones 62C01 and 117C06 were categorized as epitope category 2, which permits high affinity binding to the dominant human LIGHT allele variant 214E, but binding to the minor allele variant 214K is either reduced more than 20 fold or completely abolished. Lastly, antibody clones 14B09, 13H04, and 42A02 were identified to be epitope category 3 binders, where antibodies recognize both human LIGHT allele variants (214E and 214K) with similar high apparent affinity. Interestingly, antibodies of epitope category 2 and 3 compete with each other for hLIGHT binding. However, due to the differential binding profile where epitope category 2 antibodies cannot recognize the minor allele variant of LIGHT and epitope category 3 antibodies can, (while not wishing to be bound by any theory) we conclude that antibodies of epitope category 2 and 3 must bind separate epitopes on the surface of the LIGHT molecule. Antibodies of epitope categories 1 and 3 do not compete with each other and (while not wishing to be bound by any theory) we conclude that they must therefore bind different epitopes. Also, antibodies of epitope category 1 and 2 antibodies do not compete with each other and (while not wishing to be bound by any theory) we conclude that they must therefore bind different epitopes.

The data from this cross-binding study is summarized in Table 3:

TABLE 3

| Experiment ID | Clone ID | Epitope | Ab Footprint | hLIGHT 214E Binder | hLIGHT 214K Binder |
|---|---|---|---|---|---|
| KM044-2 | 31A10 | 1 | A | yes | yes |
| KM044-2 | 62C01 | 2 | B | yes | no |
| KM050 | 29C09 | 1 | A | yes | yes |
| KM050 | 14B09 | 3 | B | yes | yes |
| KM050 | 13H04 | 3 | B | yes | yes |
| KM050 | 42A02 | 3 | B | yes | yes |
| KM050 | 117C06 | 2 | B | yes | no |
| KM050 | 144F05 | 1 | A | yes | yes |

Materials and Methods

Antibody Competition SPR:

All antibodies tested in the competition SPR were in human IgG4(PE) format (see Example 5 for re-formatting methods). To investigate antibodies that may share the same binding region on LIGHT, an SPR based assay was carried out on the ProteOn™ XPR36 Array System. Anti-human IgG antibody (Jackson Immunoresearch, 109-005-008, 109-006-008 and 309-006-008) was immobilised on the GLC biosensor surface, and the assay performed as above was immobilised a GLC biosensor chip using standard amine coupling. The anti-human IgG surface was used as a capture surface to capture test antibodies as "ligands" for analysis. Using the ProteOn™ XPR36 Array System ability to address the capture surface in either the vertical or horizontal orientation the assay was carried out as follows. The "Ligand" antibodies were captured in the vertical orientation, and then a 1 in 1000 dilution of mouse serum was used to block the capture surface in the horizontal orientation. LIGHT was then passed over the capture surface in the horizontal orientation and bound to the captured ligand antibody, after which the same ligand antibody was passed over the "antibody-LIGHT" complex, (LIGHT is a trimer, so this ensures all available LIGHT molecules are bound to by the Ligand antibody), again the second application of the ligand antibody was in the vertical orientation. Then the analyte antibody was passed over the "antibody-LIGHT ligand complex" in the horizontal orientation, if no binding is seen then the Abs share a similar epitope, if binding does occur then the Abs do not share a similar epitope. Binding/no-binding is determined by monitoring the sensorgrams, which were double referenced using a non-LIGHT binding antibody as a control sample and was included with every set of ligand antibodies run. After the interactions had finished the anti-mouse IgG capture surface was regenerated using 10 mM glycine, pH1.7, leaving the capture surface available for another round of analysis. The assay was run at 25° C. using HBS-EP as running buffer.

Example 5

Sequence Recovery of Lead Antibody Candidates

After the selection and characterization of lead candidates, their fully human variable domains were recovered using RT-PCR using a mixture of forward and reverse primers. Antibodies were reformatted into a human IgG4 backbone and expressed using a transient expression system in CHO-S cells. A summary of all sequences is displayed in the Sequence Listings and Table 4.

TABLE 4

| Clone Information | | | Sequence Composition | | | | | |
|---|---|---|---|---|---|---|---|---|
| Experiment ID | Clone ID | Rearrangement HC | nt | aa | k/l | Rearrangement LC | nt | aa |
| KM044-2 | 31A10 | V4-4*02/D6-19*01/J6*02 | 12 | 8 | Kappa | V1D-13/J05*01 | 9 | 6 |
| KM044-2 | 62C01 | V3-23*04/D3-10*01/J3*02 | 6 | 1 | Kappa | V1D-12*02/J4*01 | 5 | 2 |
| KM050 | 29C09 | V1-8*01/D3-16*02/J3*02 | 5 | 4 | Lambda | V3-10*01/J1*01 | 1 | 0 |
| KM050 | 14B09 | V1-3*01/01-14*01/J5*02 | 5 | 4 | Lambda | V2-23*02/J3*01 | 6 | 3 |
| KM050 | 13H04 | V1-18*01/D1-1*01/J5*02 | 4 | 3 | Lambda | V2-23*02/J3*02 | 5 | 3 |
| KM050 | 42A02 | V3-23*04/D3-10*01/J4*02 | 9 | 6 | Lambda | V3-21*01/J3*02 | 6 | 4 |
| KM050 | 117C06 | V1-18*01/J5*02 | 12 | 7 | Kappa | V3-20*01/J2*04 | 3 | 1 |
| KM050 | 144F05 | V4-4*02/D6-13*01/J6*02 | 8 | 6 | Kappa | V1-33*01/J4*01 | 1 | 1 | nt—nucleotide
aa—amino acid
Indicates numbers of changes from germline segment sequences Materials and Methods RNA Isolation from Hybridoma Cells:

Total RNA was extracted from hybridoma cells using TRIzol™ Reagent (Invitrogen). The quantity and quality of the isolated RNA was analysed spectrophotometrically.

Antibody Variable Domain Recovery by RT-PCR:

Selected clones were used for preparing total RNA, which was used in an RT-PCR reaction to recover the heavy chain V-regions. IgG specific reverse primers and Ig leader sequence specific forward primer sets or alternatively IgG specific reverse primers and Ig 5' untranslated region (UTR) sequence specific forward primer sets were used for the heavy chains. Kappa constant region specific reverse primers and Kappa leader sequence specific forward primer sets or alternatively Kappa constant region specific reverse primers and Kappa 5'UTR sequence specific forward primer sets were used for the Kappa light chains. Lambda specific 3'UTR reverse primers and Lambda leader sequence specific forward primer sets or alternatively Lambda specific 3'UTR reverse primers and Lambda 5'UTR sequence specific forward primer sets or alternatively Lambda constant region specific reverse primers and Lambda leader sequence specific forward primer sets or alternatively Lambda constant region specific reverse primers and Lambda 5'UTR sequence specific forward primer sets were used for the Lambda light chains. The RT-PCR products were separated by agarose gel electrophoresis with the DNA of the predicted size being sequenced in the forward and reverse directions. Alternatively, the RT-PCR products were subcloned into a cloning vector and DNA of individual colonies submitted for sequencing.

Re-Formatting of Antibodies with IgG4 Backbone

The heavy chain variable region coding sequences were codon optimised for mammalian expression and fused in frame with the codon optimized Human IgG4-PE constant region by overlap extension PCR and then cloned into a pXC-18.4 expression plasmid (Lonza) using standard restriction enzyme digestion and ligation. The kappa light chain variable region coding sequences in frame with the human kappa constant region or the full length lambda light chain coding sequences were codon optimized for mammalian expression and cloned into a pXC-17.4 expression plasmid (Lonza) using standard restriction enzyme digestion and ligation. For the simultaneous expression of the heavy and light chains the vectors pXC-17.4 and pXC-18.4 were fused into one single vector using standard restriction enzyme digestion and ligation.

All constructs were sequenced to ensure their correct sequence composition.

Example 6

Determining Effect of Anti-LIGHT Antibodies on Activation of T Cells in Dendritic Cell-T-Cell Mixed Lymphocyte Reaction Dendritic cells are generated from monocytic precursors. Monocytic precursors are isolated from peripheral blood mononuclear cells (PBMCs) isolated using Ficoll-Paque plus (GE Healthcare) density gradient centrifugation from leukoreduction system chambers (NHSBT). Monocytes are isolated from PBMCs using negative selection magnetic separation beads (Miltenyi). Monocytes are cultured with cytokines GM-CSF (Peprotech) at 100 ng/ml and IL-4 (Peprotech) at 100 ng/ml for 7 days in culture media (RPMI (Gibco) supplemented with 10% v/v FBS). After seven days, cells are removed using cell dissociation media (Gibco) and a cell scraper and are used immediately or cryopreserved for future use. T cells are isolated from allogeneic PBMC using negative selection magnetic separation beads (Miltenyi).

Dendritic cells are pre-incubated with mitomycin C (Sigma) at 10 µg/ml in PBS for one hour at 37° C. Cells are then washed 3 times in PBS centrifuging at 300×g for 3 minutes, aspirating the supernatant after each wash. Allogeneic T cells are added to a 96-well plate in RPMI supplemented with 10% v/v FBS, then dendritic cells are added at a defined ratio of dendritic cells/T cells ranging from 1:1 and 4:1 based on number of cells/well. The cells are incubated for five days at 37° C. After five days TNF-α, IFN-γ, and IL-2 are measured by duoset ELISA (R&D Systems) according to manufacturer's recommendations. Proliferation is measured by CFSE dilution according to manufacturer's recommendations.

Determining Effect of Anti-LIGHT Antibodies in Allogenic PBMC Mixed Lymphocyte Reaction PBMCs are isolated from leukoreduction system chambers (NHSBT) using Ficoll-Paque plus (GE Healthcare) density gradient centrifugation. PBMC are pre-incubated with mitomycin C (Sigma) at 10 µg/ml in PBS for one hour at 37° C. Cells are then washed 3 times in PBS centrifuging at 300×g for 3 minutes, aspirating the supernatant after each wash. Allogeneic PBMC (not treated with mitomycin C) are added to a 96-well plate in RPMI supplemented with 10% v/v FBS at a concentration of 1×10E06/ml, 100 µl/well. Mitomycin C treated PBMC are then added to allogeneic PBMC (not treated with mitomycin C) in 96-well plate at a final cell ratio in range of 1:1 to 4:1 mitomycin C treated to non mitomycin C based on number of cells/well. The cells are incubated for five days at 37° C./5% CO2. After five days TNF-α, IFN-γ, and IL-2 are measured by duoset ELISA (R&D Systems) according to manufacturer's recommendations. Proliferation is measured by CFSE dilution according to manufacturer's recommendations.

Example 7

Antigen Preparation, Immunization Procedures, and Hybridoma Generation

The following Example provides a description of the generation and identification of a further panel of anti-human LIGHT monoclonal antibodies using the KyMouse™ system as discussed above. Detailed descriptions can be found in Example 1. Antibodies 18E04 and 98C07 were isolated from hybridomas generated using splenocytes from mice immunised using a RIMMS regime, as described in Example 1.

Cloning of Antibodies from Single B Cells (BCT)

Transgenic mice from group 4 (Immunization Procedures) were used here. Murine tissue isolation and preparation, and enrichment of B cells were performed as per Example 1 method above. Additionally, antigen-specific B cells were single cell sorted in 96 well plates containing lysis buffer. Lysates were subjected to RT-PCR and the resulting heavy chain and light chain products sent for sequencing.

Sequences were transfected into CHO cells for expression. Supernatants were collected 5 days post-transfection and screened as per hybridoma supernatants, described in Example 8.

Example 8

Hybridoma Supernatant Screening

After generation of hybridoma clones, the hybridoma supernatant was assessed in a sequential primary and secondary screen and appropriate hybridoma clones selected based on criteria of antibody binding to hLIGHT and receptor neutralization activity. A detailed description of the screening, and the selection of hits by primary and secondary screening, can be found in Example 2. Antibody clones 18E04 and 98C07 were selected in this manner.

Antibodies were defined as a secondary hit when antibodies in hybridoma supernatant bound to hLIGHT-214E, but not necessarily hLIGHT-214K, with high apparent affinity as well as cross-reacting with recombinant cynomolgus monkey LIGHT. Additionally antibodies in the supernatant had to at least neutralize one of LIGHT's receptors, i.e.: LTβR or HVEM, in at least one of the two assays tested (i.e., HTRF or flow cytometry based assay).

For antibodies generated using BCT, the screening cascade was as described in Example 2, with amendments described below. Two BCT clones were also selected for the lead panel based on primary and secondary screen, and SPR analysis. Desired selection criteria for BCT clones were devised by the inventors (see details in Example 9). Antibodies 01C02 and 01C06 were selected in this manner.

Wells containing BCT clones were selected if antibodies present in the supernatant could bind natively displayed hLIGHT-214E expressed on the cell surface of CHO-S cells or to recombinantly expressed human LIGHT-214E. In addition, the inventors decided to analyse supernatants by SPR to evaluate apparent affinity of the antibodies to recombinant trimeric human LIGHT. Lastly the inventors decided to assess the ability of each antibody to neutralize recombinantly expressed hLIGHT-214E binding to HVEM using a receptor neutralisation HTRF assay. Clones meeting certain selection criteria (see further description below) using data from the aforementioned assays were then re-formatted with a human constant region, that was non FcR-binding, and hinge region-stabilised (IgG4(PE)) to allow further characterization.

Materials and Methods

Primary Screen—Binding to Cell Expressed Human LIGHT-214E:

For antibody clones 18E04 and 98C07, screening was performed as per Example 2. A selection criterion of greater than or equal to 5.0 percent response was applied to define a well as a hit.

Calculation of Percentage Effect from Primary Screen ($LI$ – COR) and HTRF (Using 800% Resp values ($LI$ – COR) or 665/620 nm ratio (see equation 2) (HTRF)

Equation 1

$$\text{Percent effect} = \frac{(\text{sample well} - \text{non-specific binding}) \times 100}{(\text{total binding} - \text{non-specfic binding})}$$

Non-specific binding = values from wells containing isotype control mouse $IgG1$ Total Binding = values from wells containing reference antibody For antibodies generating using BCT, the same method was used with the following modification: as antibody-producing cells were cultured in CHO media, positive control reference antibody, and isotype control antibody were diluted in CHO media (CD CHO medium (Gibco) and 8 mM L-glutamine).

Primary Screen: Binding to Recombinant Human LIGHT-214E:

For clones screened from hybridoma (18E04 and 98C07), methods are as described in Example 2.

For clones screened from BCT, a modified version of the method in Example 2 was used. 5 µl of 20 nM biotinylated hLIGHT-214E diluted in HTRF buffer (PBS (Sigma)+0.53M KF (Sigma)+0.1% w/v BSA (Sigma) was pre-incubated with 5 µl of Streptavidin D2 (Cisbio) diluted 1:100 in HTRF assay buffer for 1 hr at room temperature. 5 µl of CHO supernatant or 5 µl of reference antibody or mouse IgG1 isotype control diluted to 5 nM working concentration in CHO media was transferred to a white 384 well low volume non-binding surface polystyrene plate (Greiner). 5 al goat anti-mouse IgG (Southern Biotech) labelled with europium cryptate (Cisbio) diluted 1:1000 in HTRF assay buffer, for final dilution 1:4000, was added. The plate was left to incubate in dark for 2 hours prior to reading time resolved fluorescence at 620 nm and 665 nm emission wavelengths using an EnVision plate reader (Perkin Elmer). Analysis was performed as described for hybridoma.

Data were analysed by calculating 665/620 ratio and percent effect for each sample according to equation 2 and equation 1 respectively.

Calculation of 665/620 ratio

Equation 2

665/620 ratio=(sample 665/620 nm value)×10000

For clones derived from hybridoma, a selection criterion of greater than or equal to 20 percent effect was applied by the inventors to define a well as a hit from recombinant hLIGHT-214E binding. For clones derived from BCT a selection criterion of greater than or equal to 10 percent effect was applied by the inventors to define a well as a hit from recombinant hLIGHT-214E binding.

Secondary Screen: Binding to Cell Expressed and Recombinant Human LIGHT-214E

As described previously, supernatants were screened to assess whether the secreted antibodies that bind to CHO-S expressed hLIGHT-214E, may also bind to CHO-S expressed hLIGHT-214K (a), in some cases bind to untransfected CHO-S cells (b), whether they neutralise recombinant LTβR-Fc or HVEM-Fc binding to CHO-S hLIGHT-214E (c) and ability to neutralise LTβR-Fc or HVEM-Fc binding to recombinant biotinylated hLIGHT-214E (d).

Binding to CHO-S Expressed hLIGHT and Receptor Neutralisation (Assays a, b, and c):

Hybridoma derived clones were screened as per Example 2.

Percentage of receptor binding (FACS)     Equation 3

Based on geomean fluorescence

% of Receptor binding =

$$\frac{\text{sample value} - \text{non-specific binding}}{\text{total binding} - \text{non-specific binding}} \times 100$$

Non-specific binding = No antibody, no receptor

Total binding = receptor (LTβR or HVEM) only binding (no inhibitor) + isotype control at 1 μg/ml

Secondary Screen—HTRF Ligand/Receptor Neutralisation (Assay d):

Hybridoma clones were screened as described in Example 2.

For clones derived from BCT, supernatants from CHO cells were tested for the ability to neutralize recombinantly expressed hLIGHT-214E binding to HVEM using a receptor neutralisation HTRF assay. The assay was performed as described in Example 2 with the following modifications. To wells used to define total binding, 5 μl of LIGHT (10 nM working, 2.5 nM final) and 5 μl of CHO media) were added. To wells used to define non-specific binding (receptor only) 10 μl of CHO media was added. Data were analysed as per hybridoma clones.

665/620 ratio (2) = sample 665/620 nm value     Equation 4

Percentage of receptor binding (HTRF)     Equation 5

Based on calculation of 665/620 ratio (2) (equation 4)

% of Receptor binding =

$$\frac{\text{sample value} - \text{non-specific binding}}{\text{total binding} - \text{non-specific binding}} \times 100$$

Non-specific binding = receptor and reference antibody at 300 nM

Total binding = receptor (HVEM or LTβR)

and LIGHT (no inhibitor)

Hit Criteria Selection from Secondary Screening:

Hits were selected based on binding and neutralisation assays. Hits in CHO-S LIGHT-214E/HVEM-Fc or LTβR-Fc were defined by the inventors as <70% receptor binding to CHO-S LIGHT-214E cells by FACS. Hits in flag-LIGHT/HVEM-Fc or flag-LIGHT/LTβR-Fc HTRF neutralisation assays were defined as clones with <90% receptor binding. Binding to CHO-S LIGHT-214E and in some cases to CHO-LIGHT 214K were defined as >2*background (mouse IgG1 binding) geomean. For BCT, <40% receptor binding to flag-LIGHT/HVEM by HTRF neutralisation assay was considered to be a hit. Cross-reactivity with cynomolgus LIGHT, and binding to native and/or recombinant hLIGHT 214E was also required for progression of BCT hits. Apparent affinity measurements by SPR were also considered.

Example 9

Antibody Lead Characterization

Figure 4A:
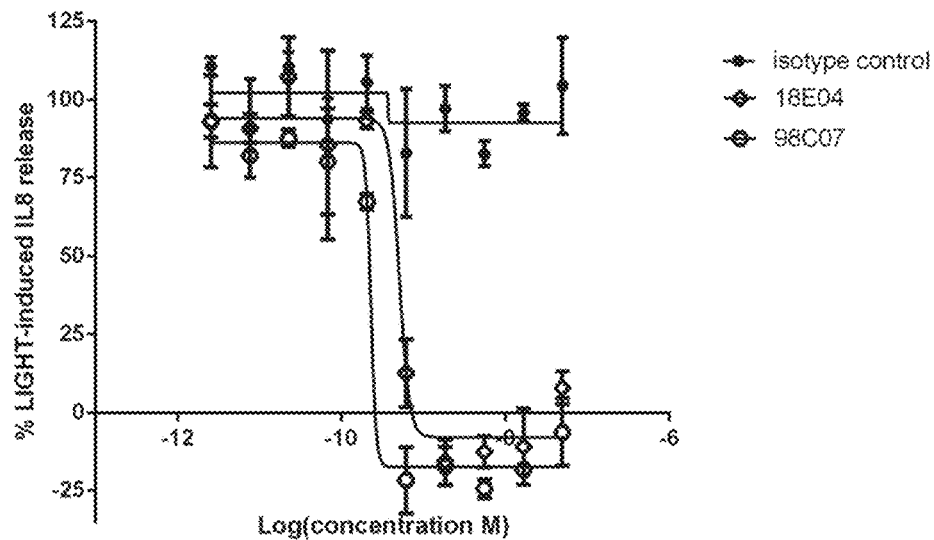
FIGS. 4A-4B.
Figure 4B:
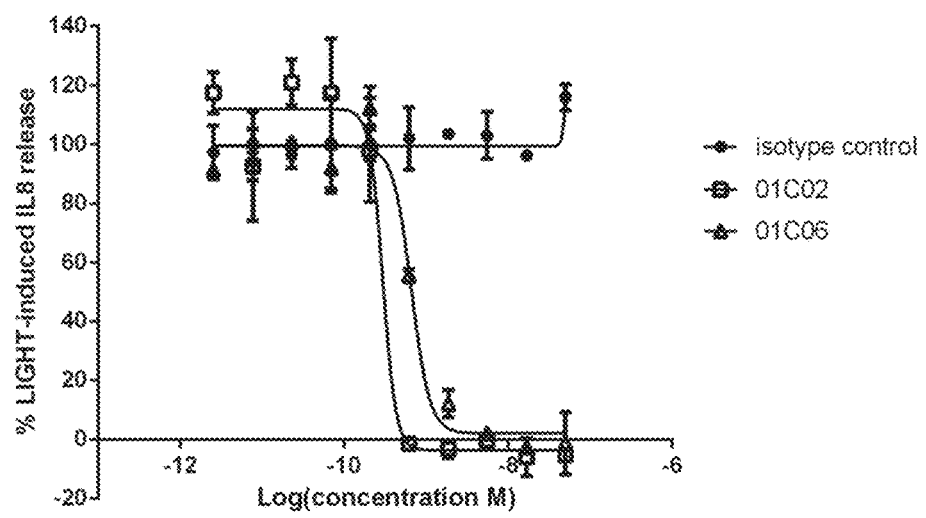
Figure 5:
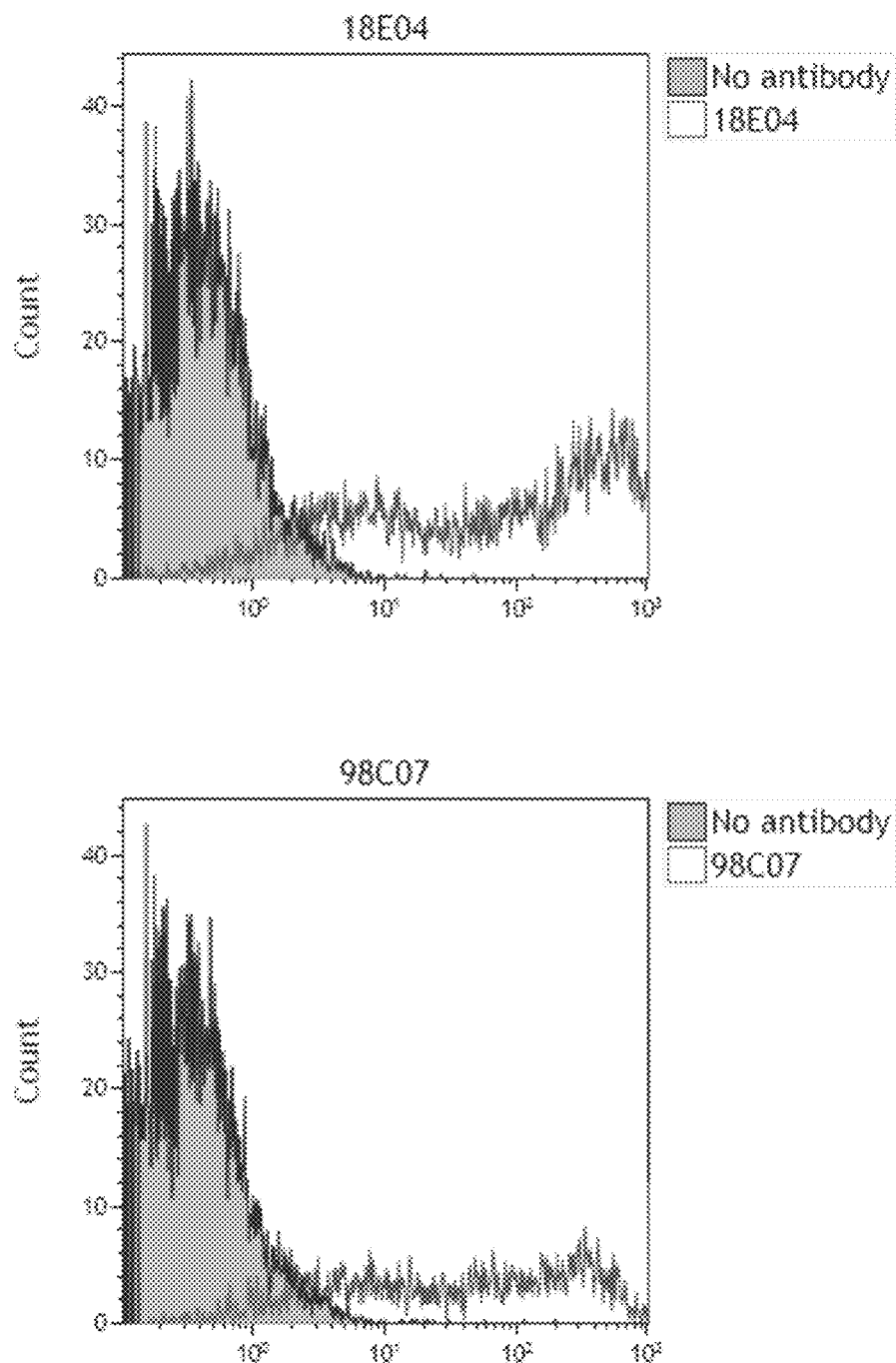
FIG. 5.
Figure 5:
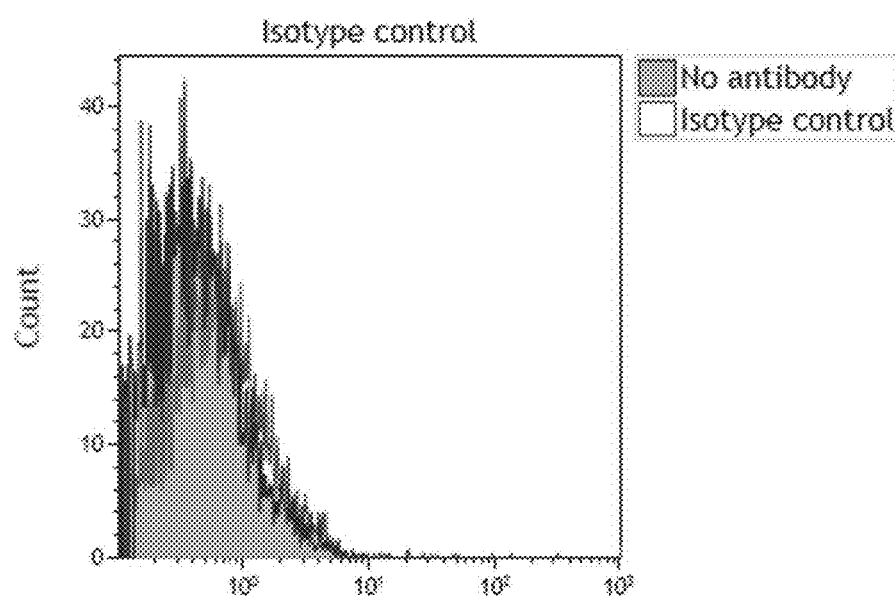

Selected wells were expanded and murine C/human V chimeric antibodies purified using a standard Protein G based affinity chromatography purification (see Example 3). The two hybridoma-derived clones and the two BCT clones were subjected to various assays to assess their ability to block hLIGHT binding to its receptors HVEM and LTβR, as well as the ability of each antibody to bind to human as well as cynomolgus monkey LIGHT with high apparent affinity FIG. 4A shows the ability of the additional hybridoma clones to block hLIGHT-induced IL-8 release by HT29 cells. FIG. 4B shows the results of the clones generated by BCT. Data from FIG. 4 is from a single experiment which is representative of at least two independent experiments. FIG. 5 shows binding of lead hybridoma clones at 0.64 μg/ml to CHO-S-hLIGHT 214E cells compared to secondary detection antibody only. In FIG. 5 the term "no antibody" specifies the use of no primary antibody used but not the lack of the secondary detection antibody. Data from FIG. 5 is derived from a single experiment. An isotype control (mouse IgG1/Kappa, Sigma M9269) was run alongside to demonstrate specificity.

Additionally, antibodies were tested for their ability to neutralize the binding of recombinant hLIGHT to its receptors, either human HVEM or human LTβR, in an HTRF assay as outlined.

Figure 6A:
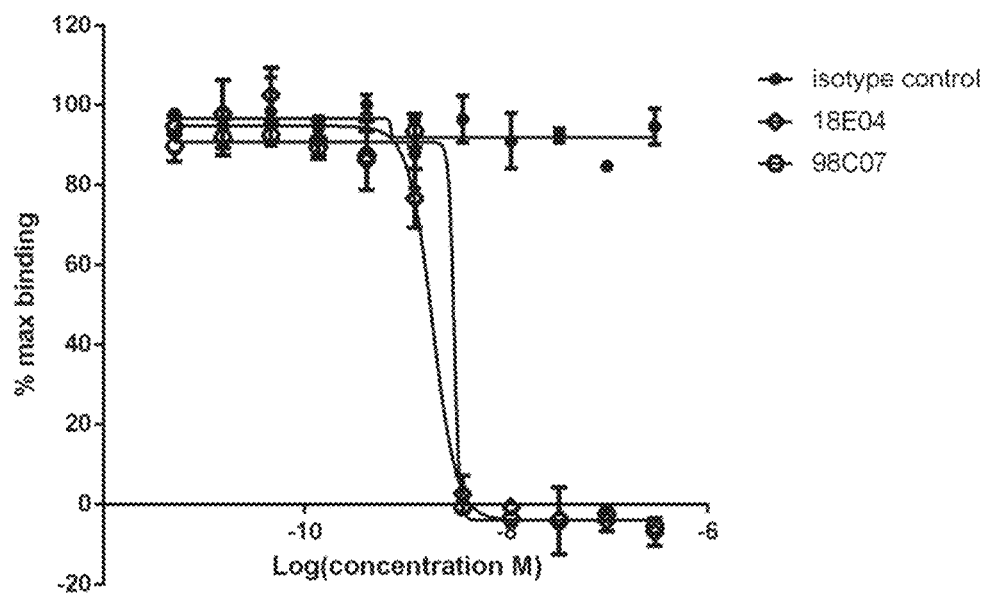
FIGS. 6A-6D.
Figure 6B:
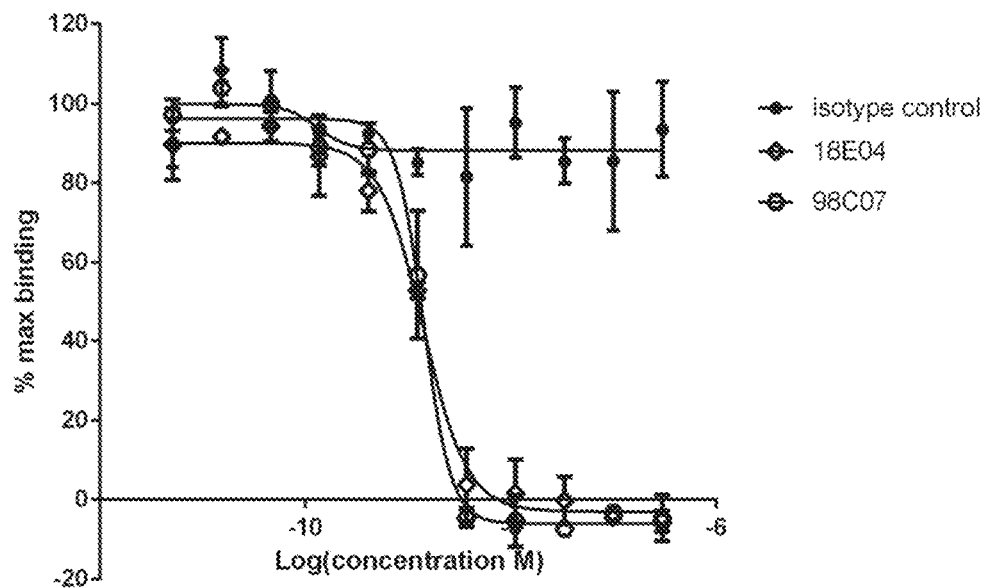
Figure 6C:
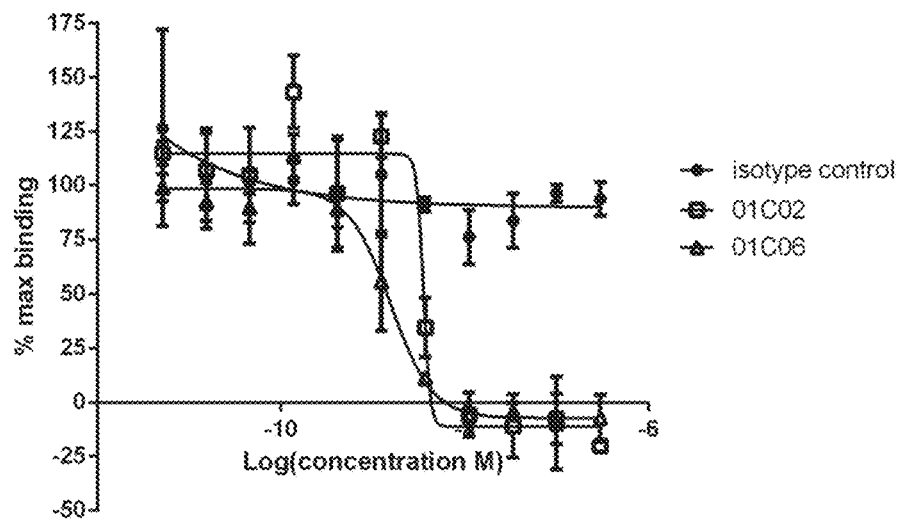
Figure 6D:
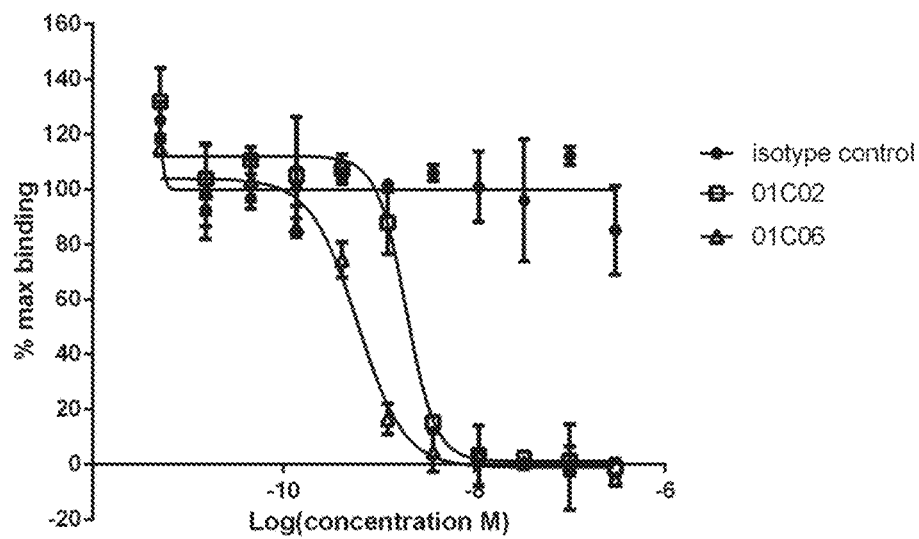

FIG. 6A shows the neutralization of LTβR binding to recombinant hLIGHT-214E by the additional hybridoma clones. FIG. 6B shows neutralization of HVEM binding to hLIGHT. Both FIGS. 6A and 6B are derived from a single experiment which is representative of at least two independent experiments. An isotype control mouse IgG1 antibody (Sigma M9269) was run in both assays. Lead antibodies were again subjected to SPR analysis evaluating the apparent affinity to hLIGHT as well as the level of cross-reactivity to cynomolgus monkey LIGHT. Cross-reactivity to mouse LIGHT was absent. FIG. 6C shows neutralization of LTβR binding to hLIGHT by BCT-derived clones, and FIG. 6D shows neutralization of HVEM binding. A summary of the additional lead candidate antibodies can be seen in Table 5.

TABLE 5 mAb Lead Summary

| Clone Information | | Binding- SPR | | | | Binding | Receptor Neutralization | | | |
| --- | --- | --- | --- | --- | --- | --- | --- | --- | --- | --- |
| | | Human LIGHT | Human LIGHT | Cynomolgus | Murine | FACS Human | HT29 IL-8 release, | HVEM | LTBR | |
| Experiment ID | Clone ID | in nM (214E) | in nM (214K) | LIGHT in nM | LIGHT in nM | LIGHT (214E) | IC50 (M) †† | HTRF IC50 (M)† | HTRF IC50 (M)† | Kappa/ lambda |
| KM050 | $ 98C07 | 0.045 | 296 | 0.257 | no binding | yes | 1.66E-10‡ | 1.08E-09≠ | 2.06E-09≠ | Kappa |
| KM050 | $ 18E04 | CNROR* | 2.33 | 3.11 | no binding | yes | 3.27E-10 | 1.32E-09 | 1.64E-09 | Lambda |
| KM044-1 | #01C02 | CNROR* | CNROR* | CNROR* | no binding | n.d. | 2.61E-10 | 1.64E-09 | 3.48E-09 | Kappa |
| KM044-1 | #01C06 | CNROR* | CNROR* | CNROR* | no binding | n.d. | 5.56E-10 | 6.98E-10 | 2.07E-09 | Kappa |

Antibodies in IgG4(PE) format
$ antibodies purified from hybridoma supernatant (mouse IgG)
*cannot resolve off-rate (ie, very high affinity)
n.d. not determined
†Numbers in this column (except 98C07) represent an average of two independent experiments
≠Number in this box represents an average of at least three independent experiments
†† Numbers in this column (except 98C07) represent an average of two independent experiments
‡Number in this box represents an average of three independent experiments Materials and Methods:
Purification of Antibodies from Hybridoma Supernatant:
Antibodies were purified as per Example 3.
Re-Formatting of BCT-Derived Antibodies
Antibodies 01C02 and 01C06 were re-formatted with a hinge-region stabilised, non-FcR-binding human constant region (IgG4(PE)) as per Example 10. All assays in this Example were performed with these re-formatted antibodies.
Inhibition of LIGHT Induced IL8 Release from HT29 Cells:
This assay was performed as per Example 3.

Binding of Antibodies Purified from Hybridoma Supernatant to CHO-S Expressed hLIGHT Binding of antibodies purified from hybridoma supernatant was carried out as described herein.

HTRF Ligand/Receptor Neutralisation:

Analysis of antibodies 18E04 and 98C07 was performed as per Example 3.

For analysis of BCT-derived clones re-formatted with a human IgG4(PE) constant region, the assay was performed as per Example 3, with the following modifications: HVEM-Fc and LTβR-Fc were labelled with AlexaFluor 647, and an anti-Flag K antibody (Cisbio) was used for detection.

Surface Plasmon Resonance Analysis:

For hybridoma-derived clones, this was performed as per Example 3. For BCT-derived clones, anti-human IgG (Jackson Immunoresearch, 109-005-008, 109-006-008 and 309-006-008) was immobilised on the biosensor surface. The remainder of the assay was performed as before.

Example 10

Sequence Recovery of Lead Antibody Candidates

After the selection and characterization of lead candidates, their fully human variable domains were recovered using RT-PCR using a mixture of forward and reverse primers. Antibodies were reformatted into a human IgG4 backbone and expressed using a transient expression system in CHO-S cells. A summary of all sequences is displayed in the Sequence Listing (Table 6).

TABLE 6

| Clone Information | | Sequence Composition | | | | | |
| --- | --- | --- | --- | --- | --- | --- | --- |
| Experiment ID | Clone ID | Rearrangement HC | nt | aa | k/l | Rearrangement LC | nt | aa |
| KM050 | 18E04 | V1-8*01/D4-17*01/J4*02 | 10 | 8 | lambda | V3-10*01/J2*01 | 2 | 0 |
| KM050 | 98C07 | V3-11*01/D1-26*01/J4*02 | 8 | 4 | kappa | V1-16*02/J3*01 | 2 | 1 |
| KM044-1 | 01C02 | V1-18*01/D2-21*02/J4*02 | 15 | 8 | Kappa | V1-9*01/J4*01 | 4 | 2 |
| KM044-1 | 01C06 | V3-11*01/D3-10*01/J6*02 | 10 | 7 | Kappa | V1D-13*01/J4*01 | 13 | 8 | nt—nucleotide
aa—amino acid
Indicates numbers of changes from germline segment sequences Materials and Methods
RNA Isolation from Hybridoma Cells:
Methods are as described in Example 5.
Antibody Variable Domain Recovery by RT-PCR:
Methods are as described in Example 5.
Re-Formatting of Antibodies with Human IgG4 Backbone
Methods are as described in Example 5.

Example 11

Antibody Binding Characterization Study

Antibody cross-blocking experiments using SPR demonstrated that the isolated antibodies fall into 3 epitope categories. Antibody clones 01C06 and 18E04 bind to epitope category 1 and can recognize both LIGHT allele variants (214E & 214K) with similar apparent affinity. Antibody clone 98C07 was categorized as epitope category 2, which permits high affinity binding to the dominant human LIGHT allele variant 214E, but binding to the minor allele variant 214K is either reduced more than 20 fold or completely abolished. Lastly, antibody 01C02 was identified to be an epitope category 3 binder, which recognizes both human LIGHT allele variants (214E and 214K) with similar high apparent affinity. Interestingly, antibodies of epitope category 2 and 3 compete with each other for hLIGHT binding. However, due to the differential binding profile where epitope category 2 antibodies cannot recognize the minor allele variant of LIGHT and epitope category 3 antibodies can, antibodies of epitope category 2 and 3 must bind separate epitopes on the surface of the LIGHT molecule. Antibodies of epitope category 1 and 3 antibodies do not compete with each other and must therefore bind different epitopes.

The data from this cross-binding study is summarized in Table 7:

| Experiment ID | Clone ID | Epitope | hLIGHT 214E Binder | hLIGHT 214K Binder |
|---|---|---|---|---|
| KM050 | 98C07 | 2 | yes | no |
| KM050 | 18E04 | 1 | yes | yes |
| KM044-1 | 01C02 | 3 | yes | yes |
| KM044-1 | 01C06 | 1 | yes | yes |

Materials and Methods
Antibody Competition SPR:
Competition SPR assay was performed as described in Example 4. All antibodies were re-formatted with a human IgG4(PE) backbone as described in Example 5.

Example 12

Assessment of Lead Antibody Binding to Rabbit LIGHT

Figure 7:
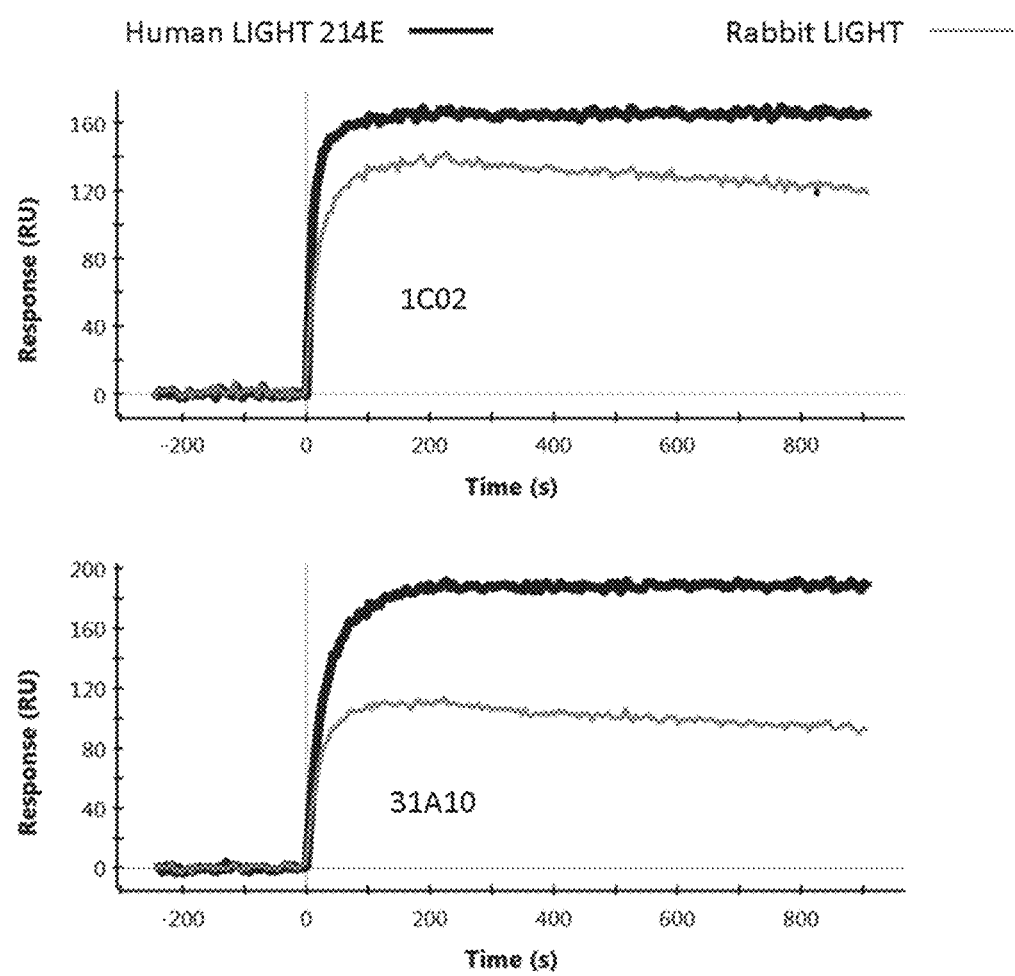
FIG. 7.
Figure 7:
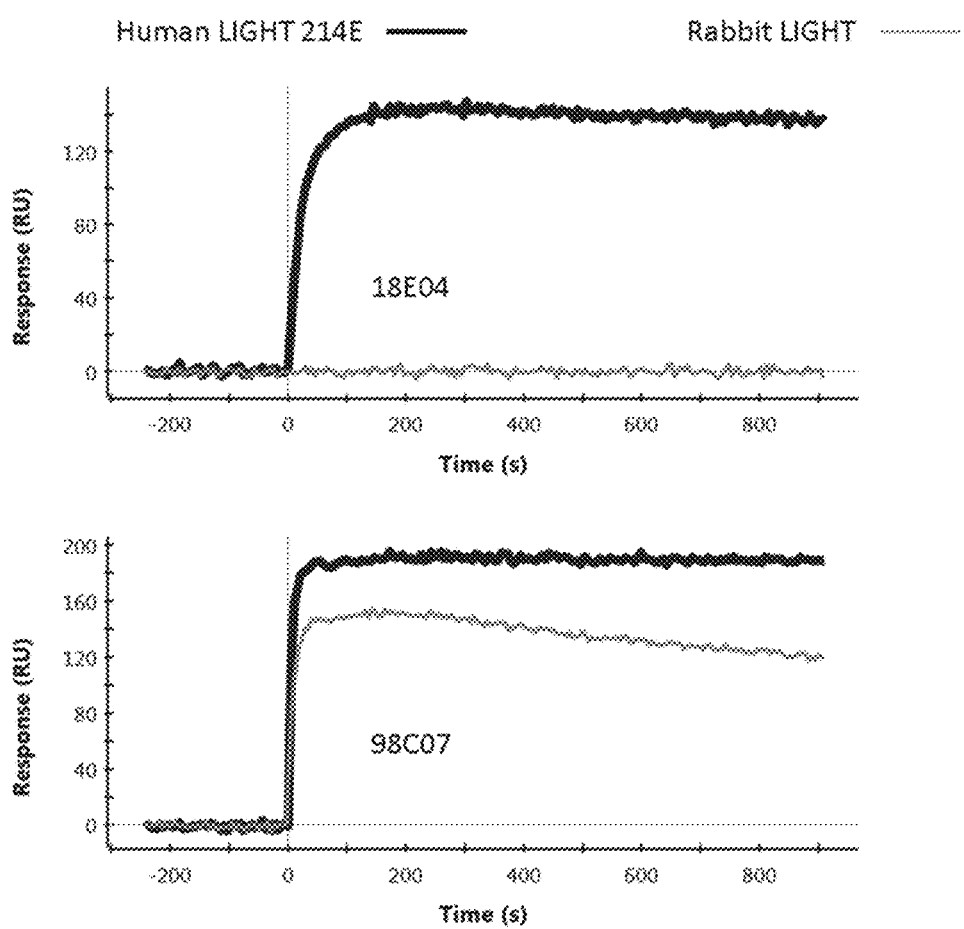
Figure 7:
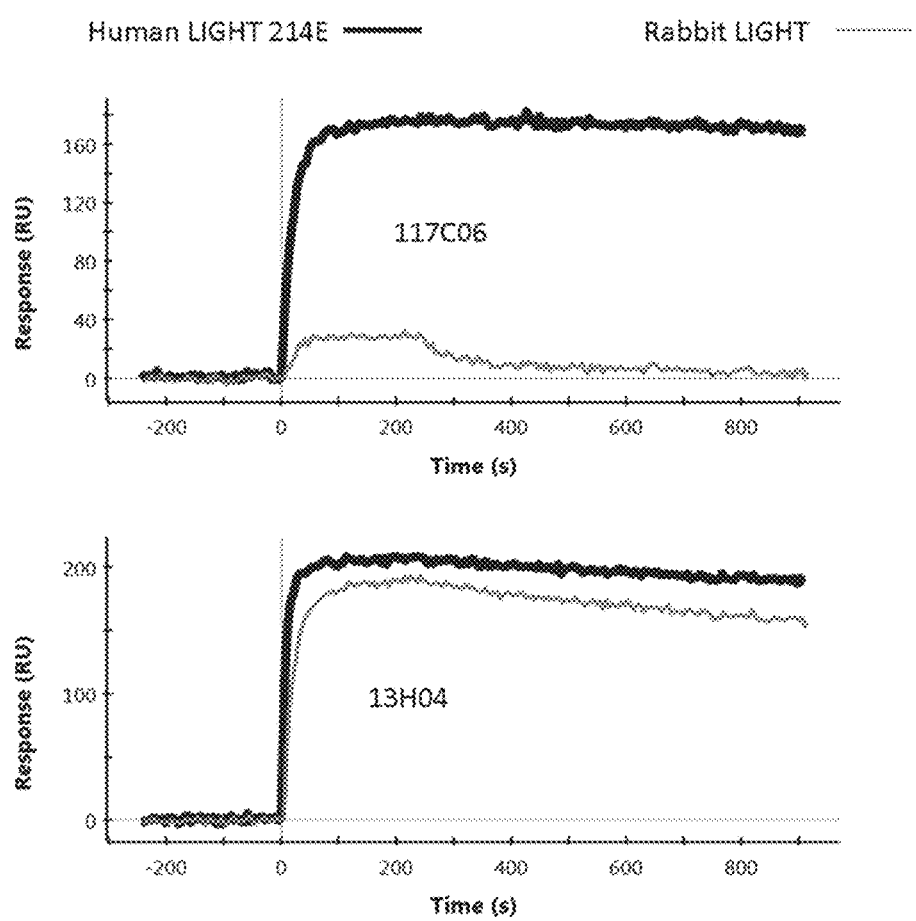
Figure 7:
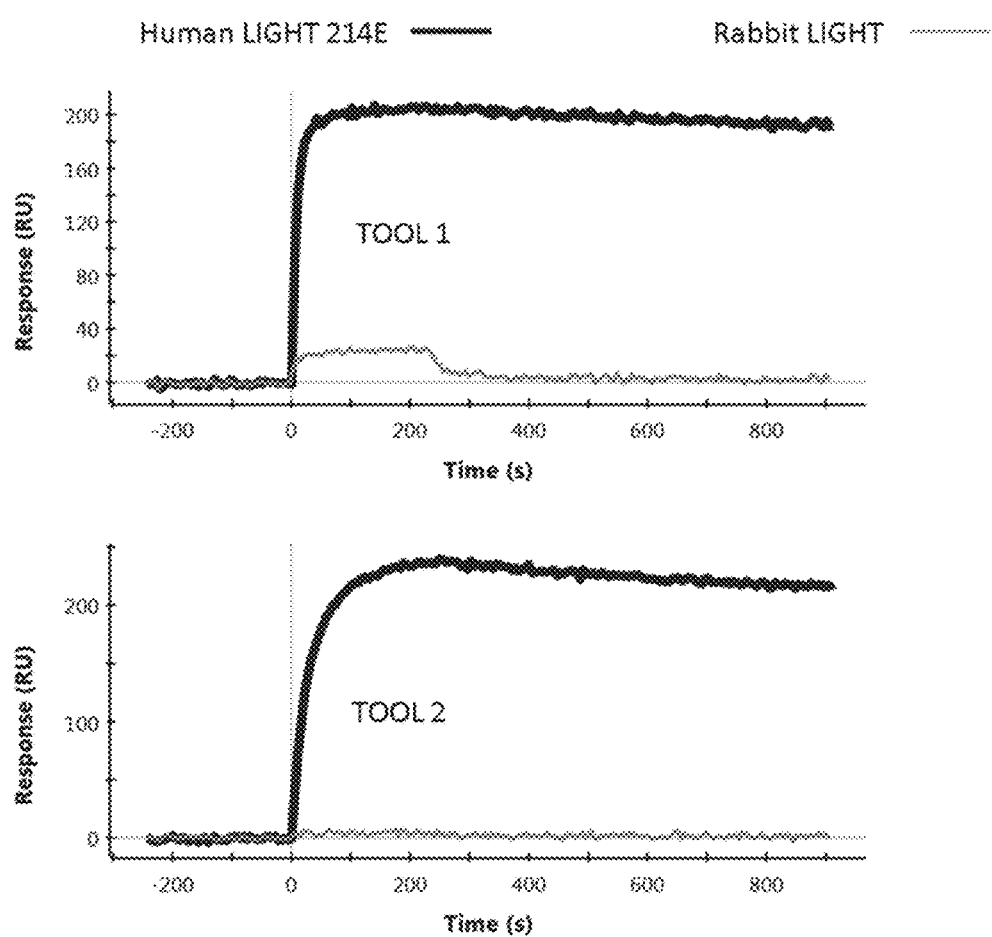
Figure 7:
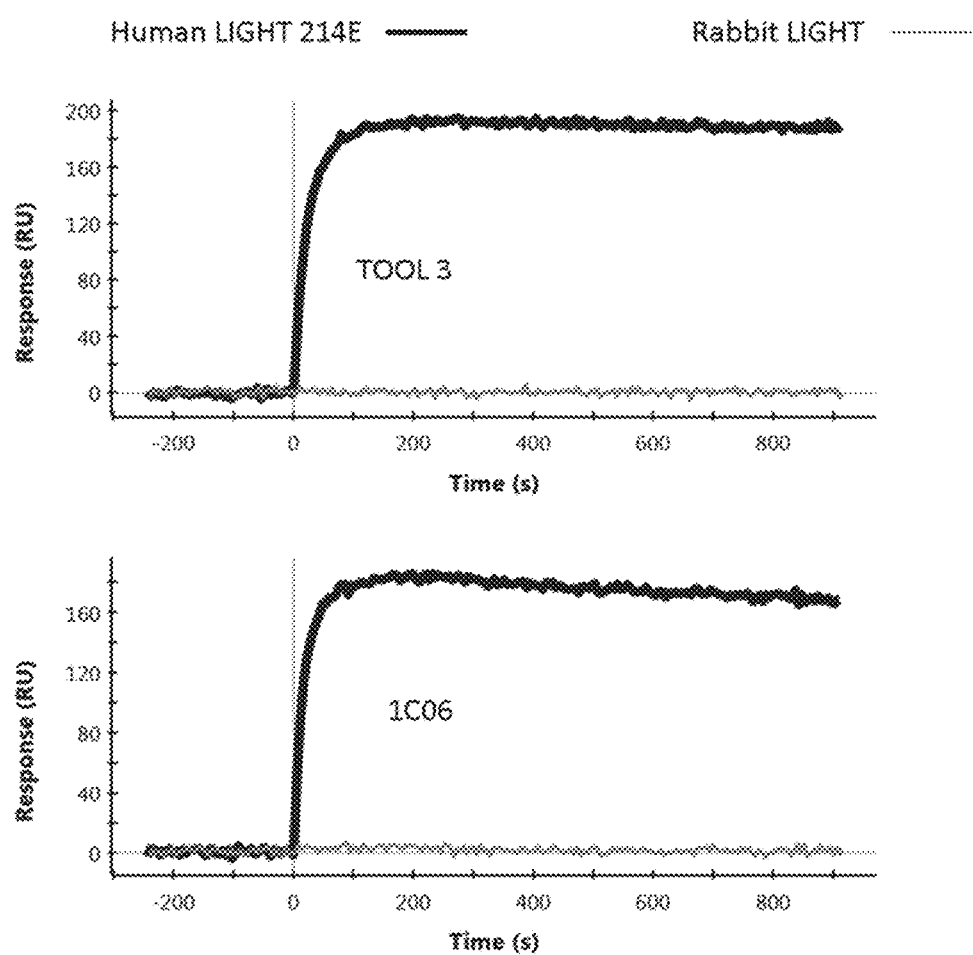
Figure 7:
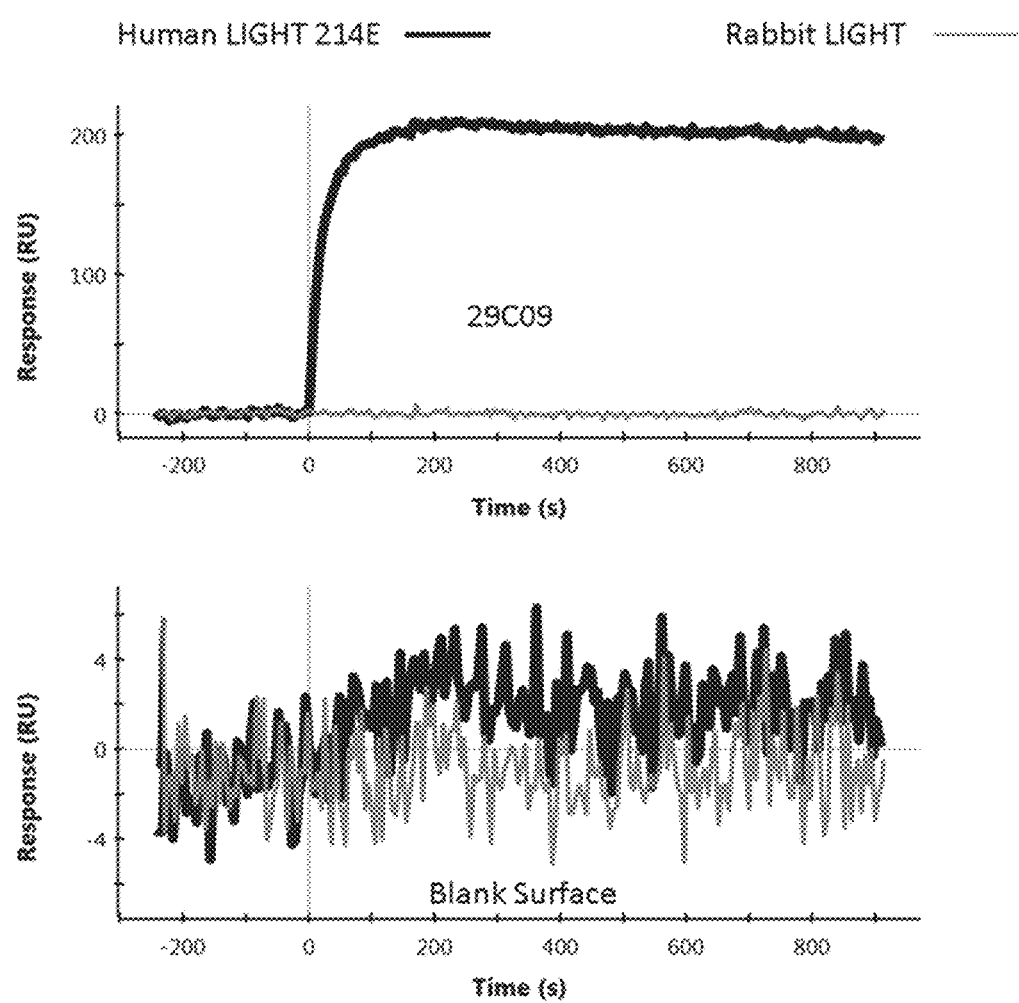

The top eight antibodies, based on IC50 values, were assessed for binding to rabbit LIGHT. As the lead mAbs do not bind mouse LIGHT, binding to rabbit LIGHT would provide more options in terms of animal models. Lead antibodies were analysed by SPR, alongside three tool mAbs. Results are shown in FIG. 7. Four out of eight lead antibodies were shown to bind human and rabbit LIGHT proteins (SEQ ID NOs: 308 and 423 respectively) with broadly similar kinetics. Interestingly, the tool antibodies do not bind rabbit LIGHT. The four binders were selected as the final lead panel; 1C02, 13H04, 98C07 and 31A10. These four antibodies are also distributed amongst the three epitope categories, as described in Examples 4 and 11.

Materials and Methods
Binding of the human LIGHT 214E and rabbit LIGHT proteins was carried out using surface plasmon resonance (SPR), using the ProteOn XPR36 Array System (BioRad). A mix of three anti-human antibodies—Jackson Labs 109-005-008, 109-006-008 and 309-006-008 were immobilised on a GLC chip at a concentration of 25 g/ml in 10 mM acetate, pH4.5 by primary amine coupling. This created a capture surface suitable for capturing human antibodies. The LIGHT antibodies were captured on this anti-human IgG surface, and then human and rabbit LIGHT proteins were passed over captured LIGHT Abs at a concentration of 200 nM. A buffer injection was used to double reference the LIGHT binding sensorgrams. The assay was run at 25° C., using HBS-EP as running buffer.

Example 13

Characterisation of Final Lead Panel

Figure 8A:
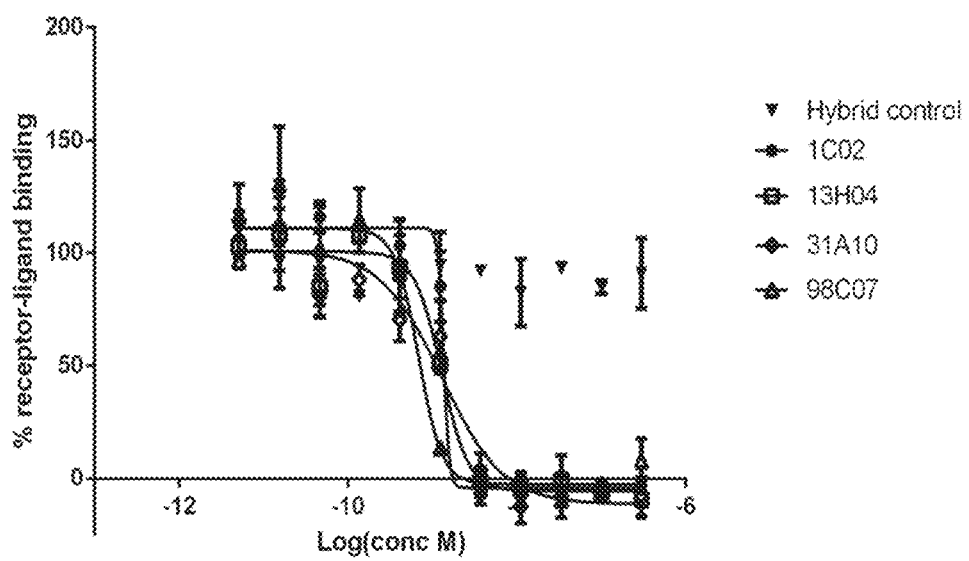
FIGS. 8A-8C.
Figure 8B:
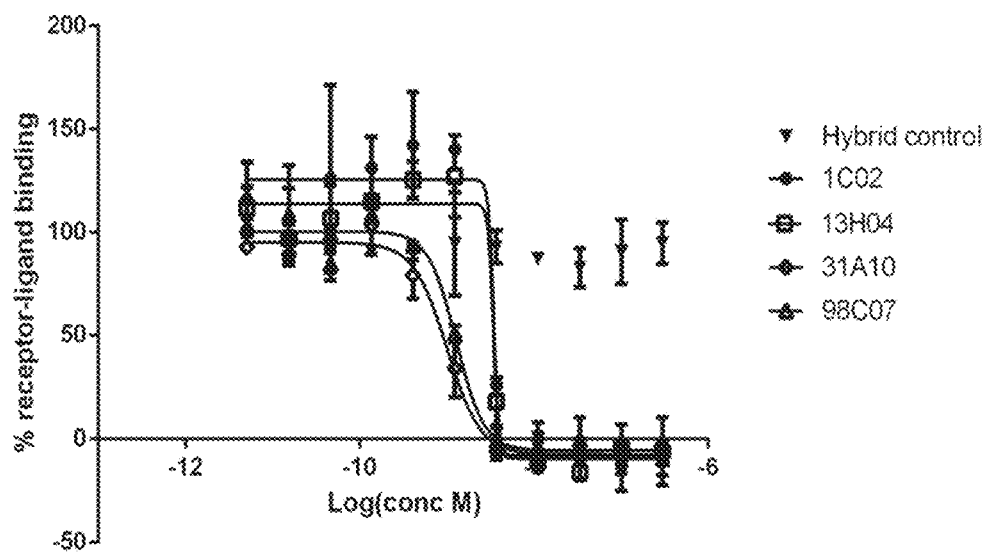
Figure 8C:
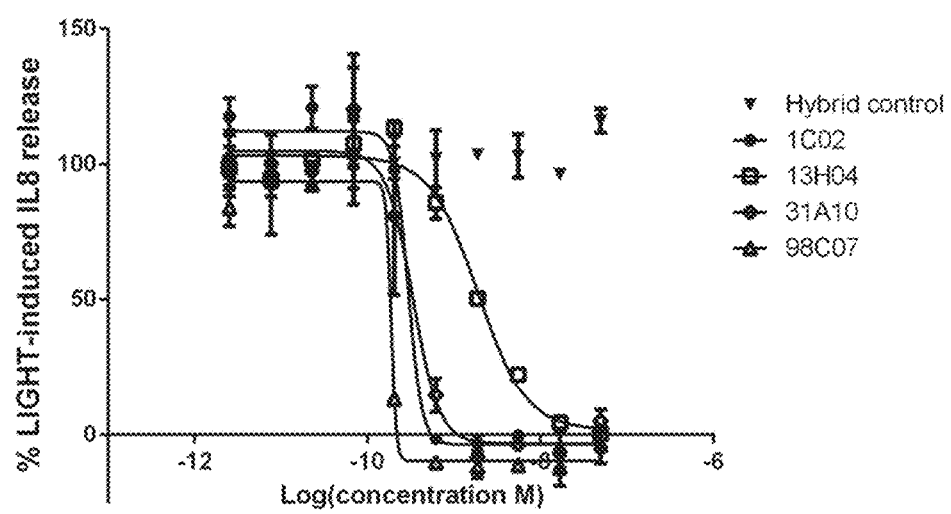

The final IgG4(PE) format lead panel was analysed for neutralization activity as in Example 3. Antibodies were tested for their ability to neutralize LIGHT binding to its receptors, HVEM and LTβR, in an HTRF assay. Antibodies were also tested for their ability to neutralize LIGHT-induced IL-8 release by HT29 colon carcinoma cells. Results and a summary of lead mAb characteristics are shown in FIG. 8 and Table 8.

TABLE 8

| | LIGHT binding by SPR | | | | | Receptor Neutralization (mean of n = 2) | | |
|---|---|---|---|---|---|---|---|---|
| Clone ID | Human 214E (nM at 37° C.) | Human 214K (nM at 37° C.) | Cynomolgus (nM at 37° C.) | Rabbit (25° C.) | Epitope Category | HT29 IL-8 release, IC50 (nM) | HVEM HTRF, IC50 (nM) | LTPR HTRF, IC50 (nM) |
| 31A10 | CNROR | CNROR | CNROR | Yes | 1 | 0.29 | 1.15 | 2.19 |
| 13H04 | 0.293 | 0.401 | 0.207 | Yes | 3 | 1.22 | 1.29 | 3.15 |
| 1C02 | CNROR | 0.822 | CNROR | Yes | 3 | 0.26 | 1.64 | 3.48 |
| 98C07 | 0.018 | No binding | 0.202 | Yes | 2 | 0.18 | 0.82 | 1.62 |

CNROR— cannot resolve off-rate

The final lead panel possesses excellent binding and neutralization characteristics. All leads neutralized LIGHT-induced IL-8 release, with sub-nanomolar IC50 values for three of the four leads. All four leads neutralized binding of LIGHT to soluble HVEM and LTβR with IC50 values less than 5 nM. The four leads bind both human and cynomolgus LIGHT with sub-nanomolar affinities, and all leads, except 98C07, bind both the major and minor human LIGHT variants.

Materials and Methods
HTRF assays were performed as per Example 3, with the following modifications: HVEM-Fc and LTβR-Fc were labelled with AlexaFluor 647, and an anti-Flag K antibody (Cisbio) was used for detection.
HT29 IL-8 release assays were performed as per Example 3. SPR was performed as per BCT-derived clones as described in Example 9.
Light Sequences
Human LIGHT-214E (Native, Non-Codon Optimized Sequences)

Nucleotide Sequence
[SEQ ID NO: 299]
Atggaggaga gtgtcgtacg gccctcagtg tttgtggtgg

```
atggacagac cgacatccca ttcacgaggc tgggacgaag ccaccggaga cagtcgtgca gtgtggcccg ggtgggtctg ggtctcttgc tgttgctgat gggggctggg ctggccgtcc aaggctggtt cctcctgcag ctgcactggc gtctaggaga gatggtcacc cgcctgcctg acggacctgc aggctcctgg gagcagctga tacaagagcg aaggtctcac gaggtcaacc cagcagcgca tctcacaggg gccaactcca gcttgaccgg cagcggggggg ccgctgttat gggagactca gctgggcctg gccttcctga ggggcctcag ctaccacgat ggggcccttg tggtcaccaa agctggctac tactacatct actccaaggt gcagctgggc ggtgtgggct gcccgctggg cctggccagc accatcaccc acggcctcta caagcgcaca ccccgctacc ccgaggagct ggagctgttg gtcagccagc agtcaccctg cggacgggcc accagcagct cccgggtctg gtgggacagc agcttcctgg gtggtgtggt cacacctggag gctggggagg aggtggtcgt ccgtgtgctg gatgaacgcc tggttcgact gcgtgatggt acccggtctt acttcggggc tttcatggtg
```

Amino Acid Sequence
[SEQ ID NO: 300]
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGE<u>E</u>VVVRVLDERLVRLRDGTRSYFGAFMV

<u>Doubleunderline</u>: Allele Variant
Human LIGHT-214K (Native, Non-Codon Optimized Sequences)

Nucleotide Sequence
[SEQ ID NO: 301]
```
Atggaggaga gtgtcgtacg gccctcagtg tttgtggtgg atggacagac cgacatccca ttcacgaggc tgggacgaag ccaccggaga cagtcgtgca gtgtggcccg ggtgggtctg ggtctcttgc tgttgctgat gggggctggg ctggccgtcc aaggctggtt cctcctgcag ctgcactggc gtctaggaga gatggtcacc cgcctgcctg acggacctgc aggctcctgg gagcagctga tacaagagcg aaggtctcac gaggtcaacc cagcagcgca tctcacaggg gccaactcca gcttgaccgg cagcggggggg ccgctgttat gggagactca gctgggcctg gccttcctga ggggcctcag ctaccacgat ggggcccttg tggtcaccaa agctggctac tactacatct actccaaggt gcagctgggc ggtgtgggct gcccgctggg cctggccagc accatcaccc acggcctcta caagcgcaca ccccgctacc ccgaggagct ggagctgttg gtcagccagc agtcaccctg cggacgggcc accagcagct cccgggtctg gtgggacagc agcttcctgg gtggtgtggt acacctggag gctggggag<u>a</u> aggtggtcgt ccgtgtgctg gatgaacgcc tggttcgact gcgtgatggt acccggtctt acttcggggc tttcatggtg
```

Amino Acid Sequence
[SEQ ID NO: 302]
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGE<u>K</u>VVVRVLDERLVRLRDGTRSYFGAFMV

<u>Doubleunderline</u>: Allele Variant
Human LIGHT-214E (Codon Optimized Sequences—Version 1)

Human LIGHT as used to make stable cell lines (MEF cells used for immunization, CHO cells for screening), codon optimized, This LIGHT is full length with extracellular domain, transmembrane domain and cytoplasmic tail.

Nucleotide Sequence
[SEQ ID NO: 303]
ATGGAAGAGTCCGTCGTGCGGCCCTCCGTGTTCGTGGTGGATGGCCAGAC

CGACATCCCCTTCACCAGACTGGGCCGGTCCCACAGACGGCAGTCTTGCT

CTGTGGCTAGAGTGGGCCTGGGCCTCCTGCTGCTGCTGATGGGAGCTGGA

CTGGCTGTGCAGGGCTGGTTTCTGCTGCAGCTGCATTGGCGGCTGGGCGA

GATGGTCACCAGGCTGCCTGATGCCCTGCTGGCTCTTGGGAGCAGCTGA

TCCAGGAACGGCGGTCCCACGAAGTGAATCCTGCCGCTCATCTGACCGGC

GCCAACTCTTCCCTGACCGGATCTGGTGGACCCCTGCTGTGGGAGACTCA

GCTGGGCCTGGCTTTCCTGCGGGGCCTGTCTTACCATGATGGCGCCCTGG

TCGTGACCAAGGCCGGCTACTACTACATCTACTCCAAGGTGCAGCTGGGC

GGCGTGGGCTGTCCTCTGGGACTGGCTTCTACCATCACCCACGGCCTGTA

CAAGCGGACCCCCAGATACCCCGAGGAACTGGAACTGCTGGTGTCCCAGC

AGTCCCCTTGTGGCAGAGCCACCTCCTCCAGCAGAGTGTGGTGGGACTCC

TCTTTCCTGGGCGGGGTGGTGCATCTGGAAGCCGGCGAA<u>G</u>AGGTGGTCGT

GCGGGTGCTGGATGAGAGACTCGTGCGGCTGAGGGACGGCACCAGAAGCT

ACTTCGGCGCCTTTATGGTG

Amino Acid Sequence
[SEQ ID NO: 304]
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGE<u>E</u>VVVRVLDERLVRLRDGTRSYFGAFMV

<u>Doubleunderline</u>: Allele Variant
Human LIGHT-214K (Codon Optimized Sequences—Version 1)

Human LIGHT as used to make stable cell lines (MEF cells used for immunization, CHO cells for screening), codon optimized, This LIGHT is full length with extracellular domain, transmembrane domain and cytoplasmic tail.

Nucleotide Sequence
[SEQ ID NO: 305]
ATGGAAGAGTCCGTCGTGCGGCCCTCCGTGTTCGTGGTGGATGGCCAGAC

CGACATCCCCTTCACCAGACTGGGCCGGTCCCACAGACGGCAGTCTTGCT

CTGTGGCTAGAGTGGGCCTGGGCCTCCTGCTGCTGCTGATGGGAGCTGGA

CTGGCTGTGCAGGGCTGGTTTCTGCTGCAGCTGCATTGGCGGCTGGGCGA

GATGGTCACCAGGCTGCCTGATGGCCCTGCTGGCTCTTGGGAGCAGCTGA

TCCAGGAACGGCGGTCCCACGAAGTGAATCCTGCCGCTCATCTGACCGGC

GCCAACTCTTCCCTGACCGGATCTGGTGGACCCCTGCTGTGGGAGACTCA

GCTGGGCCTGGCTTTCCTGCGGGGCCTGTCTTACCATGATGGCGCCCTGG

TCGTGACCAAGGCCGGCTACTACTACATCTACTCCAAGGTGCAGCTGGGC

GGCGTGGGCTGTCCTCTGGGACTGGCTTCTACCATCACCCACGGCCTGTA

CAAGCGGACCCCCAGATACCCCGAGGAACTGGAACTGCTGGTGTCCCAGC

AGTCCCCTTGTGGCAGAGCCACCTCCTCCAGCAGAGTGTGGTGGGACTCC

TCTTTCCTGGGCGGGTGGTGCATCTGGAAGCCGGCGAA<u>A</u>AGGTGGTCGT

GCGGGTGCTGGATGAGAGACTCGTGCGGCTGAGGGACGGCACCAGAAGCT

ACTTCGGCGCCTTTATGGTG

Amino Acid Sequence
[SEQ ID NO: 306]
MEESVVRPSVFVVDGQTDIPFTRLGRSHRRQSCSVARVGLGLLLLLMGAG

LAVQGWFLLQLHWRLGEMVTRLPDGPAGSWEQLIQERRSHEVNPAAHLTG

ANSSLTGSGGPLLWETQLGLAFLRGLSYHDGALVVTKAGYYYIYSKVQLG

GVGCPLGLASTITHGLYKRTPRYPEELELLVSQQSPCGRATSSSRVWWDS

SFLGGVVHLEAGE<u>K</u>VVVRVLDERLVRLRDGTRSYFGAFMV

<u>Doubleunderline</u>: Allele Variant
Human LIGHT-214E (Codon Optimized Sequences—Version 2; Includes FLAG Tag)
Human LIGHT as used to express recombinant LIGHT in CHO cells (includes cleavable FLAG tag), also codon optimized.

Nucleotide Sequence
[SEQ ID NO: 307]
ATGGGCTGGTCCTGCATCATCCTGTTCCTGGTGGCCACCGCTACCGGCGT

GCATTCCATGGACTACAAGGACGACGACGACAAGGGCGGAGGATCCGGAG

GAGGCTCCGGAGGCGGATCCATTGAGGGCAGGGATGGACCTGCCGGATCC

TGGGAGCAGCTGATCCAGGAGAGGCGGTCCCACGAAGTGAATCCCGCCGC

TCACCTGACCGGAGCCAATAGCTCCCTCACAGGATCCGGCGGACCTCTGC

TGTGGGAAACCCAACTGGGACTCGCCTTCCTGAGGGGCCTCTCCTACCAC

GATGGCGCTCTGGTCGTGACCAAGGCCGGCTACTACTACATCTACTCCAA

GGTGCAGCTGGGCGGAGTGGGATGTCCTCTGGGACTGGCCAGCACCATCA

CCCATGGCCTCTACAAGAGGACCCCTAGGTATCCTGAGGAACTGGAGCTG

CTGGTGAGCCAGCAGTCCCCTTGCGGAAGGGCTACCAGCTCCTCCAGGGT

GTGGTGGGATTCCTCCTTCCTGGGAGGAGTCGTGCACCTGGAGGCTGGCG

AG<u>A</u>AGGTCGTGGTGAGGGTGCTGGACGAGAGGCTGGTGCGGCTCAGGGAT

GGCACAAGGTCCTACTTCGGCGCCTTCATGGTG

<u>Doubleunderline</u>: Allele Variant

Amino Acid Sequence
[SEQ ID NO: 308]
<u>MGWSCIILFLVATATGVHSM</u>*DYKDDDDK*<u>*GGGSGGGSGGGS*</u>IEGRDGPAGS

WEQLIQERRSHEVNPAAHLTGANSSLTGSGGPLLWETQLGLAFLRGLSYH

DGALVVTKAGYYYIYSKVQLGGVGCPLGLASTITHGLYKRTPRYPEELEL

LVSQQSPCGRATSSSRVWWDSSFLGGVVHLEAGE<u>E</u>VVVRVLDERLVRLRD

GTRSYFGAFMV

Underlined: IgK leader peptide
Italics: FLAG tag
<u>*Underlined italics*</u>: Linker
Bold <u>underlined</u>: FXa cleavage site
Bold: hLIGHT-214E Extracellular Domain (Asp74-Val240)
<u>Doubleunderline</u>: Allele Variant
Human LIGHT-214K (Codon Optimized Sequences—Version 2; Includes FLAG Tag)
Human LIGHT as used to express recombinant LIGHT in CHO cells (includes cleavable FLAG tag), also codon optimized.

Nucleotide Sequence
[SEQ ID NO: 309]
ATGGGCTGGTCCTGCATCATCCTGTTCCTGGTGGCCACCGCTACCGGCGT

GCATTCCATGGACTACAAGGACGACGACGACAAGGGCGGAGGATCCGGAG

GAGGCTCCGGAGGCGGATCCATTGAGGGCAGGGATGGACCTGCCGGATCC

TGGGAGCAGCTGATCCAGGAGAGGCGGTCCCACGAAGTGAATCCCGCCGC

TCACCTGACCGGAGCCAATAGCTCCCTCACAGGATCCGGCGGACCTCTGC

TGTGGGAAACCCAACTGGGACTCGCCTTCCTGAGGGGCCTCTCCTACCAC

GATGGCGCTCTGGTCGTGACCAAGGCCGGCTACTACTACATCTACTCCAA

GGTGCAGCTGGGCGGAGTGGGATGTCCTCTGGGACTGGCCAGCACCATCA

CCCATGGCCTCTACAAGAGGACCCCTAGGTATCCTGAGGAACTGGAGCTG

CTGGTGAGCCAGCAGTCCCCTTGCGGAAGGGCTACCAGCTCCTCCAGGGT

GTGGTGGGATTCCTCCTTCCTGGGAGGAGTCGTGCACCTGGAGGCTGGCG

AG<u>A</u>AGGTCGTGGTGAGGGTGCTGGACGAGAGGCTGGTGCGGCTCAGGGAT

GGCACAAGGTCCTACTTCGGCGCCTTCATGGTG

Amino Acid Sequence
[SEQ ID NO: 310]
<u>MGWSCIILFLVATATGVHSM</u>*DYKDDDDK*<u>*GGGSGGGSGGGS*</u>IEGRDGPAGS

WEQLIQERRSHEVNPAAHLTGANSSLTGSGGPLLWETQLGLAFLRGLSYH

DGALVVTKAGYYYIYSKVQLGGVGCPLGLASTITHGLYKRTPRYPEELEL

LVSQQSPCGRATSSSRVWWDSSFLGGVVHLEAGE<u>K</u>VVVRVLDERLVRLRD

GTRSYFGAFMV

Underlined: IgK leader peptide
Italics: FLAG tag
<u>*Underlined italics*</u>: Linker
Bold <u>underlined</u>: FXa cleavage site Bold: hLIGHT-214E Extracellular Domain (Asp74-Val240)
Doubleunderline: Allele Variant
An Amino Acid Sequence of a Rabbit LIGHT Protein

[SEQ ID NO: 423]
DYKDDDDKGGGSGGGSGGGSIEGRDQDTGSWEQLVQARRSHKASPAAHLT
GANSSSMGTGGPLLWETQLGLAFLRGLGYHDGALVTTQAGYYYIYSKVQL
GGVGCPQGLATDLPVTHGLYKRTTRYPEELELLVSRRSPCGRAASSRVWW
DSSFLGGVVHLEAGEEVVVRVLEEQLVRLRDGTRSYFGAFMV

Where:-
(SEQ ID NO: 425)
DYKDDDDK = FLAG Tag;

(SEQ ID NO: 426)
GGGSGGGSGGGS = GS Linker;

IEGR=Factor Xa cleavage site (SEQ ID NO: 427); and remaining sequence is LIGHT protein sequence.

SEQUENCE LISTING

| SEQ ID NO: | SEQUENCE |
|---|---|
| 1 | caggtgcagc tgcaggagtc gggcccagga ctggtgaagc cttcggggac cctgtccctc acctgcgctg tctctggtgg ctccatcagc agtattaatt ggtggaattg ggtccgccag cccccaggga aggggctgga gtggattggg gaagtctctc atagtgggat caccaactat aacccgtccc tcaagagtcg agtcaccatg tcagtagaca aggccaagaa tcagttctcc ctgaagctga actctgtgac cgccgcggac acggccgtgt attattgtgc gagagaaagg gcagtggctg actaccacgg tatggacgtc tggggccaag ggaccacggt caccgtctcc tca |
| 2 | Gln Val Gln Leu Gln Glu Ser Gly Pro Gly Leu Val Lys Pro Ser Gly Thr Leu Ser Leu Thr Cys Ala Val Ser Gly Gly Ser Ile Ser Ser Ile Asn Trp Trp Asn Trp Val Arg Gln Pro Pro Gly Lys Gly Leu Glu Trp Ile Gly Glu Val Ser His Ser Gly Ile Thr Asn Tyr Asn Pro Ser Leu Lys Ser Arg Val Thr Met Ser Val Asp Lys Ala Lys Asn Gln Phe Ser Leu Lys Leu Asn Ser Val Thr Ala Ala Asp Thr Ala Val Tyr Tyr Cys Ala Arg Glu Arg Ala Val Ala Asp Tyr His Gly Met Asp Val Trp Gly Gln Gly Thr Thr Val Thr Val Ser Ser |
| 3 | ggtggctcca tcagcagtat taattgg |
| 4 | Gly Gly Ser Ile Ser Ser Ile Asn Trp |
| 5 | gtctctcata gtgggatcac c |
| 6 | Val Ser His Ser Gly Ile Thr |
| 7 | gcgagagaaa gggcagtggc tgactaccac ggtatggacg tc |
| 8 | Ala Arg Glu Arg Ala Val Ala Asp Tyr His Gly Met Asp Val |
| 9 | agtattaatt ggtggaat |
| 10 | Ser Ile Asn Trp Trp Asn |
| 11 | gaagtctctc atagtgggat caccaactat aacccgtccc tcaagagt |
| 12 | Glu Val Ser His Ser Gly Ile Thr Asn Tyr Asn Pro Ser Leu Lys Ser |
| 13 | aaagggcagt ggctgactac cacggtatgg acgtc |
| 14 | Glu Arg Ala Val Ala Asp Tyr His Gly Met Asp Val |
| 15 | gccatccagt tgacccagtc tccatcctcc ctgtctgcat ctgtgggaga tagagtcacc atcacttgcc gggcaagtca gggcattagc agtgctttag cctggtttca gcagaaacca gggaaacctc ctaagctcct gatctttgat gcctccgatt tggaaagtgg ggtctcatca aggttcagcg gcagtggatc tgggacagat ttcactctca ccatcagcag cctgcagcct ggagattttg caacttatta ctgtcaacag tttaatagtt acccgatcac cttcggccaa gggacacgac tggagatcaa a |
| 16 | Ala Ile Gln Leu Thr Gln Ser Pro Ser Ser Leu Ser Ala Ser Val Gly Asp Arg Val Thr Ile Thr Cys Arg Ala Ser Gln Gly Ile Ser Ser Ala Leu Ala Trp Phe Gln Gln Lys Pro Gly Lys Pro Pro Lys Leu Leu Ile Phe Asp Ala Ser Asp Leu Glu Ser Gly Val Ser Ser Arg Phe Ser Gly Ser Gly Ser Gly Thr Asp Phe Thr Leu Thr Ile Ser Ser Leu Gln Pro Gly Asp Phe Ala Thr Tyr Tyr Cys Gln Gln Phe Asn Ser Tyr Pro Ile Thr Phe Gly Gln Gly Thr Arg Leu Glu Ile Lys |
| 17 | cagggcatta gcagtgct |
| 18 | Gln Gly Ile Ser Ser Ala |

SEQUENCE LISTING

| SEQ ID NO: | SEQUENCE |
|---|---|
| 19 | Gatgcctcc |
| 20 | Asp Ala Ser |
| 21 | ctgcagcctg gagattttgc aacttattac tgtcaacagt ttaatagtta cccgatcacc |
| 22 | Gln Gln Phe Asn Ser Tyr Pro Ile Thr |
| 23 | cgggcaagtc agggcattag cagtgcttta gcc |
| 24 | Arg Ala Ser Gln Gly Ile Ser Ser Ala Leu Ala |
| 25 | gatgcctccg atttggaaag t |
| 26 | Asp Ala Ser Asp Leu Glu Ser |
| 27 | ctgcagcctg gagattttgc aacttattac tgtcaacagt ttaatagtta cccgatcacc |
| 28 | Gln Gln Phe Asn Ser Tyr Pro Ile Thr |
| 29 | caggtgcagt tggtggagtc tggggggaggc ttggtcaagc ctggagggtc cctgagactc tcctgtgcag cctctggatt cacctttcagt gactactaca tgagctggat ccgccaggct ccagggaagg gactggagtg ggtttcatac attagtagaa gtagtttcat atactactca gagtctgtga agggccgatt caccatctcc aggacaacg ccaagaactc actgtatctg caaatgaaca gcctgagagc cgaggacacg gccgtgtatt actgtgcgcg atgggagcta tccccttttg actactgggg ccagggaacc ctggtcaccg tctcctca |
| 30 | Gln Val Gln Leu Val Glu Ser Gly Gly Gly Leu Val Lys Pro Gly Gly Ser Leu Arg Leu Ser Cys Ala Ala Ser Gly Phe Thr Phe Ser Asp Tyr Tyr Met Ser Trp Ile Arg Gln Ala Pro Gly Lys Gly Leu Glu Trp Val Ser Tyr Ile Ser Arg Ser Ser Phe Ile Tyr Tyr Ser Glu Ser Val Lys Gly Arg Phe Thr Ile Ser Arg Asp Asn Ala Lys Asn Ser Leu Tyr Leu Gln Met Asn Ser Leu Arg Ala Glu Asp Thr Ala Val Tyr Tyr Cys Ala Arg Trp Glu Leu Ser Pro Phe Asp Tyr Trp Gly Gln Gly Thr Leu Val Thr Val Ser Ser |
| 31 | ggattcacct tcagtgacta ctac |
| 32 | Gly Phe Thr Phe Ser Asp Tyr Tyr |
| 33 | attagtagaa gtagtttcat a |
| 34 | Ile Ser Arg Ser Ser Phe Ile |
| 35 | gcgcgatggg agctatcccc ttttgactac |
| 36 | Ala Arg Trp Glu Leu Ser Pro Phe Asp Tyr |
| 37 | gactactaca tgagc |
| 38 | Asp Tyr Tyr Met Ser |
| 39 | tacattagta gaagtagttt catatactac tcagagtctg tgaagggc |
| 40 | Tyr Ile Ser Arg Ser Ser Phe Ile Tyr Tyr Ser Glu Ser Val Lys Gly |
| 41 | tgggagctat ccccttttga ctac |
| 42 | Trp Glu Leu Ser Pro Phe Asp Tyr |
| 43 | gacatccaga tgacccagtc tccatcctca ctgtctgcat ctgtaggaga cagagtcacc atcacttgtc ggcgagtca gggcattagc aattatttag cctggtttca gcagaaacca gggaaagccc ctaagtccct gatctatgct gcatccagtt tgcaaagtgg ggtcccatca aagttcagcg gcagtggatc tgggacagat ttcactctca ccatcagcag cctgcagcct gaagattttg caacttattt ctgccaacag tataatactt acccattcac tttcggccct gggaccaaag tggatatcaa a |
| 44 | Asp Ile Gln Met Thr Gln Ser Pro Ser Ser Leu Ser Ala Ser Val Gly Asp Arg Val Thr Ile Thr Cys Arg Ala Ser Gln Gly Ile Ser Asn Tyr Leu Ala Trp Phe Gln Gln Lys Pro Gly Lys Ala Pro Lys Ser Leu Ile Tyr Ala Ala Ser Ser Leu Gln Ser Gly Val Pro Ser Lys Phe Ser Gly Ser Gly Ser Gly Thr Asp Phe Thr Leu Thr Ile Ser Ser Leu Gln Pro Glu Asp Phe Ala Thr Tyr Phe Cys Gln Gln Tyr Asn Thr Tyr Pro Phe Thr Phe Gly Pro Gly Thr Lys Val Asp Ile Lys |

SEQUENCE LISTING

| SEQ ID NO: | SEQUENCE |
|---|---|
| 45 | cagggcatta gcaattat |
| 46 | Gln Gly Ile Ser Asn Tyr |
| 47 | Gctgcatcc |
| 48 | Ala Ala Ser |
| 49 | caacagtata atacttaccc attcact |
| 50 | Gln Gln Tyr Asn Thr Tyr Pro Phe Thr |
| 51 | cgggcgagtc agggcattag caattattta gcc |
| 52 | Arg Ala Ser Gln Gly Ile Ser Asn Tyr Leu Ala |
| 53 | gctgcatcca gtttgcaaag t |
| 54 | Ala Ala Ser Ser Leu Gln Ser |
| 55 | caacagtata atacttaccc attcact |
| 56 | Gln Gln Tyr Asn Thr Tyr Pro Phe Thr |
| 57 | gaggtgcagc tggtggagtc tgggggaggc ttggtacagc ctgggggtc cctgagactc tcctgtgcag cctctggatt cacctttagc agctatgtca tgagctgggt ccgccaggct ccagggaagg gctggagtg ggtctcagtt attagttcta gtggtgttac cacgtactac gcagactccg tgaagggccg attcaccatc tccagagaca attccaagaa cacgctgtat ctgcaaatga acagcctgag agccgaggag acggccgtat attactgtgc gaaagggaac tatgggtcgg ggagttttg tgactactgg ggccaggaa ccccggtcac cgtctcctca |
| 58 | Glu Val Gln Leu Val Glu Ser Gly Gly Gly Leu Val Gln Pro Gly Gly Ser Leu Arg Leu Ser Cys Ala Ala Ser Gly Phe Thr Phe Ser Ser Tyr Val Met Ser Trp Val Arg Gln Ala Pro Gly Lys Gly Leu Glu Trp Val Ser Val Ile Ser Ser Ser Gly Val Thr Thr Tyr Tyr Ala Asp Ser Val Lys Gly Arg Phe Thr Ile Ser Arg Asp Asn Ser Lys Asn Thr Leu Tyr Leu Gln Met Asn Ser Leu Arg Ala Glu Glu Thr Ala Val Tyr Tyr Cys Ala Lys Gly Asn Tyr Gly Ser Gly Ser Phe Cys Asp Tyr Trp Gly Gln Gly Thr Pro Val Thr Val Ser Ser |
| 59 | ggattcacct ttagcagcta tgtc |
| 60 | Gly Phe Thr Phe Ser Ser Tyr Val |
| 61 | attagttcta gtggtgttac cacg |
| 62 | Ile Ser Ser Ser Gly Val Thr Thr |
| 63 | gcgaaaggga actatgggtc ggggagtttt tgtgactac |
| 64 | Ala Lys Gly Asn Tyr Gly Ser Gly Ser Phe Cys Asp Tyr |
| 65 | agctatgtca tgagc |
| 66 | Ser Tyr Val Met Ser |
| 67 | gttattagtt ctagtggtgt taccacgtac tacgcagact ccgtgaaggg c |
| 68 | Val Ile Ser Ser Ser Gly Val Thr Thr Tyr Tyr Ala Asp Ser Val Lys Gly |
| 69 | gggaactatg gtcggggag ttttgtgac tac |
| 70 | Gly Asn Tyr Gly Ser Gly Ser Phe Cys Asp Tyr |
| 71 | tcctatgtgc tgactcagcc accctcagtg tcagtggccc caggaaagac ggccaggatt acctgtgggg gaaacaacat tggaagtaaa agtgtgcact ggtaccagca gaggccaggc caggccccta tactggtcat ctattatgat agcgaccggc cctcagggat ccctgagcga ttctctggct ccaactctgg gaactcggcc accctgacca tcagcaggggt cgaagccggg gatgaggccg actatcactg tcaggtgtgg gaaagtagta gtgatcatcc ggtgttcggc ggagggacca agctgaccgt ccta |

| SEQ ID NO: | SEQUENCE |
|---|---|
| 72 | Ser Tyr Val Leu Thr Gln Pro Pro Ser Val Ser Val Ala Pro Gly Lys<br>Thr Ala Arg Ile Thr Cys Gly Gly Asn Asn Ile Gly Ser Lys Ser Val<br>His Trp Tyr Gln Gln Arg Pro Gly Gln Ala Pro Ile Leu Val Ile Tyr<br>Tyr Asp Ser Asp Arg Pro Ser Gly Ile Pro Glu Arg Phe Ser Gly Ser<br>Asn Ser Gly Asn Ser Ala Thr Leu Thr Ile Ser Arg Val Glu Ala Gly<br>Asp Glu Ala Asp Tyr His Cys Gln Val Trp Glu Ser Ser Asp His<br>Pro Val Phe Gly Gly Gly Thr Lys Leu Thr Val Leu |
| 73 | aacattggaa gtaaaagt |
| 74 | Asn Ile Gly Ser Lys Ser |
| 75 | Tatgatagc |
| 76 | Tyr Asp Ser |
| 77 | caggtgtggg aaagtagtag tgatcatccg gtg |
| 78 | Gln Val Trp Glu Ser Ser Ser Asp His Pro Val |
| 79 | gggggaaaca acattggaag taaaagtgtg cac |
| 80 | Gly Gly Asn Asn Ile Gly Ser Lys Ser Val His |
| 81 | tatgatagcg accggccctc a |
| 82 | Tyr Asp Ser Asp Arg Pro Ser |
| 83 | caggtgtggg aaagtagtag tgatcatccg gtg |
| 84 | Gln Val Trp Glu Ser Ser Ser Asp His Pro Val |
| 85 | caggagcagc tggtgcagtc tggggctgag gtgaagaagc ctgggccctc agtgaaggtc<br>tcctgcaagg cttctggata cactttcacc agttatgata tcaactgggt gcgacaggcc<br>actggacaag ggcttgagtg gatgggatgg atgaacccta acagtggtta cacaggctat<br>gcacagaagt tccagggcag agtcaccatg accaggaaca cctccataag aacagtctac<br>atggagctga gcagcctgag atctgaggac acggccgtgt attactgtgc gagaggaggg<br>gagactttt atatctgggg ccaagggaca atggtcaccg tctcttca |
| 86 | Gln Glu Gln Leu Val Gln Ser Gly Ala Glu Val Lys Lys Pro Gly Ala<br>Ser Val Lys Val Ser Cys Lys Ala Ser Gly Tyr Thr Phe Thr Ser Tyr<br>Asp Ile Asn Trp Val Arg Gln Ala Thr Gly Gln Gly Leu Glu Trp Met<br>Gly Trp Met Asn Pro Asn Ser Gly Tyr Thr Gly Tyr Ala Gln Lys Phe<br>Gln Gly Arg Val Thr Met Thr Arg Asn Thr Ser Ile Arg Thr Val Tyr<br>Met Glu Leu Ser Ser Leu Arg Ser Glu Asp Thr Ala Val Tyr Tyr Cys<br>Ala Arg Gly Gly Glu Thr Phe Asp Ile Trp Gly Gln Gly Thr Met Val<br>Thr Val Ser Ser |
| 87 | ggatacactt tcaccagtta tgat |
| 88 | Gly Tyr Thr Phe Thr Ser Tyr Asp |
| 89 | atgaaccta acagtggtta caca |
| 90 | Met Asn Pro Asn Ser Gly Tyr Thr |
| 91 | gcgagaggag gggagacttt tgatatc |
| 92 | Ala Arg Gly Gly Glu Thr Phe Asp Ile |
| 93 | agttatgata tcaac |
| 94 | Ser Tyr Asp Ile Asn |
| 95 | tggatgaacc ctaacagtgg ttacacaggc tatgcacaga agttccaggg c |
| 96 | Trp Met Asn Pro Asn Ser Gly Tyr Thr Gly Tyr Ala Gln Lys Phe Gln<br>Gly |
| 97 | ggaggggaga cttttgatat c |
| 98 | Gly Gly Glu Thr Phe Asp Ile |

SEQUENCE LISTING

| SEQ ID NO: | SEQUENCE |
|---|---|
| 99 | tcctatgagc tgacacagcc accctcggtg tcagtgtccc caggacaaac ggccaggatc acctgctctg gagatgcatt gccaaaaaaa tatgcttatt ggtaccagca gaagtcaggc caggcccctg tgctggtcat ctatgaggac agcaaacgac cctccgggat ccctgagaga ttctctggct ccagctcagg gacaatggcc accttgacta tcagtggggc ccaggtggag gatgaagctg actactactg ttactcaaca gacagcagtg ataatcatag tgtcttcgga actgggacca aggtcaccgt ccta |
| 100 | Ser Tyr Glu Leu Thr Gln Pro Pro Ser Val Ser Val Ser Pro Gly Gln Thr Ala Arg Ile Thr Cys Ser Gly Asp Ala Leu Pro Lys Lys Tyr Ala Tyr Trp Tyr Gln Gln Lys Ser Gly Gln Ala Pro Val Leu Val Ile Tyr Glu Asp Ser Lys Arg Pro Ser Gly Ile Pro Glu Arg Phe Ser Gly Ser Ser Ser Gly Thr Met Ala Thr Leu Thr Ile Ser Gly Ala Gln Val Glu Asp Glu Ala Asp Tyr Tyr Cys Tyr Ser Thr Asp Ser Ser Asp Asn His Ser Val Phe Gly Thr Gly Thr Lys Val Thr Val Leu |
| 101 | gcattgccaa aaaaatat |
| 102 | Ala Leu Pro Lys Lys Tyr |
| 103 | Gaggacagc |
| 104 | Glu Asp Ser |
| 105 | tactcaacag acagcagtga taatcatagt gtc |
| 106 | Tyr Ser Thr Asp Ser Ser Asp Asn His Ser Val |
| 107 | tctggagatg cattgccaaa aaaatatgct tat |
| 108 | Ser Gly Asp Ala Leu Pro Lys Lys Tyr Ala Tyr |
| 109 | gaggacagca acgaccctc c |
| 110 | Glu Asp Ser Lys Arg Pro Ser |
| 111 | tactcaacag acagcagtga taatcatagt gtc |
| 112 | Tyr Ser Thr Asp Ser Ser Asp Asn His Ser Val |
| 113 | caggtccagc ttgtgcagtc tggggctgag gtgaagaagc ctgggcctc agtgaaggtt tcctgcaggg cttctggata caccttcact agctatctta tgcattggg gcgccaggcc cccggacaaa ggcttgagtg gatgggatgg atcaacgttg gcaatggtaa cacaaaatat tcacagaagt tccagggcag agtcaccatt accagggaca catccgcgag cacagcctac atggagctga gcggcctgag atctgaagac acggctgtgt attactgtgc ccggaactac tacaactggt tcgacccctg ggccaggga accctggtca ccgtctcctc a |
| 114 | Gln Val Gln Leu Val Gln Ser Gly Ala Glu Val Lys Lys Pro Gly Ala Ser Val Lys Val Ser Cys Arg Ala Ser Gly Tyr Thr Phe Thr Ser Tyr Leu Met His Trp Val Arg Gln Ala Pro Gly Gln Arg Leu Glu Trp Met Gly Trp Ile Asn Val Gly Asn Gly Asn Thr Lys Tyr Ser Gln Lys Phe Gln Gly Arg Val Thr Ile Thr Arg Asp Thr Ser Ala Ser Thr Ala Tyr Met Glu Leu Ser Gly Leu Arg Ser Glu Asp Thr Ala Val Tyr Tyr Cys Ala Arg Asn Tyr Tyr Asn Trp Phe Asp Pro Trp Gly Gln Gly Thr Leu Val Thr Val Ser Ser |
| 115 | ggatacacct tcactagcta tctt |
| 116 | Gly Tyr Thr Phe Thr Ser Tyr Leu |
| 117 | atcaacgttg gcaatggtaa caca |
| 118 | Ile Asn Val Gly Asn Gly Asn Thr |
| 119 | gcccggaact actacaactg gttcgacccc |
| 120 | Ala Arg Asn Tyr Tyr Asn Trp Phe Asp Pro |
| 121 | agctatctta tgcat |
| 122 | Ser Tyr Leu Met His |
| 123 | tggatcaacg ttggcaatgg taacacaaaa tattcacaga agttccaggg c |

SEQUENCE LISTING

| SEQ ID NO: | SEQUENCE |
|---|---|
| 124 | Trp Ile Asn Val Gly Asn Gly Asn Thr Lys Tyr Ser Gln Lys Phe Gln Gly |
| 125 | aactactaca actggttcga cccc |
| 126 | Asn Tyr Tyr Asn Trp Phe Asp Pro |
| 127 | cagtctgccc tgactcagcc tgcctccgtg tctgggtctc ctggacagtc gatcaccatc tcctgcactg gaaccagcag tgatgttggt ggttataact atgtctcctg gtaccaacag cacccaggca aagcccccaa actcatgatt tatgatgtca gtaagcggcc ctcaggggtt tctaatcgct tctctggctc caagtctggc aacacggcct ccctgacaat ctctgggctc caggctgagg acgaggctga ttattactgc ttctcatatg caggtagtag cactgtggta ttcggcggag ggaccaagct gaccgtccta |
| 128 | Gln Ser Ala Leu Thr Gln Pro Ala Ser Val Ser Gly Ser Pro Gly Gln Ser Ile Thr Ile Ser Cys Thr Gly Thr Ser Asp Val Gly Gly Tyr Asn Tyr Val Ser Trp Tyr Gln Gln His Pro Gly Lys Ala Pro Lys Leu Met Ile Tyr Asp Val Ser Lys Arg Pro Ser Gly Val Ser Asn Arg Phe Ser Gly Ser Lys Ser Gly Asn Thr Ala Ser Leu Thr Ile Ser Gly Leu Gln Ala Glu Asp Glu Ala Asp Tyr Tyr Cys Phe Ser Tyr Ala Gly Ser Ser Thr Val Val Phe Gly Gly Gly Thr Lys Leu Thr Val Leu |
| 129 | agcagtgatg ttggtggtta taactat |
| 130 | Ser Ser Asp Val Gly Gly Tyr Asn Tyr |
| 131 | Gatgtcagt |
| 132 | Asp Val Ser |
| 133 | ttctcatatg caggtagtag cactgtggta |
| 134 | Phe Ser Tyr Ala Gly Ser Ser Thr Val Val |
| 135 | actggaacca gcagtgatgt tggtggttat aactatgtct cc |
| 136 | Thr Gly Thr Ser Ser Asp Val Gly Gly Tyr Asn Tyr Val Ser |
| 137 | gatgtcagta agcggccctc a |
| 138 | Asp Val Ser Lys Arg Pro Ser |
| 139 | ttctcatatg caggtagtag cactgtggta |
| 140 | Phe Ser Tyr Ala Gly Ser Ser Thr Val Val |
| 141 | caggttcagc tggtgcagtc tggagctgag gtgaagaagc ctggggcctc agtgaaggtc tcctgcaagg cttctggtta tacctttacc agctatggta tcagctgggt gcgacaggcc cctggacaag gcttgagtg gatgggatgg atcagcgctc acaatgctaa cacaaactat gcacagaagc tccaggcag agtcaccatg accacagaca catccacgag cacagcctac atggagctga ggagcctgag atctgacgac acggccatgt attactgtgc gagactgtac cgcaactggt tcgaccctg gggccaggga accctggtca ccgtctcctc a |
| 142 | Gln Val Gln Leu Val Gln Ser Gly Ala Glu Val Lys Lys Pro Gly Ala Ser Val Lys Val Ser Cys Lys Ala Ser Gly Tyr Thr Phe Thr Ser Tyr Gly Ile Ser Trp Val Arg Gln Ala Pro Gly Gln Gly Leu Glu Trp Met Gly Trp Ile Ser Ala His Asn Ala Asn Thr Asn Tyr Ala Gln Lys Leu Gln Gly Arg Val Thr Met Thr Thr Asp Thr Ser Thr Ser Thr Ala Tyr Met Glu Leu Arg Ser Leu Arg Ser Asp Asp Thr Ala Met Tyr Tyr Cys Ala Arg Leu Tyr Arg Asn Trp Phe Asp Pro Trp Gly Gln Gly Thr Leu Val Thr Val Ser Ser |
| 143 | ggttatacct ttaccagcta tggt |
| 144 | Gly Tyr Thr Phe Thr Ser Tyr Gly |
| 145 | atcagcgctc acaatgctaa caca |
| 146 | Ile Ser Ala Asn Ala Asn Thr |
| 147 | gcgagactgt accgcaactg gttcgacccc |
| 148 | Ala Arg Leu Tyr Arg Asn Trp Phe Asp Pro |
| 149 | agctatggta tcagc |

SEQUENCE LISTING

| SEQ ID NO: | SEQUENCE |
|---|---|
| 150 | Ser Tyr Gly Ile Ser |
| 151 | tggatcagcg ctcacaatgc taacacaaac tatgcacaga agctccaggg c |
| 152 | Trp Ile Ser Ala His Asn Ala Asn Thr Asn Tyr Ala Gln Lys Leu Gln Gly |
| 153 | ctgtaccgca actggttcga cccc |
| 154 | Leu Tyr Arg Asn Trp Phe Asp Pro |
| 155 | cagtctgccc tgactcagcc tgcctccgtg tctgggtctc ctggacagtc gatcaccatc tcctgcactg gaaccagcag tgatgttggt ggttataact atgtctcctg gtaccaacag cacccaggca aagcccccaa actcatgatt tatgatgtca gtaagcggcc ctcaggggtt tctaatcgct tctctggctc caagtctggc aacacggcct ccctgacaat ctctgggctc caggctgagg acgaggctga ttattactgc tgctcatatg caggtagtag cactttgctg ttcggcggag ggaccaagct gaccgtccta |
| 156 | Gln Ser Ala Leu Thr Gln Pro Ala Ser Val Ser Gly Ser Pro Gly Gln Ser Ile Thr Ile Ser Cys Thr Gly Thr Ser Ser Asp Val Gly Gly Tyr Asn Tyr Val Ser Trp Tyr Gln Gln His Pro Gly Lys Ala Pro Lys Leu Met Ile Tyr Asp Val Ser Lys Arg Pro Ser Gly Val Ser Asn Arg Phe Ser Gly Ser Lys Ser Gly Asn Thr Ala Ser Leu Thr Ile Ser Gly Leu Gln Ala Glu Asp Glu Ala Asp Tyr Tyr Cys Cys Ser Tyr Ala Gly Ser Ser Thr Leu Leu Phe Gly Gly Gly Thr Lys Leu Thr Val Leu |
| 157 | agcagtgatg ttggtggtta taactat |
| 158 | Ser Ser Asp Val Gly Gly Tyr Asn Tyr |
| 159 | Gatgtcagt |
| 160 | Asp Val Ser |
| 161 | tgctcatatg caggtagtag cactttgctg |
| 162 | Cys Ser Tyr Ala Gly Ser Ser Thr Leu Leu |
| 163 | actggaacca gcagtgatgt tggtggttat aactatgtct cc |
| 164 | Thr Gly Thr Ser Ser Asp Val Gly Gly Tyr Asn Tyr Val Ser |
| 165 | gatgtcagta agcggccctc a |
| 166 | Asp Val Ser Lys Arg Pro Ser |
| 167 | tgctcatatg caggtagtag cactttgctg |
| 168 | Cys Ser Tyr Ala Gly Ser Ser Thr Leu Leu |
| 169 | caggttcagt tggtgcagtc tggagctgag gtgaagaagc ctggggcctc agtgaaggtc tcctgcaagg cttctggtta cacctttgtc aactttggta tcagctgggt gcgacaggcc cctggacaag gcttgagtg gatgggatgg atcagtgtta cagtggtaa cacaaactat gcacagaagc tccagggcag agtcaccttg accacagaca catccacgac cacagcctac atggaactga ggagcctgag atctgacgac acggccgttt attactgtgc gagacacaac tggaacgact actgggccca gggaaccctg gtcaccgtct cctca |
| 170 | Gln Val Gln Leu Val Gln Ser Gly Ala Glu Val Lys Lys Pro Gly Ala Ser Val Lys Val Ser Cys Lys Ala Ser Gly Tyr Thr Phe Val Asn Phe Gly Ile Ser Trp Val Arg Gln Ala Pro Gly Gln Gly Leu Glu Trp Met Gly Trp Ile Ser Val Tyr Ser Gly Asn Thr Asn Tyr Ala Gln Lys Leu Gln Gly Arg Val Thr Leu Thr Thr Asp Thr Ser Thr Thr Thr Ala Tyr Met Glu Leu Arg Ser Leu Arg Ser Asp Asp Thr Ala Val Tyr Tyr Cys Ala Arg His Asn Trp Asn Asp Tyr Trp Gly Gln Gly Thr Leu Val Thr Val Ser Ser |
| 171 | ggttacacct ttgtcaactt tggt |
| 172 | Gly Tyr Thr Phe Val Asn Phe Gly |
| 173 | atcagtgttt acagtggtaa caca |
| 174 | Ile Ser Val Tyr Ser Gly Asn Thr |

| SEQ ID NO: | SEQUENCE |
|---|---|
| 175 | gcgagacaca actggaacga ctac |
| 176 | Ala Arg His Asn Trp Asn Asp Tyr |
| 177 | aactttggta tcagc |
| 178 | Asn Phe Gly Ile Ser |
| 179 | tggatcagtg tttacagtgg taacacaaac tatgcacaga agctccaggg c |
| 180 | Trp Ile Ser Val Tyr Ser Gly Asn Thr Asn Tyr Ala Gln Lys Leu Gln Gly |
| 181 | cacaactgga acgactac |
| 182 | His Asn Trp Asn Asp Tyr |
| 183 | gaaattgtgt tgacgcagtc tccaggcacc ctgtctttgt ctccagggga aagagccacc ctctcctgca gggccagtca gagtgttagc agcagctact taacctggta ccagcagaaa cctggccagg ctcccaggct cctcatctat ggtgcatcca gcagggccac tggcatccca gacaggttca gtggcagtgg gtctgggaca gacttcactc tcaccatcag cagactggag cctgaagatt ttgcagtcta ttactgtcag cagtttggta gctcacctag ttttggccag gggaccaagc tggagatcaa a |
| 184 | Glu Ile Val Leu Thr Gln Ser Pro Gly Thr Leu Ser Leu Ser Pro Gly Glu Arg Ala Thr Leu Ser Cys Arg Ala Ser Gln Ser Val Ser Ser Ser Tyr Leu Thr Trp Tyr Gln Gln Lys Pro Gly Gln Ala Pro Arg Leu Leu Ile Tyr Gly Ala Ser Ser Arg Ala Thr Gly Ile Pro Asp Arg Phe Ser Gly Ser Gly Ser Gly Thr Asp Phe Thr Leu Thr Ile Ser Arg Leu Glu Pro Glu Asp Phe Ala Val Tyr Tyr Cys Gln Gln Phe Gly Ser Ser Pro Ser Phe Gly Gln Gly Thr Lys Leu Glu Ile Lys |
| 185 | cagagtgtta gcagcagcta c |
| 186 | Gln Ser Val Ser Ser Ser Tyr |
| 187 | Ggtgcatcc |
| 188 | Gly Ala Ser |
| 189 | cagcagtttg gtagctcacc tagt |
| 190 | Gln Gln Phe Gly Ser Ser Pro Ser |
| 191 | agggccagtc agagtgttag cagcagctac ttaacc |
| 192 | Arg Ala Ser Gln Ser Val Ser Ser Ser Tyr Leu Thr |
| 193 | ggtgcatcca gcagggccac t |
| 194 | Gly Ala Ser Ser Arg Ala Thr |
| 195 | cagcagtttg gtagctcacc tagt |
| 196 | Gln Gln Phe Gly Ser Ser Pro Ser |
| 197 | caggtgcagc tgcaggagtc gggcccagga ctggtgaagc cttcggggac cctgtccctc acctgcgctg tctctggtgg ctccatcagc agtactcact ggtggaattg ggtccgccag cccccaggga aggggctgga gtggattgga gaaatctatc atagtgggag caccaactgc aacccgtccc tcaagagtcg agtcaccata tcagtcgaca gtccaagaa ccagttctcc ctgaagatga actctgtgac cgccgcggac acggccgtgt attactgtac aaggggtggg gcagcagctg gtacgaacta cggtttggac gtctgggcc aagggaccag gtcaccgtc tcctca |
| 198 | Gln Val Gln Leu Gln Glu Ser Gly Pro Gly Leu Val Lys Pro Ser Gly Thr Leu Ser Leu Thr Cys Ala Val Ser Gly Gly Ser Ile Ser Ser Thr His Trp Trp Asn Trp Val Arg Gln Pro Pro Gly Lys Gly Leu Glu Trp Ile Gly Glu Ile Tyr His Ser Gly Ser Thr Asn Cys Asn Pro Ser Leu Lys Ser Arg Val Thr Ile Ser Val Asp Lys Ser Lys Asn Gln Phe Ser Leu Lys Met Asn Ser Val Thr Ala Ala Asp Thr Ala Val Tyr Tyr Cys Thr Arg Gly Gly Ala Ala Ala Gly Thr Asn Tyr Gly Leu Asp Val Trp Gly Gln Gly Thr Thr Val Thr Val Ser Ser |

SEQUENCE LISTING

| SEQ ID NO: | SEQUENCE |
|---|---|
| 199 | ggtggctcca tcagcagtac tcactgg |
| 200 | Gly Gly Ser Ile Ser Ser Thr His Trp |
| 201 | atctatcata gtgggagcac c |
| 202 | Ile Tyr His Ser Gly Ser Thr |
| 203 | acaaggggtg gggcagcagc tggtacgaac tacggtttgg acgtc |
| 204 | Thr Arg Gly Gly Ala Ala Ala Gly Thr Asn Tyr Gly Leu Asp Val |
| 205 | agtactcact ggtggaat |
| 206 | Ser Thr His Trp Trp Asn |
| 207 | gaaatctatc atagtgggag caccaactgc aacccgtccc tcaagagt |
| 208 | Glu Ile Tyr His Ser Gly Ser Thr Asn Cys Asn Pro Ser Leu Lys Ser |
| 209 | acaaggggtg gggcagcagc tggtacgaac tacggtttgg acgtc |
| 210 | Thr Arg Gly Gly Ala Ala Ala Gly Thr Asn Tyr Gly Leu Asp Val |
| 211 | gacatccaga tgacccagtc tccatcctcc ctgtctgcat ctgtaggaga cagagtctcc atcacttgcc aggcgagtca ggacattagc aactatttaa attggtatca gcagaaacca gggaaagccc ctaagctcct gatctacgat gcatccaatt tggaaacagg ggtcccatca aggttcagtg gaagtggatc tgggacagat ttactttca ccatcagcag cctgcagcct gaagatattg caacatatta ctgtcaacag tatgataatc tcccactcac tttcggcgga gggaccaagg tggagatcaa a |
| 212 | Asp Ile Gln Met Thr Gln Ser Pro Ser Ser Leu Ser Ala Ser Val Gly Asp Arg Val Ser Ile Thr Cys Gln Ala Ser Gln Asp Ile Ser Asn Tyr Leu Asn Trp Tyr Gln Gln Lys Pro Gly Lys Ala Pro Lys Leu Leu Ile Tyr Asp Ala Ser Asn Leu Glu Thr Gly Val Pro Ser Arg Phe Ser Gly Ser Gly Ser Gly Thr Asp Phe Thr Phe Thr Ile Ser Ser Leu Gln Pro Glu Asp Ile Ala Thr Tyr Tyr Cys Gln Gln Tyr Asp Asn Leu Pro Leu Thr Phe Gly Gly Gly Thr Lys Val Glu Ile Lys |
| 213 | caggacatta gcaactat |
| 214 | Gln Asp Ile Ser Asn Tyr |
| 215 | Gatgcatcc |
| 216 | Asp Ala Ser |
| 217 | caacagtatg ataatctccc actcact |
| 218 | Gln Gln Tyr Asp Asn Leu Pro Leu Thr |
| 219 | caggcgagtc aggacattag caactat |
| 220 | Gln Ala Ser Gln Asp Ile Ser Asn Tyr Leu Asn |
| 221 | gatgcatcca atttggaaac a |
| 222 | Asp Ala Ser Asn Leu Glu Thr |
| 223 | caacagtatg ataatctccc actcact |
| 224 | Gln Gln Tyr Asp Asn Leu Pro Leu Thr |
| 225 | gaggtgcagc tggtggagtc tgggggaggc ttggtacagc ctgggggtc cctgagactc tcctgtgcag cctctggatt cacctttagc aactatgcca tgagctgggt ccgccaggct ccagggaagg ggctggagtg ggtctcagct attagtggta gtggtggtag cacatattat gcagattccg tgaagggccg cttcaccatc tccagagaca attccaagaa cacgctgtat ctgcaaatga atagcctgag agccgaggac acggccgtat attactgtgc gaaagatatt actatggttc ggggaatcaa ctgggccaa gggacaatgg tcatcgtctc ttca |
| 226 | Glu Val Gln Leu Val Glu Ser Gly Gly Gly Leu Val Gln Pro Gly Gly Ser Leu Arg Leu Ser Cys Ala Ala Ser Gly Phe Thr Phe Ser Asn Tyr Ala Met Ser Trp Val Arg Gln Ala Pro Gly Lys Gly Leu Glu Trp Val Ser Ala Ile Ser Gly Ser Gly Gly Ser Thr Tyr Tyr Ala Asp Ser Val |

| SEQ ID NO: | SEQUENCE |
|---|---|
| | Lys Gly Arg Phe Thr Ile Ser Arg Asp Asn Ser Lys Asn Thr Leu Tyr Leu Gln Met Asn Ser Leu Arg Ala Glu Asp Thr Ala Val Tyr Tyr Cys Ala Lys Asp Ile Thr Met Val Arg Gly Ile Asn Trp Gly Gln Gly Thr Met Val Ile Val Ser Ser |
| 227 | ggattcacct ttagcaacta tgcc |
| 228 | Gly Phe Thr Phe Ser Asn Tyr Ala |
| 229 | attagtggta gtggtggtag caca |
| 230 | Ile Ser Gly Ser Gly Gly Ser Thr |
| 231 | gcgaaagata ttactatggt tcggggaatc aac |
| 232 | Ala Lys Asp Ile Thr Met Val Arg Gly Ile Asn |
| 233 | aactatgcca tgagc |
| 234 | Asn Tyr Ala Met Ser |
| 235 | gctattagtg gtagtggtgg tagcacatat tatgcagatt ccgtgaaggg c |
| 236 | Ala Ile Ser Gly Ser Gly Gly Ser Thr Tyr Tyr Ala Asp Ser Val Lys Gly |
| 237 | gatattacta tggttcgggg aatcaac |
| 238 | Asp Ile Thr Met Val Arg Gly Ile Asn |
| 239 | gacatccaga tgacccagtc tccatcttcc gtgtctgcat ctgtaggaga cagagtcacc atcacttgtc gggcgagtca gggtattagc aactggttag cctggtatca gcagaaacca gggaaagccc ctaaactcct gatctttgct gcatccagtt tgcaaagtgg ggtcccatca aggttcagcg gcagtggctc tgggacagat ttcactctca ccatcagcag cctgcagcct gaagattttg caacttacta ttgtcaacag tctaacagtt tccctctcac tttcggcgga gggaccaagg tggagatcaa a |
| 240 | Asp Ile Gln Met Thr Gln Ser Pro Ser Ser Val Ser Ala Ser Val Gly Asp Arg Val Thr Ile Thr Cys Arg Ala Ser Gln Gly Ile Ser Asn Trp Leu Ala Trp Tyr Gln Gln Lys Pro Gly Lys Ala Pro Lys Leu Leu Ile Phe Ala Ala Ser Ser Leu Gln Ser Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys Gln Gln Ser Asn Ser Phe Pro Leu Thr Phe Gly Gly Gly Thr Lys Val Glu Ile Lys |
| 241 | cagggtatta gcaactgg |
| 242 | Gln Gly Ile Ser Asn Trp |
| 243 | Gctgcatcc |
| 244 | Ala Ala Ser |
| 245 | caacagtcta acagtttccc tctcact |
| 246 | Gln Gln Ser Asn Ser Phe Pro Leu Thr |
| 247 | cgggcgagtc agggtattag caactggtta gcc |
| 248 | Arg Ala Ser Gln Gly Ile Ser Asn Trp Leu Ala |
| 249 | gctgcatcca gtttgcaaag t |
| 250 | Ala Ala Ser Ser Leu Gln Ser |
| 251 | caacagtcta acagtttccc tctcact |
| 252 | Gln Gln Ser Asn Ser Phe Pro Leu Thr |
| 253 | gcttccacca agggcccatc cgtcttcccc ctggcgccct gctccaggag cacctccgag agcacagccg ccctgggctg cctggtcaag gactacttcc ccgaaccggt gacggtgtcg tggaactcag gcgccctgac cagcggcgtg cacaccttcc cggctgtcct acagtcctca ggactctact ccctcagcag cgtggtgacc gtgccctcca gcagcttggg cacgaagacc tacacctgca acgtagatca caagcccagc aacaccaagg tggacaagag agttgagtcc |

SEQUENCE LISTING

| SEQ ID NO: | SEQUENCE |
|---|---|
| | aaatatggtc ccccatgccc atcatgccca gcacctgagt tcctgggggg accatcagtc<br>ttcctgttcc ccccaaaacc caaggacact ctcatgatct cccggacccc tgaggtcacg<br>tgcgtggtgg tggacgtgag ccaggaagac cccgaggtcc agttcaactg gtacgtggat<br>ggcgtggagg tgcataatgc caagacaaag ccgcgggagg agcagttcaa cagcacgtac<br>cgtgtggtca gcgtcctcac cgtcctgcac caggactggc tgaacggcaa ggagtacaag<br>tgcaaggtct ccaacaaagg cctcccgtcc tccatcgaga aaaccatctc caaagccaaa<br>gggcagcccc gagagccaca ggtgtacacc ctgcccccat cccaggagga gatgaccaag<br>aaccaggtca gcctgacctg cctggtcaaa ggcttctacc ccagcgacat cgccgtggag<br>tgggagagca atgggcagcc ggagaacaac tacaagacca cgcctcccgt gctggactcc<br>gacggctcct tcttcctcta cagcaggcta accgtggaca gagcaggtg gcaggagggg<br>aatgtcttct catgctccgt gatgcatgag gctctgcaca accactacac acagaagagc<br>ctctccctgt ctctgggtaa a |
| 254 | Ala Ser Thr Lys Gly Pro Ser Val Phe Pro Leu Ala Pro Cys Ser Arg<br>Ser Thr Ser Glu Ser Thr Ala Ala Leu Gly Cys Leu Val Lys Asp Tyr<br>Phe Pro Glu Pro Val Thr Val Ser Trp Asn Ser Gly Ala Leu Thr Ser<br>Gly Val His Thr Phe Pro Ala Val Leu Gln Ser Ser Gly Leu Tyr Ser<br>Leu Ser Ser Val Val Thr Val Pro Ser Ser Ser Leu Gly Thr Lys Thr<br>Tyr Thr Cys Asn Val Asp His Lys Pro Ser Asn Thr Lys Val Asp Lys<br>Arg Val Glu Ser Lys Tyr Gly Pro Pro Cys Pro Ser Cys Pro Ala Pro<br>Glu Phe Leu Gly Gly Pro Ser Val Phe Leu Phe Pro Pro Lys Pro Lys<br>Asp Thr Leu Met Ile Ser Arg Thr Pro Glu Val Thr Cys Val Val Val<br>Asp Val Ser Gln Glu Asp Pro Glu Val Gln Phe Asn Trp Tyr Val Asp<br>Gly Val Glu Val His Asn Ala Lys Thr Lys Pro Arg Glu Glu Gln Phe<br>Asn Ser Thr Tyr Arg Val Val Ser Val Leu Thr Val Leu His Gln Asp<br>Trp Leu Asn Gly Lys Glu Tyr Lys Cys Lys Val Ser Asn Lys Gly Leu<br>Pro Ser Ser Ile Glu Lys Thr Ile Ser Lys Ala Lys Gly Gln Pro Arg<br>Glu Pro Gln Val Tyr Thr Leu Pro Pro Ser Gln Glu Glu Met Thr Lys<br>Asn Gln Val Ser Leu Thr Cys Leu Val Lys Gly Phe Tyr Pro Ser Asp<br>Ile Ala Val Glu Trp Glu Ser Asn Gly Gln Pro Glu Asn Asn Tyr Lys<br>Thr Thr Pro Pro Val Leu Asp Ser Asp Gly Ser Phe Phe Leu Tyr Ser<br>Arg Leu Thr Val Asp Lys Ser Arg Trp Gln Glu Gly Asn Val Phe Ser<br>Cys Ser Val Met His Glu Ala Leu His Asn His Tyr Thr Gln Lys Ser<br>Leu Ser Leu Ser Leu Gly Lys |
| 255 | gcttccacca agggcccatc cgtcttcccc ctggcgccct gctccaggag cacctccgag<br>agcacagccg ccctgggctg cctggtcaag gactacttcc ccgaaccggt gacggtgtcg<br>tggaactcag gcgccctgac cagcggcgtg cacaccttcc cggctgtcct acagtcctca<br>ggactctact ccctcagcag cgtggtgacc gtgccctcca gcagcttggg cacgaagacc<br>tacacctgca acgtagatca caagcccagc aacaccaagg tggacaagag agttgagtcc<br>aaatatggtc ccccgtgccc atcatgccca gcacctgagt tcctgggggg accatcagtc<br>ttcctgttcc ccccaaaacc caaggacact ctcatgatct cccggacccc tgaggtcacg<br>tgcgtggtgg tggacgtgag ccaggaagac cccgaggtcc agttcaactg gtacgtggat<br>ggcgtggagg tgcataatgc caagacaaag ccgcgggagg agcagttcaa cagcacgtac<br>cgtgtggtca gcgtcctcac cgtcgtgcac caggactggc tgaacggcaa ggagtacaag<br>tgcaaggtct ccaacaaagg cctcccgtcc tccatcgaga aaaccatctc caaagccaaa<br>gggcagcccc gagagccaca ggtgtacacc ctgcccccat cccaggagga gatgaccaag<br>aaccaggtca gcctgacctg cctggtcaaa ggcttctacc ccagcgacat cgccgtggag<br>tgggagagca atgggcagcc ggagaacaac tacaagacca cgcctcccgt gctggactcc<br>gacggctcct tcttcctcta cagcaggcta accgtggaca gagcaggtg gcaggagggg<br>aatgtcttct catgctccgt gatgcatgag gctctgcaca accactacac gcagaagagc<br>ctctccctgt ctctgggtaa a |
| 256 | Ala Ser Thr Lys Gly Pro Ser Val Phe Pro Leu Ala Pro Cys Ser Arg<br>Ser Thr Ser Glu Ser Thr Ala Ala Leu Gly Cys Leu Val Lys Asp Tyr<br>Phe Pro Glu Pro Val Thr Val Ser Trp Asn Ser Gly Ala Leu Thr Ser<br>Gly Val His Thr Phe Pro Ala Val Leu Gln Ser Ser Gly Leu Tyr Ser<br>Leu Ser Ser Val Val Thr Val Pro Ser Ser Ser Leu Gly Thr Lys Thr<br>Tyr Thr Cys Asn Val Asp His Lys Pro Ser Asn Thr Lys Val Asp Lys<br>Arg Val Glu Ser Lys Tyr Gly Pro Pro Cys Pro Ser Cys Pro Ala Pro<br>Glu Phe Leu Gly Gly Pro Ser Val Phe Leu Phe Pro Pro Lys Pro Lys<br>Asp Thr Leu Met Ile Ser Arg Thr Pro Glu Val Thr Cys Val Val Val<br>Asp Val Ser Gln Glu Asp Pro Glu Val Gln Phe Asn Trp Tyr Val Asp<br>Gly Val Glu Val His Asn Ala Lys Thr Lys Pro Arg Glu Glu Gln Phe<br>Asn Ser Thr Tyr Arg Val Val Ser Val Leu Thr Val Val His Gln Asp<br>Trp Leu Asn Gly Lys Glu Tyr Lys Cys Lys Val Ser Asn Lys Gly Leu<br>Pro Ser Ser Ile Glu Lys Thr Ile Ser Lys Ala Lys Gly Gln Pro Arg<br>Glu Pro Gln Val Tyr Thr Leu Pro Pro Ser Gln Glu Glu Met Thr Lys<br>Asn Gln Val Ser Leu Thr Cys Leu Val Lys Gly Phe Tyr Pro Ser Asp<br>Ile Ala Val Glu Trp Glu Ser Asn Gly Gln Pro Glu Asn Asn Tyr Lys<br>Thr Thr Pro Pro Val Leu Asp Ser Asp Gly Ser Phe Phe Leu Tyr Ser<br>Arg Leu Thr Val Asp Lys Ser Arg Trp Gln Glu Gly Asn Val Phe Ser<br>Cys Ser Val Met His Glu Ala Leu His Asn His Tyr Thr Gln Lys Ser<br>Leu Ser Leu Ser Leu Gly Lys |

SEQUENCE LISTING

| SEQ ID NO: | SEQUENCE |
|---|---|
| 257 | gcttccacca agggcccatc cgtcttcccc ctggcgccct gctccaggag cacctccgag<br>agcacagccg ccctgggctg cctggtcaag gactacttcc ccgaaccggt gacggtgtcg<br>tggaactcag gcgccctgac cagcggcgtg cacaccttcc cggctgtcct acagtcctca<br>ggactctact ccctcagcag cgtggtgacc gtgccctcca gcagcttggg cacgaagacc<br>tacacctgca acgtagatca caagcccagc aacaccaagg tggacaagag agttgagtcc<br>aaatatggtc cccatgccc atcatgccca gcacctgagt tcctgggggg accatcagtc<br>ttcctgttcc ccccaaaacc caaggacact ctcatgatct cccggacccc tgaggtcacg<br>tgcgtggtgg tggacgtgag ccaggaagac cccgaggtcc agttcaactg gtacgtggat<br>ggcgtggagg tgcataatgc caagacaaag ccgcgggagg agcagttcaa cagcacgtac<br>cgtgtggtca gcgtcctcac cgtcctgcac caggactggc tgaacggcaa ggagtacaag<br>tgcaaggtct ccaacaaagg cctcccgtcc tcatcgaga aaccatctc caaagccaaa<br>gggcagcccc gagagccaca ggtgtacacc ctgccccat cccaggagga gatgaccaag<br>aaccaggtca gcctgacctg cctggtcaaa ggcttctacc ccagcgacat cgccgtggag<br>tgggagagca atgggcagcc ggagaacaac tacaagacca cgcctcccgt gctggactcc<br>gacggctcct tcttcctcta cagcaagctc accgtggaca agagcaggtg gcaggagggg<br>aacgtcttct catgctccgt gatgcatgag gctctgcaca accactacac gcagaagagc<br>ctctccctgt ctctgggtaa a |
| 258 | Ala Ser Thr Lys Gly Pro Ser Val Phe Pro Leu Ala Pro Cys Ser Arg<br>Ser Thr Ser Glu Ser Thr Ala Ala Leu Gly Cys Leu Val Lys Asp Tyr<br>Phe Pro Glu Pro Val Thr Val Ser Trp Asn Ser Gly Ala Leu Thr Ser<br>Gly Val His Thr Phe Pro Ala Val Leu Gln Ser Ser Gly Leu Tyr Ser<br>Leu Ser Ser Val Val Thr Val Pro Ser Ser Ser Leu Gly Thr Lys Thr<br>Tyr Thr Cys Asn Val Asp His Lys Pro Ser Asn Thr Lys Val Asp Lys<br>Arg Val Glu Ser Lys Tyr Gly Pro Pro Cys Pro Ser Cys Pro Ala Pro<br>Glu Phe Leu Gly Gly Pro Ser Val Phe Leu Phe Pro Pro Lys Pro Lys<br>Asp Thr Leu Met Ile Ser Arg Thr Pro Glu Val Thr Cys Val Val Val<br>Asp Val Ser Gln Glu Asp Pro Glu Val Gln Phe Asn Trp Tyr Val Asp<br>Gly Val Glu Val His Asn Ala Lys Thr Lys Pro Arg Glu Glu Gln Phe<br>Asn Ser Thr Tyr Arg Val Val Ser Val Leu Thr Val Leu His Gln Asp<br>Trp Leu Asn Gly Lys Glu Tyr Lys Cys Lys Val Ser Asn Lys Gly Leu<br>Pro Ser Ser Ile Glu Lys Thr Ile Ser Lys Ala Lys Gly Gln Pro Arg<br>Glu Pro Gln Val Tyr Thr Leu Pro Pro Ser Gln Glu Glu Met Thr Lys<br>Asn Gln Val Ser Leu Thr Cys Leu Val Lys Gly Phe Tyr Pro Ser Asp<br>Ile Ala Val Glu Trp Glu Ser Asn Gly Gln Pro Glu Asn Asn Tyr Lys<br>Thr Thr Pro Pro Val Leu Asp Ser Asp Gly Ser Phe Phe Leu Tyr Ser<br>Lys Leu Thr Val Asp Lys Ser Arg Trp Gln Glu Gly Asn Val Phe Ser<br>Cys Ser Val Met His Glu Ala Leu His Asn His Tyr Thr Gln Lys Ser<br>Leu Ser Leu Ser Leu Gly Lys |
| 259 | gcctccacca agggcccatc cgtcttcccc ctggcgccct gctccaggag cacctccgag<br>agcacggccg ccctgggctg cctggtcaag gactacttcc ccgaaccagt gacggtgtcg<br>tggaactcag gcgccctgac cagcggcgtg cacaccttcc cggctgtcct acagtcctca<br>ggactctact ccctcagcag cgtggtgacc gtgccctcca gcagcttggg cacgaagacc<br>tacacctgca acgtagatca caagcccagc aacaccaagg tggacaagag agttgagtcc<br>aaatatggtc cccatgccc accatgccca gcgcctgaat ttgagggggg accatcagtc<br>ttcctgttcc ccccaaaacc caaggacact ctcatgatct cccggacccc tgaggtcacg<br>tgcgtggtgg tggacgtgag ccaggaagac cccgaggtcc agttcaactg gtacgtggat<br>ggcgtggagg tgcataatgc caagacaaag ccgcgggagg agcagttcaa cagcacgtac<br>cgtgtggtca gcgtcctcac cgtcctgcac caggactggc tgaacggcaa ggagtacaag<br>tgcaaggtct ccaacaaagg cctcccgtca tcgatcgaga aaccatctc caaagccaaa<br>gggcagcccc gagagccaca ggtgtacacc ctgccccat cccaggagga gatgaccaag<br>aaccaggtca gcctgacctg cctggtcaaa ggcttctacc ccagcgacat cgccgtggag<br>tgggagagca atgggcagcc ggagaacaac tacaagacca cgcctcccgt gctggactcc<br>gacggatcct tcttcctcta cagcaggcta accgtggaca agagcaggtg gcaggagggg<br>aatgtcttct catgctccgt gatgcatgag gctctgcaca accactacac acagaagagc<br>ctctccctgt ctctgggtaa a |
| 260 | Ala Ser Thr Lys Gly Pro Ser Val Phe Pro Leu Ala Pro Cys Ser Arg<br>Ser Thr Ser Glu Ser Thr Ala Ala Leu Gly Cys Leu Val Lys Asp Tyr<br>Phe Pro Glu Pro Val Thr Val Ser Trp Asn Ser Gly Ala Leu Thr Ser<br>Gly Val His Thr Phe Pro Ala Val Leu Gln Ser Ser Gly Leu Tyr Ser<br>Leu Ser Ser Val Val Thr Val Pro Ser Ser Ser Leu Gly Thr Lys Thr<br>Tyr Thr Cys Asn Val Asp His Lys Pro Ser Asn Thr Lys Val Asp Lys<br>Arg Val Glu Ser Lys Tyr Gly Pro Pro Cys Pro Ser Cys Pro Ala Pro<br>Glu Phe Glu Gly Gly Pro Ser Val Phe Leu Phe Pro Pro Lys Pro Lys<br>Asp Thr Leu Met Ile Ser Arg Thr Pro Glu Val Thr Cys Val Val Val<br>Asp Val Ser Gln Glu Asp Pro Glu Val Gln Phe Asn Trp Tyr Val Asp<br>Gly Val Glu Val His Asn Ala Lys Thr Lys Pro Arg Glu Glu Gln Phe<br>Asn Ser Thr Tyr Arg Val Val Ser Val Leu Thr Val Leu His Gln Asp<br>Trp Leu Asn Gly Lys Glu Tyr Lys Cys Lys Val Ser Asn Lys Gly Leu<br>Pro Ser Ser Ile Glu Lys Thr Ile Ser Lys Ala Lys Gly Gln Pro Arg<br>Glu Pro Gln Val Tyr Thr Leu Pro Pro Ser Gln Glu Glu Met Thr Lys |

| SEQ ID NO: | SEQUENCE |
|---|---|
| | Asn Gln Val Ser Leu Thr Cys Leu Val Lys Gly Phe Tyr Pro Ser Asp<br>Ile Ala Val Glu Trp Glu Ser Asn Gly Gln Pro Glu Asn Asn Tyr Lys<br>Thr Thr Pro Pro Val Leu Asp Ser Asp Gly Ser Phe Phe Leu Tyr Ser<br>Arg Leu Thr Val Asp Lys Ser Arg Trp Gln Glu Gly Asn Val Phe Ser<br>Cys Ser Val Met His Glu Ala Leu His Asn His Tyr Thr Gln Lys Ser<br>Leu Ser Leu Ser Leu Gly Lys |
| 261 | gcctccacca agggacctag cgtgttccct ctcgcccct gttccaggtc cacaagcgag<br>tccaccgctg ccctcggctg tctggtgaaa gactactttc ccgagcccgt gaccgtctcc<br>tggaatagcg gagccctgac ctccggcgtg cacacatttc ccgccgtgct gcagagcagc<br>ggactgtata gcctgagcag cgtggtgacc gtgcccagct ccagcctcgg caccaaaacc<br>tacacctgca acgtggacca caagccctcc aacaccaagg tggacaagcg ggtggagagc<br>aagtacggcc ccccttgccc tccttgtcct gcccctgagt tcgagggagg accctccgtg<br>ttcctgtttc ccccaaaacc caaggacacc ctgatgatct cccggacacc cgaggtgacc<br>tgtgtggtcg tggacgtcag ccaggaggac ccgaggtgc agttcaactg gtatgtggac<br>ggcgtggagg tgcacaatgc caaaaccaag cccagggagg agcagttcaa ttccacctac<br>agggtggtga gcgtgctgac cgtcctgcat caggattgga tgaacggcaa ggagtacaag<br>tgcaaggtgt ccaacaaggg actgcccagc tccatcgaga gaccatcag caaggctaag<br>gccagccga gggagcccca ggtgtatacc ctgcctccta gccaggaaga gatgaccaag<br>aaccaagtgt ccctgacctg cctggtgaag ggattctacc cctccgacat cgccgtggag<br>tgggagagca atggccagcc cgagaacaac tacaaaacaa ccccctccgt gctcgatagc<br>gacggcagct tctttctcta cagccggctg acagtggaca agagcaggtg gcaggaggc<br>aacgtgttct cctgttccgt gatgcacgag gccctgcaca atcactacac ccagaagagc<br>ctctccctgt ccctgggcaa g |
| 262 | gccagcacca agggcccttc cgtgttcccc ctggcccctt gcagcaggag cacctccgaa<br>tccacagctg ccctgggctg tctggtgaag gactactttc ccgagcccgt gaccgtgagc<br>tggaacagcg gcgctctgac atccggcgtc cacacctttc ctgccgtcct gcagtcctcc<br>ggcctctact ccctgtcctc cgtggtgacc gtgcctagct cctccctcgg caccaagacc<br>tacacctgta acgtggacca caaaccctcc aacaccaagg tggacaaacg ggtcgagagc<br>aagtacggcc ctccctgccc tccttgtcct gccccgagt cgaaggcgg acccagcgtg<br>ttcctgttcc ctcctaagcc caaggacacc ctcatgatca gccggacacc cgaggtgacc<br>tgcgtggtgg tggatgtgag ccaggaggac cctgaggtcc agttcaactg gtatgtggat<br>ggcgtggagg tgcacaacgc caagacaaag ccccgggaag agcagttcaa ctccacctac<br>agggtggtca gcgtgctgac cgtgctgcat caggactggc tgaacggcaa ggagtacaag<br>tgcaaggtca gcaataaggg actgcccagc agcatcgaga agaccatctc caaggctaaa<br>ggccagcccc gggaacctca ggtgtacacc ctgcctccca gccaggagga gatgaccaag<br>aaccaggtga gcctgacctg cctggtgaag ggattctacc cttccgacat cgccgtggag<br>tgggagtcca acggccagcc cgagaacaat tataagacca cccctcccgt cctcgacagc<br>gacggatcct tctttctgta ctccaggctg accgtggata agtccaggtg gcaggaaggc<br>aacgtgttca gctgctccgt gatgcacgag gccctgcaca atcactacac ccagaagtcc<br>ctgagcctgt ccctgggaaa g |
| 263 | gcctccacca agggcccatc cgtcttcccc ctggcgccct gctccaggag cacctccgag<br>agcacggccg ccctgggctg cctggtcaag gactacttcc ccgaaccagt gacggtgtcg<br>tggaactcag gcgccctgac cagcggcgtg cacacctcc cggctgtcct acagtcctca<br>ggactctact ccctcagcag cgtggtgacc gtgcctcca gcagcttggg cacgaagacc<br>tacacctgca acgtagatca caagcccagc aacaccaagg tggacaagag agttgagtcc<br>aaatatggtc ccccatgccc accatgccca gcgcctccag ttgcggggg accatcagtc<br>ttcctgttcc cccaaaacc caaggacact ctcatgatct cccggacccc tgaggtcacg<br>tgcgtggtgg tggacgtgag ccaggaagac cccgaggtcc agttcaactg gtacgtggat<br>ggcgtggagg tgcataatgc caagacaaag ccgcgggagg agcagttcaa cagcacgtac<br>cgtgtggtca gcgtcctcac cgtcctgcac caggactggc tgaacggcaa ggagtacaag<br>tgcaaggtct ccaacaaagg cctcccgtca tcgatcgaga aaaccatctc caaagccaaa<br>gggcagcccc gagagccaca ggtgtacacc ctgccccat cccaggagga gatgaccaag<br>aaccaggtca gcctgacctg cctggtcaaa ggcttctacc ccagcgacat cgccgtggag<br>tgggagagca atgggcagcc ggagaacaac tacaagacca cgcctcccgt gctggactcc<br>gacggatcct tcttcctcta cagcaggcta accgtggaca agagcaggtg gcaggagggg<br>aatgtcttct catgctccgt gatgcatgag gctctgcaca accactacac acagaagagc<br>ctctccctgt ctctgggtaa a |
| 264 | Ala Ser Thr Lys Gly Pro Ser Val Phe Pro Leu Ala Pro Cys Ser Arg<br>Ser Thr Ser Glu Ser Thr Ala Ala Leu Gly Cys Leu Val Lys Asp Tyr<br>Phe Pro Glu Pro Val Thr Val Ser Trp Asn Ser Gly Ala Leu Thr Ser<br>Gly Val His Thr Phe Pro Ala Val Leu Gln Ser Ser Gly Leu Tyr Ser<br>Leu Ser Ser Val Val Thr Val Pro Ser Ser Ser Leu Gly Thr Lys Thr<br>Tyr Thr Cys Asn Val Asp His Lys Pro Ser Asn Thr Lys Val Asp Lys<br>Arg Val Glu Ser Lys Tyr Gly Pro Pro Cys Pro Pro Cys Pro Ala Pro<br>Pro Val Ala Gly Gly Pro Ser Val Phe Leu Phe Pro Pro Lys Pro Lys<br>Asp Thr Leu Met Ile Ser Arg Thr Pro Glu Val Thr Cys Val Val Val<br>Asp Val Ser Gln Glu Asp Pro Glu Val Gln Phe Asn Trp Tyr Val Asp<br>Gly Val Glu Val His Asn Ala Lys Thr Lys Pro Arg Glu Glu Gln Phe<br>Asn Ser Thr Tyr Arg Val Val Ser Val Leu Thr Val Leu His Gln Asp<br>Try Leu Asn Gly Lys Glu Tyr Lys Cys Lys Val Ser Asn Lys Gly Leu |

| SEQ ID NO: | SEQUENCE |
|---|---|
| | Pro Ser Ser Ile Glu Lys Thr Ile Ser Lys Ala Lys Gly Gln Pro Arg<br>Glu Pro Gln Val Tyr Thr Leu Pro Pro Ser Gln Glu Glu Met Thr Lys<br>Asn Gln Val Ser Leu Thr Cys Leu Val Lys Gly Phe Tyr Pro Ser Asp<br>Ile Ala Val Glu Trp Glu Ser Asn Gly Gln Pro Glu Asn Asn Tyr Lys<br>Thr Thr Pro Pro Val Leu Asp Ser Asp Gly Ser Phe Phe Leu Tyr Ser<br>Arg Leu Thr Val Asp Lys Ser Arg Trp Gln Glu Gly Asn Val Phe Ser<br>Cys Ser Val Met His Glu Ala Leu His Asn His Tyr Thr Gln Lys Ser<br>Leu Ser Leu Ser Leu Gly Lys |
| 265 | gcctccacca agggcccatc ggtcttcccc ctggcaccct cctccaagag cacctctggg<br>ggcacagcgg ccctgggctg cctggtcaag gactacttcc ccgaaccggt gacggtgtcg<br>tggaactcag gcgccctgac cagcggcgtg cacaccttcc cggctgtcct acagtcctca<br>ggactctact ccctcagcag cgtggtgacc gtgccctcca gcagcttggg cacccagacc<br>tacatctgca acgtgaatca caagcccagc aacaccaagg tggacaagaa agtggagccc<br>aaatcttgtg acaaaactca cacatgccca ccgtgcccag cacctgaact cgcggggggca<br>ccgtcagtct tcctcttccc cccaaaaccc aaggacaccc tcatgatctc ccggacccct<br>gaggtcacat gcgtggtggt ggacgtgagc cacgaagacc ctgaggtcaa gttcaactgg<br>tacgtggacg gcgtggaggt gcataatgcc aagacaaagc cgcgggagga gcagtacaac<br>agcacgtacc gtgtggtcag cgtcctcacc gtcctgcacc aggactggct gaatggcaag<br>gagtacaagt gcaaggtctc caacaaagcc ctcccagccc ccatcgagaa aaccatctcc<br>aaagccaaag ggcagccccg agaaccacag gtgtacaccc tgcccccatc ccgggatgag<br>ctgaccaaga accaggtcag cctgacctgc ctggtcaaag gcttctatcc cagcgacatc<br>gccgtggagt gggagagcaa tgggcagccg gagaacaact acaagaccac gcctcccgtg<br>ctggactccg acggctcctt cttcctctac agcaagctca ccgtggacaa gagcaggtgg<br>cagcagggga acgtcttctc atgctccgtg atgcatgagg ctctgcacaa ccactacacg<br>cagaagagcc tctccctgtc tccgggtaaa |
| 266 | Ala Ser Thr Lys Gly Pro Ser Val Phe Pro Leu Ala Pro Ser Ser Lys<br>Ser Thr Ser Gly Gly Thr Ala Ala Leu Gly Cys Leu Val Lys Asp Tyr<br>Phe Pro Glu Pro Val Thr Val Ser Trp Asn Ser Gly Ala Leu Thr Ser<br>Gly Val His Thr Phe Pro Ala Val Leu Gln Ser Ser Gly Leu Tyr Ser<br>Leu Ser Ser Val Val Thr Val Pro Ser Ser Ser Leu Gly Thr Gln Thr<br>Tyr Ile Cys Asn Val Asn His Lys Pro Ser Asn Thr Lys Val Asp Lys<br>Lys Val Glu Pro Lys Ser Cys Asp Lys Thr His Thr Cys Pro Pro Cys<br>Pro Ala Pro Glu Leu Ala Gly Ala Pro Ser Val Phe Leu Phe Pro Pro<br>Lys Pro Lys Asp Thr Leu Met Ile Ser Arg Thr Pro Glu Val Thr Cys<br>Val Val Val Asp Val Ser His Glu Asp Pro Glu Val Lys Phe Asn Trp<br>Tyr Val Asp Gly Val Glu Val His Asn Ala Lys Thr Lys Pro Arg Glu<br>Glu Gln Tyr Asn Ser Thr Tyr Arg Val Val Ser Val Leu Thr Val Leu<br>His Gln Asp Trp Leu Asn Gly Lys Glu Tyr Lys Cys Lys Val Ser Asn<br>Lys Ala Leu Pro Ala Pro Ile Glu Lys Thr Ile Ser Lys Ala Lys Gly<br>Gln Pro Arg Glu Pro Gln Val Tyr Thr Leu Pro Pro Ser Arg Asp Glu<br>Leu Thr Lys Asn Gln Val Ser Leu Thr Cys Leu Val Lys Gly Phe Tyr<br>Pro Ser Asp Ile Ala Val Glu Trp Glu Ser Asn Gly Gln Pro Glu Asn<br>Asn Tyr Lys Thr Thr Pro Pro Val Leu Asp Ser Asp Gly Ser Phe Phe<br>Leu Tyr Ser Lys Leu Thr Val Asp Lys Ser Arg Trp Gln Gln Gly Asn<br>Val Phe Ser Cys Ser Val Met His Glu Ala Leu His Asn His Tyr Thr<br>Gln Lys Ser Leu Ser Leu Ser Pro Gly Lys |
| 267 | cgtacggtgg ccgctccctc cgtgttcatc ttcccacctt ccgacgagca gctgaagtcc<br>ggcaccgctt ctgtcgtgtg cctgctgaac aacttctacc cccgcgaggc caaggtgcag<br>tggaaggtgg acaacgccct gcagtccggc aactcccagg aatccgtgac cgagcaggac<br>tccaaggaca gcacctactc cctgtcctcc accctgaccc tgtccaaggc cgactacgag<br>aagcacaagg tgtacgcctg cgaagtgacc caccagggcc tgtctagccc cgtgaccaag<br>tctttcaacc ggggcgagtg t |
| 268 | Arg Thr Val Ala Ala Pro Ser Val Phe Ile Phe Pro Pro Ser Asp Glu<br>Gln Leu Lys Ser Gly Thr Ala Ser Val Val Cys Leu Leu Asn Asn Phe<br>Tyr Pro Arg Glu Ala Lys Val Gln Trp Lys Val Asp Asn Ala Leu Gln<br>Ser Gly Asn Ser Gln Glu Ser Val Thr Glu Gln Asp Ser Lys Asp Ser<br>Thr Tyr Ser Leu Ser Ser Thr Leu Thr Leu Ser Lys Ala Asp Tyr Glu<br>Lys His Lys Val Tyr Ala Cys Glu Val Thr His Gln Gly Leu Ser Ser<br>Pro Val Thr Lys Ser Phe Asn Arg Gly Glu Cys |
| 269 | cgaactgtgg ctgcaccatc tgtcttcatc ttcccgccat ctgatgagca gttgaaatct<br>ggaactgcct ctgttgtgtg cctgctgaat aacttctatc ccagagaggc caaagtacag<br>tggaaggtgg ataacgccct ccaatcggt aactcccagg agagtgtcac agagcaggag<br>agcaaggaca gcacctacag cctcagcagc accctgacgc tgagcaaagc agactacgag<br>aaacacaaag tctacgcgcg cgaagtcacc catcagggcc tgagctcgcc cgtcacaaag<br>agcttcaaca ggggagagtg t |
| 270 | Arg Thr Val Ala Ala Pro Ser Val Phe Ile Phe Pro Pro Ser Asp Glu<br>Gln Leu Lys Ser Gly Thr Ala Ser Val Val Cys Leu Leu Asn Asn Phe<br>Tyr Pro Arg Glu Ala Lys Val Gln Trp Lys Val Asp Asn Ala Leu Gln |

SEQUENCE LISTING

| SEQ ID NO: | SEQUENCE |
|---|---|
| | Ser Gly Asn Ser Gln Glu Ser Val Thr Glu Gln Glu Ser Lys Asp Ser<br>Thr Tyr Ser Leu Ser Ser Thr Leu Thr Leu Ser Lys Ala Asp Tyr Glu<br>Lys His Lys Val Tyr Ala Gly Glu Val Thr His Gln Gly Leu Ser Ser<br>Pro Val Thr Lys Ser Phe Asn Arg Gly Glu Cys |
| 271 | cgaactgtgg ctgcaccatc tgtcttcatc ttcccgccat ctgatgagca gttgaaatct<br>ggaactgcct ctgttgtgtg cctgctgaat aacttctatc ccagagaggc caaagtacag<br>cggaaggtgg ataacgccct ccaatcgggt aactcccagg agagtgtcac agagcaggag<br>agcaaggaca gcacctacag cctcagcagc accctgacgc tgagcaaagc agactacgag<br>aaacacaaag tctacgcctg cgaagtcacc catcagggcc tgagctcgcc cgtcacaaag<br>agcttcaaca ggggagagtg t |
| 272 | Arg Thr Val Ala Ala Pro Ser Val Phe Ile Phe Pro Pro Ser Asp Glu<br>Gln Leu Lys Ser Gly Thr Ala Ser Val Val Cys Leu Leu Asn Asn Phe<br>Tyr Pro Arg Glu Ala Lys Val Gln Arg Lys Val Asp Asn Ala Leu Gln<br>Ser Gly Asn Ser Gln Glu Ser Val Thr Glu Gln Glu Ser Lys Asp Ser<br>Thr Tyr Ser Leu Ser Ser Thr Leu Thr Leu Ser Lys Ala Asp Tyr Glu<br>Lys His Lys Val Tyr Ala Cys Glu Val Thr His Gln Gly Leu Ser Ser<br>Pro Val Thr Lys Ser Phe Asn Arg Gly Glu Cys |
| 273 | cgaactgtgg ctgcaccatc tgtcttcatc ttcccgccat ctgatgagca gttgaaatct<br>ggaactgcct ctgttgtgtg cctgctgaat aacttctatc ccagagaggc caaagtacag<br>tggaaggtgg ataacgccct ccaatcgggt aactcccagg agagtgtcac agagcaggac<br>agcaaggaca gcacctacag cctcagcagc accctgacgc tgagcaaagc agactacgag<br>aaacacaaac tctacgcctg cgaagtcacc catcagggcc tgagctcgcc cgtcacaaag<br>agcttcaaca ggggagagtg t |
| 274 | Arg Thr Val Ala Ala Pro Ser Val Phe Ile Phe Pro Pro Ser Asp Glu<br>Gln Leu Lys Ser Gly Thr Ala Ser Val Val Cys Leu Leu Asn Asn Phe<br>Tyr Pro Arg Glu Ala Lys Val Gln Trp Lys Val Asp Asn Ala Leu Gln<br>Ser Gly Asn Ser Gln Glu Ser Val Thr Glu Gln Asp Ser Lys Asp Ser<br>Thr Tyr Ser Leu Ser Ser Thr Leu Thr Leu Ser Lys Ala Asp Tyr Glu<br>Lys His Lys Leu Tyr Ala Cys Glu Val Thr His Gln Gly Leu Ser Ser<br>Pro Val Thr Lys Ser Phe Asn Arg Gly Glu Cys |
| 275 | cgaactgtgg ctgcaccatc tgtcttcatc ttcccgccat ctgatgagca gttgaaatct<br>ggaactgcct ctgttgtgtg cctgctgaat aacttctatc ccagagaggc caaagtacag<br>tggaaggtgg ataacgccct ccaatcgggt aactcccagg agagtgtcac agagcaggac<br>agcaaggaca gcacctacag cctcagcaac accctgacgc tgagcaaagc agactacgag<br>aaacacaaag tctacgcctg cgaagtcacc catcagggcc tgagctcgcc cgtcacaaag<br>agcttcaaca ggggagagtg c |
| 276 | Arg Thr Val Ala Ala Pro Ser Val Phe Ile Phe Pro Pro Ser Asp Glu<br>Gln Leu Lys Ser Gly Thr Ala Ser Val Val Cys Leu Leu Asn Asn Phe<br>Tyr Pro Arg Glu Ala Lys Val Gln Trp Lys Val Asp Asn Ala Leu Gln<br>Ser Gly Asn Ser Gln Glu Ser Val Thr Glu Gln Asp Ser Lys Asp Ser<br>Thr Tyr Ser Leu Ser Asn Thr Leu Thr Leu Ser Lys Ala Asp Tyr Glu<br>Lys His Lys Val Tyr Ala Cys Glu Val Thr His Gln Gly Leu Ser Ser<br>Pro Val Thr Lys Ser Phe Asn Arg Gly Glu Cys |
| 277 | cccaaggcca accccacggt cactctgttc ccgccctcct ctgaggagct ccaagccaac<br>aaggccacac tagtgtgtct gatcagtgac ttctacccgg gagctgtgac agtggcttgg<br>aaggcagatg gcagccccgt caaggcggga gtggagacga ccaaaccctc caaacagagc<br>aacaacaagt acgcggccag cagctacctg agcctgacgc cgagcagtg gaagtccac<br>agaagctaca gctgccaggt cacgcatgaa gggagcaccg tggagaagac agtggcccct<br>acagaatgtt ca |
| 278 | Pro Lys Ala Asn Pro Thr Val Thr Leu Phe Pro Pro Ser Ser Glu Glu<br>Leu Gln Ala Asn Lys Ala Thr Leu Val Cys Leu Ile Ser Asp Phe Tyr<br>Pro Gly Ala Val Thr Val Ala Trp Lys Ala Asp Gly Ser Pro Val Lys<br>Ala Gly Val Glu Thr Thr Lys Pro Ser Lys Gln Ser Asn Asn Lys Tyr<br>Ala Ala Ser Ser Tyr Leu Ser Leu Thr Pro Glu Gln Trp Lys Ser His<br>Arg Ser Tyr Ser Cys Gln Val Thr His Glu Gly Ser Thr Val Glu Lys<br>Thr Val Ala Pro Thr Glu Cys Ser |
| 279 | ggtcagccca aggccaaccc cactgtcact ctgttcccgc cctcctctga ggagctccaa<br>gccaacaagg ccacactagt gtgtctgatc agtgacttct acccgggagc tgtgacagtg<br>gcctggaagg cagatggcag ccccgtcaag gcgggagtgg agaccaccaa accctccaaa<br>cagagcaaca acaagtacgc ggccagcagc tacctgagcc tgacgcccga gcagtggaag<br>tcccacagaa gctacagctg ccaggtcacg catgaaggga gcaccgtgga agacagtg<br>gcccctacag aatgttca |
| 280 | Gly Gln Pro Lys Ala Asn Pro Thr Val Thr Leu Phe Pro Pro Ser Ser<br>Glu Glu Leu Gln Ala Asn Lys Ala Thr Leu Val Cys Leu Ile Ser Asp |

SEQUENCE LISTING

| SEQ ID NO: | SEQUENCE |
|---|---|
| | Phe Tyr Pro Gly Ala Val Thr Val Ala Trp Lys Ala Asp Gly Ser Pro Val Lys Ala Gly Val Glu Thr Thr Lys Pro Ser Lys Gln Ser Asn Asn Lys Tyr Ala Ala Ser Ser Tyr Leu Ser Leu Thr Pro Glu Gln Trp Lys Ser His Arg Ser Tyr Ser Cys Gln Val Thr His Glu Gly Ser Thr Val Glu Lys Thr Val Ala Pro Thr Glu Cys Ser |
| 281 | ggtcagccca aggccaaccc cactgtcact ctgttcccgc cctcctctga ggagctccaa gccaacaagg ccacactagt gtgtctgatc agtgacttct acccgggagc tgtgacagtg gcctggaagg cagatggcag ccccgtcaag gcgggagtgg agaccaccaa accctccaaa cagagcaaca acaagtacgc ggccagcagc tacctgagcc tgacgcccga gcagtggaag tcccacagaa gctacagctg ccaggtcacg catgaaggga gcaccgtgga agacagtg gcccctacag aatgttca |
| 282 | Gly Gly Cys Cys Ala Gly Cys Cys Thr Ala Ala Gly Gly Cys Cys Gly Cys Thr Cys Thr Thr Cys Thr Gly Thr Gly Ala Cys Cys Cys Thr Gly Thr Thr Cys Cys Cys Cys Cys Cys Ala Thr Cys Cys Thr Cys Cys Gly Ala Gly Gly Ala Ala Cys Thr Cys Gly Ala Gly Gly Cys Thr Ala Ala Cys Ala Ala Gly Gly Cys Cys Ala Cys Cys Thr Cys Gly Thr Gly Thr Gly Cys Cys Thr Gly Ala Thr Cys Ala Gly Cys Gly Ala Cys Thr Thr Cys Thr Ala Cys Cys Cys Thr Gly Gly Cys Gly Cys Cys Gly Thr Gly Ala Cys Cys Gly Thr Gly Gly Cys Cys Thr Gly Gly Ala Ala Gly Gly Cys Cys Gly Ala Cys Thr Cys Cys Ala Gly Cys Cys Cys Thr Gly Thr Cys Ala Ala Ala Gly Cys Cys Gly Gly Cys Gly Thr Gly Gly Ala Gly Ala Cys Cys Ala Cys Cys Ala Cys Cys Cys Thr Cys Cys Ala Ala Gly Thr Cys Thr Cys Cys Ala Ala Cys Ala Ala Cys Ala Ala Gly Thr Ala Cys Gly Cys Gly Cys Cys Thr Cys Cys Ala Gly Cys Thr Ala Thr Cys Thr Cys Thr Cys Cys Cys Thr G

| SEQ ID NO: | SEQUENCE |
|---|---|
| | Ala Gly Val Glu Thr Thr Thr Pro Ser Lys Gln Ser Asn Asn Lys Tyr<br>Ala Ala Ser Ser Tyr Leu Ser Leu Thr Pro Glu Gln Trp Lys Ser His<br>Lys Ser Tyr Ser Cys Gln Val Thr His Glu Gly Ser Thr Val Glu Lys<br>Thr Val Ala Pro Thr Glu Cys Ser |
| 289 | ggtcagccca aggctgcccc ctcggtcact ctgttcccac cctcctctga ggagcttcaa<br>gccaacaagg ccacactggt gtgtctcata agtgacttct acccggggcc agtgacagtt<br>gcctggaagg cagatagcag ccccgtcaag gcggggtgg agaccaccac accctccaaa<br>caaagcaaca acaagtacgc ggccagcagc tacctgagcc tgacgcctga gcagtggaag<br>tcccacaaaa gctacagctg ccaggtcacg catgaaggga gcaccgtgga agacagtg<br>gcccctacgg aatgttca |
| 290 | Gly Gln Pro Lys Ala Ala Pro Ser Val Thr Leu Phe Pro Pro Ser Ser<br>Glu Glu Leu Gln Ala Asn Lys Ala Thr Leu Val Cys Leu Ile Ser Asp<br>Phe Tyr Pro Gly Pro Val Thr Val Ala Trp Lys Ala Asp Ser Ser Pro<br>Val Lys Ala Gly Val Glu Thr Thr Thr Pro Ser Lys Gln Ser Asn Asn<br>Lys Tyr Ala Ala Ser Ser Tyr Leu Ser Leu Thr Pro Glu Gln Trp Lys<br>Ser His Lys Ser Tyr Ser Cys Gln Val Thr His Glu Gly Ser Thr Val<br>Glu Lys Thr Val Ala Pro Thr Glu Cys Ser |
| 291 | ggtcagccca aggctgcccc ctcggtcact ctgttcccac cctcctctga ggagcttcaa<br>gccaacaagg ccacactggt gtgtctcata agtgacttct acccgggagc cgtgacagtg<br>gcctggaagg cagatagcag ccccgtcaag gcgggagtgg agaccaccac accctccaaa<br>caaagcaaca acaagtacgc ggccagcagc tacctgagcc tgacgcctga gcagtggaag<br>tcccacaaaa gctacagctg ccaggtcacg catgaaggga gcaccgtgga agacagtg<br>gcccctacag aatgttca |
| 292 | Gly Gln Pro Lys Ala Ala Pro Ser Val Thr Leu Phe Pro Pro Ser Ser<br>Glu Glu Leu Gln Ala Asn Lys Ala Thr Leu Val Cys Leu Ile Ser Asp<br>Phe Tyr Pro Gly Ala Val Thr Val Ala Trp Lys Ala Asp Ser Ser Pro<br>Val Lys Ala Gly Val Glu Thr Thr Thr Pro Ser Lys Gln Ser Asn Asn<br>Lys Tyr Ala Ala Ser Ser Tyr Leu Ser Leu Thr Pro Glu Gln Trp Lys<br>Ser His Lys Ser Tyr Ser Cys Gln Val Thr His Glu Gly Ser Thr Val<br>Glu Lys Thr Val Ala Pro Thr Glu Cys Ser |
| 293 | ggtcagccca aggctgcccc ctcggtcact ctgttcccgc cctcctctga ggagcttcaa<br>gccaacaagg ccacactggt gtgtctcata agtgacttct acccgggagc cgtgacagtg<br>gcctggaagg cagatagcag ccccgtcaag gcgggagtgg agaccaccac accctccaaa<br>caaagcaaca acaagtacgc ggccagcagc tacctgagcc tgacgcctga gcagtggaag<br>tcccacagaa gctacagctg ccaggtcacg catgaaggcc gcaccgtgga agacagtg<br>gcccctacag aatgttca |
| 294 | Gly Gln Pro Lys Ala Ala Pro Ser Val Thr Leu Phe Pro Pro Ser Ser<br>Glu Glu Leu Gln Ala Asn Lys Ala Thr Leu Val Cys Leu Ile Ser Asp<br>Phe Tyr Pro Gly Ala Val Thr Val Ala Trp Lys Ala Asp Ser Ser Pro<br>Val Lys Ala Gly Val Glu Thr Thr Thr Pro Ser Lys Gln Ser Asn Asn<br>Lys Tyr Ala Ala Ser Ser Tyr Leu Ser Leu Thr Pro Glu Gln Trp Lys<br>Ser His Arg Ser Tyr Ser Cys Gln Val Thr His Glu Gly Ser Thr Val<br>Glu Lys Thr Val Ala Pro Thr Glu Cys Ser |
| 295 | ggtcagccca aggctgcccc atcggtcact ctgttcccgc cctcctctga ggagcttcaa<br>gccaacaagg ccacactggt gtgcctgatc agtgacttct acccgggagc tgtgaaagtg<br>gcctggaagg cagatggcag ccccgtcaac acgggagtgg agaccaccac accctccaaa<br>cagagcaaca acaagtacgc ggccagcagc tacctgagcc tgacgcctga gcagtggaag<br>tcccacagaa gctacagctg ccaggtcacg catgaaggga gcaccgtgga agacagtg<br>gcccctgcag aatgttca |
| 296 | Gly Gln Pro Lys Ala Ala Pro Ser Val Thr Leu Phe Pro Pro Ser Ser<br>Glu Glu Leu Gln Ala Asn Lys Ala Thr Leu Val Cys Leu Ile Ser Asp<br>Phe Tyr Pro Gly Ala Val Lys Val Ala Trp Lys Ala Asp Gly Ser Pro<br>Val Asn Thr Gly Val Glu Thr Thr Thr Pro Ser Lys Gln Ser Asn Asn<br>Lys Tyr Ala Ala Ser Ser Tyr Leu Ser Leu Thr Pro Glu Gln Trp Lys<br>Ser His Arg Ser Tyr Ser Cys Gln Val Thr His Glu Gly Ser Thr Val<br>Glu Lys Thr Val Ala Pro Ala Glu Cys Ser |
| 297 | ggtcagccca aggctgcccc atcggtcact ctgttcccac cctcctctga ggagcttcaa<br>gccaacaagg ccacactggt gtgtctcgta agtgacttct acccgggagc cgtgacagtg<br>gcctggaagg cagatggcag ccccgtcaag gtgggagtgg agaccaccaa accctccaaa<br>caaagcaaca acaagtatgc ggccagcagc tacctgagcc tgacgcccga gcagtggaag<br>tcccacagaa gctacagctg ccgggtcacg catgaaggga gcaccgtgga agacagtg<br>gcccctgcag aatgctct |
| 298 | Gly Gln Pro Lys Ala Ala Pro Ser Val Thr Leu Phe Pro Pro Ser Ser<br>Glu Glu Leu Gln Ala Asn Lys Ala Thr Leu Val Cys Leu Val Ser Asp |

SEQUENCE LISTING

| SEQ ID NO: | SEQUENCE |
|---|---|
| | Phe Tyr Pro Gly Ala Val Thr Val Ala Trp Lys Ala Asp Gly Ser Pro<br>Val Lys Val Gly Val Glu Thr Thr Lys Pro Ser Lys Gln Ser Asn Asn<br>Lys Tyr Ala Ala Ser Ser Tyr Leu Ser Leu Thr Pro Glu Gln Trp Lys<br>Ser His Arg Ser Tyr Ser Cys Arg Val Thr His Glu Gly Ser Thr Val<br>Glu Lys Thr Val Ala Pro Ala Glu Cys Ser |
| 299 | atggaggaga gtgtcgtacg gccctcagtg tttgtggtgg atggacagac cgacatccca<br>ttcacgaggc tgggacgaag ccaccggaga cagtcgtgca gtgtggcccg ggtgggtctg<br>ggtctcttgc tgttgctgat gggggctggg ctggccgtcc aaggctggtt cctcctgcag<br>ctgcactggc gtctaggaga gatggtcacc cgcctgcctg acggacctgc aggctcctgg<br>gagcagctga tacaagagcg aaggtctcac gaggtcaacc cagcagcgca tctcacaggg<br>gccaactcca gcttgaccgg cagcggggggg ccgctgttat gggagactca gctgggcctg<br>gccttcctga ggggcctcag ctaccacgat gggccctttg tggtcaccaa agctggctac<br>tactacatct actccaaggt gcagctgggc ggtgtgggct gcccgctggg cctggccagc<br>accatcaccc acggcctcta caagcgcaca cccgctaccc cgaggagct ggagctgttg<br>gtcagccagc agtcaccctg cggacgggcc accagcagct cccgggtctg gtgggacagc<br>agcttcctgg gtggtgtggt acacctggag gctggggagg aggtggtcgt ccgtgtgctg<br>gatgaacgcc tggttcgact gcgtgatggt acccggtctt acttcggggc tttcatgtgt |
| 300 | Met Glu Glu Ser Val Val Arg Pro Ser Val Phe Val Val Asp Gly Gln<br>Thr Asp Ile Pro Phe Thr Arg Leu Gly Arg Ser His Arg Arg Gln Ser<br>Cys Ser Val Ala Arg Val Gly Leu Gly Leu Leu Leu Leu Leu Met Gly<br>Ala Gly Leu Ala Val Gln Gly Trp Phe Leu Leu Gln Leu His Trp Arg<br>Leu Gly Glu Met Val Thr Arg Leu Pro Asp Gly Pro Ala Gly Ser Trp<br>Glu Gln Leu Ile Gln Glu Arg Arg Ser His Glu Val Asn Pro Ala Ala<br>His Leu Thr Gly Ala Asn Ser Ser Leu Thr Gly Ser Gly Gly Pro Leu<br>Leu Trp Glu Thr Gln Leu Gly Leu Ala Phe Leu Arg Gly Leu Ser Tyr<br>His Asp Gly Ala Leu Val Val Thr Lys Ala Gly Tyr Tyr Tyr Ile Tyr<br>Ser Lys Val Gln Leu Gly Gly Val Gly Cys Pro Leu Gly Leu Ala Ser<br>Thr Ile Thr His Gly Leu Tyr Lys Arg Thr Pro Arg Tyr Pro Glu Glu<br>Leu Glu Leu Leu Val Ser Gln Gln Ser Pro Cys Gly Arg Ala Thr Ser<br>Ser Ser Arg Val Trp Trp Asp Ser Ser Phe Leu Gly Gly Val Val His<br>Leu Glu Ala Gly Glu Glu Val Val Arg Val Leu Asp Glu Arg Leu<br>Val Arg Leu Arg Asp Gly Thr Arg Ser Tyr Phe Gly Ala Phe Met Val |
| 301 | atggaggaga gtgtcgtacg gccctcagtg tttgtggtgg atggacagac cgacatccca<br>ttcacgaggc tgggacgaag ccaccggaga cagtcgtgca gtgtggcccg ggtgggtctg<br>ggtctcttgc tgttgctgat gggggctggg ctggccgtcc aaggctggtt cctcctgcag<br>ctgcactggc gtctaggaga gatggtcacc cgcctgcctg acggacctgc aggctcctgg<br>gagcagctga tacaagagcg aaggtctcac gaggtcaacc cagcagcgca tctcacaggg<br>gccaactcca gcttgaccgg cagcggggggg ccgctgttat gggagactca gctgggcctg<br>gccttcctga ggggcctcag ctaccacgat gggccctttg tggtcaccaa agctggctac<br>tactacatct actccaaggt gcagctgggc ggtgtgggct gcccgctggg cctggccagc<br>accatcaccc acggcctcta caagcgcaca cccgctaccc cgaggagct ggagctgttg<br>gtcagccagc agtcaccctg cggacgggcc accagcagct cccgggtctg gtgggacagc<br>agcttcctgg gtggtgtggt acacctggag gctggggaga aggtggtcgt ccgtgtgctg<br>gatgaacgcc tggttcgact gcgtgatggt acccggtctt acttcggggc tttcatgtgt |
| 302 | Met Glu Glu Ser Val Val Arg Pro Ser Val Phe Val Val Asp Gly Gln<br>Thr Asp Ile Pro Phe Thr Arg Leu Gly Arg Ser His Arg Arg Gln Ser<br>Cys Ser Val Ala Arg Val Gly Leu Gly Leu Leu Leu Leu Leu Met Gly<br>Ala Gly Leu Ala Val Gln Gly Trp Phe Leu Leu Gln Leu His Trp Arg<br>Leu Gly Glu Met Val Thr Arg Leu Pro Asp Gly Pro Ala Gly Ser Trp<br>Glu Gln Leu Ile Gln Glu Arg Arg Ser His Glu Val Asn Pro Ala Ala<br>His Leu Thr Gly Ala Asn Ser Ser Leu Thr Gly Ser Gly Gly Pro Leu<br>Leu Trp Glu Thr Gln Leu Gly Leu Ala Phe Leu Arg Gly Leu Ser Tyr<br>His Asp Gly Ala Leu Val Val Thr Lys Ala Gly Tyr Tyr Tyr Ile Tyr<br>Ser Lys Val Gln Leu Gly Gly Val Gly Cys Pro Leu Gly Leu Ala Ser<br>Thr Ile Thr His Gly Leu Tyr Lys Arg Thr Pro Arg Tyr Pro Glu Glu<br>Leu Glu Leu Leu Val Ser Gln Gln Ser Pro Cys Gly Arg Ala Thr Ser<br>Ser Ser Arg Val Trp Trp Asp Ser Ser Phe Leu Gly Gly Val Val His<br>Leu Glu Ala Gly Glu Lys Val Val Arg Val Leu Asp Glu Arg Leu<br>Val Arg Leu Arg Asp Gly Thr Arg Ser Tyr Phe Gly Ala Phe Met Val |
| 303 | atggaagagt ccgtcgtgcg gccctccgtg ttcgtggtgg atggccagac cgacatcccc<br>ttcaccagac tgggccggtc ccacagacgg cagtcttgct ctgtggctag agtgggcctg<br>ggcctcctgc tgctgctgat gggagctgga ctggctgtgc agggctggtt tctgctgcag<br>ctgcattggc ggctgggcga gatggtcacc aggctgcctg atgggcctgc tggctcttgg<br>gagcagctga tccaggaacg gcggtcccac gaagtgaatc ctgccgctca tctgaccggc<br>gccaactctt ccctgaccgg atctggtgga ccctgctgt gggagactca gctgggcctg<br>gctttcctgc ggggcctgtc ttaccatgat ggcgcccttgt tcgtgaccaa ggccggctac<br>tactacatct actccaaggt gcagctgggc ggcgtgggct gtcctctggg actggcttct<br>accatcaccc acggcctgta caagcggacc cccagatacc cgaggaact ggaactgctg<br>gtgtcccagc agtcccttg tggcagagcc acctcctcca gcagagtgtg gtgggactcc |

| SEQ ID NO: | SEQUENCE |
|---|---|
| | tctttcctgg gcggggtggt gcatctggaa gccggcgaag aggtggtcgt gcgggtgctg<br>gatgagagac tcgtgcggct gagggacggc accagaagct acttcggcgc ctttatggtg |
| 304 | Met Glu Glu Ser Val Val Arg Pro Ser Val Phe Val Val Asp Gly Gln<br>Thr Asp Ile Pro Phe Thr Arg Leu Gly Arg Ser His Arg Arg Gln Ser<br>Cys Ser Val Ala Arg Val Gly Leu Gly Leu Leu Leu Leu Leu Met Gly<br>Ala Gly Leu Ala Val Gln Gly Trp Phe Leu Leu Gln Leu His Trp Arg<br>Leu Gly Glu Met Val Thr Arg Leu Pro Asp Gly Pro Ala Gly Ser Trp<br>Glu Gln Leu Ile Gln Glu Arg Arg Ser His Glu Val Asn Pro Ala Ala<br>His Leu Thr Gly Ala Asn Ser Ser Leu Thr Gly Ser Gly Gly Pro Leu<br>Leu Trp Glu Thr Gln Leu Gly Leu Ala Phe Leu Arg Gly Leu Ser Tyr<br>His Asp Gly Ala Leu Val Val Thr Lys Ala Gly Tyr Tyr Tyr Ile Tyr<br>Ser Lys Val Gln Leu Gly Gly Val Gly Cys Pro Leu Gly Leu Ala Ser<br>Thr Ile Thr His Gly Leu Tyr Lys Arg Thr Pro Arg Tyr Pro Glu Glu<br>Leu Glu Leu Leu Val Ser Gln Gln Ser Pro Cys Gly Arg Ala Thr Ser<br>Ser Ser Arg Val Trp Trp Asp Ser Ser Phe Leu Gly Gly Val Val His<br>Leu Glu Ala Gly Glu Glu Val Val Arg Val Leu Asp Glu Arg Leu<br>Val Arg Leu Arg Asp Gly Thr Arg Ser Tyr Phe Gly Ala Phe Met Val |
| 305 | atggaagagt ccgtcgtgcg gccctccgtg ttcgtggtgg atggccagac cgacatcccc<br>ttcaccagac tgggccggtc ccacagacgg cagtcttgct ctgtggctag agtgggcctg<br>ggcctcctgc tgctgctgat gggagctgga ctggctgtgc agggctggtt tctgctgcag<br>ctgcattggc ggctgggcga gatggtcacc aggctgcctg atggccctgc tggctcttgg<br>gagcagctga tccaggaacg gcgtcccac gaagtgaatc ctgccgctca tctgaccggc<br>gccaactctt ccctgaccgg atctggtgga ccctgctgt gggagactga gctgggcctg<br>gctttcctgc ggggcctgtc ttaccatgat ggcgccctgg tcgtgaccaa ggccggctac<br>tactacatct actccaaggt gcagctgggc ggcgtgggct gtcctctggg actggcttct<br>accatcaccc acggcctgta caagcggacc cccagatacc ccgaggaact ggaactgctg<br>gtgtcccagc agtcccttg tggcagagcc acctcctcca gcagagtgtg gtgggactcc<br>tctttcctgg gcggggtggt gcatctggaa gccggcgaag aggtggtcgt gcgggtgctg<br>gatgagagac tcgtgcggct gagggacggc accagaagct acttcggcgc ctttatggtg |
| 306 | Met Glu Glu Ser Val Val Arg Pro Ser Val Phe Val Val Asp Gly Gln<br>Thr Asp Ile Pro Phe Thr Arg Leu Gly Arg Ser His Arg Arg Gln Ser<br>Cys Ser Val Ala Arg Val Gly Leu Gly Leu Leu Leu Leu Leu Met Gly<br>Ala Gly Leu Ala Val Gln Gly Trp Phe Leu Leu Gln Leu His Trp Arg<br>Leu Gly Glu Met Val Thr Arg Leu Pro Asp Gly Pro Ala Gly Ser Trp<br>Glu Gln Leu Ile Gln Glu Arg Arg Ser His Glu Val Asn Pro Ala Ala<br>His Leu Thr Gly Ala Asn Ser Ser Leu Thr Gly Ser Gly Gly Pro Leu<br>Leu Trp Glu Thr Gln Leu Gly Leu Ala Phe Leu Arg Gly Leu Ser Tyr<br>His Asp Gly Ala Leu Val Val Thr Lys Ala Gly Tyr Tyr Tyr Ile Tyr<br>Ser Lys Val Gln Leu Gly Gly Val Gly Cys Pro Leu Gly Leu Ala Ser<br>Thr Ile Thr His Gly Leu Tyr Lys Arg Thr Pro Arg Tyr Pro Glu Glu<br>Leu Glu Leu Leu Val Ser Gln Gln Ser Pro Cys Gly Arg Ala Thr Ser<br>Ser Ser Arg Val Trp Trp Asp Ser Ser Phe Leu Gly Gly Val Val His<br>Leu Glu Ala Gly Glu Lys Val Val Arg Val Leu Asp Glu Arg Leu<br>Val Arg Leu Arg Asp Gly Thr Arg Ser Tyr Phe Gly Ala Phe Met Val |
| 307 | atgggctggt cctgcatcat cctgttcctg gtggccaccg ctaccggcgt gcattccatg<br>gactacaagg acgacgacga caagggcgga ggatccgag gaggccgg aggcggatcc<br>attgagggca gggatggacc tgccctgtcc tgggagcagc tgatccagga gaggcggtcc<br>cacgaagtga atcccgccgc tcacctgacc ggagccaata gctccctcac aggatccggc<br>ggacctctgc tgtgggaaac ccaactggga ctcgccttcc tgaggggcct ctcctaccac<br>gatggcgctc tggtcgtgac caaggccggc tactactaca tctactccaa ggtgcagctg<br>ggcggagtgg gatgtcctct gggactggcc agcaccatca cccatggcct ctacaagagg<br>accctaggt atcctgagga actggagctg ctggtgagcc agcagtcccc ttgcggaagg<br>gctaccagct cctccagggt gtggtgggat tcctccttcc tgggaggagt cgtgcacctg<br>gaggctggcg aggaggtcgt ggtgagggtg ctggacgaga ggctggtgcg gctcagggat<br>ggcacaaggt cctacttcgg cgccttcatg gtg |
| 308 | Met Gly Trp Ser Cys Ile Ile Leu Phe Leu Val Ala Thr Ala Thr Gly<br>Val His Ser Met Asp Tyr Lys Asp Asp Asp Asp Lys Gly Gly Gly Ser<br>Gly Gly Gly Ser Gly Gly Gly Ser Ile Glu Gly Arg Asp Gly Pro Ala<br>Gly Ser Trp Glu Gln Leu Ile Gln Glu Arg Arg Ser His Glu Val Asn<br>Pro Ala Ala His Leu Thr Gly Ala Asn Ser Ser Leu Thr Gly Ser Gly<br>Gly Pro Leu Leu Trp Glu Thr Gln Leu Gly Leu Ala Phe Leu Arg Gly<br>Leu Ser Tyr His Asp Gly Ala Leu Val Val Thr Lys Ala Gly Tyr Tyr<br>Tyr Ile Tyr Ser Lys Val Gln Leu Gly Gly Val Gly Cys Pro Leu Gly<br>Leu Ala Ser Thr Ile Thr His Gly Leu Tyr Lys Arg Thr Pro Arg Tyr<br>Pro Glu Glu Leu Glu Leu Leu Val Ser Gln Gln Ser Pro Cys Gly Arg<br>Ala Thr Ser Ser Ser Arg Val Trp Trp Asp Ser Ser Phe Leu Gly Gly<br>Val Val His Leu Glu Ala Gly Glu Glu Val Val Arg Val Leu Asp<br>Glu Arg Leu Val Arg Leu Arg Asp Gly Thr Arg Ser Tyr Phe Gly Ala<br>Phe Met Val |

SEQUENCE LISTING

| SEQ ID NO: | SEQUENCE |
|---|---|
| 309 | atgggctggt cctgcatcat cctgttcctg gtggccaccg ctaccggcgt gcattccatg<br>gactacaagg acgacgacga caagggcgga ggatccggag gaggctccgg aggcggatcc<br>attgagggca gggatggacc tgccgatcc tgggagcagc tgatccagga gaggcggtcc<br>cacgaagtga atcccgccgc tcacctgacc ggagccaata gctccctcac aggatccggc<br>ggacctctgc tgtgggaaac ccaactggga ctcgccttcc tgaggggcct ctcctaccac<br>gatggcgctc tggtcgtgac caaggccggc tactactaca tctactccaa ggtgcagctg<br>ggcggagtgg atgtcctct gggactggcc agcaccatca cccatggcct ctacaagagg<br>accctaggt atcctgagga actggagctg ctggtgagcc agcagtcccc ttgcggaagg<br>gctaccagct cctccaggt gtggtgggat tcctccttcc tgggaggagt cgtgcacctg<br>gaggctggcg agaaggtcgt ggtgagggtg ctggacgaga ggctggtgcg gctcagggat<br>ggcacaaggt cctacttcgg cgccttcatg gtg |
| 310 | Met Gly Trp Ser Cys Ile Ile Leu Phe Leu Val Ala Thr Ala Thr Gly<br>Val His Ser Met Asp Tyr Lys Asp Asp Asp Lys Gly Gly Gly Ser<br>Gly Gly Gly Ser Gly Gly Gly Ser Ile Glu Gly Arg Asp Gly Pro Ala<br>Gly Ser Trp Glu Gln Leu Ile Gln Glu Arg Arg Ser His Glu Val Asn<br>Pro Ala Ala His Leu Thr Gly Ala Asn Ser Ser Leu Thr Gly Ser Gly<br>Gly Pro Leu Leu Trp Glu Thr Gln Leu Gly Leu Ala Phe Leu Arg Gly<br>Leu Ser Tyr His Asp Gly Ala Leu Val Val Thr Lys Ala Gly Tyr Tyr<br>Tyr Ile Tyr Ser Lys Val Gln Leu Gly Gly Val Gly Cys Pro Leu Gly<br>Leu Ala Ser Thr Ile Thr His Gly Leu Tyr Lys Arg Thr Pro Arg Tyr<br>Pro Glu Glu Leu Glu Leu Leu Val Ser Gln Gln Ser Pro Cys Gly Arg<br>Ala Thr Ser Ser Ser Arg Val Trp Trp Asp Ser Ser Phe Leu Gly Gly<br>Val Val His Leu Glu Ala Gly Glu Lys Val Val Val Arg Val Leu Asp<br>Glu Arg Leu Val Arg Leu Arg Asp Gly Thr Arg Ser Tyr Phe Gly Ala<br>Phe Met Val |

SEQUENCE CORRELATION TABLE

| SEQ ID NO: | | Human Gene Segment(s) Used | |
|---|---|---|---|
| 1 | 31A10 | IgHV4-4*02/<br>IgHD6-19*01/<br>IgHJ6*02 | VH Nucleotide Sequence |
| 2 | | | VH Amino Acid Sequence |
| 3 | | | HCDR1 Nucleotide Sequence (IMGT) |
| 4 | | | HCDR1 Amino Acid Sequence (IMGT) |
| 5 | | | HCDR2 Nucleotide Sequence (IMGT) |
| 6 | | | HCDR2 Amino Acid Sequence (IMGT) |
| 7 | | | HCDR3 Nucleotide Sequence (IMGT) |
| 8 | | | HCDR3 Amino Acid Sequence (IMGT) |
| 9 | | | HCDR1 Nucleotide Sequence (KABAT) |
| 10 | | | HCDR1 Amino Acid Sequence (KABAT) |
| 11 | | | HCDR2 Nucleotide Sequence (KABAT) |
| 12 | | | HCDR2 Amino Acid Sequence (KABAT) |
| 13 | | | HCDR3 Nucleotide Sequence (KABAT) |
| 14 | | | HCDR3 Amino Acid Sequence (KABAT) |
| 15 | | IgKV1D-13/<br>J5*01 | VL Nucleotide Sequence |
| 16 | | | VL Amino Acid Sequence |
| 17 | | | LCDR1 Nucleotide Sequence (IMGT) |
| 18 | | | LCDR1 Amino Acid Sequence (IMGT) |
| 19 | | | LCDR2 Nucleotide Sequence (IMGT) |
| 20 | | | LCDR2 Amino Acid Sequence (IMGT) |
| 21 | | | LCDR3 Nucleotide Sequence (IMGT) |
| 22 | | | LCDR3 Amino Acid Sequence (IMGT) |
| 23 | | | LCDR1 Nucleotide Sequence (KABAT) |
| 24 | | | LCDR1 Amino Acid Sequence (KABAT) |
| 25 | | | LCDR2 Nucleotide Sequence (KABAT) |
| 26 | | | LCDR2 Amino Acid Sequence (KABAT) |
| 27 | | | LCDR3 Nucleotide Sequence (KABAT) |
| 28 | | | LCDR3 Amino Acid Sequence (KABAT) |
| 29 | 98C07 | IgHV3-11*01/<br>IgHD1-26*-01/<br>IgHJ4*02 | VH Nucleotide Sequence |
| 30 | | | VH Amino Acid Sequence |
| 31 | | | HCDR1 Nucleotide Sequence (IMGT) |
| 32 | | | HCDR1 Amino Acid Sequence (IMGT) |
| 33 | | | HCDR2 Nucleotide Sequence (IMGT) |
| 34 | | | HCDR2 Amino Acid Sequence (IMGT) |
| 35 | | | HCDR3 Nucleotide Sequence (IMGT) |
| 36 | | | HCDR3 Amino Acid Sequence (IMGT) |
| 37 | | | HCDR1 Nucleotide Sequence (KABAT) |
| 38 | | | HCDR1 Amino Acid Sequence (KABAT) |
| 39 | | | HCDR2 Nucleotide Sequence (KABAT) |
| 40 | | | HCDR2 Amino Acid Sequence (KABAT) |
| 41 | | | HCDR3 Nucleotide Sequence (KABAT) |
| 42 | | | HCDR3 Amino Acid Sequence (KABAT) |
| 43 | | IgKV1-16*02/<br>IgKJ3*01 | VL Nucleotide Sequence |
| 44 | | | VL Amino Acid Sequence |
| 45 | | | LCDR1 Nucleotide Sequence (IMGT) |
| 46 | | | LCDR1 Amino Acid Sequence (IMGT) |
| 47 | | | LCDR2 Nucleotide Sequence (IMGT) |
| 48 | | | LCDR2 Amino Acid Sequence (IMGT) |
| 49 | | | LCDR3 Nucleotide Sequence (IMGT) |
| 50 | | | LCDR3 Amino Acid Sequence (IMGT) |
| 51 | | | LCDR1 Nucleotide Sequence (KABAT) |
| 52 | | | LCDR1 Amino Acid Sequence (KABAT) |
| 53 | | | LCDR2 Nucleotide Sequence (KABAT) |
| 54 | | | LCDR2 Amino Acid Sequence (KABAT) |
| 55 | | | LCDR3 Nucleotide Sequence (KABAT) |
| 56 | | | LCDR3 Amino Acid Sequence (KABAT) |

SEQUENCE CORRELATION TABLE

| SEQ ID NO: | | Human Gene Segment(s) Used | |
|---|---|---|---|
| 57 | 42A02 | V3-23*04/ D3-10*01/ J4*02 | VH Nucleotide Sequence |
| 58 | | | VH Amino Acid Sequence |
| 59 | | | HCDR1 Nucleotide Sequence (IMGT) |
| 60 | | | HCDR1 Amino Acid Sequence (IMGT) |
| 61 | | | HCDR2 Nucleotide Sequence (IMGT) |
| 62 | | | HCDR2 Amino Acid Sequence (IMGT) |
| 63 | | | HCDR3 Nucleotide Sequence (IMGT) |
| 64 | | | HCDR3 Amino Acid Sequence (IMGT) |
| 65 | | | HCDR1 Nucleotide Sequence (KABAT) |
| 66 | | | HCDR1 Amino Acid Sequence (KABAT) |
| 67 | | | HCDR2 Nucleotide Sequence (KABAT) |
| 68 | | | HCDR2 Amino Acid Sequence (KABAT) |
| 69 | | | HCDR3 Nucleotide Sequence (KABAT) |
| 70 | | | HCDR3 Amino Acid Sequence (KABAT) |
| 71 | | IgLV3-21*01/ IgLJ3*02 | VL Nucleotide Sequence |
| 72 | | | VL Amino Acid Sequence |
| 73 | | | LCDR1 Nucleotide Sequence (IMGT) |
| 74 | | | LCDR1 Amino Acid Sequence (IMGT) |
| 75 | | | LCDR2 Nucleotide Sequence (IMGT) |
| 76 | | | LCDR2 Amino Acid Sequence (IMGT) |
| 77 | | | LCDR3 Nucleotide Sequence (IMGT) |
| 78 | | | LCDR3 Amino Acid Sequence (IMGT) |
| 79 | | | LCDR1 Nucleotide Sequence (KABAT) |
| 80 | | | LCDR1 Amino Acid Sequence (KABAT) |
| 81 | | | LCDR2 Nucleotide Sequence (KABAT) |
| 82 | | | LCDR2 Amino Acid Sequence (KABAT) |
| 83 | | | LCDR3 Nucleotide Sequence (KABAT) |
| 84 | | | LCDR3 Amino Acid Sequence (KABAT) |
| 85 | 29C09 | IgHV1-8*01/ IgHD3-16*02/ IgHJ3*02 | VH Nucleotide Sequence |
| 86 | | | VH Amino Acid Sequence |
| 87 | | | HCDR1 Nucleotide Sequence (IMGT) |
| 88 | | | HCDR1 Amino Acid Sequence (IMGT) |
| 89 | | | HCDR2 Nucleotide Sequence (IMGT) |
| 90 | | | HCDR2 Amino Acid Sequence (IMGT) |
| 91 | | | HCDR3 Nucleotide Sequence (IMGT) |
| 92 | | | HCDR3 Amino Acid Sequence (IMGT) |
| 93 | | | HCDR1 Nucleotide Sequence (KABAT) |
| 94 | | | HCDR1 Amino Acid Sequence (KABAT) |
| 95 | | | HCDR2 Nucleotide Sequence (KABAT) |
| 96 | | | HCDR2 Amino Acid Sequence (KABAT) |
| 97 | | | HCDR3 Nucleotide Sequence (KABAT) |
| 98 | | | HCDR3 Amino Acid Sequence (KABAT) |
| 99 | | IgLV3-10*01/ IgLJ1*01 | VL Nucleotide Sequence |
| 100 | | | VL Amino Acid Sequence |
| 101 | | | LCDR1 Nucleotide Sequence (IMGT) |
| 102 | | | LCDR1 Amino Acid Sequence (IMGT) |
| 103 | | | LCDR2 Nucleotide Sequence (IMGT) |
| 104 | | | LCDR2 Amino Acid Sequence (IMGT) |
| 105 | | | LCDR3 Nucleotide Sequence (IMGT) |
| 106 | | | LCDR3 Amino Acid Sequence (IMGT) |
| 107 | | | LCDR1 Nucleotide Sequence (KABAT) |
| 108 | | | LCDR1 Amino Acid Sequence (KABAT) |
| 109 | | | LCDR2 Nucleotide Sequence (KABAT) |
| 110 | | | LCDR2 Amino Acid Sequence (KABAT) |
| 111 | | | LCDR3 Nucleotide Sequence (KABAT) |
| 112 | | | LCDR3 Amino Acid Sequence (KABAT) |
| 113 | 14B09 | IgHV1-3*01/ IgHD1-14*01/ IgHJ5*02 | VH Nucleotide Sequence |
| 114 | | | VH Amino Acid Sequence |
| 115 | | | HCDR1 Nucleotide Sequence (IMGT) |
| 116 | | | HCDR1 Amino Acid Sequence (IMGT) |
| 117 | | | HCDR2 Nucleotide Sequence (IMGT) |
| 118 | | | HCDR2 Amino Acid Sequence (IMGT) |
| 119 | | | HCDR3 Nucleotide Sequence (IMGT) |
| 120 | | | HCDR3 Amino Acid Sequence (IMGT) |
| 121 | | | HCDR1 Nucleotide Sequence (KABAT) |
| 122 | | | HCDR1 Amino Acid Sequence (KABAT) |
| 123 | | | HCDR2 Nucleotide Sequence (KABAT) |
| 124 | | | HCDR2 Amino Acid Sequence (KABAT) |
| 125 | | | HCDR3 Nucleotide Sequence (KABAT) |
| 126 | | | HCDR3 Amino Acid Sequence (KABAT) |
| 127 | | IgLV2-23*02/ IgLJ3*01 | VL Nucleotide Sequence |
| 128 | | | VL Amino Acid Sequence |
| 129 | | | LCDR1 Nucleotide Sequence (IMGT) |
| 130 | | | LCDR1 Amino Acid Sequence (IMGT) |
| 131 | | | LCDR2 Nucleotide Sequence (IMGT) |
| 132 | | | LCDR2 Amino Acid Sequence (IMGT) |
| 133 | | | LCDR3 Nucleotide Sequence (IMGT) |
| 134 | | | LCDR3 Amino Acid Sequence (IMGT) |
| 135 | | | LCDR1 Nucleotide Sequence (KABAT) |
| 136 | | | LCDR1 Amino Acid Sequence (KABAT) |
| 137 | | | LCDR2 Nucleotide Sequence (KABAT) |
| 138 | | | LCDR2 Amino Acid Sequence (KABAT) |
| 139 | | | LCDR3 Nucleotide Sequence (KABAT) |
| 140 | | | LCDR3 Amino Acid Sequence (KABAT) |
| 141 | 13H04 | IgHV1-18*01/ IgHD1-1*01/ IgHJ5*02 | VH Nucleotide Sequence |
| 142 | | | VH Amino Acid Sequence |
| 143 | | | HCDR1 Nucleotide Sequence (IMGT) |
| 144 | | | HCDR1 Amino Acid Sequence (IMGT) |
| 145 | | | HCDR2 Nucleotide Sequence (IMGT) |
| 146 | | | HCDR2 Amino Acid Sequence (IMGT) |
| 147 | | | HCDR3 Nucleotide Sequence (IMGT) |
| 148 | | | HCDR3 Amino Acid Sequence (IMGT) |
| 149 | | | HCDR1 Nucleotide Sequence (KABAT) |
| 150 | | | HCDR1 Amino Acid Sequence (KABAT) |
| 151 | | | HCDR2 Nucleotide Sequence (KABAT) |
| 152 | | | HCDR2 Amino Acid Sequence (KABAT) |
| 153 | | | HCDR3 Nucleotide Sequence (KABAT) |
| 154 | | | HCDR3 Amino Acid Sequence (KABAT) |
| 155 | | IgLV2-23*02/ IgLJ3*02 | VL Nucleotide Sequence |
| 156 | | | VL Amino Acid Sequence |
| 157 | | | LCDR1 Nucleotide Sequence (IMGT) |
| 158 | | | LCDR1 Amino Acid Sequence (IMGT) |
| 159 | | | LCDR2 Nucleotide Sequence (IMGT) |
| 160 | | | LCDR2 Amino Acid Sequence (IMGT) |
| 161 | | | LCDR3 Nucleotide Sequence (IMGT) |
| 162 | | | LCDR3 Amino Acid Sequence (IMGT) |
| 163 | | | LCDR1 Nucleotide Sequence (KABAT) |
| 164 | | | LCDR1 Amino Acid Sequence (KABAT) |
| 165 | | | LCDR2 Nucleotide Sequence (KABAT) |
| 166 | | | LCDR2 Amino Acid Sequence (KABAT) |
| 167 | | | LCDR3 Nucleotide Sequence (KABAT) |
| 168 | | | LCDR3 Amino Acid Sequence (KABAT) |
| 169 | 117C06 | IgHV1-18*01/ IgHJ5*02 | VH Nucleotide Sequence |
| 170 | | | VH Amino Acid Sequence |
| 171 | | | HCDR1 Nucleotide Sequence (IMGT) |
| 172 | | | HCDR1 Amino Acid Sequence (IMGT) |
| 173 | | | HCDR2 Nucleotide Sequence (IMGT) |
| 174 | | | HCDR2 Amino Acid Sequence (IMGT) |
| 175 | | | HCDR3 Nucleotide Sequence (IMGT) |

SEQUENCE CORRELATION TABLE

| SEQ ID NO: | Human Gene Segment(s) Used | | Description |
|---|---|---|---|
| 176 | | | HCDR3 Amino Acid Sequence (IMGT) |
| 177 | | | HCDR1 Nucleotide Sequence (KABAT) |
| 178 | | | HCDR1 Amino Acid Sequence (KABAT) |
| 179 | | | HCDR2 Nucleotide Sequence (KABAT) |
| 180 | | | HCDR2 Amino Acid Sequence (KABAT) |
| 181 | | | HCDR3 Nucleotide Sequence (KABAT) |
| 182 | | | HCDR3 Amino Acid Sequence (KABAT) |
| 183 | | IgKV3-20*01/ IgKJ2*04 | VL Nucleotide Sequence |
| 184 | | | VL Amino Acid Sequence |
| 185 | | | LCDR1 Nucleotide Sequence (IMGT) |
| 186 | | | LCDR1 Amino Acid Sequence (IMGT) |
| 187 | | | LCDR2 Nucleotide Sequence (IMGT) |
| 188 | | | LCDR2 Amino Acid Sequence (IMGT) |
| 189 | | | LCDR3 Nucleotide Sequence (IMGT) |
| 190 | | | LCDR3 Amino Acid Sequence (IMGT) |
| 191 | | | LCDR1 Nucleotide Sequence (KABAT) |
| 192 | | | LCDR1 Amino Acid Sequence (KABAT) |
| 193 | | | LCDR2 Nucleotide Sequence (KABAT) |
| 194 | | | LCDR2 Amino Acid Sequence (KABAT) |
| 195 | | | LCDR3 Nucleotide Sequence (KABAT) |
| 196 | | | LCDR3 Amino Acid Sequence (KABAT) |
| 197 | 144F05 | IgHV4-4*02/ IgHD6-13*01/ IgHJ6*02 | VH Nucleotide Sequence |
| 198 | | | VH Amino Acid Sequence |
| 199 | | | HCDR1 Nucleotide Sequence (IMGT) |
| 200 | | | HCDR1 Amino Acid Sequence (IMGT) |
| 201 | | | HCDR2 Nucleotide Sequence (IMGT) |
| 202 | | | HCDR2 Amino Acid Sequence (IMGT) |
| 203 | | | HCDR3 Nucleotide Sequence (IMGT) |
| 204 | | | HCDR3 Amino Acid Sequence (IMGT) |
| 205 | | | HCDR1 Nucleotide Sequence (KABAT) |
| 206 | | | HCDR1 Amino Acid Sequence (KABAT) |
| 207 | | | HCDR2 Nucleotide Sequence (KABAT) |
| 208 | | | HCDR2 Amino Acid Sequence (KABAT) |
| 209 | | | HCDR3 Nucleotide Sequence (KABAT) |
| 210 | | | HCDR3 Amino Acid Sequence (KABAT) |
| 211 | | IgKV1-33*01/ IgKJ4*01 | VL Nucleotide Sequence |
| 212 | | | VL Amino Acid Sequence |
| 213 | | | LCDR1 Nucleotide Sequence (IMGT) |
| 214 | | | LCDR1 Amino Acid Sequence (IMGT) |
| 215 | | | LCDR2 Nucleotide Sequence (IMGT) |
| 216 | | | LCDR2 Amino Acid Sequence (IMGT) |
| 217 | | | LCDR3 Nucleotide Sequence (IMGT) |
| 218 | | | LCDR3 Amino Acid Sequence (IMGT) |
| 219 | | | LCDR1 Nucleotide Sequence (KABAT) |
| 220 | | | LCDR1 Amino Acid Sequence (KABAT) |
| 221 | | | LCDR2 Nucleotide Sequence (KABAT) |
| 222 | | | LCDR2 Amino Acid Sequence (KABAT) |
| 223 | | | LCDR3 Nucleotide Sequence (KABAT) |
| 224 | | | LCDR3 Amino Acid Sequence (KABAT) |
| 225 | 62C01 | IgHV3-23*04/ IgHD3-10*01/ IgHJ3*02 | VH Nucleotide Sequence |
| 226 | | | VH Amino Acid Sequence |
| 227 | | | HCDR1 Nucleotide Sequence (IMGT) |
| 228 | | | HCDR1 Amino Acid Sequence (IMGT) |
| 229 | | | HCDR2 Nucleotide Sequence (IMGT) |
| 230 | | | HCDR2 Amino Acid Sequence (IMGT) |
| 231 | | | HCDR3 Nucleotide Sequence (IMGT) |
| 232 | | | HCDR3 Amino Acid Sequence (IMGT) |
| 233 | | | HCDR1 Nucleotide Sequence (KABAT) |
| 234 | | | HCDR1 Amino Acid Sequence (KABAT) |
| 235 | | | HCDR2 Nucleotide Sequence (KABAT) |
| 236 | | | HCDR2 Amino Acid Sequence (KABAT) |
| 237 | | | HCDR3 Nucleotide Sequence (KABAT) |
| 238 | | | HCDR3 Amino Acid Sequence (KABAT) |
| 239 | | IgKV1D-12*02/ IgKJ4*01 | VL Nucleotide Sequence |
| 240 | | | VL Amino Acid Sequence |
| 241 | | | LCDR1 Nucleotide Sequence (IMGT) |
| 242 | | | LCDR1 Amino Acid Sequence (IMGT) |
| 243 | | | LCDR2 Nucleotide Sequence (IMGT) |
| 244 | | | LCDR2 Amino Acid Sequence (IMGT) |
| 245 | | | LCDR3 Nucleotide Sequence (IMGT) |
| 246 | | | LCDR3 Amino Acid Sequence (IMGT) |
| 247 | | | LCDR1 Nucleotide Sequence (KABAT) |
| 248 | | | LCDR1 Amino Acid Sequence (KABAT) |
| 249 | | | LCDR2 Nucleotide Sequence (KABAT) |
| 250 | | | LCDR2 Amino Acid Sequence (KABAT) |
| 251 | | | LCDR3 Nucleotide Sequence (KABAT) |
| 252 | | | LCDR3 Amino Acid Sequence (KABAT) |
| 253 | Human IgG4 heavy chain constant region #1 | IGHG*01 | VH Nucleotide Sequence |
| 254 | | | VH Amino Acid Sequence |
| 255 | Human IgG4 heavy chain constant region #2 | IGHG*02 | VH Nucleotide Sequence |
| 256 | | | VH Amino Acid Sequence |
| 257 | Human IgG4 heavy chain constant region #3 | IGHG*03 | VH Nucleotide Sequence |
| 258 | | | VH Amino Acid Sequence |
| 259 | IgG4 heavy chain constant region | | VH Nucleotide Sequence—Synthetic Version A |
| 260 | IgG4 heavy chain constant region | | VH Amino Acid Sequence—Encoded by Synthetic Version A, B & C |
| 261 | IgG4 heavy chain constant region | | VH Nucleotide Sequence—Synthetic Version B |
| 262 | IgG4 heavy chain constant region | | VH Nucleotide Sequence—Synthetic Version C |
| 263 | IgG4 heavy chain constant region | | VH Nucleotide Sequence—Synthetic Version D |
| 264 | | | VH Amino Acid Sequence—encoded by Synthetic Version D |
| 265 | Human IgG1 heavy chain constant region | | VH Nucleotide Sequence |
| 266 | | | VH Amino Acid Sequence |
| 267 | Human $C_K$ constant region | IGKC*01 | VL Nucleotide Sequence |
| 268 | | | VL Amino Acid Sequence |
| 269 | Human $C_K$ constant region | IGKC*02 | $C_K$ Nucleotide Sequence |

SEQUENCE CORRELATION TABLE

| SEQ ID NO: | Human constant region | Gene Segment(s) Used | Description |
|---|---|---|---|
| 270 | | | $C_K$ Amino Acid Sequence |
| 271 | Human $C_K$ constant region | IGKC*03 | $C_K$ Nucleotide Sequence |
| 272 | | | $C_K$ Amino Acid Sequence |
| 273 | Human $C_K$ constant region | IGKC*04 | $C_K$ Nucleotide Sequence |
| 274 | | | $C_K$ Amino Acid Sequence |
| 275 | Human $C_K$ constant region | IGKC*05 | $C_K$ Nucleotide Sequence |
| 276 | | | $C_K$ Amino Acid Sequence |
| 277 | Human Cλ constant region | IGCλ1*01 | Cλ Nucleotide Sequence |
| 278 | | | Cλ Amino Acid Sequence |
| 279 | Human Cλ constant region | IGCλ1*02 | Cλ Nucleotide Sequence |
| 280 | | | Cλ Amino Acid Sequence |
| 281 | Human Cλ constant region | IGCλ2*01 | Cλ Nucleotide Sequence—Version A |
| 282 | | | Cλ Nucleotide Sequence—Version B |
| 283 | | | Cλ Nucleotide Sequence—Version C |
| 284 | | | Cλ Amino Acid Sequence—Encoded by Version A, B & C |
| 285 | Human Cλ constant region | IGCλ2*02 | Cλ Nucleotide Sequence |
| 286 | | | Cλ Amino Acid Sequence |
| 287 | Human Cλ constant region | IGCλ3*01 | Cλ Nucleotide Sequence |
| 288 | | | Cλ Amino Acid Sequence |
| 289 | Human Cλ constant region | IGCλ3*02 | Cλ Nucleotide Sequence |
| 290 | | | Cλ Amino Acid Sequence |
| 291 | Human Cλ constant region | IGCA3*03 | Cλ Nucleotide Sequence |
| 292 | | | Cλ Amino Acid Sequence |
| 293 | Human Cλ constant region | IGCλ3*04 | Cλ Nucleotide Sequence |
| 294 | | | Cλ Amino Acid Sequence |
| 295 | Human Cλ constant region | IGCλ6*01 | Cλ Nucleotide Sequence |
| 296 | | | Cλ Amino Acid Sequence |
| 297 | Human Cλ constant region | IGCλ7*02 | Cλ Nucleotide Sequence |
| 298 | | | Cλ Amino Acid Sequence |
| 299 | Human LIGHT-214E (Native, Non-codon optimized sequences) | | Nucleotide Sequence |
| 300 | | | Amino Acid Sequence |
| 301 | Human LIGHT-214K (Native, Non-codon optimized sequences) | | Nucleotide Sequence |
| 302 | | | Amino Acid Sequence |
| 303 | Human LIGHT-214E (Codon optimized sequences—Version 1) | | Nucleotide Sequence |
| 304 | | | Amino Acid Sequence |
| 305 | Human LIGHT-214K (Codon optimized sequences—Version 1) | | Nucleotide Sequence |
| 306 | | | Amino Acid Sequence |
| 307 | Human LIGHT-214E (Codon optimized sequences—Version 2; Includes FLAG Tag) | | Nucleotide Sequence |
| 308 | | | Amino Acid Sequence |
| 309 | Human LIGHT-214K (Codon optimized sequences—Version 2; Includes FLAG Tag) | | Nucleotide Sequence |
| 310 | | | Amino Acid Sequence |

IMGT indicates that CDR is determined using IMGT nomenclature;
KABAT indicates that CDR is determined using Kabat nomenclature.
The numbering in the sequence correlation table takes precedence over any inconsistent numbering elsewhere in this text.

FURTHER SEQUENCE LISTING

| | | SEQ ID NO: |
|---|---|---|
| 18E04 | | |
| VH nt | CAGGTGCTGCTGGTGCAGTCTGGGGCTGAGGTAAAGAAGCCTGGGGCCTCAGTGAAGGTCTCCTGCAAGGCTTCTGGAT ACACCTTCACCCATTTTGATATCAACTGGGTGCGACAGGCCACTGGACAAGGGCTTGAGTGGATGGATGGATGAACCC TGACAGTGATAACACAGACTATGCACAGGAGTTCCAGGGCAGAGTCACCATGACCAGGGACACCTCCATAAGCACAGCC TACATGGAGCTGAGCAGCCTGAGATCTGAGGACACGGCCGTGTATTACTGTGCGAGAGGGGGGACTACCCTAGACTACT GGGGCCAGGGAACCCTGGTCACCGTCTCCTCAG | 311 |

| | | SEQ ID NO: |
|---|---|---|
| VH aa | QVLLVQSGAEVKKPGASVKVSCKASGYTFTHFDINWVRQATGQGLEWMGWMNPDSDNTDYAQEFQGRVTMTRDTSISTA YMELSSLRSEDTAVYYCARGGTTLDYWGQGTLVTVSS | 312 |
| VL nt | TCCTATGAGCTGACACAGCCACCCTCGGTGTCAGTGTCCCCAGGACAAACGGCCAGGATCACCTGCTCTGGAGATGCAT TGCCAAAAAATATGCTTATTGGTACCAGCAGAAGTCAGGCCAGGCCCCTGTACTGGTCATCTATGAGGACAGCAAACG ACCCTCCGGGATCCCTGAGAGATTCTCTGGCTCCAGCTCAGGGACAATGGCCACCTTGACTATCAGTGGGGCCCAGGTG GAGGATGAAGCTGACTACTACTGTTACTCAACAGACAGCAGTGATAATCATGTGATATTCGGCGGAGGGACCAAGCTGA CCGTCCTAG | 313 |
| VL aa | SYELTQPPSVSVSPGQTARITCSGDALPKKYAYWYQQKSGQAPVLVIYEDSKRPSGIPERFSGSSSGTMATLTISGAQV EDEADYYCYSTDSSDNHVIFGGGTKLTVL | 314 |
| HCDR1 IMGT | GGATACACCTTCACCCATTTTGAT | 315 |
| HCDR1 Kabat | CATTTTGATATCAAC | 316 |
| HCDR2 IMGT | ATGAACCCTGACAGTGATAACACA | 317 |
| HCDR2 Kabat | TGGATGAACCCTGACAGTGATAACACAGACTATGCACAGGAGTTCCAGGGC | 318 |
| HCDR3 IMGT | GCGAGAGGGGGGACTACCCTAGACTAC | 319 |
| HCDR3 Kabat | GGGGGGACTACCCTAGACTAC | 320 |
| LCDR1 IMGT | GCATTGCCAAAAAATAT | 321 |
| LCDR1 Kabat | TCTGGAGATGCATTGCCAAAAAATATGCTTAT | 322 |
| LCDR2 IMGT | GAGGACAGC | 323 |
| LCDR2 Kabat | GAGGACAGCAAACGACCCTCC | 324 |
| LCDR3 IMGT | TACTCAACAGACAGCAGTGATAATCATGTGATA | 325 |
| LCDR3 Kabat | TACTCAACAGACAGCAGTGATAATCATGTGATA | 326 |
| HCDR1 IMGT | GYTFTHFD | 327 |
| HCDR1 Kabat | HFDIN | 328 |
| HCDR2 IMGT | MNPDSDNT | 329 |
| HCDR2 Kabat | WMNPDSDNTDYAQEFQG | 330 |
| HCDR3 IMGT | ARGGTTLDY | 331 |
| HCDR3 Kabat | GGTTLDY | 332 |
| LCDR1 IMGT | ALPKKY | 333 |
| LCDR1 Kabat | SGDALPKKYAY | 334 |
| LCDR2 IMGT | EDS | 335 |
| LCDR2 Kabat | EDSKRPS | 336 |
| LCDR3 IMGT | YSTDSSDNHVI | 337 |
| LCDR3 Kabat | YSTDSSDNHVI | 338 |
| 98C07 | | |
| VH nt | CAGGTGCAGTTGGTGGAGTCTGGGGGAGGCTTGGTCAAGCCTGGAGGGTCCCTGAGACTCTCCTGTGCAGCCTCTGGAT TCACCTTCAGTGACTACTACATGAGCTGGATCCGCCAGGCTCCAGGGAAGGGACTGGAGTGGGTTTCATACATTAGTAG AAGTAGTTTCATATACTACTCAGAGTCTGTGAAGGGCCGATTCACCATCTCCAGGGACAACGCCAAGAACTCACTGTAT CTGCAAATGAACAGCCTGAGAGCCGAGGACACGGCCGTGTATTACTGTGCGCGATGGGAGCTATCCCCTTTTGACTACT GGGGCCAGGGAACCCTGGTCACCGTCTCCTCAG | 339 |
| VH aa | QVQLVESGGGLVKPGGSLRLSCAASGFTFSDYYMSWIRQAPGKGLEWVSYISRSSFIYYSESVKGRFTISRDNAKNSLY LQMNSLRAEDTAVYYCARWELSPFDYWGQGTLVTVSS | 340 |
| VL nt | GACATCCAGATGACCCAGTCTCCATCCTCACTGTCTGCATCTGTAGGAGACAGAGTCACCATCACTTGTCGGGCGAGTC AGGGCATTAGCAATTATTTAGCCTGGTTTCAGCAGAAACCAGGGAAAGCCCCTAAGTCCCTGATCTATGCTGCATCCAG | 341 |

| | FURTHER SEQUENCE LISTING | SEQ ID NO: |
|---|---|---|
| | TTTGCAAAGTGGGGTCCCATCAAAGTTCAGCGGCAGTGGATCTGGGACAGATTTCACTCTCACCATCAGCAGCCTGCAG CCTGAAGATTTTGCAACTTATTTCTGCCAACAGTATAATACTTACCCATTCACTTTCGGCCCTGGGACCAAAGTGGATA TCAAAC | |
| VL aa | DIQMTQSPSSLSASVGDRVTITCRASQGISNYLAWFQQKPGKAPKSLIYAASSLQSGVPSKFSGSGSGTDFTLTISSLQ PEDFATYFCQQYNTYPFTFGPGTKVDIK | 342 |
| HCDR1 IMGT | GGATTCACCTTCAGTGACTACTAC | 343 |
| HCDR1 Kabat | GACTACTACATGAGC | 344 |
| HCDR2 IMGT | ATTAGTAGAAGTAGTTTCATA | 345 |
| HCDR2 Kabat | TACATTAGTAGAAGTAGTTTCATATACTACTCAGAGTCTGTGAAGGGC | 346 |
| HCDR3 IMGT | GCGCGATGGGAGCTATCCCCTTTTGACTAC | 347 |
| HCDR3 Kabat | TGGGAGCTATCCCCTTTTGACTAC | 348 |
| LCDR1 IMGT | CAGGGCATTAGCAATTAT | 349 |
| LCDR1 Kabat | CGGGCGAGTCAGGGCATTAGCAATTATTTAGCC | 350 |
| LCDR2 IMGT | GCTGCATCC | 351 |
| LCDR2 Kabat | GCTGCATCCAGTTTGCAAAGT | 352 |
| LCDR3 IMGT | CAACAGTATAATACTTACCCATTCACT | 353 |
| LCDR3 Kabat | CAACAGTATAATACTTACCCATTCACT | 354 |
| HCDR1 IMGT | GFTFSDYY | 355 |
| HCDR1 Kabat | DYYMS | 356 |
| HCDR2 IMGT | ISRSSFI | 357 |
| HCDR2 Kabat | YISRSSFIYYSESVKG | 358 |
| HCDR3 IMGT | ARWELSPFDY | 359 |
| HCDR3 Kabat | WELSPFDY | 360 |
| LCDR1 IMGT | QGISNY | 361 |
| LCDR1 Kabat | RASQGISNYLA | 362 |
| LCDR2 IMGT | AAS | 363 |
| LCDR2 Kabat | AASSLQS | 364 |
| LCDR3 IMGT | QQYNTYPFT | 365 |
| LCDR3 Kabat | QQYNTYPFT | 366 |
| | 1C02 | |
| VH nt | CAGGTTCAGCTGGTGCAATCTGGAGCTGAGGTGCAGAAGCCTGGGGCCTCAGTGATGGTCTCCTGCAAGGCTTCTGGTT ACACCTTTACCTATTATGGTATCAGCTGGGTGCGACAGGCCCCTGGACAAGGGCTTGAGTGGATGGGATGGATCAGCGC TAACAGTGGTAACACAAACTATGCACAGAAGTTCCAGGGCAGAGTCACCATGACCACAGACACATCCACGAACACAGCC TACATGGAACTAAGGAGCCTGAGAACTGACGACACGGCCGTTTATTACTGTGCGAAAGGGGGGGTCGCAGTCCTTGAGT ATTGGGGCCAGGGAACCCTGGTCACCGTCTCCTCAG | 367 |
| VH aa | QVQLVQSGAEVQKPGASVMVSCKASGYTFTYYGISWVRQAPGQGLEWMGWISANSGNTNYAQKFQGRVTMTTDTSTNTA YMELRSLRTDDTAVYYCAKGGVAVLEYWGQGTLVTVSS | 368 |
| VL nt | GACATCCAGTTGACCCAGTCTCCATCCTTCCTGTCTGCATCTGTAGGAGACAGAGTCACCATCACTTGCTGGGCCAGTC AGGGCATTAGCAGTTATTTAGCCTGGTATCAGCAAAAACCAGGGAAGCCCCTAACTCCTGATCTATGtTGCATCCAC TTTGCAAAGTGGGGTCCCATCAAGTTCAGCGGCAGTGGATCTGGGACAGAATTCACTCTCACAATCAGCAGCCTGCAG CCTGAAGATTTTGCAACTTATTACTGTCAACAGCTTAAGATTTACCCACTCACTTTCGGCGGAGGGACCAAGGTGGAGA TCAAAC | 369 |

| | FURTHER SEQUENCE LISTING | SEQ ID NO: |
|---|---|---|
| VL aa | DIQLTQSPSFLSASVGDRVTITCWASQGISSYLAWYQQKPGKAPNLLIYVASTLQSGVPSRFSGSGSGTEFTLTISSLQ PEDFATYYCQQLKIYPLTFGGGTKVEIK | 370 |
| HCDR1 IMGT | GGTTACACCTTTACCTATTATGGT | 371 |
| HCDR1 Kabat | TATTATGGTATCAGC | 372 |
| HCDR2 IMGT | ATCAGCGCTAACAGTGGTAACACA | 373 |
| HCDR2 Kabat | TGGATCAGCGCTAACAGTGGTAACACAAACTATGCACAGAAGTTCCAGGGC | 374 |
| HCDR3 IMGT | GCGAAAGGGGGGGTCGCAGTCCTTGAGTAT | 375 |
| HCDR3 Kabat | GGGGGGGTCGCAGTCCTTGAGTAT | 376 |
| LCDR1 IMGT | CAGGGCATTAGCAGTTAT | 377 |
| LCDR1 Kabat | TGGGCCAGTCAGGGCATTAGCAGTTATTTAGCC | 378 |
| LCDR2 IMGT | GTTGCATCC | 379 |
| LCDR2 Kabat | GTTGCATCCACTTTGCAAAGT | 380 |
| LCDR3 IMGT | CAACAGCTTAAGATTTACCCACTCACT | 381 |
| LCDR3 Kabat | CAACAGCTTAAGATTTACCCACTCACT | 382 |
| HCDR1 IMGT | GYTFTYYG | 383 |
| HCDR1 Kabat | YYGIS | 384 |
| HCDR2 IMGT | ISANSGNT | 385 |
| HCDR2 Kabat | WISANSGNTNYAQKFQG | 386 |
| HCDR3 IMGT | AKGGVAVLEY | 387 |
| HCDR3 Kabat | GGVAVLEY | 388 |
| LCDR1 IMGT | QGISSY | 389 |
| LCDR1 Kabat | WASQGISSYLA | 390 |
| LCDR2 IMGT | VAS | 391 |
| LCDR2 Kabat | VASTLQS | 392 |
| LCDR3 IMGT | QQLKIYPLT | 393 |
| LCDR3 Kabat | QQLKIYPLT | 394 |

| 1C06 | | |
|---|---|---|
| VH nt | CAGGTGCAGCTGGTGGAGTCTGGGGGAGGCTTGGTCAAGCCTGGAGGGTCCCTGAGACTCTCCTGTGCAGCCTCTGGAT TCACCTTCAGTGACTACTACATGAACTGGATCCGCCAGGCTCCAGGGAAGGGGCTGGAGTGGATTGCAGACATTAGTAG TCGTGACAATACCATTTACTACGCAGACTCTGTGAAGGGCCGATTCACCATCTCCAGGGACAACGCCAAGAACTCACTG TATCTGCAAATGAACAGTCTGAGAGCCGAGGACACGGCCGTGTATTACTGTGCGAGAGAGAGGGGGTTCGGGGACTACT TCGGTATGGACGTCTGGGGCCAAGGGACCACGGTCACCGTCTCCTCA | 395 |
| VH aa | QVQLVESGGGLVKPGGSLRLSCAASGFTFSDYYMNWIRQAPGKGLEWIADISSRDNTIYYADSVKGRFTISRDNAKNSL YLQMNSLRAEDTAVYYCARERGFGDYFGMDVWGQGTTVTVSS | 396 |
| VL nt | GCCATCCAGTTGACCCAGTCTCCATCCTCCCTGTCTGCATCTGTAGGAGACAGAGTCACCATCGCTTGCCGGGCAAGTC AGGACATTAGCAGTGCTTTAGCCTGGTTCCGGCAGACACCAGGGAAAACTCCTAAGCTCCTGATCTATGATGCCTCCAG TTTGGAAAGTGGAGTCCCATCAAGGTTCCTCGGCAGTGGATCTGGGACAGATTTCACTCTCACCATCAGCAGCCTGCAG CCTGAAGATTTTGCAATTTATTACTGTCAACAGTTTAACACTTACCCTCTCACTTTCGGCGGAGGGACCAAGGTGGAGA TCAAAC | 397 |
| VL aa | AIQLTQSPSSLSASVGDRVTIACRASQDISSALAWFRQTPGKTPKLLIYDASSLESGVPSRFLGSGSGTDFTLTISSLQ PEDFAIYYCQQFNTYPLTFGGGTKVEIK | 398 |

FURTHER SEQUENCE LISTING

| | | SEQ ID NO: |
|---|---|---|
| HCDR1 IMGT | GGATTCACCTTCAGTGACTACTAC | 399 |
| HCDR1 Kabat | GACTACTACATGAAC | 400 |
| HCDR2 IMGT | ATTAGTAGTCGTGACAATACCATT | 401 |
| HCDR2 Kabat | GACATTAGTAGTCGTGACAATACCATTTACTACGCAGACTCTGTGAAGGGC | 402 |
| HCDR3 IMGT | GCGAGAGAGAGGGGGTTCGGGGACTACTTCGGTATGGACGTC | 403 |
| HCDR3 Kabat | GAGAGGGGGTTCGGGGACTACTTCGGTATGGACGTC | 404 |
| LCDR1 IMGT | CAGGACATTAGCAGTGCT | 405 |
| LCDR1 Kabat | CGGGCAAGTCAGGACATTAGCAGTGCTTTAGCC | 406 |
| LCDR2 IMGT | GATGCCTCC | 407 |
| LCDR2 Kabat | GATGCCTCCAGTTTGGAAAGT | 408 |
| LCDR3 IMGT | CAACAGTTTAACACTTACCCTCTCACT | 409 |
| LCDR3 Kabat | CAACAGTTTAACACTTACCCTCTCACT | 410 |
| HCDR1 IMGT | GFTFSDYY | 411 |
| HCDR1 Kabat | DYYMN | 412 |
| HCDR2 IMGT | ISSRDNTI | 413 |
| HCDR2 Kabat | DISSRDNTIYYADSVKG | 414 |
| HCDR3 IMGT | ARERGFGDYFGMDV | 415 |
| HCDR3 Kabat | ERGFGDYFGMDV | 416 |
| LCDR1 IMGT | QDISSA | 417 |
| LCDR1 Kabat | RASQDISSALA | 418 |
| LCDR2 IMGT | DAS | 419 |
| LCDR2 Kabat | DASSLES | 420 |
| LCDR3 IMGT | QQFNTYPLT | 421 |
| LCDR3 Kabat | QQFNTYPLT | 422 |
| Rabbit LIGHT Extracellular Domain | | 423 |

The invention claimed is:

1. An antibody or a fragment thereof, that specifically binds to human lymphotoxin-like, exhibits inducible expression and competes with HSV glycoprotein D for HVEM, a receptor expressed by T lymphocytes 214E allele (214E hLIGHT), competes for binding to said 214E hLIGHT with the antibody 01C02 comprises the HCDR1, HCDR2, HCDR3, LCDR1, LCDR2, and LCDR3 of 01C02.

2. The antibody or antibody fragment according to claim 1, wherein the antibody or fragment comprises variable domains that i. specifically bind both 214E hLIGHT and lymphotoxin-like, exhibits inducible expression and competes with HSV glycoprotein D for HVEM, a receptor expressed by T lymphocytes 214K allele (214K hLIGHT), ii. compete with an antibody comprising the variable regions of 01C02 for binding 214E hLIGHT, and iii. do not compete with an antibody comprising the variable regions of an antibody selected from 01C06 and 18E04 for binding to 214E hLIGHT; or wherein the antibody or fragment comprises variable domains that iv. specifically bind both 214E hLIGHT and 214K hLIGHT, v. compete with an antibody comprising the variable regions of 31A10 for binding 214E hLIGHT and vi. compete with an antibody comprising the variable regions of 01C02 for binding to 214E hLIGHT.

3. The antibody or fragment of claim 1, wherein (ii), (iii), (v) and (vi) are determined using the variable domains in a human IgG4 antibody format.

4. The antibody or fragment of claim 1, wherein the antibody is in a human IgG4 format.

5. The antibody or fragment of claim 1, comprising a VH domain that comprises an amino acid sequence at least 95% identical to SEQ ID NO: 368.

6. The antibody or fragment of claim 1, comprising a VL domain that comprises an amino acid sequence at least 95% identical to SEQ ID NO: 370.

7. The antibody or fragment of claim 1 comprising lambda light chain variable domains.

8. The antibody or fragment of claim 1, wherein the antibody or fragment competes with mAb664 for binding to 214E hLIGHT.

9. The antibody or fragment of claim 1, wherein the hLIGHT is human cell surface-expressed hLIGHT.

10. The antibody or fragment of claim 1, wherein the antibody or fragment decreases IL-8 secretion from human epithelial cells expressing a receptor for 214E hLIGHT in vitro.

11. The antibody or fragment of claim 10, wherein the cells are primary cells.

12. The antibody or fragment of claim 1, wherein the antibody or fragment specifically binds SEQ ID NO: 423 and SEQ ID NO: 308, wherein binding affinity to human LIGHT extracellular protein is at least the affinity of binding to rabbit LIGHT extracellular protein.

13. The antibody or fragment of claim 1, wherein the antibody or fragment inhibits binding of 214E hLIGHT to a human HVEM and/or human lymphotoxin β receptor with an IC50 of $1\times10^{-8}$ or less in a HTRF assay.

14. A pharmaceutical composition comprising the antibody or fragment of claim 1 and a diluent, excipient or carrier; and optionally further comprising an anti-inflammatory drug.

15. A kit comprising the antibody or fragment of claim 1 and means for genotyping a human as positive or negative for a nucleotide sequence encoding 214E hLIGHT polypeptide and/or means for phenotyping a human as positive or negative for a 214E hLIGHT polypeptide.

16. A kit comprising the antibody or fragment of claim 1 and means for genotyping a human as positive or negative for a nucleotide sequence encoding 214K hLIGHT polypeptide and/or means for phenotyping a human as positive or negative for a 214K hLIGHT polypeptide.

17. An isolated nucleic acid that encodes the HCDR3 of the antibody recited in claim 1.

18. The isolated nucleic acid of claim 17 comprising a nucleotide sequence that is at least 95% identical, to a sequence selected from SEQ ID NOs: 375, 376, 147, 153, 7 and 13.

19. A vector comprising the isolated nucleic acid of claim 17.

20. A host cell comprising the isolated nucleic acid of claim 17.

21. The isolated nucleic acid of claim 17, comprising a nucleotide sequence that is 100% identical, to a sequence selected from SEQ ID NOs: 375, 376, 147, 153, 7 and 13.

22. An isolated nucleic acid that encodes the VH domain and/or a VL domain, or encodes a heavy chain or a light chain, of an antibody recited in claim 1.

23. The isolated nucleic acid of claim 22 comprising a nucleotide sequence that is at least 95% identical, to a sequence selected from SEQ ID NOs: 367, 1 and 141.

24. The isolated nucleic acid of claim 22 comprising a nucleotide sequence that is at least 95% identical to a sequence selected from SEQ ID NOs: 369, 15 and 155.

25. A method of treating or preventing a human lymphotoxin-like, exhibits inducible expression and competes with HSV glycoprotein D for HVEM, a receptor expressed by T lymphocytes (hLIGHT)-mediated disease or condition in a human by decreasing one, more or all of:

i. the secretion of a cytokine selected from IL-2, TNF alpha and interferon gamma in the human;

ii. the proliferation of leukocytes of the human; and iii. the binding of hLIGHT by human epithelial cells expressing a receptor for hLIGHT;

wherein the method comprises administering to said human a therapeutically effective amount of an antibody or fragment that specifically binds to hLIGHT, wherein the antibody or fragment is according to claim 1.

26. The method claim 25, wherein the human has been genotyped as positive for a nucleotide sequence encoding 214E hLIGHT polypeptide and/or wherein the human has been phenotyped as positive for a 214E hLIGHT polypeptide.

27. The method of claim 25, wherein the disease or condition is selected from the group consisting of an inflammatory bowel disease (IBD), Crohn's disease, rheumatoid arthritis, psoriasis, bronchiolitis, gingivitis, transplant rejection, allogeneic transplant rejection, graft-versus-host disease (GvHD), asthma, adult respiratory distress syndrome (ARDS), septic shock, ulcerative colitis, Sjogren's syndrome and airway inflammation.

28. The antibody or fragment of claim 1, comprising a VH domain that comprises the amino acid sequence of SEQ ID NO: 368.

29. The antibody or fragment of claim 1, comprising a VL domain that comprises the amino acid sequence of SEQ ID NO: 370.

30. The antibody or fragment of claim 1, wherein the competition is determined using surface plasmon resonance (SPR).

* * * * *